US012808892B2

(12) United States Patent
Nguyen et al.

(10) Patent No.: US 12,808,892 B2
(45) **Date of Patent: *Nov. 24, 2026**

(54) INSTRUMENT FOR PROCESSING CARTRIDGE FOR PERFORMING ASSAYS IN A CLOSED SAMPLE PREPARATION AND REACTION SYSTEM

(71) Applicant: Roche Molecular Systems, Inc., Pleasanton, CA (US)

(72) Inventors: Michael Thomas Nguyen, Carlsbad, CA (US); Sean Ford, Oceanside, CA (US); Nikolas James Hansen, La Jolla, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 18/649,862

(22) Filed: Apr. 29, 2024

(65) Prior Publication Data

US 2024/0345115 A1 Oct. 17, 2024

Related U.S. Application Data

(63) Continuation of application No. 17/685,318, filed on Mar. 2, 2022, now Pat. No. 12,000,847, which is a (Continued)

(51) Int. Cl.
*G01N 35/00* (2006.01)
*B01L 3/00* (2006.01)
(Continued)

(52) U.S. Cl.
CPC .................. *G01N 35/00732* (2013.01); *B01L 3/502715* (2013.01); *B01L 3/50273* (2013.01);
(Continued)

(58) Field of Classification Search
CPC ....... G01N 35/00732; G01N 35/00029; G01N 35/00871; G01N 2035/00148;
(Continued)

(56) References Cited

U.S. PATENT DOCUMENTS

D60,340 S 2/1922 Grier
D202,013 S 8/1965 Hamilton
(Continued)

FOREIGN PATENT DOCUMENTS

CA 3036572 A1 3/2018
DE 102005032134 A1 1/2007
(Continued)

OTHER PUBLICATIONS

EP: Examination Report dated Oct. 27, 2021 in European Patent Application No. 17781237.7.
(Continued)

*Primary Examiner* — John Mcguirk
(74) *Attorney, Agent, or Firm* — Snell & Wilmer, L.L.P.; April Wurster

(57) ABSTRACT

In one embodiment, a diagnostic system includes an instrument coupled to a client device and having at least one sample processing bay. The diagnostic system has a software architecture including instrument software (ISW) associated with the instrument. The ISW receives an assay definition file (ADF) that has a control file and an assay analysis module (AAM) file. The processing bay prepares and senses the sample according to parameters in the OPUS file and then generates sensor scan data. The diagnostic system then analyzes the sensor scan data and prepares a report according to the AAM file.

21 Claims, 79 Drawing Sheets

Related U.S. Application Data continuation of application No. 15/708,847, filed on Sep. 19, 2017, now Pat. No. 11,300,578.

(60) Provisional application No. 62/396,449, filed on Sep. 19, 2016.

(51) Int. Cl.
*C12Q 1/6888* (2018.01)
*B01L 7/00* (2006.01)
*G01N 35/04* (2006.01)

(52) U.S. Cl.
CPC ...... *B01L 3/502738* (2013.01); *C12Q 1/6888* (2013.01); *G01N 35/00029* (2013.01); *G01N 35/00871* (2013.01); *B01L 7/52* (2013.01); *B01L 2200/04* (2013.01); *B01L 2200/10* (2013.01); *B01L 2300/123* (2013.01); *B01L 2300/18* (2013.01); *B01L 2300/1822* (2013.01); *B01L 2300/1827* (2013.01); *B01L 2400/0427* (2013.01); *B01L 2400/0481* (2013.01); *B01L 2400/0683* (2013.01); *G01N 2035/00148* (2013.01); *G01N 2035/00326* (2013.01); *G01N 2035/00376* (2013.01); *G01N 2035/00841* (2013.01); *G01N 2035/00851* (2013.01); *G01N 2035/0477* (2013.01)

(58) Field of Classification Search
CPC .......... G01N 2035/00326; G01N 2035/00376; G01N 2035/00841; G01N 2035/00851; G01N 2035/0477; B01L 3/502715; B01L 3/50273; B01L 3/502738; B01L 7/52; B01L 2200/04; B01L 2200/10; B01L 2300/123; B01L 2300/18; B01L 2300/1822; B01L 2300/1827; B01L 2400/0427; B01L 2400/0481; B01L 2400/0683; C12Q 1/6888; C12Q 1/686
See application file for complete search history.

(56) References Cited

U.S. PATENT DOCUMENTS

D234,404 S 2/1975 Merril
4,065,263 A 12/1977 Woodbridge, III
D253,126 S 10/1979 Baxter
4,225,410 A 9/1980 Pace
D268,130 S 3/1983 Easton
4,469,863 A 9/1984 Ts'o et al.
D287,760 S 1/1987 Discko, Jr.
4,654,127 A 3/1987 Baker
4,887,455 A 12/1989 Payne et al.
5,034,506 A 7/1991 Summerton et al.
5,089,233 A 2/1992 DaVaney
D327,363 S 6/1992 Farb
5,216,141 A 6/1993 Benner
5,235,033 A 8/1993 Summerton et al.
5,284,568 A 2/1994 Pace
5,320,808 A 6/1994 Holen
D350,478 S 9/1994 Fuller et al.
D351,996 S 11/1994 Kalvelage
5,386,023 A 1/1995 Sanghvi et al.
5,591,578 A 1/1997 Meade et al.
5,602,240 A 2/1997 De Mesmaeker et al.
5,625,292 A 4/1997 Crook et al.
5,637,684 A 6/1997 Cook et al.
5,644,048 A 7/1997 Yau
5,681,702 A 10/1997 Collins et al.
5,705,348 A 1/1998 Meade et al.
5,770,365 A 6/1998 Lane et al.
5,781,024 A 7/1998 Blomberg et al.
5,807,701 A 9/1998 Payne et al.
5,824,473 A 10/1998 Meade et al.
5,837,546 A 11/1998 Allen
5,882,497 A 3/1999 Persaud et al.
D407,983 S 4/1999 Hui
5,968,329 A 10/1999 Anderson
6,013,170 A 1/2000 Meade
6,013,459 A 1/2000 Meade
6,023,961 A 2/2000 Discenzo
6,033,601 A 3/2000 Persaud et al.
6,063,573 A 5/2000 Kayyem
6,090,933 A 7/2000 Kayyem et al.
6,096,273 A 8/2000 Kayyem et al.
6,117,290 A 9/2000 Say
6,180,064 B1 1/2001 Persaud et al.
6,190,858 B1 2/2001 Persaud et al.
6,192,351 B1 2/2001 Persaud
6,221,583 B1 4/2001 Kayyem et al.
6,232,062 B1 5/2001 Kayyem et al.
6,236,951 B1 5/2001 Payne et al.
6,244,096 B1 6/2001 Lewis et al.
6,248,229 B1 6/2001 Meade
6,264,825 B1 7/2001 Blackburn et al.
6,265,155 B1 7/2001 Meade et al.
6,290,839 B1 9/2001 Kayyem et al.
6,361,958 B1 3/2002 Shieh et al.
6,376,232 B1 4/2002 Payne et al.
6,387,707 B1 5/2002 Seul et al.
6,431,016 B1 8/2002 Payne
6,432,723 B1 8/2002 Plaxco et al.
6,479,240 B1 11/2002 Kayyem et al.
6,495,323 B1 12/2002 Kayyem et al.
6,518,024 B2 2/2003 Choong et al.
6,541,617 B1 4/2003 Bamdad et al.
6,565,727 B1 5/2003 Shenderov
6,596,483 B1 7/2003 Choong et al.
6,600,026 B1 7/2003 Yu
6,602,400 B1 8/2003 Choong et al.
6,627,412 B1 9/2003 Manning et al.
6,642,046 B1 11/2003 McGarry et al.
6,655,010 B1 12/2003 Hatfield et al.
6,661,434 B1 12/2003 MacPhail
6,673,533 B1 1/2004 Wohlstadter et al.
6,686,150 B1 2/2004 Blackburn et al.
6,740,518 B1 5/2004 Duong et al.
6,753,143 B2 6/2004 Tao et al.
6,761,816 B1 7/2004 Blackburn et al.
6,773,566 B2 8/2004 Shenderov
6,824,669 B1 11/2004 Li et al.
6,833,267 B1 12/2004 Kayyem
6,875,619 B2 4/2005 Blackburn
6,942,771 B1 9/2005 Kayyem
6,951,759 B2 10/2005 Travers et al.
6,960,467 B2 11/2005 Shieh et al.
6,977,151 B2 12/2005 Kayyem et al.
7,014,992 B1 3/2006 Kayyem et al.
7,018,523 B2 3/2006 Meade
7,045,285 B1 5/2006 Kayyem et al.
7,056,669 B2 6/2006 Kayyem et al.
7,087,148 B1 8/2006 Blackburn et al.
7,090,804 B2 8/2006 Kayyem et al.
7,125,668 B2 10/2006 Kayyem et al.
7,160,678 B1 1/2007 Kayyem et al.
7,172,897 B2 2/2007 Blackburn et al.
D546,201 S 7/2007 Bhavnani
7,255,780 B2 8/2007 Shenderov
7,267,939 B2 9/2007 Meade
7,312,087 B2 12/2007 Duong et al.
7,381,525 B1 6/2008 Kayyem et al.
7,381,533 B2 6/2008 Kayyem et al.
7,384,749 B2 6/2008 Kayyem et al.
7,393,645 B2 7/2008 Kayyem et al.
7,439,014 B2 10/2008 Pamula et al.
7,514,228 B2 4/2009 Meade
7,534,331 B2 5/2009 Kayyem
7,560,237 B2 7/2009 O'Connor et al.
7,566,534 B2 7/2009 Meade
7,579,145 B2 8/2009 Meade
D599,832 S 9/2009 Chapin et al.
D600,503 S 9/2009 Ragsdale et al.
7,582,419 B2 9/2009 Meade

(56) References Cited

U.S. PATENT DOCUMENTS 7,595,153 B2 9/2009 Meade
7,601,507 B2 10/2009 O'Connor et al.
7,655,129 B2 2/2010 Blackburn et al.
7,713,711 B2 5/2010 O'Connor et al.
7,727,723 B2 6/2010 Pollack et al.
7,759,073 B2 7/2010 O'Connor et al.
7,763,471 B2 7/2010 Pamula et al.
7,815,871 B2 10/2010 Pamula et al.
7,816,121 B2 10/2010 Pollack et al.
7,820,391 B2 10/2010 Chunlin
7,822,510 B2 10/2010 Paik et al.
7,851,184 B2 12/2010 Pollack et al.
7,863,035 B2 1/2011 Clemens et al.
7,901,947 B2 3/2011 Pollack et al.
7,919,330 B2 4/2011 de Guzman et al.
7,935,481 B1 5/2011 Umek et al.
7,939,021 B2 5/2011 Smith et al.
7,943,030 B2 5/2011 Shenderov
7,998,436 B2 8/2011 Pollack et al.
8,007,739 B2 8/2011 Pollack et al.
8,012,743 B2 9/2011 Bamdad et al.
8,041,463 B2 10/2011 Pollack et al.
8,048,628 B2 11/2011 Pollack et al.
8,088,578 B2 1/2012 Hua et al.
8,093,062 B2 1/2012 Winger
8,114,661 B2 2/2012 O'Connor et al.
8,137,917 B2 3/2012 Pollack et al.
8,202,686 B2 6/2012 Pamula et al.
8,208,146 B2 6/2012 Srinivasan et al.
8,268,246 B2 9/2012 Srinivasan et al.
D669,191 S 10/2012 Handique
8,304,253 B2 11/2012 Yi et al.
8,313,698 B2 11/2012 Pollack et al.
8,313,895 B2 11/2012 Pollack et al.
8,317,990 B2 11/2012 Pamula et al.
8,349,276 B2 1/2013 Pamula et al.
8,364,315 B2 1/2013 Sturmer et al.
8,388,909 B2 3/2013 Pollack et al.
8,389,297 B2 3/2013 Pamula et al.
8,394,641 B2 3/2013 Winger
8,426,213 B2 4/2013 Eckhardt et al.
8,440,392 B2 5/2013 Pamula et al.
8,454,905 B2 6/2013 Pope et al.
8,460,528 B2 6/2013 Pollack et al.
8,470,606 B2 6/2013 Srinivasan et al.
8,481,125 B2 7/2013 Yi et al.
8,492,168 B2 7/2013 Srinivasan et al.
8,541,176 B2 9/2013 Pamula et al.
8,541,177 B2 9/2013 Chan
8,614,087 B2 12/2013 Drader
D702,364 S 4/2014 Iqbal et al.
8,709,787 B2 4/2014 Handique
9,132,423 B2 9/2015 Battrell et al.
9,222,623 B2 12/2015 Wright et al.
9,254,489 B2 2/2016 Lin et al.
9,410,663 B2 8/2016 Wright et al.
9,453,613 B2 9/2016 Wright et al.
9,498,778 B2 11/2016 Corey et al.
9,500,663 B2 11/2016 Tieman et al.
9,598,722 B2 3/2017 Wright et al.
9,873,120 B2 1/2018 Wright
9,874,542 B2 1/2018 Umek et al.
9,891,215 B2 2/2018 Kayyem et al.
9,945,738 B2 4/2018 Shadpour et al.
9,957,553 B2 5/2018 Kayyem et al.
10,001,476 B2 6/2018 Wood et al.
D845,503 S 4/2019 Jensen et al.
10,495,656 B2 12/2019 Kayyem et al.
D881,409 S 4/2020 Kayyem et al.
10,935,561 B2 3/2021 Nguyen et al.
10,948,450 B2 3/2021 Uhegbu
11,300,578 B2 4/2022 Nguyen et al.
D1,012,871 S 1/2024 Yi
12,000,847 B2 * 6/2024 Nguyen ............... C12Q 1/6888
2002/0107647 A1 8/2002 Anderson et al.
2002/0137238 A1 9/2002 Mockel et al.
2004/0009607 A1 1/2004 Goodman
2004/0024051 A1 2/2004 Holton
2004/0101191 A1 5/2004 Seul et al.
2004/0189311 A1 9/2004 Glezer et al.
2005/0136552 A1 6/2005 Buechler
2006/0192015 A1 8/2006 DiGiovanna
2007/0143313 A1 6/2007 Cotner
2007/0198213 A1 8/2007 Parvin
2007/0241068 A1 10/2007 Pamula et al.
2007/0242105 A1 10/2007 Srinivasan et al.
2007/0275415 A1 11/2007 Srinivasan et al.
2008/0038164 A1 2/2008 Satou et al.
2008/0230386 A1 9/2008 Srinivasan et al.
2008/0274513 A1 11/2008 Shenderov et al.
2009/0117571 A1 5/2009 Solanki
2009/0155902 A1 6/2009 Pollack et al.
2009/0202390 A1 8/2009 Iizumi et al.
2009/0263834 A1 10/2009 Sista et al.
2009/0304944 A1 12/2009 Sudarsan et al.
2010/0010602 A1 1/2010 Wedan et al.
2010/0025250 A1 2/2010 Pamula et al.
2010/0028984 A1 2/2010 Duong et al.
2010/0032293 A1 2/2010 Pollack et al.
2010/0048410 A1 2/2010 Shenderov et al.
2010/0068764 A1 3/2010 Sista et al.
2010/0084270 A1 4/2010 Vulto
2010/0087012 A1 4/2010 Shenderov
2010/0106206 A1 4/2010 Aghassian et al.
2010/0116640 A1 5/2010 Pamula et al.
2010/0120130 A1 5/2010 Srinivasan et al.
2010/0130369 A1 5/2010 Shenderov et al.
2010/0190263 A1 7/2010 Srinivasan et al.
2010/0194408 A1 8/2010 Sturmer et al.
2010/0206094 A1 8/2010 Shenderov
2010/0236928 A1 9/2010 Srinivasan et al.
2010/0236929 A1 9/2010 Pollack et al.
2010/0270156 A1 10/2010 Srinivasan et al.
2010/0279374 A1 11/2010 Sista et al.
2010/0282608 A1 11/2010 Srinivasan et al.
2010/0291578 A1 11/2010 Pollack et al.
2010/0295685 A1 11/2010 Parvin
2010/0307917 A1 12/2010 Srinivasan et al.
2010/0323405 A1 12/2010 Pollack et al.
2011/0076692 A1 3/2011 Sista et al.
2011/0086377 A1 4/2011 Thwar et al.
2011/0091989 A1 4/2011 Sista et al.
2011/0097763 A1 4/2011 Pollack et al.
2011/0104725 A1 5/2011 Pamula et al.
2011/0104747 A1 5/2011 Pollack et al.
2011/0104816 A1 5/2011 Pollack et al.
2011/0113901 A1 5/2011 Gonzalez
2011/0114490 A1 5/2011 Pamula et al.
2011/0160808 A1 6/2011 Lyden et al.
2011/0180571 A1 7/2011 Srinivasan et al.
2011/0186433 A1 8/2011 Pollack et al.
2011/0201099 A1 8/2011 Anderson
2011/0203930 A1 8/2011 Pamula et al.
2011/0209998 A1 9/2011 Shenderov
2011/0269239 A1 11/2011 Diessel et al.
2011/0270220 A1 11/2011 Genosar
2011/0303542 A1 12/2011 Srinivasan et al.
2011/0311980 A1 12/2011 Pollack et al.
2012/0018306 A1 1/2012 Srinivasan et al.
2012/0038477 A1 2/2012 Torgerson et al.
2012/0044299 A1 2/2012 Winger
2012/0046203 A1 2/2012 Walsh et al.
2012/0109531 A1 * 5/2012 Knafel ............. G05B 19/41865
702/19
2012/0132528 A1 5/2012 Shenderov et al.
2012/0165238 A1 6/2012 Pamula et al.
2012/0178091 A1 7/2012 Glezer et al.
2012/0181186 A1 7/2012 Bertin et al.
2012/0182562 A1 7/2012 Yang et al.
2012/0261264 A1 10/2012 Srinivasan et al.
2012/0282602 A1 11/2012 Drader et al.
2012/0330866 A1 12/2012 Parvin
2013/0017544 A1 1/2013 Eckhardt et al.
2013/0018611 A1 1/2013 Sturmer

(56) References Cited

U.S. PATENT DOCUMENTS

| | | | |
|---|---|---|---|
| 2013/0053666 | A1 | 2/2013 | Hughes et al. |
| 2013/0059366 | A1 | 3/2013 | Pollack et al. |
| 2013/0118901 | A1 | 5/2013 | Pollack et al. |
| 2013/0130369 | A1 | 5/2013 | Wilson et al. |
| 2013/0130936 | A1 | 5/2013 | Eckhardt |
| 2013/0146461 | A1 | 6/2013 | Pamula et al. |
| 2013/0164742 | A1 | 6/2013 | Pollack et al. |
| 2013/0178374 | A1 | 7/2013 | Eckhardt et al. |
| 2013/0178968 | A1 | 7/2013 | Sturmer et al. |
| 2013/0203606 | A1 | 8/2013 | Pollack et al. |
| 2013/0217103 | A1 | 8/2013 | Bauer |
| 2013/0217113 | A1 | 8/2013 | Srinivasan et al. |
| 2013/0225450 | A1 | 8/2013 | Pollack et al. |
| 2013/0225452 | A1 | 8/2013 | Pollack et al. |
| 2013/0230875 | A1 | 9/2013 | Pamula et al. |
| 2013/0233425 | A1 | 9/2013 | Srinivasan et al. |
| 2013/0233712 | A1 | 9/2013 | Pamula et al. |
| 2013/0252262 | A1 | 9/2013 | Srinivasan et al. |
| 2013/0257625 | A1 | 10/2013 | Holle |
| 2014/0125352 | A1 | 5/2014 | Franke et al. |
| 2014/0154792 | A1 | 6/2014 | Moynihan et al. |
| 2014/0170735 | A1 | 6/2014 | Holmes et al. |
| 2014/0194305 | A1 | 7/2014 | Kayyem et al. |
| 2014/0252079 | A1 | 9/2014 | Bjerke et al. |
| 2014/0273187 | A1 | 9/2014 | Johnson et al. |
| 2014/0322706 | A1 | 10/2014 | Kayyem et al. |
| 2014/0336083 | A1 | 11/2014 | Khattak et al. |
| 2014/0370609 | A1 | 12/2014 | Frank et al. |
| 2015/0087559 | A1 | 3/2015 | Putnam et al. |
| 2015/0184235 | A1 | 7/2015 | Reda |
| 2015/0323555 | A1 | 11/2015 | Kayyem et al. |
| 2015/0331037 | A1 | 11/2015 | Liu et al. |
| 2015/0340718 | A1 | 11/2015 | Barton |
| 2016/0097764 | A1 | 4/2016 | Taslim et al. |
| 2016/0129437 | A1 | 5/2016 | Kayyem et al. |
| 2016/0129445 | A1 | 5/2016 | Corey et al. |
| 2016/0130640 | A1 | 5/2016 | Wright et al. |
| 2016/0142407 | A1 | 5/2016 | Chun |
| 2016/0169578 | A1 | 6/2016 | Linney, II |
| 2016/0169956 | A1 | 6/2016 | Kim |
| 2016/0209837 | A1 | 7/2016 | Kim |
| 2017/0036210 | A1 | 2/2017 | Corey et al. |
| 2019/0232279 | A1 | 8/2019 | Jensen et al. |

FOREIGN PATENT DOCUMENTS

| | | | |
|---|---|---|---|
| EP | 0222612 | A2 | 5/1987 |
| EP | 002210401-0002 | | 4/2013 |
| EP | 002618330-0001 | | 2/2015 |
| JP | 201456575 | A | 3/2014 |
| WO | 1999037819 | A2 | 7/1999 |
| WO | 2004027549 | A2 | 4/2004 |
| WO | 2012064761 | A2 | 5/2012 |
| WO | 2015191916 | A1 | 12/2015 |
| WO | 2018053501 | A1 | 3/2018 |

OTHER PUBLICATIONS

US: Final Office Action dated Oct. 5, 2021 in U.S. Appl. No. 15/708,847.

US: Non-Final Office Action dated Jun. 15, 2021 in U.S. Appl. No. 15/708,847.

WO: International Search Report and Written Opinion dated Dec. 11, 2017 in PCT/US2017/052248.

Beaucage et al., "Tetrahedron Report No. 329: The Functionalization of Oligonucleotides via Phosphoramidite Derivatives," Tetrahedron vol. 49, No. 10, pp. 1925-1963 (1993).

Bolli et al., ".alpha.-Bicyclo-DNA: Synthesis, Characterization, and Pairing Properties of .alpha.-DNA-Analogues with Restricted Conformational Flexibility in the Sugar-Phosphate Backbone," American Chemical Society, pp. 100-117 (1994).

Brill et al., "Synthesis of Oligodeoxynucleoside Phosphorodithioates via Thioamidites," J. Am. Chem. Soc., pp. 2321-2322 (1989).

Carlsson et al., "Screening for Genetic Mutations" Letters to Nature, vol. 380, p. 207 (Mar. 1996).

Cobas® eplex System Transition Lifecycle Strategy. posted May 3, 2024 [online], [retrieved Apr. 29, 2025]. Retrieved from internet, https://scholarworks.calstate.edu/downloads/pc289r855 (Year: 2024).

Dempcy et al., "Synthesis of a Thymidyl Pentamer of Deoxyribonucleic Guanidine and Binding Studies with DNA Homopolynucleotides," Proc. Natl. Acad. Sci. USA, vol. 92, pp. 6097-6101 (Jun. 1995).

Dobson et al., "Emerging Technologies for Point-of-Care Genetic Testing," Future Drugs Ltd (www.future-drugs.com), 10.1586/14737159.7.4.359, Expert Rev. Mol. Diagn., pp. 359-370 (2007).

Doebler et al., "Continuous-Flow, Rapid Lysis Devices for Biodefense Nucleic Acid Diagnostic Systems," The Association for Laboratory Automation (JALA), pp. 119-125 (Jun. 2009).

Egholm et al., "Peptide Nucleic Acids (PNA). Oligonucleotide Analogues with an Achiral Peptide Backbone," J.Am.Chem.Soc., pp. 1895-1897 (1992).

Egholm et al., "PNA hybridizes to complementary oligonucleotides obeying the Watson-Crick hydrogen-bonding rules," Letters to Nature, pp. 566-568 (1993).

Erickson et al., "Integrated Microfluidic Devices," Elsevier B.V., 16 pages (2003).

Findlay et al., "Automated Closed-Vessel System for in Vitro Diagnostics Based on Polymerase Chain Reaction," Clinical Chemistry, 39:9, pp. 1927-1933, 1993).

Focke et al., "Lab-on-a-Foil: Microfluidics on Thin and Flexible Films," The Royal Society of Chemistry, pp. 1365-1386 (2010).

GenMark ePlex Cartridge Manufacturing Tour, posted Nov. 19, 2020 [online], [retrieved Apr. 29, 2025]. Retrieved from internet, https:// www.youtube.com/watch?v=A5u0ep9K410 (Year: 2020).

Herdewijn et al., "Hexopyranosyl-Like Oligonucleotides," American Chemical Society, pp. 80-99 (1994).

Horn et al., "Oligonucleotides with Alternating Anionic and Cationic Phosphoramidate Linkages: Synthesis and Hybridization of Stereo-Uniform Isomers," Tetrahedron Letters, vol. 37, No. 6, pp. 743-746 (1996).

Jeffs et al., "Unusual Confirmation of a 3-Thioformacetal Linkage in a DNA Duples," Journal of Biomolecular NMR, pp. 17-34 (1994).

Jenkins et al., "The Biosynthesis of Carbocyclic Nucleosides," Chemical Society Reviews, pp. 169-176 (Jan. 1995).

Kiedrowski et al., "Parabolic Growth of a Self-Replicating Hexadeoxynucleotide Bearing a 3'-5' Phosphoamidate Linkage," Angew Chem. Intl. Ed. English 30, pp. 423-426 (1991).

Koshkin et al., "LNA (Locked Nucleic Acid): An RNA Mimic Forming Exceedingly Stable LNA: LNA Duplexes," J. Am. Chem. Soc., vol. 120, pp. 13252-13253 (1998).

Letsinger et al., "Cationic Oligonucleotides," J. Am. Chem. Soc., pp. 4470-4471 (1988).

Letsinger et al., "Effects of Pendant Groups at Phosphorus on Binding Properties of d-APA Analogues," Nucleic Acids Research vol. 14, No. 8, pp. 3487-3499 (1986).

Letsinger et al., "Hybridization of Alternating Cationic/ Anionic Oligonucleotides to RNA Segments," Nucleosides & Nucleotides vol. 13, No. 6&7, pp. 1597-1605 (1994).

Letsinger et al., "Phosphoramidate Analogues of Oligonucleotides," J. Org. Chem, vol. 35, No. 1, pp. 3800-3803 (1970).

Liang, Stephen et al., Empiric Antimicrobial Therapy in Severe Sepsis and Septic Shock: Optimizing Pathogen Clearance, Curr Infect Dis Rep., Jul. 2015, 17(7): 493.

Locharla et al., "Variable length mixed radix MDC FFT/IFFT processor for MIMO-OFDM application" IET Comput. Digit. Tech., 12(1) 9-19 (2018).

Maddry et al., "Synthesis of Nonionic Oligonucleotide Analogues," American Chemical Society, pp. 40-51 (1994).

Mag et al., "Synthesis and Selective Cleavage of a Oligodeoxynucleotide Containing a Bridged Internucleotide 5 Phosphorothioate Linkage," Nucleic Acids Research, vol. 19 No. 7, pp. 1437-1441 (1991).

Malic et al., "Current State of Intellectual Property in Microfluidic Nucleic Acid Analysis," McGill University, Bentham Science Publishers, 18 pages (2007).

(56) References Cited

OTHER PUBLICATIONS

Mechanisms Information/ Worksheets, World Association of Technology Teachers, 2 pages (Mar. 2, 2011). (animated display viewable at https://web.archive.org/web/20110302093447/http://www.technologystudent.c-om/cams/flat1 .htm).
Meier et al., "Peptide Nucleic Acids (PNA's)—Unusual Properties of Nonionic Oligonucleotide Analogues," Angew Intl. Ed. English 31, No. 8, pp. 1008-1010 (1992).
Mesmaeker et al., "Comparison of Rigid and Flexible Backbones in Antisense Oligonucleotides," Bioorganic & Medicinal Chem. Letters, vol. 4, No. 3, pp. 395-398 (1994).
Mesmaeker et al., "Novel Backbone Replacements for Oligonucleotides," American Chemical Society, pp. 24-39 (1994).
Oleophobic: The definition of "oleophobic" provided by the online dictionary at Merriam-webster.com [retrieved on Dec. 7, 2017]. Retrieved from the Internet: <URL: www.merriamwebster.com/medical/oleophobic>. (Year: 2017).
Paddle: The definition of "paddle" provided by the online dictionary at dictionary.com [retrieved on Jan. 31, 2018]. Retrieved from the Internet: <URL: www.dictionary.com/browse/paddle>.
Pauwels et al., "Biological Activity of New 2-5A Analogues," Chemica Scripta, vol. 26, pp. 141-145 (1986).
Philips SureSigns VSi Spot Check Patient Monitor Introduction, posted Aug. 25, 2021 [online], [retrieved Apr. 29, 2025]. Retrieved from internet, https://www.youtube.com/watch?v=7pF3QbpDLCs (Year: 2021).
Rawls "Optimistic About Antisense," C&EN, pp. 35-39 (Jun. 1997).
Respiratory Pathogen (RP) Panel. Online, published date unknown. Retrieved on Dec. 23, 2018 from URL: https://www.genmarkdx.com/solutions/panels/eplex- panels/respiratory-pathogen-panel/.
Ryan, "Flat Plate Cam/ Linear Cam" [retrieved on Aug. 5, 2014] http://web.archive.org/web/20110302093447/http://www.technologystude nt.co- m/cams/flat1 .htm, 3 pages.
Sawai, "Synthesis and Properties of Oligoadenylic Acids Containing 2'-5' Phosphoramide Linkage," Chemistry Letters, pp. 805-808 (1984).
Sipherd, "The third-leading cause of death in US most doctors don't want you to know about" CNBC: Modern Medicine, Feb. 22, 2018, available at https://www.cnbc.com/2018/02/22/medical-errors-third-leading-cause-of-death-in-america.html.
Sprinzl et al., "Enzymatic Incorporation of ATP and CTP Analogues into the 3' end of RNA," Eur. J Biochem 81, pp. 579-589 (1977).
USB Charger, Asometech 100W 8 Port Multiple USB Charging Station with 4 Quick Charge 3.0, posted May 4, 2022 [online], [ retrieved Apr. 29, 2025]. Retrieved from internet, https://www.amazon.com/Charger-ASOMETECH-Multiple-Charging-Wireless/dp/ B09ZHV9GK1/ref (Year: 2022).
Vandeventer et al., "Mechanical Disruption of Lysis-Resistant Bacterial Cells by Use of a Miniature, Low-Power, Disposable Device," American Society for Microbiology, Journal of Clinical Microbiology, 49:7, pp. 2533-2539 (Jul. 2011).
Wolff et al., "Single-Tube Nested PCR with Room-Temperature-Stable Reagents," Cold Spring Harbor Laboratory Press ISSN, 1054-9803/95, vol. 4, pp. 376-379 and source page (1995).

* cited by examiner

Standard

Wide vent

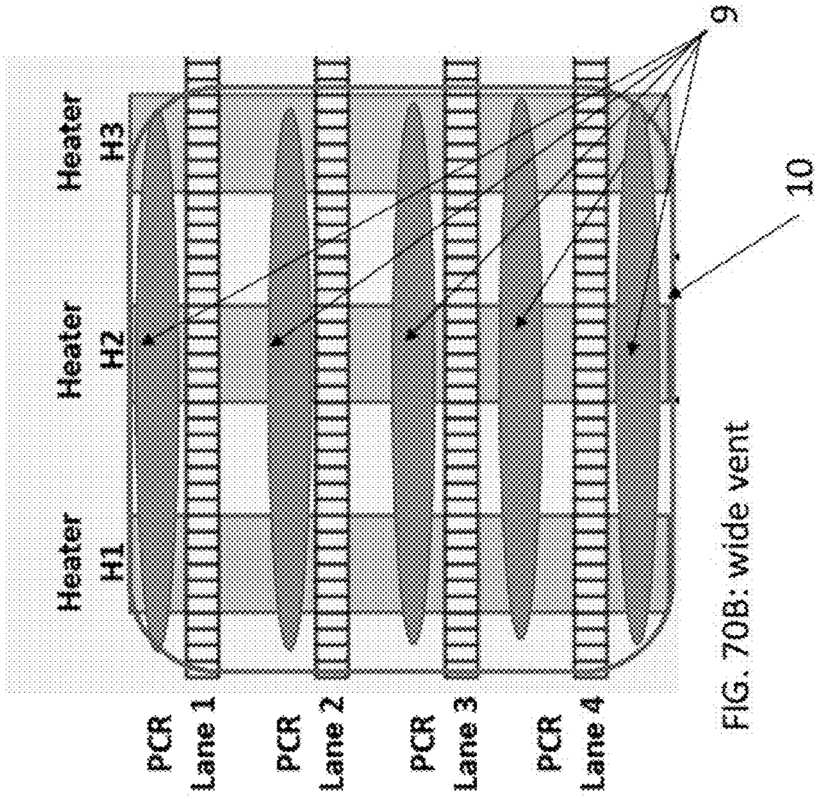
FIG. 70B: wide vent
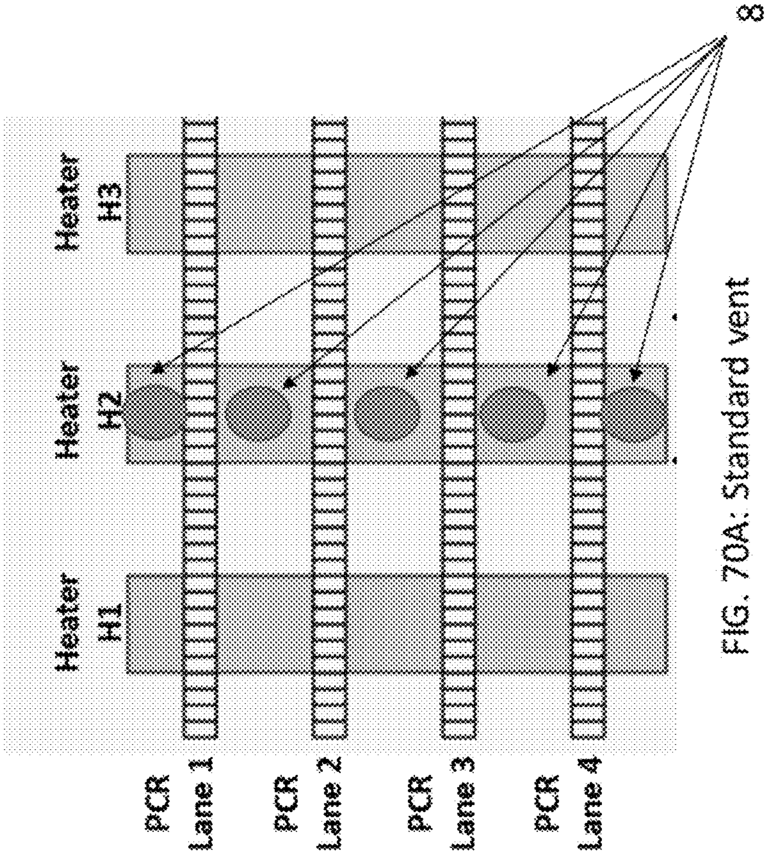
FIG. 70A: Standard vent

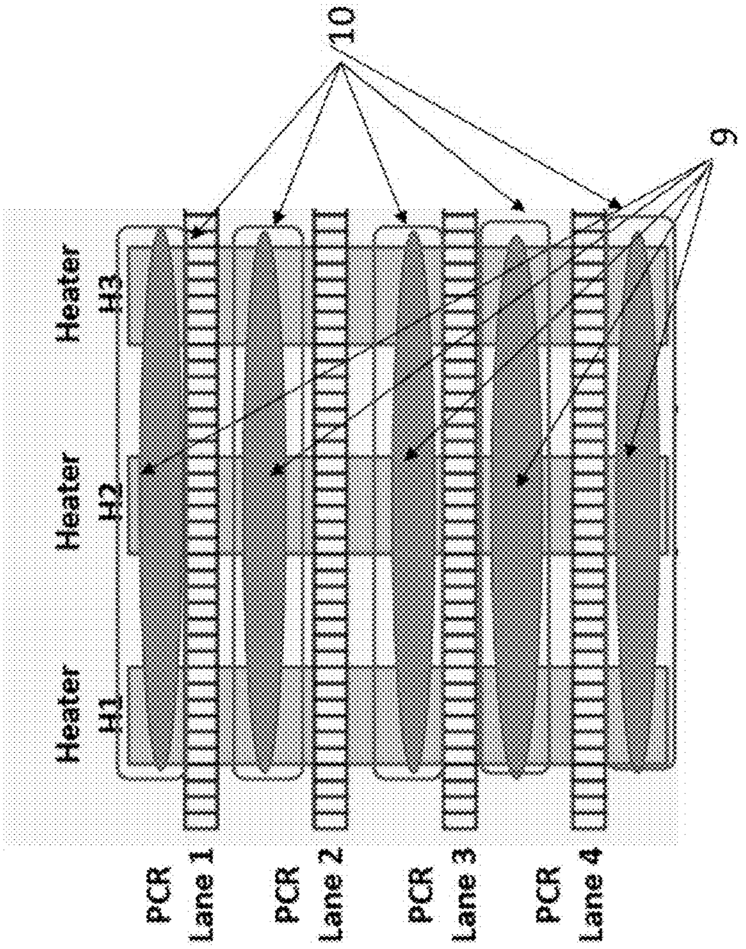
FIG. 70C: wide vent

FIGS. 71A-C: Validity-
excluding DNF, Detection, LRM, and SEF
- *Excluded 11 STP and 12 WTP runs*
Overall Validity
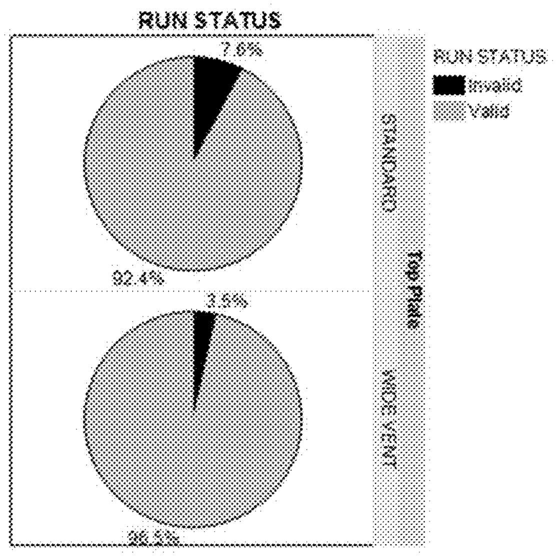
FIG. 71A
Validity by PQ Lot
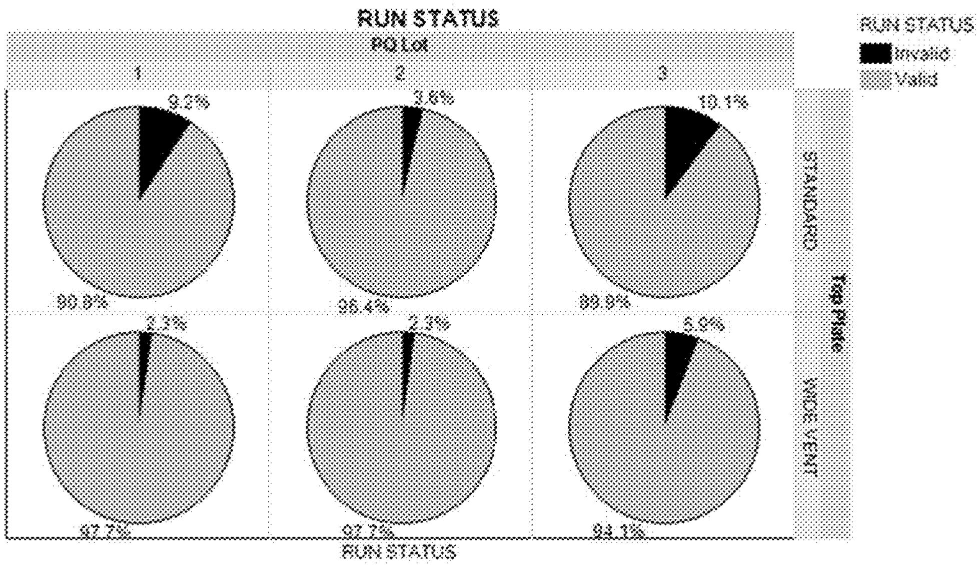
FIG. 71B
| Top Plate | | All | PQ 1 | PQ 2 | PQ 3 |
|---|---|---|---|---|---|
| STP | Invalid | 31 | 12 | 5 | 14 |
| | Total Runs | 406 | 130 | 137 | 139 |
| WTP | Invalid | 14 | 3 | 3 | 8 |
| | Total Runs | 398 | 131 | 132 | 135 |
FIG. 71C FIGS. 71D-F: Pinning Rates
excluding DNF, Detection, LRM, and SEF

- *Excluded 11 STP and 12 WTP runs*

Overall Pinning

Pinning by PQ Lot

Validity by Category and PQ Lot

FIGS. 71G-H: Pinning Rate comparison-

* *In controlled build, Mix3,4,5*

Overall Pinning

Pinning by Sample Mix

FIGS. 72A-C: Comparison of Temperature Profile during PCR
Thermistor temperature profile at standard PCR set points
FIG. 72A Heater 1
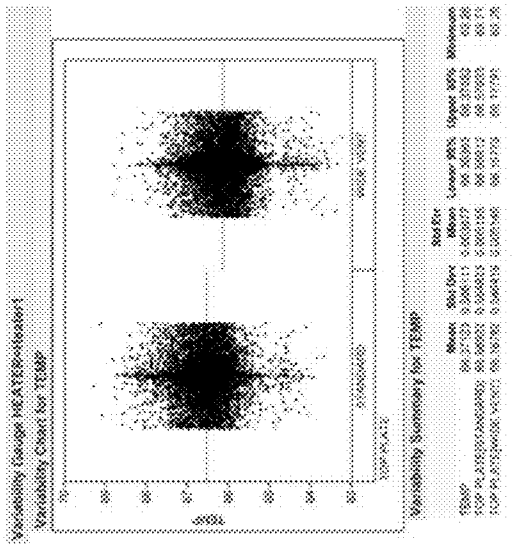
Delta = - 0.40 C
FIG. 72B Heater 2
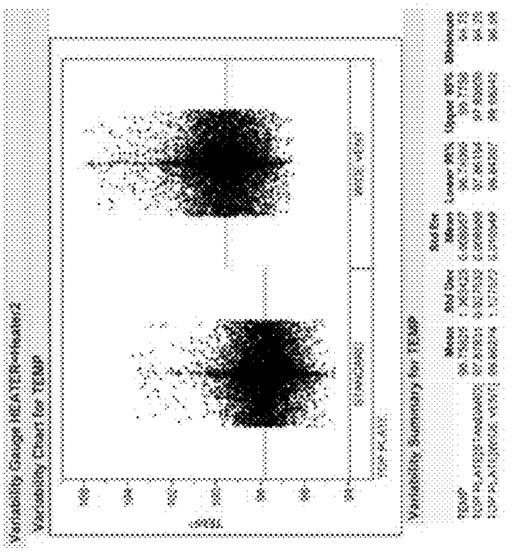
Delta = + 1.78 C
FIG. 72C Heater 3
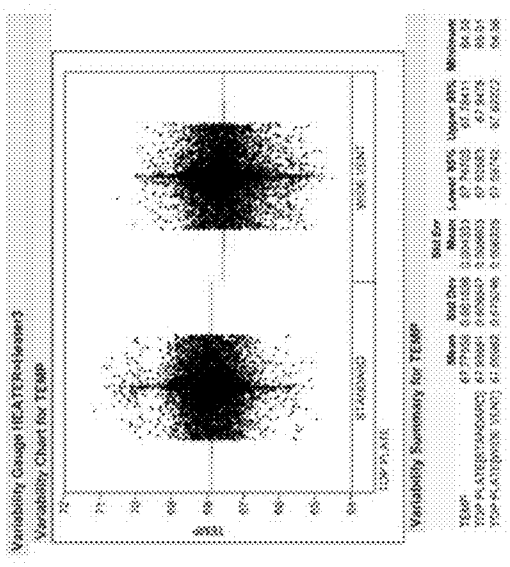
Delta = - 0.33 C
- Assessment of thermistor temperature on PCR heaters (after RTD stabilized)

FIGS. 73A-C: Comparison of Heater2 Temperature
Droplet temperature assessed by liquid crystals on PCR lanes
- Assessed by droplet color change in response to changing heater set points
- Droplet temperature is 1-2°C higher in wide vent than in standard top plate cartridges
FIG. 73C
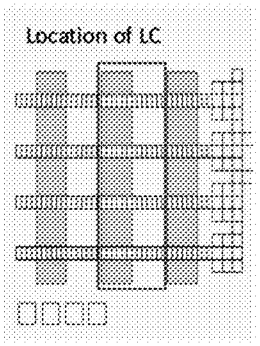
FIG. 73A: Lane 1
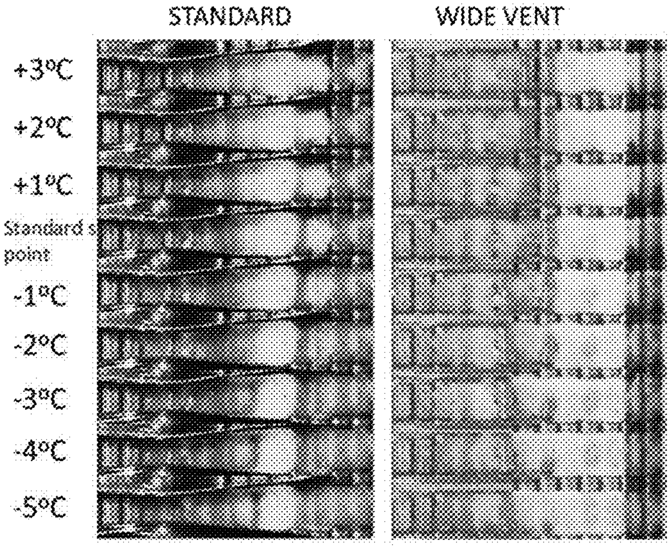
FIG 73B: Lane 4
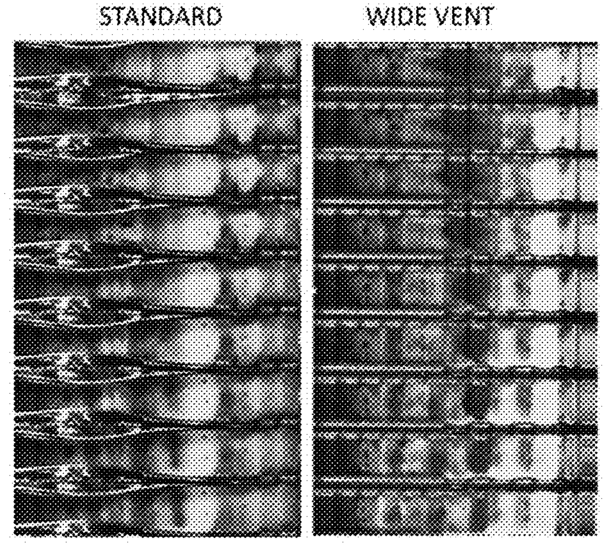
| Ink L/N | Red starts | Green starts | Blue starts | Clearing point |
| --- | --- | --- | --- | --- |
| 150324-4 | 93.6 | 94.3 | 97.8 | 125 |

FIGS. 74A-C: Assess PCR Temperature on Heater 2

Oil temperature assessed by thermocouples placed on top plate inside cartridge-

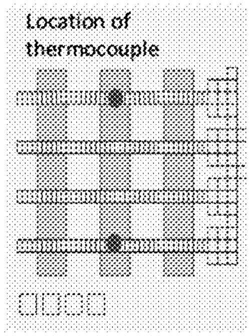

FIG. 74A

FIG. 74C

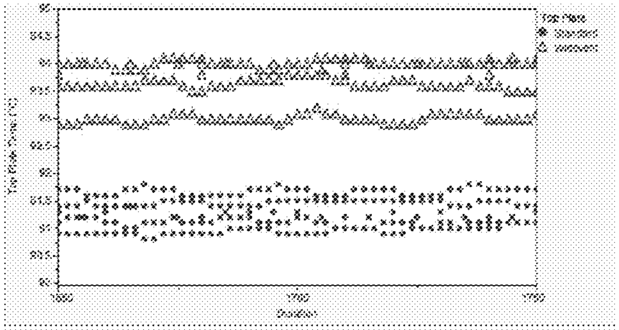

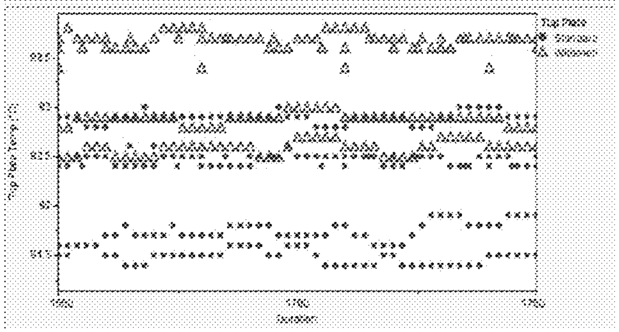

FIG. 74B

- Experiment setup
  - Thermocouples were placed inside the cartridge on the top plate surface on OCR lanes 1 and 4 at heater 2 area
  - Open bays runs were carried out in the environmental chamber set to 40°C mimicking internal temperature of ePlex instruments
  - Temperatures during PCR cycle time as logged by the thermocouple were analyzed
- Results:
  - The mean of the "stabilized temperature" across 4 independent runs in standard or wide vent top plate are compared
    - Wide vent TP – 93.4°C
    - Standard TP – 91.7°C
    - Δ=1.7°C
  - Cartridges with wide vent top plate is hotter in heater 2 area than those with standard top plate

FIGS. 75A-D: Impact of Heater2 Temperature on Assay Performance

Titrated Heater2 temperature in standard top plate

- Evaluate impact of heater 2 temperature on assay performance in consumables with standard top plate
- Experiment set up
  - Three different protocols that differ only by H2 temperature set during PCR
    - Control: H2 at 95.9°C
    - H2 + 1C: H2 at 96.9°C
    - H2 - 1C: H2 at 95°C
  - Negative NPS samples spiked with organisms at 1x LoD
- Results:
  - Most targets tolerate the temperature change with minimal change in signal level
  - One target had higher signal when H2 is set to 1°C hotter. This is in line with the higher signal observed in wide vent consumables, suggesting droplet in wide vent consumables likely have higher H2 temperature at standard PCR parameter setting H2 titration on Standard TP

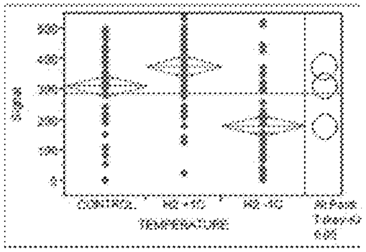

FIG. 75A

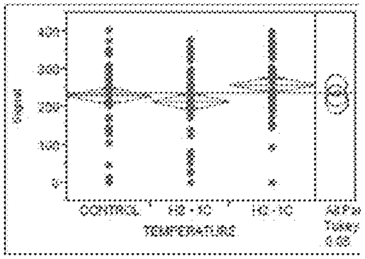

FIG. 75B

WVTP vs STP
at standard temp

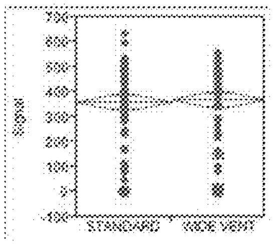

FIG. 75C

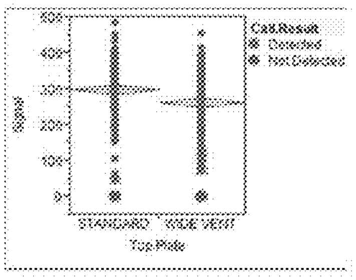

FIG. 75D

FIGS. 76A-B: Optimized PCR Temperature Set Point for Wide Vent

Decrease heater2 to 95°C

FIG. 76A

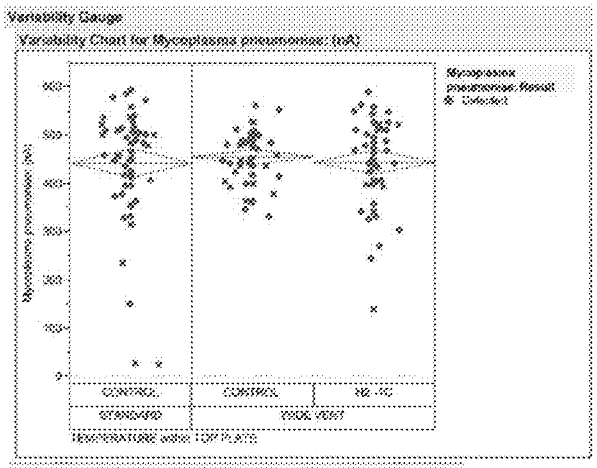

| | CONDITION | TOP PLATE | TEMPERATURE | N Rows | N(Detected) |
|---|---|---|---|---|---|
| 1 | A | STANDARD | CONTROL | 59 | 59 |
| 2 | B | WIDE VENT | CONTROL | 49 | 49 |
| 3 | C | WIDE VENT | H2-1C | 51 | 51 |

FIG. 76B

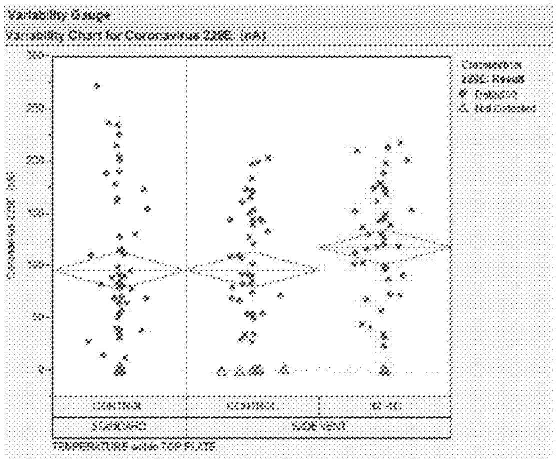

| | CONDITION | TOP PLATE | TEMPERATURE | N Rows | N(Detected) | N(Not Detected) | % FALSE NEG |
|---|---|---|---|---|---|---|---|
| 1 | A | STANDARD | CONTROL | 59 | 53 | 6 | 10.2% |
| 2 | B | WIDE VENT | CONTROL | 49 | 43 | 6 | 12.2% |
| 3 | C | WIDE VENT | H2-1C | 51 | 47 | 4 | 7.8% |

- Compare assay performance, using negative NPS sample with spiked organisms at 1x LoD
  - Standard top plate consumables running with standard PCR condition (STANDARD CONTROL)
  - wide vent top plate consumables running with standard PCR condition (WIDE VENT CONTROL)
  - wide vent top plate consumables running with the new PCR condition with H2 temperature set to 95°C (WIDE VENT H2-1C)
- Lower PCR heater2 temperature on wide vent top plate consumables improved signal in some targets, although no impact on positivity rates in the test set (n=~200).

FIGS. 77A-B: Overall Validity

Overall Validity

| Validity Category | STANDARD | WIDE VENT |
|---|---|---|
| Other | 25 | 30 |
| Pinning | 41 | 7 |
| Valid | 623 | 624 |
| TOTAL | 689 | 661 |

- Higher validity in WVTP (94.4%) than STP (90.8%) (*p=0.038, one-tailed Fisher's exact test*)

FIGS. 77C-E: Pinning Rates

- Significant improvement in pinning by WVTP (1.1%) than STP (6.0%) (*p*<.0001, *one-tailed Fisher's exact test*)

FIGS. 78A-C: Evolution of Wide Vent Top Plate Design
- Version 1 wide vent top plate
  - Vents bubble effectively on open bay
  - Oil wicking problems in consumable
- Version 2 wide vent top plate
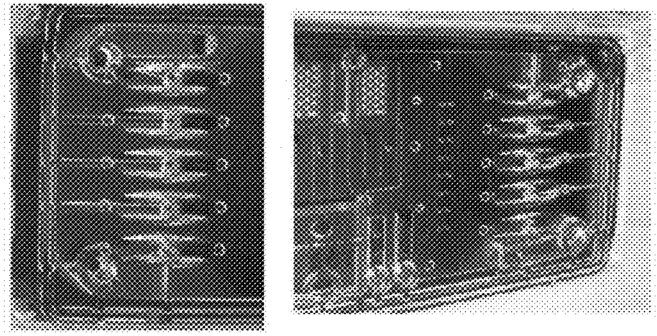
FIG. 78A: Standard
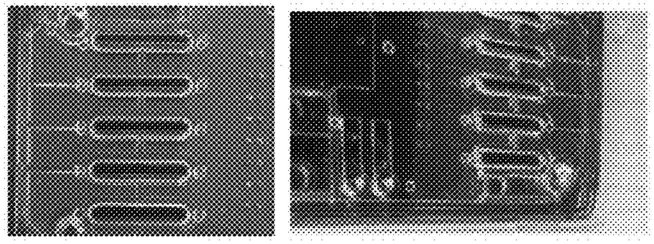
FIG. 78B: Wide v1
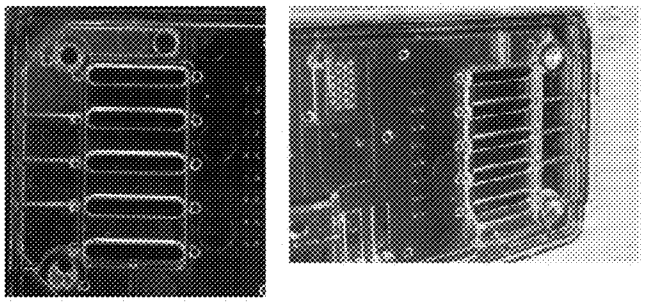
FIG. 78C: Wide v2

INSTRUMENT FOR PROCESSING CARTRIDGE FOR PERFORMING ASSAYS IN A CLOSED SAMPLE PREPARATION AND REACTION SYSTEM

CROSS REFERENCE OF RELATED APPLICATION

This application is a continuation of U.S. patent application Ser. No. 17/685,318 filed on Mar. 2, 2022, which is a continuation of U.S. patent application Ser. No. 15/708,847 filed on Sep. 19, 2017, which claims the benefit under 35 U.S.C. § 119(e) of the filing date of U.S. Patent Application Ser. No. 62/396,449 filed Sep. 19, 2016, the disclosure of which is incorporated herein by reference.

FIELD OF THE INVENTION

This subject matter of this disclosure relates to systems and methods for providing clinical and molecular diagnostics in an integrated, multiplex device that provides sample-to-answer results. In particular, the disclosure relates to a diagnostic system having a software architecture that includes an assay definition file (ADF) that enables a single instrument design to process and analyze a very wide range of fluid samples.

BACKGROUND OF INVENTION

One major challenge in the area of clinical and molecular diagnostics is the ability to have a "sample to answer" system that requires minimal sample handling and preparation and minimal requirements for trained clinical lab personnel. While many systems have been proposed, to date there are virtually no such commercial systems that adequately meet these requirements. Another major challenge is to have a system that enables the timely processing of many different types of fluid samples without requiring different kinds of specialized equipment. Aspects of the present invention provide such an integrated, multiplex system.

SUMMARY OF THE INVENTION

Aspects of the disclosure are directed to software architecture and controls systems for a diagnostic system, such as the diagnostic system described in co-pending U.S. patent application Ser. No. 14/538,565, the disclosure of which is incorporated herein by reference in its entirety. Such diagnostic systems may provide molecular diagnostic methods and compositions based on the detection of target analytes, including nucleic acids, and may be complete integrated "sample to answer" systems, in contrast with current commercial systems that require some off chip handling of the sample, generally including sample extraction (cell lysis, for example), and sample preparation prior to detection. Thus, in accordance with aspects of the current system, a sample is loaded onto a test platform and the target analyte sample is extracted, amplified as necessary (for example, when the target analyte is a nucleic acid using polymerase chain reaction (PCR) techniques, although isothermal amplification methods can be utilized as well), and then detected using electrochemical detection, all on a microfluidic platform, generally referred to herein as a "multiplex cartridge" or a "fluid sample processing cartridge."

A particular utility of the present system is the ease and rapidity of this integrated system. For example, there are no more than 2 operations required before introduction of the sample to the system, which allows for both ease of use and no requirement for highly trained lab personnel. In some embodiments there are no more than 1 operation required before introduction of the sample into the system. A significant benefit to the present system is also the speed from sample to answer, which, in some embodiments, is generally no more than about 45-90 minutes from sample introduction to reporting of assay results, with most results being reported in roughly 60-70 minutes or less. This represents a significant advantage to both labs and doctors relying on quick analyses for diagnosis and start of appropriate treatments. In addition, as outlined below, the ability of running not only multiple tests which are highly multiplexed on a single cartridge but the ability to analyze multiple cartridges in a completely random access way is a significant advantage in a clinical lab setting. A further advantage of the present system is that it can be used for point-of-care (POC) diagnostics.

Accordingly, aspects of the present invention are directed to integrated systems that allow for the detection of target analytes from samples.

For example, aspects of the invention are embodied in a fluid sample processing cartridge comprising a substrate, a sample well formed in the substrate, a closure, a deformable fluid chamber supported on the substrate, a mixing well formed in the substrate, and a driven mixing apparatus disposed within the mixing well. The sample well is configured to receive a volume of fluid sample, and the closure is configured to be selectively placed over the sample well. The deformable fluid chamber is configured to hold a fluid therein when in an un-deformed state and to collapse upon application of an external compression force to expel at least a portion of the fluid from the fluid chamber. The deformable fluid chamber is in fluid communication with the sample well via a channel formed in the substrate. The mixing well is in fluid communication with the sample well via a channel formed in the substrate and comprises a first peripheral wall and a first floor defining a well and a fluid inlet snorkel extending up a side of the first peripheral wall extending from the channel communicating the mixing well to the sample well and terminating below a top edge of the first peripheral wall. The driven mixing apparatus is constructed and arranged to mix the contents of the mixing well.

According to further aspects of the invention, the fluid inlet snorkel extends up an outer surface of the first peripheral wall and terminates at an opening formed in the first peripheral wall.

According to further aspects of the invention, the sample well comprises a second peripheral wall and a second floor defining a well and a fluid inlet snorkel extending up a side of the second peripheral wall and terminating below a top edge of the second peripheral wall.

According to further aspects of the invention, the mixing well further comprises an exit port comprising one or more openings formed in the floor of the mixing well, wherein the floor tapers downwardly toward the exit port.

According to further aspects of the invention, the driven mixing apparatus comprises a first impeller rotatably disposed within the mixing well and a gear configured to be drivingly engaged by a mating gear of an instrument into which the liquid sample processing cartridge is inserted and to rotate the first impeller when engaged by the mating gear.

According to further aspects of the invention, the sample processing cartridge further comprises a lysis chamber containing a plurality of lysis beads, the lysis chamber being formed in the substrate and disposed along the channel connecting the mixing well and the sample well whereby fluid flowing from the sample well to the mixing well will flow through the lysis chamber, and a bead mixer disposed at least partially within the lysis chamber and constructed and arranged to agitate the lysis beads and fluid flowing through the lysis chamber.

According to further aspects of the invention, the sample processing cartridge further comprises a first optical interface comprising an enlarged portion of the channel connecting the lysis chamber to the sample well and a second optical interface comprising an enlarged portion of the channel connecting the lysis chamber to the mixing well.

According to further aspects of the invention, the bead mixer comprises a motor mounted within the substrate and a second impeller disposed within the lysis chamber and mounted on an output shaft of the motor.

According to further aspects of the invention, the lysis chamber includes a fluid inlet and a fluid outlet and further comprises a mesh filter disposed over each of the fluid inlet and the fluid outlet and configured to retain the lysis beads within the lysis chamber.

According to further aspects of the invention, the sample processing cartridge further comprises a pressure port formed in the substrate and configured to couple the substrate to an external fluid pressure source and a channel formed in the substrate connecting the pressure port to the sample-well.

According to further aspects of the invention, the sample processing cartridge further comprises a waste chamber formed in the substrate, the waste chamber being in fluid communication with the mixing well via a channel formed in the substrate, a fluid exit port formed in the substrate, the fluid exit port being in fluid communication with the mixing well via a channel formed in the substrate, a first externally actuatable control valve disposed within the substrate and constructed and arranged to selectively permit or prevent fluid flow from the mixing well to the waste chamber and a second externally actuatable control valve disposed within the substrate and constructed and arranged to selectively permit or prevent fluid flow from the mixing well to the fluid exit port.

According to further aspects of the invention, the sample processing cartridge further comprises a capture chamber disposed along a channel connecting the mixing well and the waste chamber According to further aspects of the invention, the sample processing cartridge further comprises a passive valve assembly disposed within the substrate and a pressure port formed in the substrate and in pressure communication with the passive valve assembly by a pressure conduit formed in the substrate. The passive valve assembly is constructed and arranged to be closed and prevent fluid flow from the mixing well when pressure within the mixing well is not higher than a threshold pressure and to open and permit fluid flow from the mixing well when pressure within the mixing well rises above the threshold pressure. When the pressure port is closed, pressure within the mixing well is allowed to reach the threshold pressure that will open the passive valve assembly and permit fluid flow from the mixing well, and when the pressure port is open, pressure within the mixing cannot not reach the threshold pressure so the passive valve assembly is closed.

According to further aspects of the invention, the sample processing cartridge further comprises a lance blister associated with the deformable fluid chamber. The lance blister is connected or connectable to the associated deformable fluid chamber and contains a bead retained within the lance blister by a breakable septum. The lance blister is configured to collapse upon application of an external compression force to thereby push the bead through the breakable septum.

According to further aspects of the invention, the sample processing cartridge further comprises an external shroud externally enclosing at least a portion of the cartridge.

According to further aspects of the invention, the sample processing cartridge further comprises a plurality of deformable fluid chambers, and each of the fluid chambers contains one or more substances selected from the group consisting of a lysis buffer, a wash buffer, an oil, a rehydration buffer, target capture beads, and a binding buffer.

According to further aspects of the invention, the sample processing cartridge further comprises a first fluid exit port formed in the substrate, the first fluid exit port being in fluid communication with the mixing well via a channel formed in the substrate, a second fluid exit port formed in the substrate, and at least two deformable fluid chambers. One of the two deformable fluid chambers is in fluid communication with the mixing well via a channel formed in the substrate, and the other of the two deformable fluid chambers is in fluid communication with the second fluid exit port via a channel formed in the substrate that is different from the channel communicating the first fluid exit port with the mixing well.

According to further aspects of the invention, the deformable fluid chamber in fluid communication with the mixing well contains a lysis buffer, a wash buffer, target capture beads, or a binding buffer, and the deformable fluid chamber in fluid communication with the second fluid exit contains an oil or a rehydration buffer.

Further aspects of the invention are embodied in a fluid sample processing cartridge comprising a sample preparation module comprising and a reaction module. The sample preparation module comprises a substrate, a sample well formed in the substrate and configured to receive a volume of fluid sample, a closure configured to be selectively placed over the sample well, a first deformable fluid chamber supported on the substrate and configured to hold a fluid therein when in an undeformed state and to collapse upon application of an external compression force to expel at least a portion of the fluid from the first fluid chamber, the first deformable fluid chamber being in fluid communication with the sample well via a channel formed in the substrate, a mixing well formed in the substrate, the mixing well being in fluid communication with the sample well via a channel formed in the substrate, a driven mixing apparatus disposed within the mixing well and constructed and arranged to mix the contents of the mixing well, and a first fluid exit port formed in the substrate, the first fluid exit port being in fluid communication with the mixing well via a channel formed in the substrate. The reaction module is attached to the sample preparation module and is configured to receive a fluid from the sample preparation module via the fluid exit port formed in the sample preparation module. The reaction module comprises a top plate comprising a top surface, a raised wall at least partially circumscribing the top surface and in fluid sealing contact with a surface of the sample preparation module to form an interstitial space between the top surface and the surface of the sample preparation module, a sample chamber fluidly coupled to the first fluid exit port of the sample preparation module, a reagent chamber, and a detection chamber, and a fluidic processing panel coupled to a bottom surface of the top plate and defining a reaction and processing space between the fluidic processing panel and the top plate. The reaction and processing space is open or openable to the sample chamber, the reaction chamber, and the detection chamber.

According to further aspects of the invention, the reaction module includes an inlet port through which fluid sample enters the sample chamber and including a gap between the first fluid exit port of the sample preparation module and the inlet port of the sample chamber, the gap being open to the interstitial space.

According to further aspects of the invention, the first fluid exit port of the sample preparation module comprises an outlet channel formed through a frustoconical nipple.

According to further aspects of the invention, reaction module of the fluid sample processing cartridge further comprising an electrosensor array disposed in each detection chamber.

According to further aspects of the invention, the top plate of the reaction module further comprises one or more bubble traps, each bubble trap comprising a bubble capture hood open to the reaction and processing space and a vent opening open to the interstitial space.

According to further aspects of the invention, the top plate of the reaction module further comprises one or more vents which omit bubble traps, each vent being a direct opening above the reaction and processing space and each vent open to the interstitial space. Each vent or each plurality of vents comprising a rib.

According to further aspects of the invention, the sample preparation module further comprises a second deformable fluid chamber supported on the substrate and configured to hold a fluid therein when in an undeformed state and to collapse upon application of an external compression force to expel at least a portion the fluid from the fluid chamber and a second fluid exit port formed in the substrate. The second fluid exit port is in fluid communication with the second deformable fluid chamber via a channel formed in the substrate, and the reaction and processing space is fluidly coupled to the second fluid exit port of the sample preparation module.

According to further aspects of the invention, the mixing well comprises a peripheral wall and a floor defining a well and a fluid inlet snorkel extending up a side of the peripheral wall extending from the channel communicating the mixing well to the sample well and terminating below a top edge of the peripheral wall.

According to further aspects of the invention, the fluid inlet snorkel extends up an outer surface of the peripheral wall and terminates at an opening formed in the peripheral wall.

According to further aspects of the invention, the mixing well further comprises an exit port comprising one or more openings formed in the floor of the mixing well, and the floor tapers downwardly toward the exit port.

According to further aspects of the invention, the driven mixing apparatus comprises a first impeller rotatably disposed within the mixing well and a gear configured to be drivingly engaged by a mating gear of an instrument into which the liquid sample processing cartridge is inserted and to rotate the first impeller when engaged by the mating gear.

According to further aspects of the invention, the sample preparation module further comprises a lysis chamber comprising a plurality of lysis beads, the lysis chamber being formed in the substrate and disposed along the channel connecting the mixing well and the sample well whereby fluid flowing from the sample well to the mixing well will flow through the lysis chamber, and a bead mixer disposed at least partially within the lysis chamber and constructed and arranged to agitate the lysis beads and fluid flowing through the lysis chamber.

According to further aspects of the invention, the bead mixer comprises a motor mounted within the substrate and a second impeller disposed within the lysis chamber and mounted on an output shaft of the motor.

According to further aspects of the invention, the fluid sample processing cartridge further comprises a first optical interface comprising an enlarged portion of the channel connecting the lysis chamber to the sample well and a second optical interface comprising an enlarged portion of the channel connecting the lysis chamber to the mixing well.

According to further aspects of the invention, the lysis chamber includes a fluid inlet and a fluid outlet and further comprises a mesh filter disposed over each of the fluid inlet and the fluid outlet and configured to retain the lysis beads within the lysis chamber.

According to further aspects of the invention, the sample preparation module further comprises a pressure port formed in the substrate and configured to couple the substrate to an external fluid pressure source and a channel formed in the substrate connecting the pressure port to the sample well.

According to further aspects of the invention, the sample preparation module further comprises a waste chamber formed in the substrate, the waste chamber being in fluid communication with the mixing well via a channel formed in the substrate, a first externally actuatable control valve disposed within the substrate and constructed and arranged to selectively permit or prevent fluid flow from the mixing well to the waste chamber, and a second externally actuatable control valve disposed within the substrate and constructed and arranged to selectively permit or prevent fluid flow from the mixing well to the exit port.

According to further aspects of the invention, the sample preparation module further comprises a capture chamber disposed along a channel connecting the mixing well and the waste chamber.

According to further aspects of the invention, the sample preparation module further comprises a passive valve assembly disposed within the substrate and constructed and arranged to be closed and prevent fluid flow from the mixing well when pressure within the mixing well is not higher than a threshold pressure and to open and permit fluid flow from the mixing well when pressure within the mixing well rises above the threshold pressure and a pressure port formed in the substrate and in pressure communication with the passive valve assembly by a pressure conduit formed in the substrate. When the pressure port is closed, pressure within the mixing well is allowed to reach the threshold pressure that will open the passive valve assembly and permit fluid flow from the mixing well, and when the pressure port is open pressure within the mixing well cannot reach the threshold pressure so the passive valve assembly is closed.

According to further aspects of the invention, the sample preparation module further comprises a lance blister associated with the deformable fluid chamber. The lance blister is connected or connectable to the associated deformable fluid chamber and contains a bead retained within the lance blister by a breakable septum. The lance blister is configured to collapse upon application of an external compression force to thereby push the bead through the breakable septum.

According to further aspects of the invention, an external shroud externally encloses at least a portion of the cartridge.

According to further aspects of the invention, the sample preparation module further comprises a plurality of deformable fluid chambers, and each of the fluid chambers contains a substance selected from the group consisting of a lysis buffer, a wash buffer, an oil, a rehydration buffer, target capture beads, and a binding buffer.

Additional aspects of the invention are embodied in an instrument configured to process a fluid sample processing cartridge including a deformable fluid chamber supported on a planar substrate and configured to hold a fluid therein when in an undeformed state and to collapse upon application of an external compression force to expel at least a portion of the fluid from the fluid chamber. The instrument comprises a cartridge carriage assembly a cartridge carriage assembly configured to receive and hold a fluid sample processing cartridge inserted into the instrument. A heating and control assembly is disposed adjacent the cartridge carriage assembly and is configured for movement with respect to the cartridge carriage assembly between a first position not in operative contact with the cartridge carried within the cartridge carriage assembly and a second position in operative contact with the cartridge carried within the cartridge carriage assembly. One or more movable magnet assemblies are each mounted for movement with respect to the cartridge independently of the heating and control assembly between a first position applying substantially no magnetic force to the cartridge and a second position applying magnetic force to corresponding discrete portions of the cartridge. A cam block assembly is configured for powered movement and is operatively coupled to the heating and control assembly for converting powered movement of the cam block assembly into movement of the heating and control assembly with respect to the cartridge carriage assembly between the first position of the heating and control assembly and the second position of the heating and control assembly. The cam block assembly is operatively coupled to the one or more moveable magnet assemblies for converting powered movement of the cam block assembly into movement of each magnet assembly with respect to cartridge carriage assembly between the first position of the magnet assembly and the second position of the magnet assembly. A deformable chamber compression assembly is configured to selectively apply an external compression force to the deformable fluid chamber to collapse the deformable chamber and expel at least a portion of the fluid from the fluid chamber.

According to further aspects of the invention, the heating and control assembly comprises one or more heater assemblies configured to apply a thermal gradient to corresponding discrete portions of the cartridge when the heating and control assembly is in the second position and e connector board including one or more electrical connector elements configured to effect an electrical connection between the instrument and the cartridge when the heating and control assembly is in the second position.

According to further aspects of the invention, the deformable chamber compression assembly comprises a cam follower plate configured for powered movement in a first direction that is generally parallel to the plane of the substrate and a compression mechanism associated with the deformable chamber of the cartridge and configured to apply a force compressing the chamber against the substrate by movement in a second direction having a component that is generally normal to the plane of the substrate. The cam follower plate is operatively coupled to the compression mechanism to convert movement of the cam follower plate in the first direction into movement of the compression mechanism in the second direction to thereby apply an external compression force to the chamber.

According to further aspects of the invention, the instrument further comprises a pneumatic pump and a pneumatic port connected to the pneumatic pump, wherein the pneumatic port is configured to couple the pneumatic pump to a pressure port of the fluid sample processing cartridge when the cartridge is inserted into the instrument.

According to further aspects of the invention, the instrument further comprises an optical detector configured to detect fluid flow through a part of the fluid sample processing cartridge According to further aspects of the invention, the fluid sample processing cartridge includes a driven mixing apparatus including a drive gear, and the instrument further comprises a mixing motor assembly including a powered driving gear. The mixing motor is moveable between a first position in which the driving gear is not engaged with the drive gear of the driven mixing apparatus and a second position in which the driving gear is operatively engaged with the drive gear to actuate the driven mixing apparatus. The cam block assembly is operatively coupled to the mixing motor assembly for converting powered movement of the cam block assembly into movement of the mixing motor assembly between the first position of the mixing motor assembly and the second position of the mixing motor assembly.

According to further aspects of the invention, the instrument further comprises a heater cooling assembly comprising a fan and a cooling duct configured to direct air flow from the fan to a portion of one of the heater assemblies.

According to further aspects of the invention, the cartridge carriage assembly comprise a cartridge holder configured to hold a cartridge inserted therein, a cartridge latch biased into a cartridge-latching position and configured to latch onto a cartridge inserted into the cartridge holder to retain the cartridge within the cartridge holder, and a cartridge eject mechanism configured to automatically push a cartridge at least partially out of the cartridge holder when the cartridge latch is released from a cartridge-latching position.

According to further aspects of the invention, the heating and control assembly comprises a support plate on which the one or more heater assemblies and the connector board are supported. The support plate is mounted in a constrain configuration preventing horizontal movement of the support plate but permitting vertical movement of the support plate to enable movement of the heating and control assembly between its first and second positions.

According to further aspects of the invention, the heater assemblies of the heating and control assembly comprises a resistive heating element attached to the connector board and a heat spreader comprising a thermally-conductive material thermally coupled to the resistive heating element.

According to further aspects of the invention, one of the heater assemblies of the heating and control assembly comprises a thermoelectric element, a heat spreader comprising a thermally-conductive material thermally coupled to the thermoelectric element, and a heat sink including a panel that is in thermal contact with the thermoelectric element and a plurality of heat-dissipating rods.

According to further aspects of the invention, the electrical connector elements of the connector board of the heating and control assembly comprise a plurality of connector pin arrays, each connector pin array comprising a plurality of pogo pins.

According to further aspects of the invention, one of the movable magnet assemblies comprises a magnet holder mounted on a spindle so as to be rotatable about the spindle between the first position and the second position of the magnet assembly, a magnet supported on the magnet holder, an actuator bracket extending from the magnet holder, and a torsion spring configured to bias the magnet holder to a rotational position corresponding to the first position of the magnet assembly.

According to further aspects of the invention, one of the movable magnet assemblies comprises a magnet holder frame mounted on a spindle so as to be rotatable about the spindle between the first position and the second position of the magnet assembly, a magnet array disposed within the magnet holder frame, a focusing magnet disposed within an opening formed in the magnet holder frame and configured to focus magnetic forces of the magnet array, an actuator bracket extending from the magnet holder frame, and a torsion spring configured to bias the magnet holder frame to a rotational position corresponding to the first position of the magnet assembly.

According to further aspects of the invention, the cam block assembly is operatively coupled to each movable magnet assembly by a magnet actuator coupled at one portion thereof to the cam block assembly so as to be moveable by powered movement of the cam block assembly and including a tab configured to be engageable with the actuator bracket of each magnet assembly as the magnet actuator is moved with the cam block assembly to cause corresponding rotation of the magnet assembly from the first position to the second position.

According to further aspects of the invention, the cam block assembly comprises a cam frame, a cam block motor coupled to the cam frame and configured to effect powered movement of the cam frame, and first and second cam rails attached to the cam frame. Each of the cam rails has two cam slots. The cam block assembly is operatively coupled to the heating and control assembly by cam followers extending from the heating and control assembly into the cam slots such that movement of the cam frame and the cam rails with respect to the heating and control assembly causes corresponding relative movement between the cam followers and the cam slots to move the cam followers between respective first segments of the cam slots corresponding to the first position of the heating and control assembly and respective second segments of the cam slots corresponding to the second position of the heating and control assembly.

According to further aspects of the invention, the cam frame comprises a first longitudinal spar extending along one side of the heating and control assembly, a second longitudinal spar extending along an opposite side of the heating and control assembly, and a cross spar extending between the first and second longitudinal spars. Each cam rail is attached to one of the first and second longitudinal spars.

According to further aspects of the invention, the compression mechanism of the deformable chamber compression assembly comprises a cam arm having a cam surface and mounted so as to be pivotable about one end of the cam arm and a compression pad disposed at an opposite enc of the cam arm, wherein the cam arm is pivotable between a first position in which the compression pad does not contact the associated deformable chamber and a second position in which the compression pad applies a compressive force to the associated deformable chamber to at least partially collapse the chamber.

According to further aspects of the invention, the deformable chamber compression assembly further comprises a cam arm plate, and the cam arm of the compression mechanism is pivotably mounted within a slot formed in the cam arm plate for pivotable movement of the cam arm with respect to the cam arm plate. The cam surface of the cam arm projects out of the slot above a surface of the cam arm plate. The cam follower plate is operatively coupled to the compression mechanism by a cam follower element of the cam follower plate that is engaged with the cam surface of the compression mechanism during movement of the cam follower plate with respect to the cam arm plate to cause the cam arm to pivot from its first position to its second position.

According to further aspects of the invention, the cam follower plate comprises a cam groove that receives the cam surface of the cam arm projecting above the surface of the cam arm plate, and the cam follower element comprises a follower ridge disposed within the cam groove that contacts. the cam surface as the cam follower plate moves with respect to the cam arm plate to cause the cam arm to pivot from its first position to its second position.

According to further aspects of the invention, the instrument further comprises a plurality of compression mechanisms, each comprising a cam arm pivotably mounted within a slot formed in the cam arm plate and a cam arm surface, and the cam follower plate comprises a plurality of cam grooves, each cam groove being associated with at least one of the compression mechanisms and each cam groove including a follower ridge disposed within the cam groove that contacts the cam surface of the associated compression mechanism as the cam follower plate moves with respect to the cam arm plate to cause the cam arm of the associated compression mechanism to pivot from its first position to its second position.

According to further aspects of the invention, the sample processing cartridge includes a plurality of deformable fluid chambers, and the deformable chamber compression assembly comprises a plurality of compression mechanisms. Each compression mechanism is associated with one of the deformable fluid chambers, and the cam follower plate is operatively coupled to the compression mechanisms to convert movement of the cam follower plate in the first direction into movement of each of the compression mechanisms in the second direction to thereby apply an external compression force to each of the associated chambers in a specified sequence According to further aspects of the invention, the fluid sample processing cartridge includes an externally-actuatable control valve configured to selectively control fluid flow by permitting fluid flow through the valve when not externally actuated and preventing fluid flow through the valve when externally actuated. The instrument further comprises a valve actuator compression mechanism associated with the externally-actuatable control valve of the sample processing cartridge and configured to actuate the associated externally-actuatable control valve by movement in a second direction having a component that is generally normal to the plane of the substrate. The cam follower plate is operatively coupled to the valve actuator compression mechanism to convert movement of the cam follower plate in the first direction into movement of the valve actuator compression mechanism in the second direction to thereby actuate the associated externally-actuatable control valve.

The above-described aspects of the invention mostly concern advantageous mechanical and fluid-handling features. Further aspects of the invention described below concern the electronic and software architectural aspects of the above-referenced system. These electronic and software architectural aspects are all applicable to and can be advantageously integrated with the above-described aspects of the invention.

In order to provide maximum versatility and utilization, an exemplary system described herein has a very flexible software architecture that enables a very wide range of fluid samples to be optimally analyzed by utilizing an assay definition file (ADF). The ADF can define control parameters for processing a fluid sample, sensing parameters for generating scan data from the sample. and analysis parameters for analyzing the scan data.

According to an aspect of the invention, the system includes a client device that is directly, indirectly, or wirelessly coupled to an instrument. The client device can be a desktop computer, a laptop, or a tablet to name a few examples. The client device is utilized by a user to create, select, or modify a physician test order, Pending Test Order (PTO), or test order. The instrument can then utilize the test order combined with the ADF to process a fluid sample, sense an analyte or molecule, and report results from sensing.

According to further aspects of the invention, the system includes a non-transitory computer readable medium storing instructions. The system includes a processor that executes the instructions to perform software operations that are described below. The non-transitory medium can be a single storage device or it can include multiple storage devices distributed within the system. The non-transitory computer readable medium storing the instructions may include one or more of a hard disk drive, flash memory, or read-only memory (ROM) to name a few examples. The processor can be a single processor or multiple processors distributed within the system.

According to further aspects of the invention, the system includes instrument software (ISW) that is coupled to a processing bay module. The ISW receives the ADF from an external source such as a host computer. The ADF includes a command portion with control parameters (referred to herein as "OPUS") and an AAM file portion with analysis parameters. The ISW applies the OPUS portion of the ADF to the processing bay module to control processing of a fluid sample and to generate sensor scan data. For example, the OPUS portion may comprise a high level language that may communicate with firmware located in a processing bay. The processing bay module passes sensor scan data to the ISW. The ISW then applies the AAM file portion of the ADF to the sensor scan data. Application of the AAM file to the scan data by the AAM module analyzes the scan data and generates a report based on the analysis. In one embodiment, analyzing the scan data includes applying a digital filter to the scan data thereby digitally processing the scan data. In another embodiment analyzing the scan data includes applying a classifier to the scan data that identifies an analyte, identifies a molecule, identifies an organism, and/or identifies a condition.

According to further aspects of the invention, the system includes an electronic control system that operates a sample processing bay and analyzes data from the sample processing bay, the electronic control system including a processor coupled to a non-transitory computer readable medium, the non-transitory computer readable medium storing instructions directing the processor to perform steps including: (1) receive and read an assay definition file (ADF) from an external source, the ADF comprising control parameters and analysis parameters, (2) send a first set of control instructions to the sample processing bay whereby the sample processing bay operates a sample preparation module to prepare the sample for detection according to a first set of the control parameters, (2) send a second set of control instructions to the sample processing bay whereby the sample processing bay operates a sample reaction module to detect a target analyte according to a second set of the control parameters, (3) receive detection results from the sample processing bay, and (4) analyze and report results of the detection results based upon the analysis parameters.

According to further aspects of the invention, the system includes a processing bay that receives a cartridge. The ADF includes an OPUS file having control parameters that define one or more of (1) operation of mechanical features of the bay operating on the cartridge, (2) operation of mechanical features of the bay operating on a sample preparation module portion of the cartridge, (3) operation of a motor within the processing bay that drives a mechanical feature that operates upon a sample preparation module portion of the cartridge, (4) electrical signals passed through an electrical interface from the processing bay to the cartridge, (5) operation of a heating or cooling unit in the processing bay that heats or cools one or more portions of the cartridge, (6) operation of electrodes in a reaction module of the cartridge, and (7) operation of a sensor in a reaction module of the cartridge.

According to further aspects of the invention, the cartridge includes a sample preparation module configured to perform process steps on a fluid sample such as receiving the fluid sample, removing debris from the fluid sample, lysis, and removing other portions of the fluid sample that are not needed by the reaction module. The cartridge also includes a reaction module that includes fluid transport (e.g., electrowetting) electrodes and sense electrodes. The ADF includes an AAM file having parameters that define one or more of (1) which sense electrode data is to analyzed. (2) digital processing filters to be applied to the sense electrode data, (3) which electrodes are to be processed for a given digital processing filter, (4) a classifier for determining how to interpret digitally processed data, (5) call logic for determining the presence of one or more targets, and (6) aspects of a report generation.

The provision and use of an ADF file that defines both OPUS (process bay and cartridge control) parameters as well as AAM file (scan data analysis) parameters is highly advantageous over prior systems. This enables an array of similar or identical processing bays to run very wide range of assays that normally would require many different analytical machines. This allows a clinic, laboratory, or research facility the widest possible range of capabilities. This also eliminates potential capacity constraints that can exist with single purpose machines. Thus, a very wide range of critical tests can be run without bottlenecks in a facility of minimal size and capital cost Other features and characteristics of the subject matter of this disclosure, as well as the methods of operation, functions of related elements of structure and the combination of parts, and economies of manufacture, will become more apparent upon consideration of the following description and any appended claims with reference to the accompanying drawings, all of which form a part of this specification.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 69A shows the top view of a top plate 1 with five traditional dome-shaped features 2 also referred to as vent hoods wherein each vent hood has a pin-hole vent 3. These dome-shaped features are positioned on the top plate to control the size and location of bubble formation. FIG. 69B shows the bottom view 4 of the top plate 1. FIG. 69C shows the top view of a top plate 5 wherein the 5-dome-shaped features are replaced by cutout slots 6. A rib 7 surrounds the five open slots. FIG. 69D shows the bottom view 8 of the top plate 5.

FIGS. 70A-C: Shows the amplification region of a printed circuit board with circles depicting where the vents would be in the top plate. As can be seen from FIG. 70A, a standard printed circuit board has three heaters labeled H1 (anneal and extend), H2 (denature), H3 (anneal and extend), and 4 processing lanes (PCR Lane 1-PCR Lane 4) each with a small opening 8 over heater 2 (denaturation heater). FIG. 70B shows the amplification region over a printed circuit board with wide vents 9 extending across all three heaters H1, H2 and H3 and a rib 10 surrounding the plurality of vents. FIG. 70C shows the amplification region over a printed circuit board with wide vents 9 extending across all three heaters H1, H2 and H3 and a rib 10 surrounding each vent.

FIGS. 71A-C: Validity between standard and Wide Vent top plate at standard PCR conditions. FIG. 71A shows that the overall validity is over 96% when a wide vent top plate is used, whereas the overall validity is under 93% for a standard vent top plate. FIG. 71B shows the validity by lot and shows that each of the three lots tested (1, 2, and 3) had 97.7%, 97.7% and 94.1% validity respectively when a wide vent is used, while the three lots tested had 90.8%, 96.4% and 89.9% validity respectively when a standard vent is used. FIG. 71C shows the total runs and total invalids per lot for a standard vent top plate ("STD") and a wide vent top plate ("WTP").

FIG. 71D shows the overall pinning rates with standard and wide vents. Pinning is reduced from 3.7% when a standard top plate is used to about 1.0% when a wide vent top plate is used. Example 1. FIG. 71E shows the pinning rate by lot: (2.3%, 3.6%, and 5.0% for standard vent and 0.8%, 1.5%, and 0.7% for wide vent), and FIG. 71F shows the pinning rate compared to other electrowetting failures.

FIG. 71G shows data from an experiment run with Sample Mixes 3, 4, and 5 from WV-Table 2. Overall pinning was 0.6% with wide vent and 8.7% for standard vent. While pinning is reduced when a wide vent top plate is used, variability in pinning across lots is also reduced. When a wide vent top plate is used pinning consistently remains low (i.e. less than 2%—2.0%, 0.0%, and 0.0%). FIG. 71H shows that when a standard top plate is used there is variability in the pinning rate ranging from 2% to 8.2% to over 15%.

FIGS. 72A-C: Comparison of Temperature Profile during PCR. FIG. 72A shows the thermistor temperature at heater 1; FIG. 72B shows the thermistor temperature at heater 2; and FIG. 72C shows the thermistor temperature at heater 3.

FIGS. 73A-C: Comparison of Heater 2 Temperature. FIG. 73A shows the heater 2 temperature in PCR lane 1. FIG. 73B shows the heater 2 temperature in PCR lane 4. FIG. 73C shows the location of the liquid crystals over heater 2.

FIGS. 74A-C: Assess PCR Temperature on Heater 2. FIG. 74A shows the location of the thermocouples. FIG. 74B shows the temperature in lane 4 and FIG. 74C shows the temperature in lane 1.

FIGS. 75A-D: Impact of Heater 2 Temperature on Assay Performance. FIG. 75A shows the temperature of heater 2 on the standard top plate. FIG. 75B shows the temperature of heated 2 on the wide vent top plate. FIGS. 75C and 75D compared the signal when a wide vent or standard top plate is used at standard temperature (H2 at 95.9° C.).

FIGS. 76A-B: Optimized PCR Temperature Set Point for Wide Vent Top Plate. FIGS. 76A and 76B compare the signal when heater 2 is decreased to 95.0° C. with the standard and wide vent top plate.

FIGS. 78A-C: Evolution of Wide Vent Top Plate Design. FIG. 78A shows the standard vent design with bubble trapping structures. FIG. 78B shows the wide vent design with a rib around each vent. FIG. 78C shows the wide vent design with a rib around the vent region.

DEFINITIONS

Figure 1:
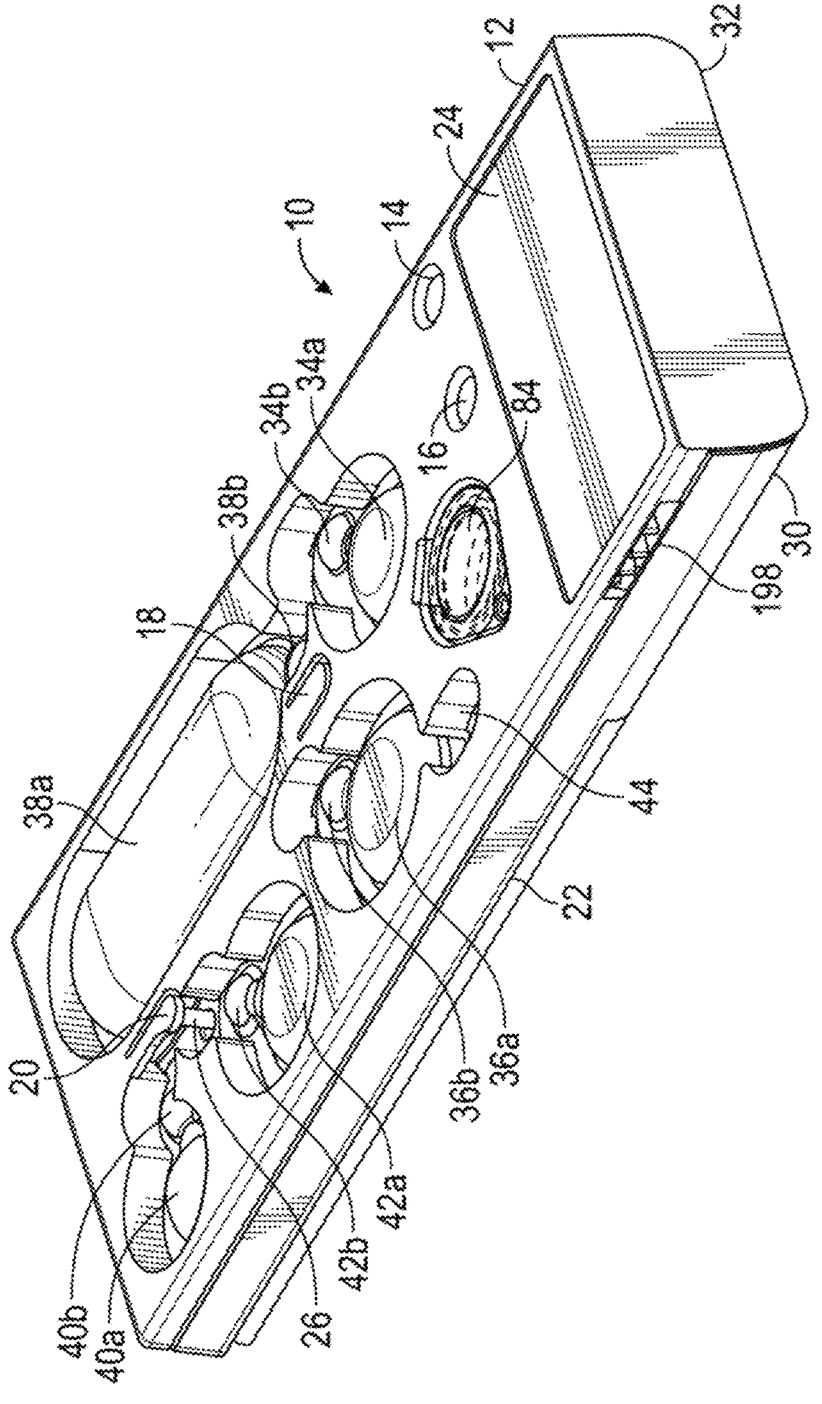
FIG. 1 is a top perspective view of a multiplex cartridge embodying aspects of the present invention.
Figure 2:
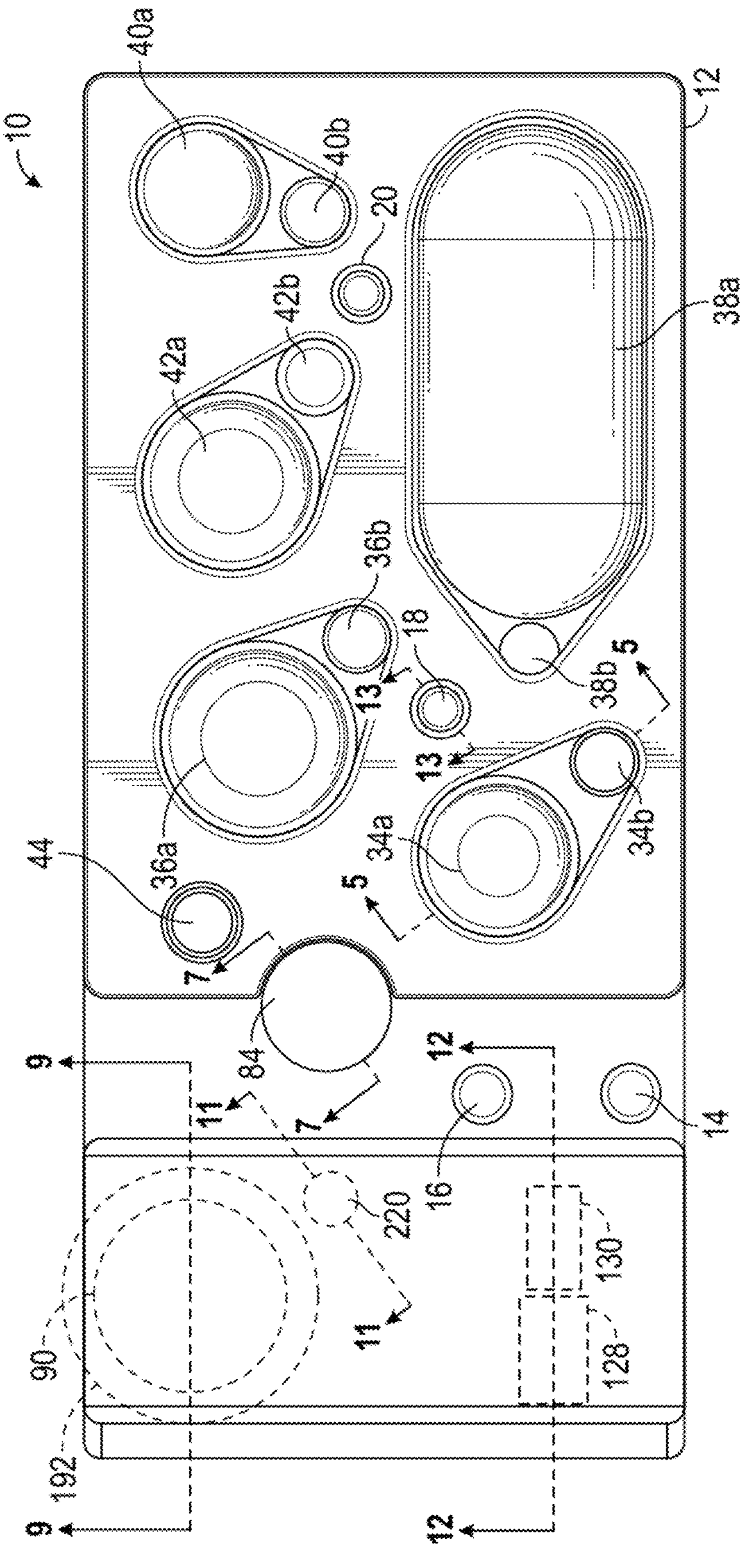
FIG. 2 is a top plan view of the multiplex cartridge.
Figure 3:
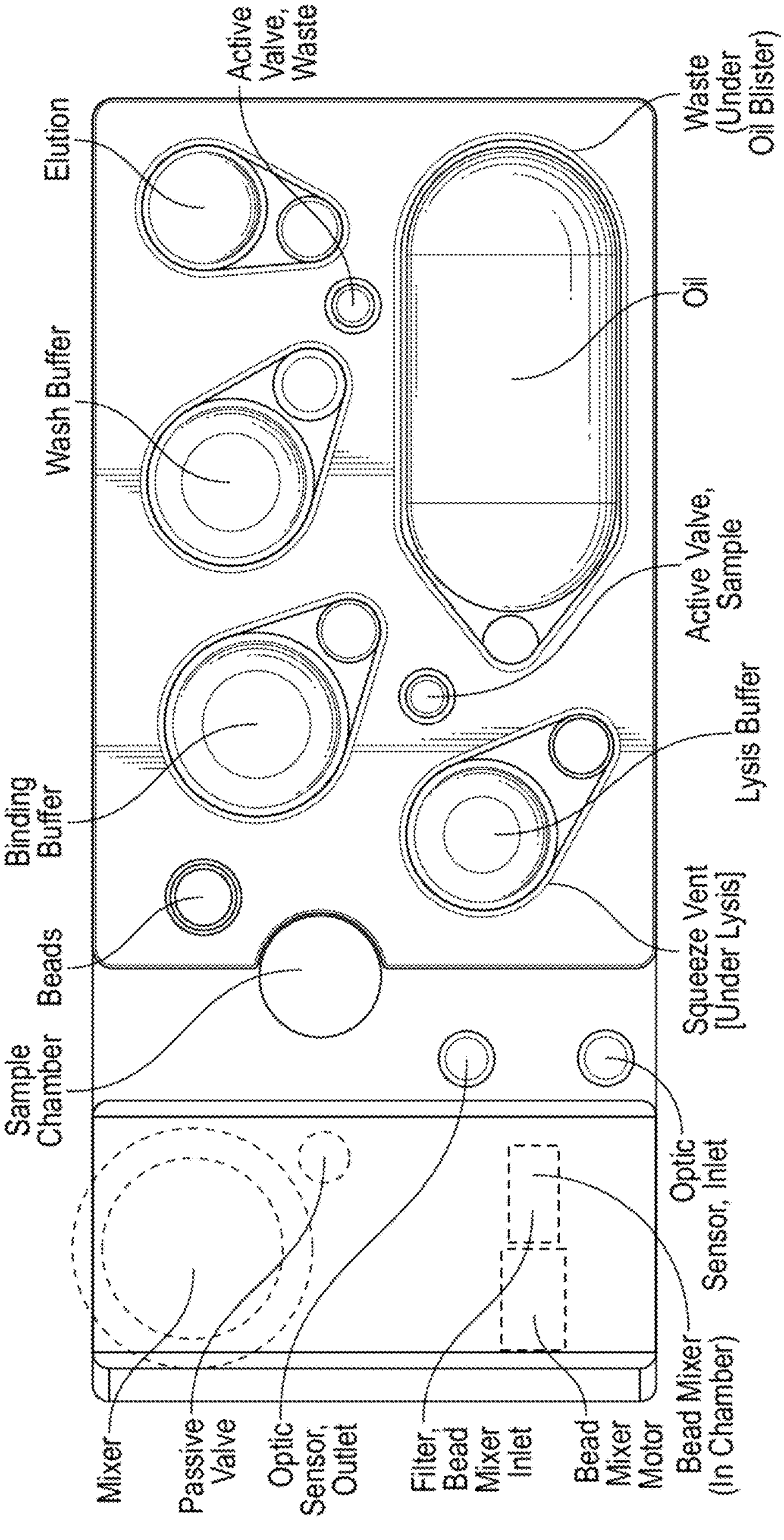
FIG. 3 is a top plan view of the multiplex cartridge annotated with identifying labels.

"OPUS" or "Opus file" or "OPUS portion" or "OPUS parameters" means control parameters of the ADF file. Specifically, the OPUS file includes both bay control and cartridge control parameters. The OPUS file includes sample processing and target detection parameters.

"AAM file" or "AAM parameters" or "AAM portion" means analysis parameters of the ADF file. Specifically, the AAM file includes scan data analysis parameters.

"ADF File" means a file that defines both OPUS and AAM file parameters.

"Electronic control system" means a system that operates a sample processing bay and analyzes data from the sample processing bay, the electronic control system includes a processor coupled to a non-transitory computer readable medium.

As used herein, the term "cartridge" means a cartridge for performing assays in a closed sample preparation and reaction system as described in U.S. Pat. No. 9,598,722 which is herein incorporated by reference in its entirety. The invention provides cartridges comprising several components, including a biochip cartage, a top plate, a liquid reagent module (LRM), and a housing that keeps the components together. The biochip cartage comprises a bottom substrate, a sample preparation zone, reagent zone, Sample Manipulation Zone, Amplification Zone, Detection Zones as further described in U.S. Patent Publication no. 2015/0323555 and U.S. Pat. No. 9,598,722 which are herein incorporated by reference in their entireties.

Consumable—Self-contained consumable cartridge that includes the necessary components to perform a single Blood Culture Identification (BCID) Panel test.

As used herein, the term RP Panel means Respiratory Panel. The RP Panel includes al of the oligonucleotides and reagents for carrying out a nucleic acid amplification reaction for the targets listed in WV-Table 1 as well as the capture and signal probes to form the hybridization complex necessary to detect the targets listed in WV-Table 1.

The term "detect", "detecting" or "detection" refers to an act of determining the existence or presence of one or more targets (e.g., microorganism nucleic acids, amplicons, etc.) in a sample. As used herein, target detection occurs when the amplicon forms a hybridization complex with the complimentary signal and capture probe. Specifically, target-specific capture probes are bound to a gold electrode in a microarray on the cartridge. The amplified target DNA hybridizes to the capture probe and to a complementary ferrocene-labeled signal probe. The electrochemical analysis determines the presence or absence of targets using voltammetry.

"Bay" or "instrument bay" or "cartridge bay" means a Stand-alone processing unit which runs a consumable. Bays as used herein are further described in U.S. patent application Ser. No. 14/062,860, U.S. Patent Publication no. 2015/0323555 and U.S. Pat. No. 9,598,722 which are herein incorporated by reference in their entireties.

"Open bay" means any bay lacking the liquid reagent module components so only cartridge-related functions can be performed.

"Rib" or "ridge" or "backbone" or "lip" or "seam" or "dam" means a raised area in the top plate. The purpose of the rib is to prevent fluid seepage The top plate can comprise a single rib surrounding a plurality of vents or each of a plurality of vents can have a single rib. The rib does not slope upwardly toward a vent opening like a bubble trap; it does not trap or direct bubbles.

"Vent region" or "venting region" means the region enclosed by the rib. As shown in FIG. 78B, the vent region encircles each vent. As shown in FIG. 78C, the vent region encircles the plurality of vents.

"Wide vent top plate" means a top plate with a vent spanning at least two thermal zones wherein the at least one vent is adjacent to at least one thermocycling pathway and wherein the at least one vent excludes bubble trap structures.

"Wide vent" or "Expanded vent" or "elongated vent" means a vent spanning at least two thermal zones wherein the at least one vent is adjacent to at least one thermocycling pathway and wherein the at least one vent excludes bubble trap structures.

RT-PCR—means Reverse Transcription Polymerase Chain Reaction

NPS—means nasopharyngeal Swab

VTM—means Viral Transport Media

Instrument—means a sample-to-answer instrument consisting of a base unit (with touchscreen interface), and up to four towers, each housing six independent bays.

nA—means nanoamp

LoD—means Limit of Detection

"Invalid Run" means failure for the cartridge to produce a valid result.

Electrowetting Failures (EWF)—means any failures to move volumes of chemistry as expected. There are subsets of EWFs that are determined by when in the assay they occurred or by the true root cause. EWF refers to generic electrowetting failure that occurs when volumes of chemistry do not move through the cartridge as expected.

Zone Fill—means when volume of chemistry fails to enter the detection zone.

Pinning—means electrowetting failure in the amplification portion of the cartridge. Drops that go in but do not come out are said to have pinned in the PCR area. Any numbering after the denotation refers to the drop or drops that were impacted by the failure.

IC Failure—means failure for internal controls to amplify. Any numbering after the denotation refers to the IC or ICs that were impacted by the failure.

DNF—means did not finish due to a particular instrument or consumable failure.

DNS—means did not start due to a particular instrument or consumable failure.

Detection—means failure to produce electrochemical signals that can be processed successfully through digital signal processing and assay analysis module (AAM) logic.

LRM Failure—means the LRM did not perform as expected. These failures include failure to open and close valves correctly, failure to deliver volumes the assay needs.

Figure 68A:
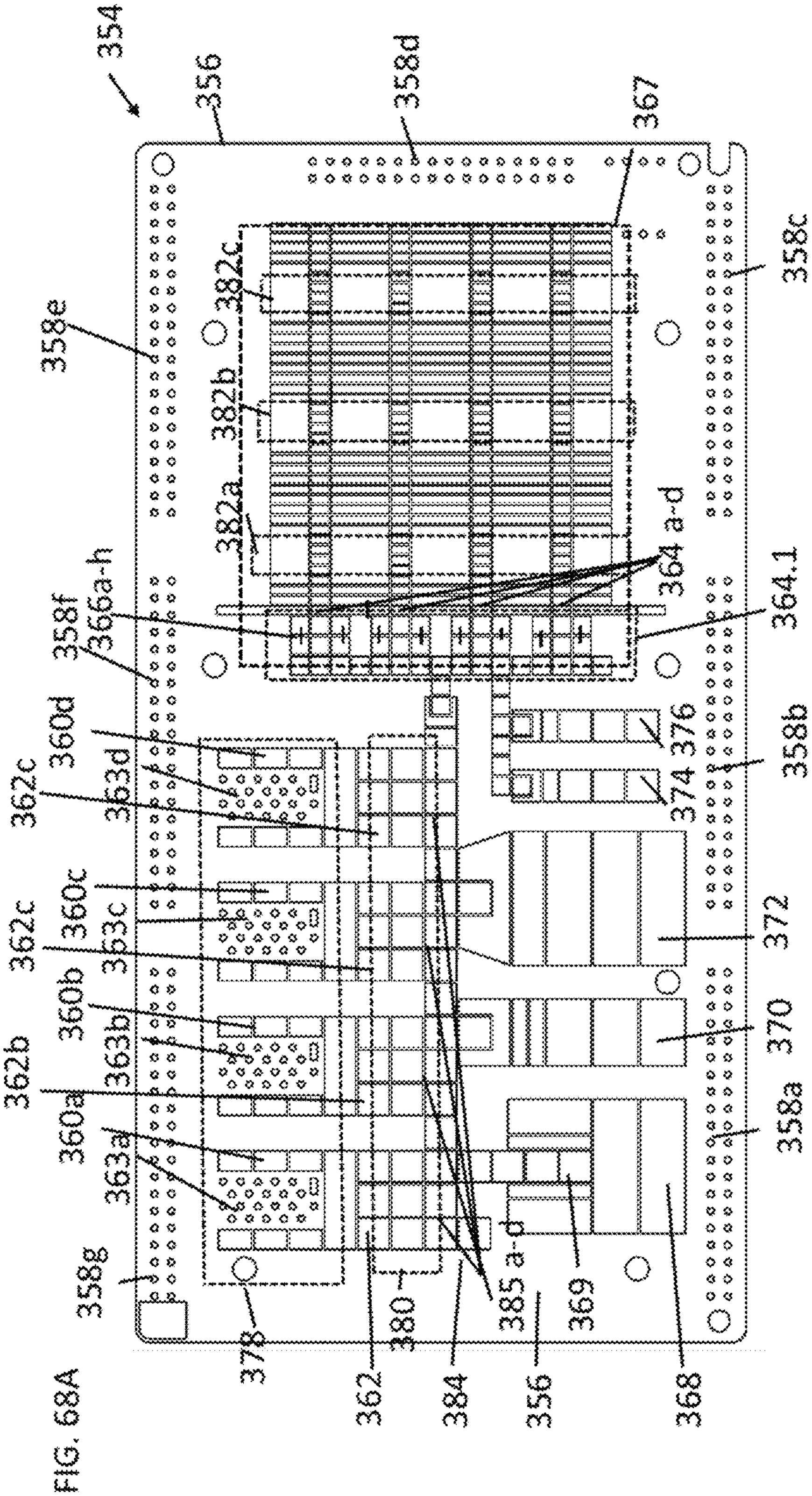
FIG. 68A is top plan view of an electrical block diagram of an exemplary system according to the present invention.
Figure 68B:
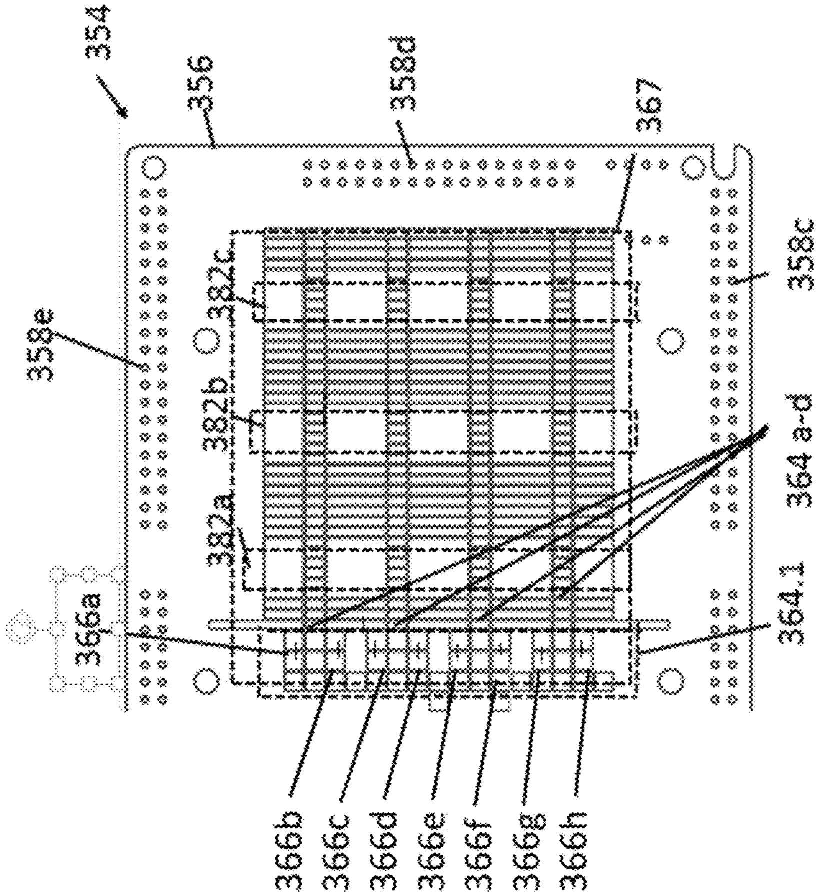
FIG. 68B is top plan view of the electrical block diagram of 68A focused on the amplification region and showing the eight primer cocktail 366*a-h* locations.
Figure 69A:
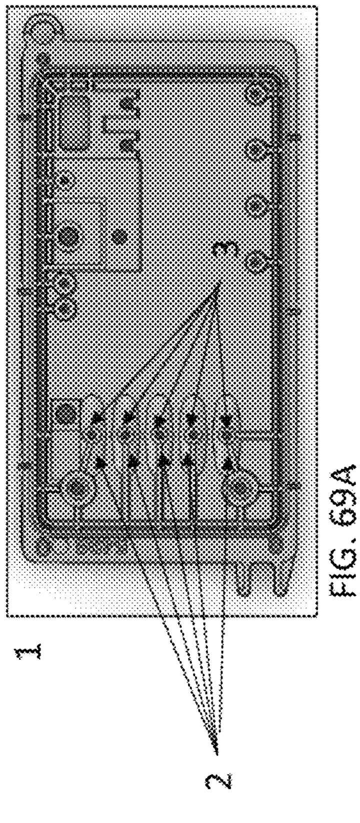
FIGS. 69A-D: Traditional vs Wide Vent Top Plate.
Figure 69B:
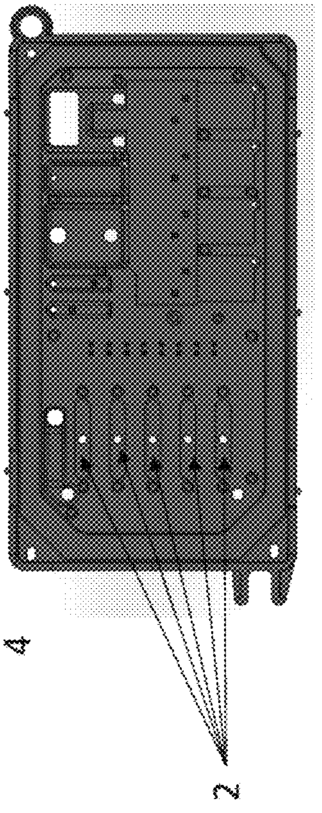
Figure 69C:
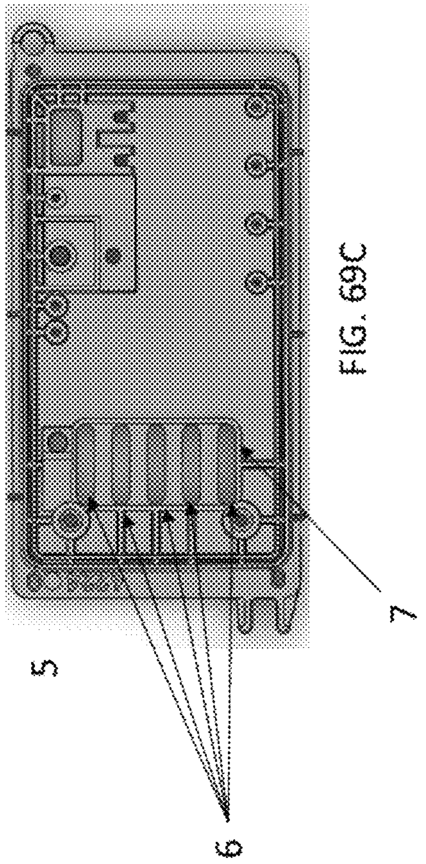
Figure 69D:
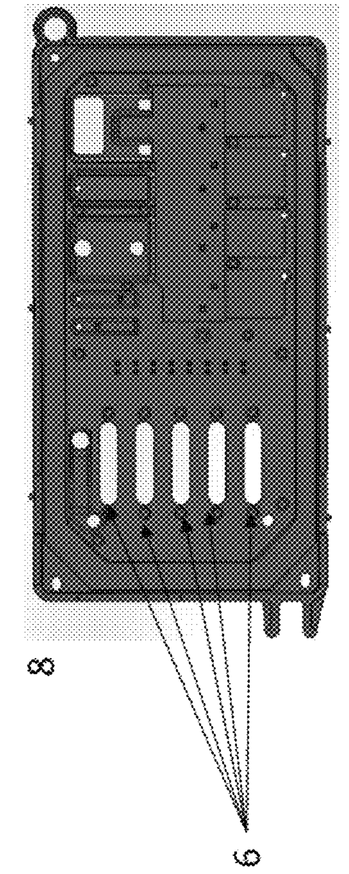

"Amplification zone" or "Amplification region" or "PCR zone" or "PCR region" means the area defined by 367 in FIGS. 68A-B and includes the thermocycling pathways 364, heater areas 382 and primer cocktail position 366.

"Bubble trapping structures" means bubble traps and bubble traps comprising a bubble capture hood.

"Standard Top Plate" means a vent over just the denature heater with bubble trapping structures.

As used herein, the term "about" means encompassing plus or minus 10%. For example, about 90% refers to a range encompassing between 81% and 99% nucleotides. As used herein, the "about" is synonymous with the term approximately.

Unless otherwise indicated or the context suggests otherwise, as used herein, "a" or "an" means "at least one" or "one or more."

The word "or" as used herein means any one member of a particular list and also includes any combination of members of that list.

DETAILED DESCRIPTION OF THE INVENTION

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the invention and are not intended to be limiting.

RELATED APPLICATIONS

This application is related to U.S. patent application Ser. No. 14/062,860. U.S. patent application Ser. No. 14/062,865 (U.S. Patent Application Publication No. 2014-0194305), and U.S. patent application Ser. No. 14/538,565 (U.S. Patent Application Publication No. 2016-0129445), the respective disclosures of which are hereby incorporated by reference.

INTRODUCTION

In general, the system includes two components: the multiplex cartridge, into which the sample is loaded and which contains various reagents, buffers, and other processing materials for performing the desired assay or other procedure, and the processing instrument into which the cartridge is inserted to perform the sample processing, detection of the target analyte(s) and reporting the detected targets.

In various embodiments, the microfluidic platform relies on the formation of microdroplets and the ability to independently transport, merge, mix and/or process the droplets. In various embodiments, such microdroplet operations are performed using electrical control of surface tension (i.e., electrowetting). In general, liquid samples are contained within a microfluidic device, known as a processing module, between two parallel plates. One plate—referred to as the fluidic processing panel—contains etched drive electrodes on its surface while the other plate contains either etched electrodes or a single, continuous plane electrode that is grounded or set to a reference potential ("biplanar electrowetting"). Hydrophobic insulation covers the electrodes and an electric field is generated between electrodes on opposing plates. This electric field creates a surface-tension gradient that causes a droplet overlapping the energized electrode to move towards that electrode. In some embodiments, the active electrowetting electrodes may be adjacent and on the same plane as the neighboring ground reference electrode, which is referred to as "coplanar electrowetting". Through proper arrangement and control of the electrodes, a droplet can be transported by successively transferring it between adjacent electrodes. The patterned electrodes can be arranged in a two dimensional array so as to allow transport of a droplet to any location covered by that array. The space surrounding the droplets may be filled with a gas such as air or an immiscible fluid such as oil, with immiscible oils being preferred in many embodiments of the present invention.

As the droplets containing the target analytes move across the surface, they can pick up reagents and buffers. For example, when dried reagents are placed on the surface (generally described herein as printed circuit board, although as will be appreciated by those in the art, additional surfaces can be used), a droplet moving through that zone will pick up and dissolve the reagent for use in a biological process, such as PCR amplification. In addition, as more fully described below, a sample preparation module positioned above the substrate, allows for specific addition of buffers and other reagents such as wash buffers, etc., as well as preparation, e.g., lysis, purification, dissolution, etc., of the sample prior to transferring the sample to the microfluidic platform.

Aspects of the present invention also involve the use of electrochemical detection of analytes of interest. Suitable electrochemical detection systems are described in U.S. Pat. Nos. 4,887,455; 5,591,578; 5,705,348; 5,770,365; 5,807,701; 5,824,473; 5,882,497; 6,013,170; 6,013,459; 6,033,601; 6,063,573; 6,090,933; 6,096,273; 6,180,064; 6,190,858; 6,192,351; 6,221,583; 6,232,062; 6,236,951; 6,248,229; 6,264,825; 6,265,155; 6,290,839; 6,361,958; 6,376,232; 6,431,016; 6,432,723; 6,479,240; 6,495,323; 6,518,024; 6,541,617; 6,596,483; 6,600,026; 6,602,400; 6,627,412; 6,642,046; 6,655,010; 6,686,150; 6,740,518; 6,753,143; 6,761,816; 6,824,669; 6,833,267; 6,875,619; 6,942,771; 6,951,759; 6,960,467; 6,977,151; 7,014,992; 7,018,523; 7,045,285; 7,056,669; 7,087,148; 7,090,804; 7,125,668; 7,160,678; 7,172,897; 7,267,939; 7,312,087; 7,381,525; 7,381,533; 7,384,749; 7,393,645; 7,514,228; 7,534,331; 7,560,237; 7,566,534; 7,579,145; 7,582,419; 7,595,153; 7,601,507; 7,655,129; 7,713,711; 7,759,073; 7,820,391; 7,863,035; 7,935,481; 8,012,743; 8,114,661 and U.S. Pub. No. 2012/01 81 186, the respective disclosures of which are expressly incorporated herein by reference.

In various embodiments processed target analyte droplets are transported to a detection zone on the fluidic processing panel, where they are specifically captured on individual detection electrodes, using systems described in numerous patents above with specific reference to U.S. Pat. Nos. 7,160,678, 7,393,645, and 7,935,481. This detection system relies on the use of label probes (in the case of nucleic acids) containing electrochemically active labels, such that the presence of the target analyte results in a positive signal, allowing detection of the pathogen, disease state, etc.

Samples

Aspects of the invention provide systems and methods for the detection of target analytes in samples to diagnose disease or infection by pathogens (e.g. bacteria, virus, fungi, etc.). As will be appreciated by those in the art, the sample solution may comprise any number of things, including, but not limited to, bodily fluids (including, but not limited to, blood, urine, serum, plasma, cerebrospinal fluid, lymph, saliva, nasopharyngeal samples, anal and vaginal secretions, feces, tissue samples including tissues suspected of containing cancerous cells, perspiration and semen of virtually any organism, with mammalian samples being preferred and human samples being particularly preferred); environmental samples (including, but not limited to, air, agricultural, water and soil samples, environmental swabs and other collection kits); biological warfare agent samples; food and beverage samples, research samples (i.e., in the case of nucleic acids, the sample may be the products, of an amplification reaction, including both target and signal amplification as is generally described in WO/1999/037819, the disclosure of which is hereby incorporated by reference, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

The multiplex cartridge may be used to detect target analytes in patient samples. By "target analyte" or "analyte" or grammatical equivalents herein is meant any molecule or compound to be detected and that can bind to a binding species, defined below. Suitable analytes include, but are not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids. lectins, carbohydrates, hormones, whole cells (including prokaryotic (such as pathogenic bacteria) and eukaryotic cells, including mammalian tumor cells), viruses, spores, etc.

In one embodiment, the target analyte is a protein ("target protein"). As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants. Particularly preferred target proteins include enzymes; drugs, cells; antibodies; antigens; cellular membrane antigens and receptors (neural, hormonal, nutrient, and cell surface receptors) or their ligands.

In a preferred embodiment, the target analyte is a nucleic acid ("target nucleic acid"). The present system finds use in the diagnosis of specific pathogens exogenous to a patient such as bacteria and viruses, as well as the diagnosis of genetic disease, such as single nucleotide polymorphisms (SNPs) that cause disease (e.g. cystic fibrosis) or are present in disease (e.g. tumor mutations).

As will be appreciated by those in the art, the present invention relies on both target nucleic acids and other nucleic acid components like capture probes and label probes used in the detection of the target nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs can be included as primers or probes that may have alternate backbones, comprising, for example, phosphoramide (Beaucage et al., Tetrahedron 49(10).T 925 (1993) and references therein; Letsinger, J. Org. Chem. 35:3800 (1970); Sprinzl et al., Eur. J. Biochem. 81:579 (1 977); Letsinger et al., Nucl. Acids Res. 14:3487 (1986); Sawai et al, Chem. Left. 805 (1984), Letsinger et al., J. Am. Chem. Soc. 1 10:4470 (1988); and Pauwels et al., Chemica *Scripta* 26: 141 91986)), phosphorothioate (Mag et al., Nucleic Acids Res. 19: 1437 (1991); and U.S. Pat. No. 5,644,048), phosphorodithioate (Briu et al, J. Am. Chem. Soc. 1 1 1:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 1 14: 1895 (1992); Meier et al., Chem. Int, Ed. Engl. 31: 1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); those with bicyclic structures including locked nucleic acids, Koshkin et al., J. Am. Chem. Soc. 120: 13252-3 (1998); non-ionic backbones (U.S. Pat. Nos. 5,386,023, 5,637,684, 5,602,240, 5,216, 141 anc. 4,469,863; Kiedrowshi et al., Angew. Chem. Intl. Ed. English 30:423 (1991); Letsinger et al., J. Am. Chem. Soc. 1 10:4470 (1988); Letsinger et al., Nucleoside & Nucleotide 13: 1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al, J. Biomolecular NMR 34: 17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention, in general for use as capture and label probes. In addition, mixtures of naturally occurring nucleic acids and analogs can be made (e.g. in general, the label probes contain a mixture of naturally occurring and synthetic nucleotides).

The nucleic acids may be single stranded or double stranded, as specified, or contain portions of both double stranded or single stranded sequence. The nucleic acids (particularly in the case of the target nucleic acids) may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, etc. One embodiment utilizes isocytosine and isoguanine in nucleic acids designed to be complementary to other probes, rather than target sequences, as this reduces non-specific hybridization, as is generally described in U.S. Pat. No. 5,681,702, disclosure of which is hereby incorporated by reference. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As will be appreciated by those in the art, a large number of analytes may be detected using the present methods; basically, any target analyte for which a binding ligand, described below, may be made may be detected using the methods of the invention.

Thus, the systems of the invention are used in assays of target analytes that then allow the diagnosis, prognosis or treatment options of disease based on the presence or absence of the target analytes. For example, the systems of the invention find use in the diagnosis or characterization of pathogen infection (including bacteria (both gram positive and gram negative bacteria, and/or the ability to distinguish between them), viruses (including the presence or absence of viral nucleic acid as well as the isotypes of the virus, for example in the case of hepatitis C virus (HCV) or respiratory viruses), fungal infection, antibiotic drug resistance, genetic diseases (including cystic fibrosis, sickle cell anemia, etc.). Included in the definition of genetic disease for the purposes of this invention are genetic conditions that do not necessarily cause disease but can result in an alternative treatment options. For example, single nucleotide polymorphisms (SNPs) in many cytochrome p450 enzymes cause different therapeutic drug processing, such as in the case of warfarin testing, where a patient may be diagnosed as a "slow", "normal" or "fast" processor, leading to different dosage regimes, or where a drug may be contraindicated for a particular patient based on the patient's genetics, or where selection between two or more drugs is aided by the knowledge of patient's genetics.

The assay can be further understood by the following numbered paragraphs:

Paragraph 1. An in vitro method for the detection and/or identification of a first human pathogen and/or genetic material thereof comprising subjecting a sample to a single multiplex polymerase chain reaction (PCR), wherein said method comprises amplification of PCR products under conditions appropriate for the substantial reduction or elimination of electrowetting failures.

Paragraph 2. The method of Paragraph 1, wherein the first human pathogen comprises respiratory viral infection.

Paragraph 3. The method of Paragraph 2, wherein the respiratory viral infection is selected from the group consisting of, Influenza A, Adenovirus, Influenza A H1 subtype, Human Bocavirus, Influenza A H3, Human Rhinovirus/Enterovirus, Influenza A 2009 H1N1 subtype, Coronavirus 229E, Influenza B, Coronavirus HKU1, Respiratory Syncytial Virus A, Coronavirus NL63, Respiratory Syncytial Virus B, Coronavirus OC43, Parainfluenza Virus 1, Coronavirus MERS, Parainfluenza Virus 2, *Bordetella pertussis*, Parainfluenza Virus 3, *Chlamydophila pneumoniae*, Parainfluenza Virus 4, *Mycoplasma pneumoniae*, Human Metapneumovirus, *Legionella pneumophila* and combinations thereof.

Paragraph 4. The method of Paragraph 2, wherein the first human pathogen comprises a gram-positive bacteria, a gram-negative bacteria or a fungal infection and wherein the gram-positive bacteria is selected from the group consisting of *Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group, *Enterococcus faecium, Streptococcus pneumonia, Lactobacillus, Streptococcus pyogenes, Listeria* and combinations thereof and wherein the gram-negative bacteria is selected from the group consisting of *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca* and combinations thereof and wherein the fungus is selected from the group consisting of *Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon* and combinations thereof.

Paragraph 5. The method of any preceding paragraph, wherein the method can further detect a second human pathogen if present in the sample.

Paragraph 6. The method of Paragraph 5, wherein the second human pathogen is a respiratory viral infection.

Paragraph 7. The method of Paragraph 6, wherein the respiratory viral infection is selected from the group comprising Influenza B, Influenza A 2009 H1N1 subtype, Parainfluenza Virus and combinations thereof.

Paragraph 8. The method of any preceding paragraph, wherein the detection method is electrochemical detection.

Paragraph 9. A microfluidic device for the detection and/or identification of a human pathogen and/or genetic material thereof comprising: a mixture of oligonucleotides and reagents for carrying out a single nucleic acid amplification reaction wherein said method comprises amplification under conditions appropriate for the substantial reduction or elimination of electrowetting failures Paragraph 10. The microfluidic device of paragraph 9, wherein the first human pathogen comprises a respiratory viral infection.

Paragraph 11. The microfluidic device of Paragraph 10, wherein the respiratory viral infection is selected from the group consisting of Influenza A, Adenovirus, Influenza A H1 subtype, Human Bocavirus, Influenza A H3, Human Rhinovirus/Enterovirus, Influenza A 2009 HIN subtype. Coronavirus 229E, Influenza B, Coronavirus HKU1, Respiratory Syncytial Virus A, Coronavirus NL63, Respiratory Syncytial Virus B, Coronavirus OC43, Parainfluenza Virus 1, Coronavirus MERS, Parainfluenza Virus 2, *Bordetella pertussis*, Parainfluenza Virus 3, *Chlamydophila pneumoniae*, Parainfluenza Virus 4, *Mycoplasma pneumoniae*, Human Metapneumovirus, *Legionella pneumophila* and combinations thereof.

Paragraph 12. The microfluidic device of any preceding Paragraph, wherein the method can further detect a second human pathogen if present in the sample.

Paragraph 13. The microfluidic device of Paragraph 12, wherein the second human pathogen is a respiratory viral infection.

Paragraph 14. The microfluidic device of Paragraph 10, wherein the first human pathogen comprises a gram-positive bacteria, a gram-negative bacteria or a fungal infection and wherein the gram-positive bacteria is selected from the group consisting of *Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group, *Enterococcus faecium, Streptococcus pneumonia, Lactobacillus, Streptococcus pyogenes, Listeria* and combinations thereof and wherein the gram-negative bacteria is selected from the group consisting of *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca* and combinations thereof and wherein the fungus is selected from the group consisting of *Candida auris, Candida albicans, Candida dubliniensis, Candida famata, Candida glabrata, Candida guilliermondii, Candida kefyr, Candida lusitaniae, Candida krusei, Candida*

*parapsilosis, Candida tropicalis, Cryptococcus gattii, Cryptococcus neoformans, Fusarium, Malassezia furfur, Rhodotorula. Trichosporon* and combinations thereof.

Paragraph 15. The microfluidic device of any preceding Paragraph, wherein the detection method is electrochemical detection.

Multiplex Cartridge

Figure 4:
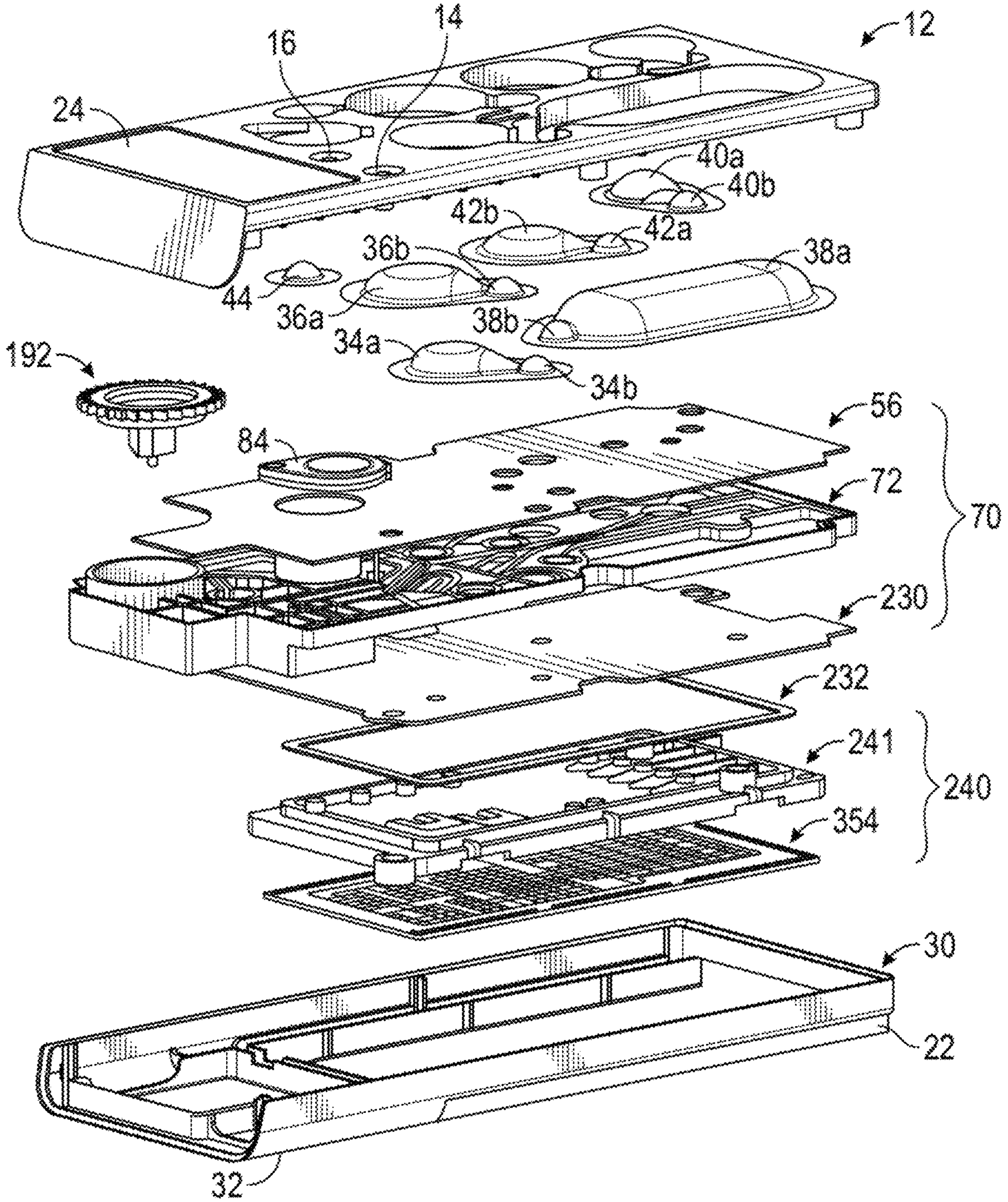
FIG. 4 is an exploded perspective view of the multiplex cartridge.

A multiplex cartridge embodying aspects of the present invention is shown in FIGS. 1-4. As shown in FIG. 4, the multiplex cartridge comprises an assembly that includes a sample preparation module 70. The sample preparation module 70 includes various wells, inlet and outlet ports, fluid channels, mixing mechanisms, valves, and other components for receiving, transporting, intermingling, mixing, and performing other processes on fluid sample materials and process fluids, such as reagents and buffers, in a manner that will be described in further detail below. The sample preparation module 70 comprises a substrate 72, with a top seal 56 secured to a top surface thereof and a bottom seal 230 secured to a bottom surface thereof. The substrate 72 includes a number of grooves or open channels formed on the top and bottom surfaces thereof. Each of the grooves may connect to one or more inlet ports comprising a blind hole formed in the top surface of the substrate 72 and/or to one or more outlet ports comprising a blind hole formed in the bottom surface of the substrate 72. This top seal 56 and bottom seal 230 cover the top and bottom, respectively, of the substrate 72 and having openings that align with the inlets and outlets formed in the substrate 72, thereby forming a network of conduits, or enclosed channels, through which a fluid—e.g., liquid, gas, solution, emulsion, liquid-solid suspension, etc.—may flow from one part of the sample preparation module 70 to another and inlet ports and outlet ports through which fluids may flow into and out of, respectively, the sample preparation module 70. In various embodiments, the sample preparation module 70 is transparent or translucent and is made from, for example, polycarbonate, polypropylene, acrylic, Mylar, acrylonitrile butadiene styrene ("ABS"), or other suitable polymers A rotary mixer 192 is operatively disposed within a mixing well 90 (described below) formed in the substrate 72. In various embodiments, the rotary mixer 192 can be used, for example, to grind up solid samples, maximize exposure of sample to capture beads, mix sample with chemical lysis buffer, mix magnetic beads with binding buffer (typically magnetic beads cannot be stored in their binding buffer and thus must be combined only at the time of use), etc.

A sample cap 84 is provided to enclose a sample well 78 (described below) formed in the substrate 72. A plurality of deformable compartments (or blisters) 34*a*, 36*a*, 38*a*, 40*a*, 42*a*, and 44 are supported on top of the substrate sample preparation module 70. Each deformable compartment may contain a fluid and may be connected to a fluid channel within the sample preparation module 70, via one of the inlet ports, by an openable connection that is initially closed to prevent fluid from flowing from the blister into the channel. Upon application of a compressive force to the exterior of the blister, increased pressure within the blister ruptures or otherwise opens or alters the openable connection to permit fluid flow from the blister into an associated inlet port and channel of the sample preparation module 70.

An upper shroud 12 is disposed over a top portion of the cartridge above the sample preparation module 70 and includes openings corresponding in number, size, and shape to the various deformable compartments supported on the sample preparation module 70. As can be appreciated from FIG. 1, the deformable compartments are recessed within the openings formed in the upper shroud 12, thereby providing some protection for the deformable compartments while allowing each compartment to be compressed from above by an actuator. In various embodiments, the upper shroud 12 further includes an inlet optical port 14 and an outlet optical port 16 to enable monitoring of fluid movement through a particular portion of the sample preparation module 70, as will be described in further detail below. The upper shroud 12 may further include a label panel 24 on which identifying information may be placed, such as, human and/or machine-readable indicia (e.g., a barcode).

The upper shroud 12 may further include valve actuator tabs, such as a sample valve actuator tab 18 and a waste valve actuator tab 20. The valve actuator tabs 18 and 20 are resilient, flexible tabs formed in the shroud that will deflect upon application of an external compressive force onto the tab. Each tab further includes a downwardly-extending actuator post—see, e.g., actuator post 26 in FIG. 1—to thereby actuate an active valve within the sample preparation module 70 and located below the respective tab 18 or 20, as will be described in further detail below.

Referring to FIG. 4, a reaction module 240 is disposed below the sample processing module 70 and, in various embodiments, may be configured to receive a processed sample from the sample processing module 70. In various embodiments, the reaction module 240 includes process fluid compartments (containing, for example, reagents, buffers, etc.), means for moving fluid droplets in a specified directed manner throughout the module, means for incubating reaction mixtures, and means for detecting target analytes (e.g., nucleic acids), The reaction module 240 may be secured to the bottom of the sample preparation module 70 by means of an adhesive gasket 232 that preferably provides a fluid-tight seal between the reaction module 240 and the sample preparation module 70. In various embodiments, the reaction module 240 comprises a top plate 241 and a bottom, a fluidic processing panel 354 secured to the bottom of the top plate 241 and which together define a gap between the bottom surface of the top plate 241 and a top surface of the fluidic processing panel 354. This gap defines fluid processing and reaction spaces within which various steps of the assay or other process are performed.

A lower shroud 30 partially encloses a bottom portion of the cartridge assembly and cooperates with the upper shroud 12 to define a relatively hard and ridged outer shell for the cartridge 10. The upper and lower shrouds may provide the cartridge 10 with an asymmetric shape so as to ensure that the cartridge 10 is inserted into a processing instrument in only one orientation. In the illustrated embodiment, the lower shroud 30 has rounded edges 32 whereas the upper shroud 12 has relatively square edges. Thus, a receiving slot of a processing instrument configured to receive the multiplex cartridge 10 and having a shape conforming to that of the shroud will ensure that the shroud is always inserted right side up into the instrument. In addition, the lower shroud 30 may include contour features, such as longitudinal side grooves 22 that extend only partially along the length of the lower shroud 30. Such grooves cooperate with corresponding features in a receiving slot of a processing instrument to ensure that the cartridge is inserted into the instrument in the proper direction.

The multiplex cartridge can be further understood by the following numbered paragraphs:

Paragraph 1: A multiplex cartridge comprising an upper shroud disposed over a sample preparation module, the sample preparation module secured to the reaction module wherein the reaction module comprises a top plate and wherein an interstitial space between the top plate and sample preparation module allows for the reduction in electrowetting errors.

Paragraph 2: A multiplex cartridge comprising an interstitial space between the top plate and sample preparation module wherein wide vents in the top plate allows for the reduction in electrowetting errors.

Deformable Fluid Compartments (Blisters)

In general, the blisters are made of a deformable material that preferably collapses upon the application of suitable pressure; that is, the materials used to form blisters do not return to their starting shape when the pressure is removed, as this could cause backflow of the applied reagents. In addition, the blisters may be used once (a single application of pressure is done during the assay) or a number of times (e.g. multiple aliquots of reagent are delivered to either a single location or multiple locations during the assay run). Each blister may contain a unique process material (e.g., buffer, reagent, immiscible liquid, etc.), or two or more blisters may contain the same process material. This redundancy may be used to deliver the same process material to multiple locations in the rest of the disposable.

Although the size, number, arrangement, and contents of the compartments is largely dictated by the assay or other process that is intended to be performed in the multiplex cartridge 10, the illustrated embodiment includes six deformable fluid compartments, or blisters: 34*a*, 36*a*, 38*a*, 40*a*. 42*a*, and 44. A deformable blister may have an associated lance blister. In the illustrated embodiment, each of deformable fluid blisters 34*a*, 36*a*, 38*a*, 40*a*, and 42*a* has an associated deformable lance cartridge, or lance blister, 34*b*, 36*b*, 38*b*, 40*b*, and 42*b*.

Operation of an embodiment of a deformable compartment is described with reference to FIG. 5, which shows a cross section of the deformable compartment 34*a*. In various embodiments, the deformable compartments of the multiplex cartridge 10 incorporate features described in commonly-owned U.S. patent application Ser. No. 14/206,867 (U.S. Pat. No. 9,222,623) entitled "Devices and Methods for Manipulating Deformable Fluid Vessels" the contents of which are hereby incorporated by reference.

When compressing a deformable compartment to displace the fluid contents thereof, sufficient compressive force must be applied to the blister to break, or otherwise open, a breakable seal that is holding the fluid within the compartment. The amount of force required to break the seal and displace the fluid contents of a compartment typically increases as the volume of the compartment increases. To limit the amount of compressive force that must be applied to a deformable compartment or blister to break or otherwise open a breakable seal that is holding the fluid within the compartment, a lance blister 34*b* is provided in association with the deformable compartment 34*a*. The deformable compartment 34*a* and the lance blister 34*b* may be connected by means of a channel, which may be initially blocked by a breakable seal. The lance blister 34*b* contains an opening device, e.g., a bead 46 (such as a steel ball bearing), enclosed within the lance blister 34*b* and supported above a fluid port 136 formed in the sample preparation module 70 by means of a breakable foil partition, or septum, that retains the bead 46 and the fluid contents within the lance blister 34*b* and the deformable compartment 34*a*. Thus, to open the deformable compartment 34*a*, a compressive force is first applied externally to the lance blister 34*b* to compress the lance blister 34*b* and force the bead 46 through the foil partition blocking the fluid port 136. After the fluid port 136 is opened, the fluid contents of the deformable compartment 34*a* can be dispensed into the fluid port 136 relatively easily by application of an external compressive force to the deformable compartment 34*a*. The amount of pressure required to compress the lance blister 34*b* and force the bead 46 through the foil partition is much less than that required to compress the primary compartment 34*a* and create sufficient pressure to open a burstable seal. Fluid flowing into the fluid port 136 will next flow through a horizontal channel 137, defined by a groove formed in a bottom surface of the substrate 72 and covered by the bottom seal 230, to a vertical channel transition 139 and from there to one or more other points within the sample preparation module 70.

The multiplex cartridge can be further understood by the following numbered paragraphs:

Paragraph 1: A multiplex cartridge comprising an upper shroud disposed over a sample preparation module comprising blisters wherein when the blisters are compressed they do not block an interstitial space between the top plate and sample preparation module so that there is a reduction in electrowetting errors.

Paragraph 2: A multiplex cartridge comprising an interstitial space between the top plate and compressed blisters wherein wide vents in the top plate allow for the reduction in electrowetting errors.

Sample Preparation Module

Various details of a sample preparation module 70 are shown in FIGS. 6-15.

Figure 6:
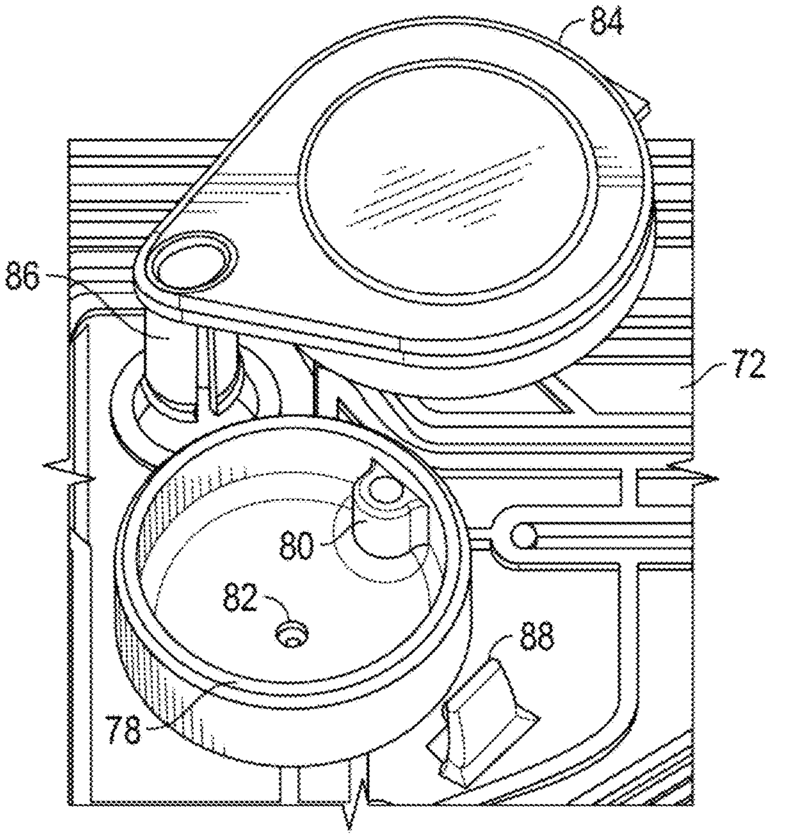
FIG. 6 is a perspective detail of a sample well and a sample cap of the multiplex cartridge.
Figure 7:
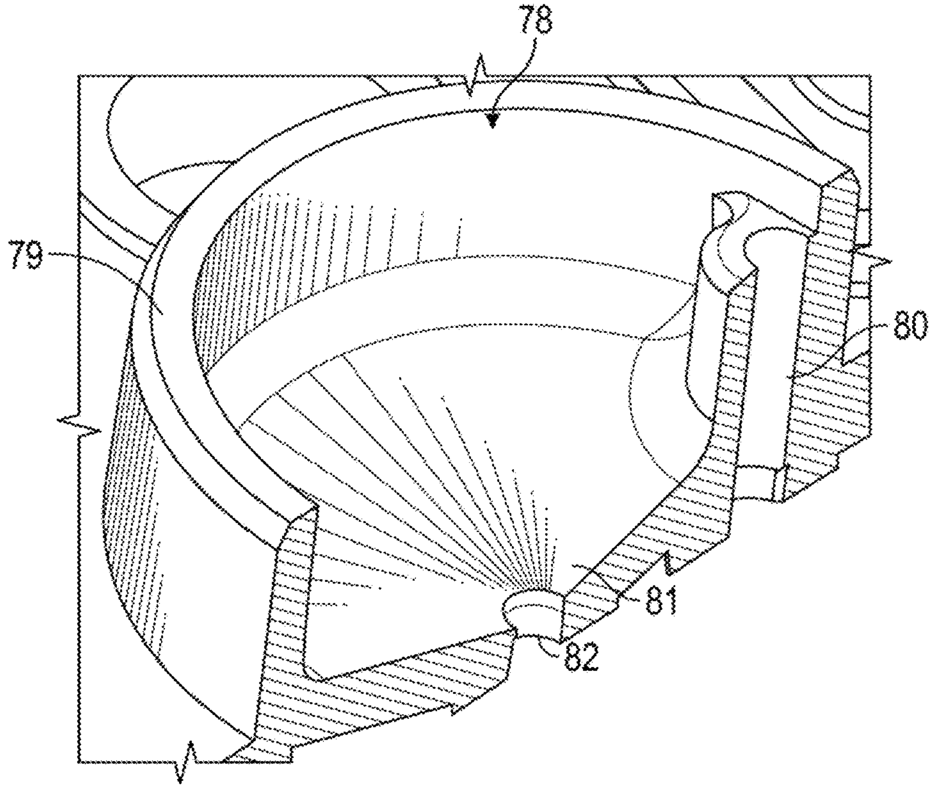
FIG. 7 is a perspective, cross sectional view of the sample well along the line 7-7 in FIG. 2.

The sample well 78 is configured to receive a fluid sample material that is to be assayed or otherwise processed in the multiplex cartridge 10. As shown in FIGS. 6 and 7, the sample well 78 may be defined by an upright peripheral wall 79 (which is circular in the illustrated embodiment) and a bottom wall, or floor 81. The sample well 78 further includes an inlet snorkel 80 extending up along the peripheral wall 79 of the sample well 78 and terminating at a position below the top of the peripheral wall. An exit port 82 is provided in the floor 81 of the well 78, and the floor 81 is preferably conical so as to taper downward toward the exit port 82.

The sample cap 84 may be provided for closing the sample well 78 after a sample material has been deposited into the sample well 78. In one embodiment, the sample cap 84 comprises a circular cover with an outer peripheral wall that fits over the upright peripheral wall 79 of the sample well 78. The sample cap 84 may include a pivot post 86 defined by radially-resilient locking tabs extending through an opening in the substrate 72 and permitting the cap 84 to be pivoted about an axis defined by the pivot post 86 relative to the sample well 78. After a sample material is deposited into the sample well 78, the sample cap 84 may be pivoted over the top of the sample well 78 and pushed down over the sample well 78. A clip, or other detent, 88, extending upwardly may be provided to catch on and securely lock the sample cap 84 when pushed down into the clip 88 and to also provide a tactile confirmation that cap 84 has been securely closed. In some embodiments, the sample cap 84 may have a bottom surface that tapers downwardly when the sample cap 84 is placed over the sample, well 78 (not shown). The conical configuration helps to reduce the amount of fluid condensate retained on the inside surface of the sample cap 84 during sample processing in the sample well 78.

Figure 8A:
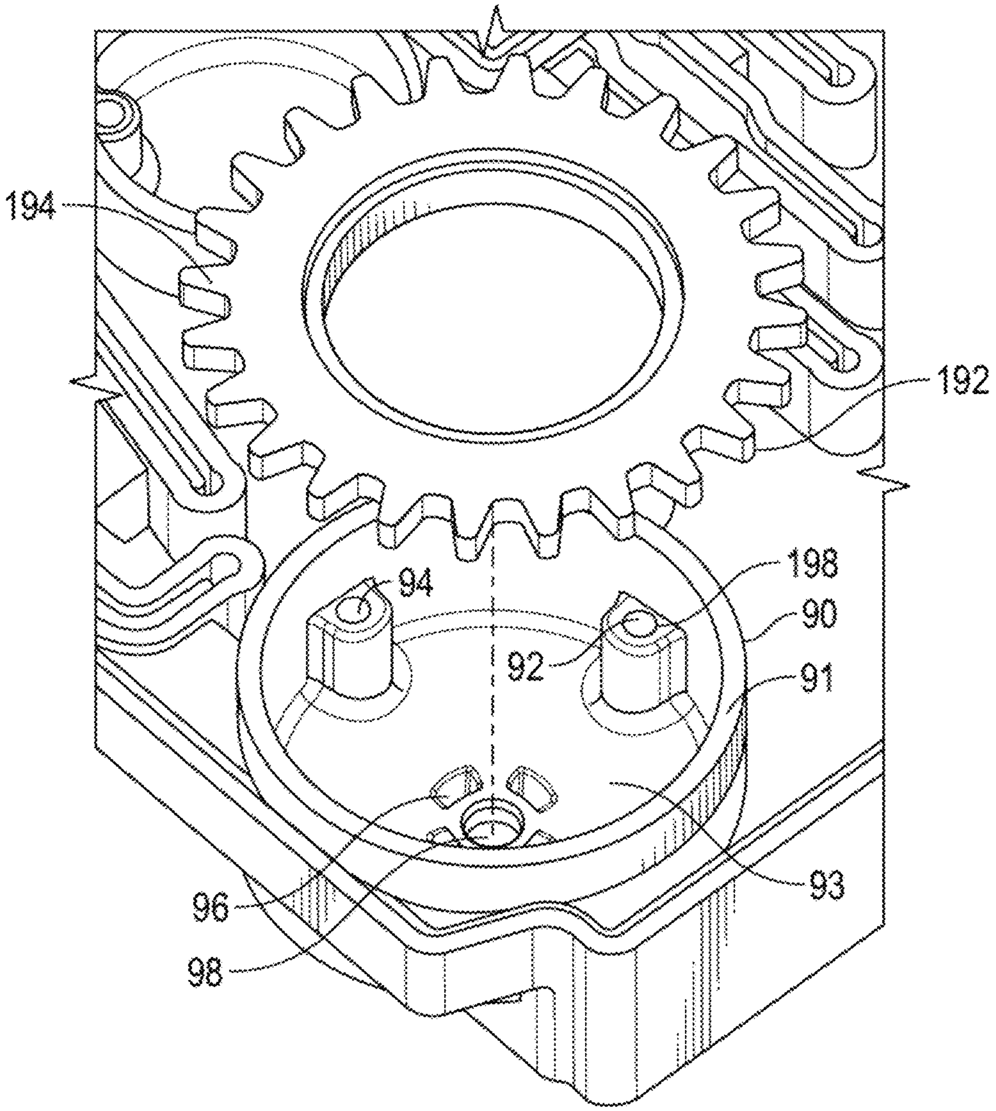
FIG. 8A is a perspective detail of a mixing well and mixer of the multiplex cartridge.
Figure 9A:
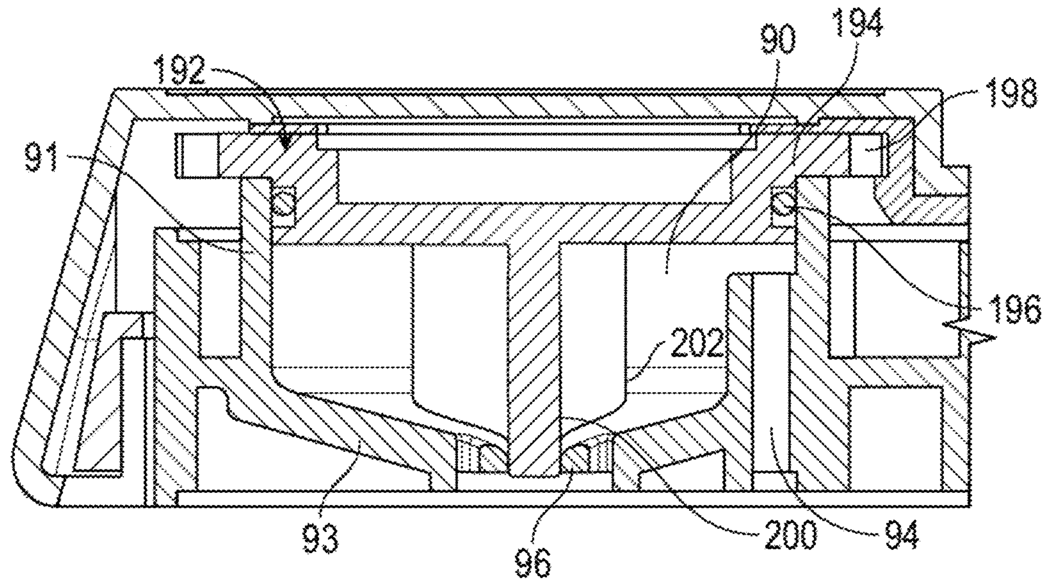
FIG. 9A is a cross sectional view of the mixing well and mixer along the line 9-9 in FIG. 2.

The sample preparation module 70 also includes a mixing well 90 formed in the substrate 72. As shown in FIGS. 8A and 9A, the mixing well 90 may be defined by an upright peripheral wall 91 (which is circular in the illustrated embodiment) and a bottom wall, or floor 93. In various embodiments, a fluid inlet snorkel 92 extends up the peripheral wall 91 of the mixing well 90 and terminates below the top of the wall 91. In various embodiments, a pressure snorkel 94 extends up another portion of the peripheral wall 91 of the mixing well 90 and terminates at a position below the top of the wall 91. An exit port 96 allows fluid to exit the mixing well 90 and may comprise a plurality of openings located near the center of a downwardly tapered portion of the floor 93 of the well 90 and surrounding a spindle seat 98 formed at the bottom center of the floor 93.

The rotary mixer 192 is disposed within the mixing well 90 and includes an upper circular disk 194 supported on an upper edge of the peripheral wall 91 of the well 90. Peripheral gear teeth 198 are formed about the periphery of the disk 194, and a portion of the teeth 198 project from an outer edge of the upper and lower shrouds 12, 30 of the multiplex cartridge 10 so as to be engageable by an external drive mechanism of a processing instrument to effect powered rotation of the rotary mixer 192. An O ring 196 is disposed within a peripheral O ring groove about the upper disk 194 below the peripheral gear teeth 198. The O ring 196 provides a seal between the rotary mixed 192 and the peripheral wall 91 of the well 90. A spindle 200 extends downwardly from the upper disk 194 and is seated within the center spindle seat 98 of the mixing well 90. A plurality of impeller blades 202 extend radially from the spindle 200.

Figure 8B:
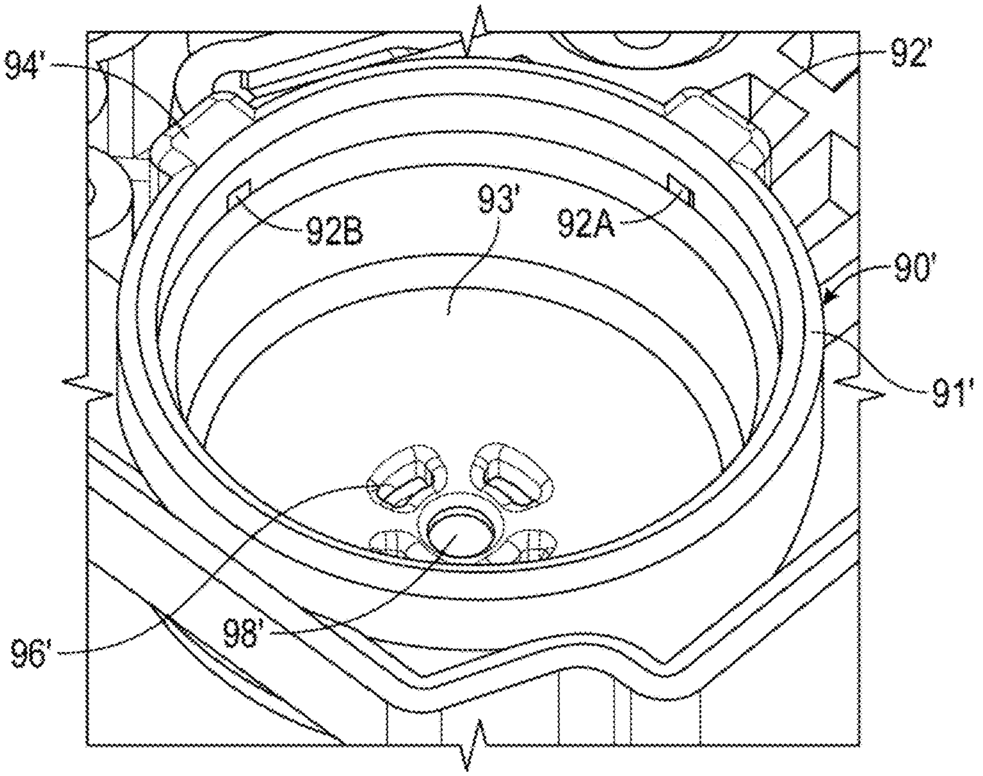
FIG. 8B is a perspective detail of an alternate mixing well of the multiplex cartridge.
Figure 8C:
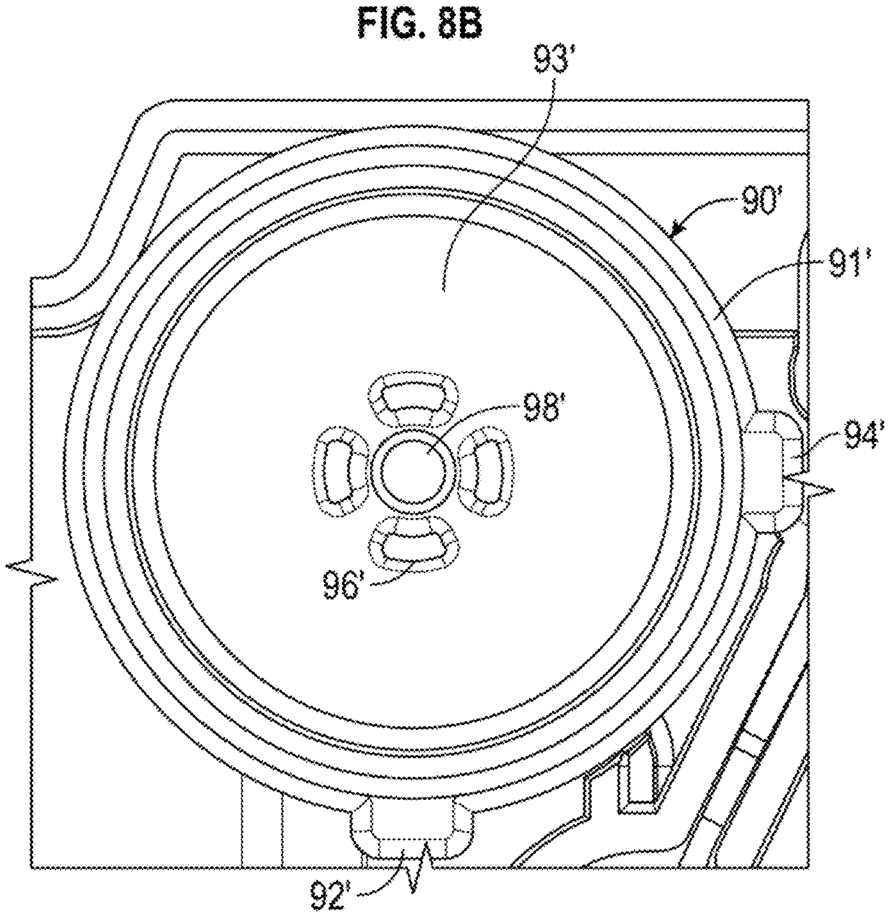
FIG. 8C is a top plan view of the mixing well of FIG. 8B.

An alternate embodiment of a mixing well 90' is shown in FIGS. 8B and 8C. As shown, mixing well 90' may be defined by an upright peripheral wall 91' (which is circular in the illustrated embodiment) and a bottom wall, or floor 93'. A fluid inlet snorkel 92' extends up an outer surface of the peripheral wall 91' of the mixing well 90' and includes an opening **92*a* below the top of the wall 91'. A pressure snorkel 94' extends up outer surface of the peripheral wall 91' of the mixing well 90' and includes an opening 94*a* below the top of the wall 91'. An exit port 96' allows fluid to exit the mixing well 90' and may comprise a plurality of openings located near the center of a downwardly tapered portion of the floor 93' of the well 90' and surrounding a spindle seat 98' formed at the bottom center of the floor 93'. The exit port 96' and spindle seat 98' may be substantially identical to the exit port 96 and spindle seat 98, respectively, of the mixing well 90**.

With the alternate mixing well 90' of FIGS. 8B and 8C, a rotary mixer disposed within the mixing well 90' may be configured with impeller blades extending radially from a spindle of the mixer substantially to the inner surface of the peripheral wall 91'. This is opposed to the configuration of the rotary mixer 192 configured for operation in the mixing well 90, in which the radial impeller blades 202 cannot extend substantially to the inner surface of the peripheral wall 91 so as to provide clearance for the snorkels 92, 94 formed on the inner surface of the peripheral wall 91. Having a mixer with impeller blades extending to the inner surface of the peripheral wall 91' may, in some circumstances, provide more complete and/or efficient mixing of the contents of the mixing well 90'.

Figure 9B:
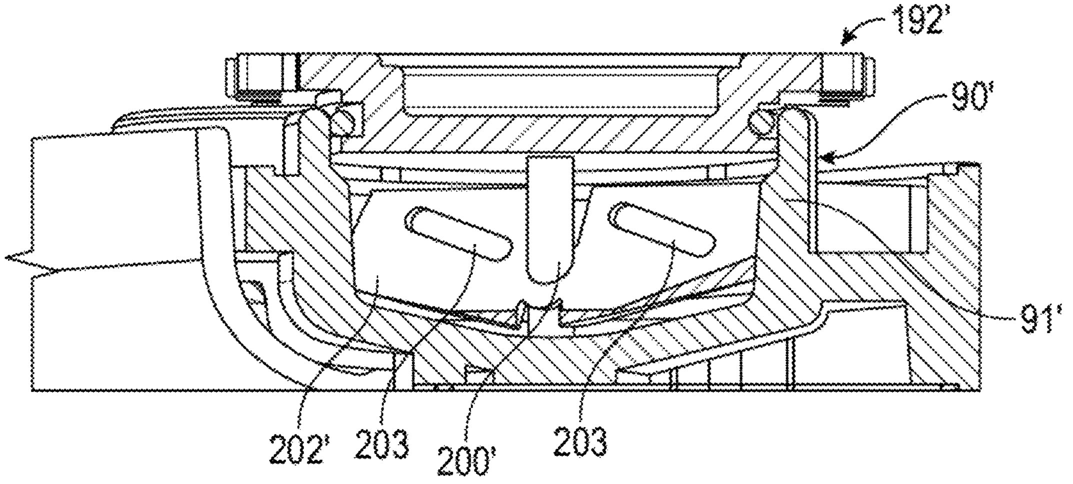
FIG. 9B is cross sectional view of the alternate mixing well of FIGS. 8B and 8C and an alternate mixer disposed therein.

Referring to FIG. 9B, the rotary mixer 192' disposed within the mixing well 90' includes an upper circular disk 194', peripheral gear teeth 198', and an O ring 196' that may be substantially identical to the circular disk 194, peripheral gear teeth 198, and an O ring 196 of the rotary mixer 192 shown in FIG. 9A. A spindle 200' extends downwardly from the upper disk 194'. Two or more impeller blades 202' extend radially from the spindle 200'. The impeller blades 202' extend substantially to the inner surface of the peripheral wall 91'. In various embodiments the impeller blades 202' may be skewed with respect to the spindle 200' and may further include openings 203 formed therein to improve the mixing efficiency of the rotary mixer 192'.

Referring again to FIG. 15, which shows a top plan view of the sample preparation module 70, the sample preparation module 70 may include alignment holes 74 and 76, or other alignment features may be provided in the sample preparation module 70, or some other portion of the multiplex cartridge 10 to facilitate alignment of the multiplex cartridge 10 with a processing instrument, for example, by means of a pin or other structure within the instrument extending into each alignment hole.

The sample preparation module 70 includes a first inlet port 136 formed in a top surface of the module by which a process fluid from the deformable compartment **34*a* may be introduced into the sample preparation module 70. In one embodiment, the deformable compartment 34*a*** contains a lysis buffer, such as water for hypotonic lysis, or a commercially available lysis buffer, such as those containing chiatropic salts such as guanidinium salts, and or high/low pH, and/or surfactants such as sodium dodecyl sulfate (SDS), TWEEN® 20 (polysorbate 20), TRITON™ X-100 (polyoxyethylene octyl phenyl ether), etc. In some cases, the lysis buffer optionally comprises reagents to disrupt undesired enzymatic activity, such as DNase and Rnase activity, which are then removed during the bead capture/elution process (although these can be separate reagents, either dried or liquid, that can be added as needed depending on the target analytes and the assay).

After cells of the sample material are lysed, it is often desirable to perform an at least partial purification, to remove other cellular and sample debris from the sample to facilitate the downstream handling and processing. Research samples in buffer do not necessarily require purification, but even there purification is typically performed. A well-known technique relies on the use of target capture beads (e.g., magnetic capture beads) that capture and immobilize the desired target analyte(s) away from the cellular and sample debris. In various implementations, capture beads and binding buffer are mixed with the sample in lysis buffer after the cells or viruses are disrupted by mechanical and/or chemical means. The capture beads may be magnetic to facilitate subsequent immobilization of the beads and the target analyte bound thereto by selective application of magnetic forces, although as will be appreciated by those in the art, other implementations may employ non-magnetic beads, such as polystyrene or silica beads (for example, beads may be captured in a zone by size or on an affinity column).

Thus, in various embodiments, the sample preparation module 70 includes a second inlet port 138 by which a process fluid from the deformable compartment **36*a* may be introduced into the sample preparation module 70. In one embodiment, the deformable compartment 36*a*** contains a binding buffer to facilitate the binding of target capture beads, such as magnetic beads, to one or more target analytes of interest.

In various embodiments, the sample preparation module 70 includes a third inlet port 140 by which a process material from the deformable compartment 44 may be introduced into the sample preparation module 70. In one embodiment, the deformable compartment 44 contains target capture beads which may comprise magnetic particles, which, in combination with a binding buffer from the deformable compartment **36*a*, binds to an analyte or analytes of interests within the sample material to thereby isolate and enable the magnetic separation of the analyte(s) of interest from the remainder of the sample material. In some embodiments, the deformable compartment 44 is absent and the mixing well 90** contains pre-dried magnetic beads.

The capture beads may be coated with a material that facilitates capture of the target analyte(s). For example, for the capture of nucleic acids, the beads can be coated with a negatively charged coating to facilitate the adsorption of positively charged nucleic acids to the surface, which are then washed with buffer and then treated with elution buffer to remove the purified nucleic acids from the beads for further processing. As will be appreciated by those in the art, there are a number of suitable, commercially available bead systems, including, for example, MagaZorb® Beads from Promega, MagMax from Life Tech, or beads from Qiagen, MoBio, BioRad, etc.

Thus, the target capture beads that may be contained in the deformable compartment 44 facilitate the purification of the desired target analyte with fluid access to a binding buffer, such as the bind buffer that may be contained in the deformable compartment 36*a*, used in conjunction with the capture beads.

In an alternate embodiment, target capture beads may be provided directly within the sample preparation module 70, for example, in the form of a lyophilized pellet placed into the mixing well 90 during assembly of the multiplex cartridge 10 and stored in the mixing well in pellet form until reconstituted by a fluid added to the mixing well 90 during use of the multiplex cartridge 10. In this alternate embodiment, the deformable blister 44 may be omitted.

In alternate implementations, capture beads may be functionalized with capture nucleic acid probes in order to either specifically or non-specifically pull out nucleic acids. For example, the beads may be functionalized with random 6-mers, to generally pull out nucleic acids, or with capture probes specific to the desired target nucleic acids. In some cases, for example when mRNA is the target, beads coated with poly-T capture probes can be used.

In various embodiments, the sample preparation module 70 further includes a fourth inlet port 142 by which process material from the deformable compartment 38*a* may be introduced into the sample preparation module 70. In one embodiment, the deformable compartment 38*a* contains an immiscible fluid (e.g., an oil, such as mineral oil, silicone oil, etc., as discussed in detail below).

In various embodiments, the sample preparation module 70 further includes a fifth inlet port 144 by which a process material from the deformable compartment 40*a* may be introduced into the substrate 72. In one embodiment, the deformable compartment 40*a* contains an elution buffer.

In various embodiments, the sample preparation module 70 further includes a sixth inlet port 146 by which process material from the deformable compartment 42*a* may be introduced into the sample preparation module 70. In one embodiment, the deformable compartment 42*a* contains a wash buffer.

In various embodiments, the sample preparation module 70 includes a first outlet port 182, a second outlet port 188, and a third outlet port 190 formed in a bottom surface of the sample preparation module 70 by which fluid can exit the module 70 and flow into the reaction module 240.

It should be noted here that the designation of inlet ports or outlet ports as the first, second, third, fourth, fifth, or sixth ports is merely to provide a convenient means for distinguishing one port from another and is not meant to be limiting, such as, for example, by specifying a particular order or sequence by which the ports may be used.

A first fluid channel 150 extends from the first inlet port 136 to the sample well 78. In the diagrams, the fluid channels are represented by parallel lines extending from point to point across the sample preparation module 70. Each channel may include one or more channel transition points, represented by a circle in the channel, one of which is indicated by reference number 151. The channel transition point represents a vertically extending section of channel extending up, from a channel section formed on the bottom of the substrate 72 to a channel section formed on the top of the substrate 72, or down, from a channel section formed on the top of the substrate 72 to a channel section formed on the bottom of the substrate 72, so that the channel may pass over or under another channel within the substrate 72.

A second fluid channel 152 extends from the sample well 78 to the lysis chamber inlet 122. A third fluid channel 156 extends from the lysis chamber outlet 124 to a fifth fluid channel 162 that extends from the third inlet port 140 to the mixing well inlet snorkel 92. A fourth fluid channel 160 extends from the second inlet port 138 to the third inlet port 140. A sixth fluid channel 164 extends from the fourth inlet port 142 to the first outlet port 182. A seventh fluid channel 166 extends from the fifth inlet port 144 to the second outlet port 188. An eighth fluid channel 168 extends from the mixing well exit port 96 to a passive valve assembly 220 (described below). A ninth fluid channel 170 extends from a passive valve cavity of the passive valve assembly 220 to a capture compartment 100. A tenth fluid channel 172 extends from an active valve assembly 204 to an active valve assembly 219. An eleventh fluid channel 174 extends from the active valve assembly 219 to a waste chamber 102. A twelfth fluid channel 176 extends from the sixth inlet port 146 to the capture compartment 100. A thirteenth fluid channel 178 extends from the capture compartment 100 to the active valve assembly 204. A fourteenth fluid channel 180 extends from the active valve assembly 204 to the third outlet 190.

It should be noted here that the designation of the various fluid channels as the first, second, third, fourth, fifth, etc. fluid channels is merely to provide a convenient means for distinguishing one port from another and is not meant to be limiting, such as, for example, by specifying a particular order or sequence in which the fluid channels may be used or a particular direction in which fluids flow through the channels.

In various embodiments, the sample preparation module 70 further includes a passive valve assembly 220 adjacent the mixing well 90. In one embodiment, the passive valve assembly 220 is configured such that the passive valve assembly 220 is closed if pressure within the mixing well 90 is below a threshold pressure and thus fluid within the mixing well 90 is retained. On the other hand, if pressure is allowed to increase within the mixing well 90, at a sufficient pressure level, above the threshold pressure, the passive valve assembly 220 will be opened, thereby permitting fluid within the mixing well to escape via the exit port 96 and the eighth fluid channel 168 connecting the mixing well exit port 96 to the passive valve assembly 220.

Figure 10:
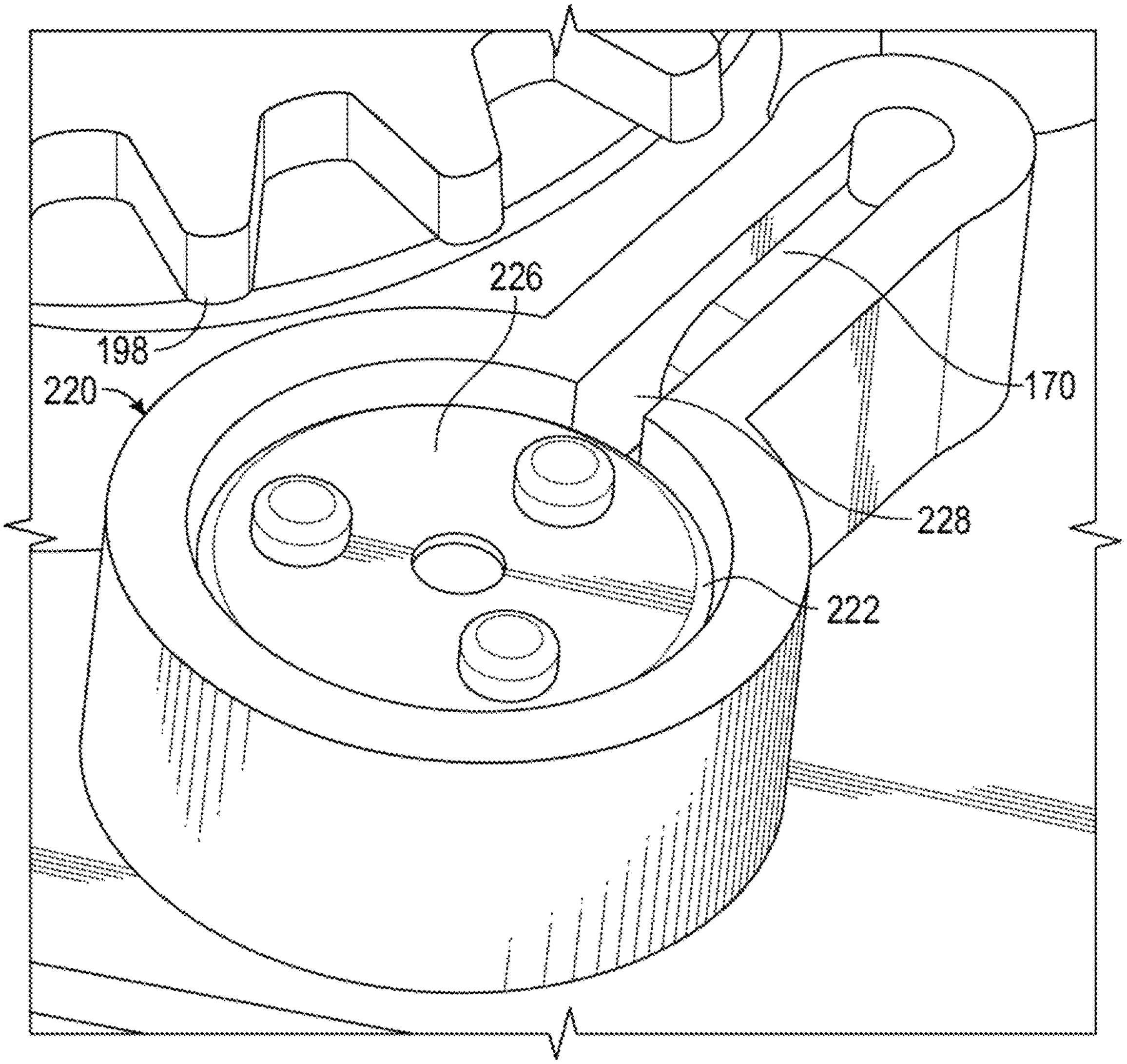
FIG. 10 is a perspective detail of a passive valve of the multiplex cartridge.
Figure 11:
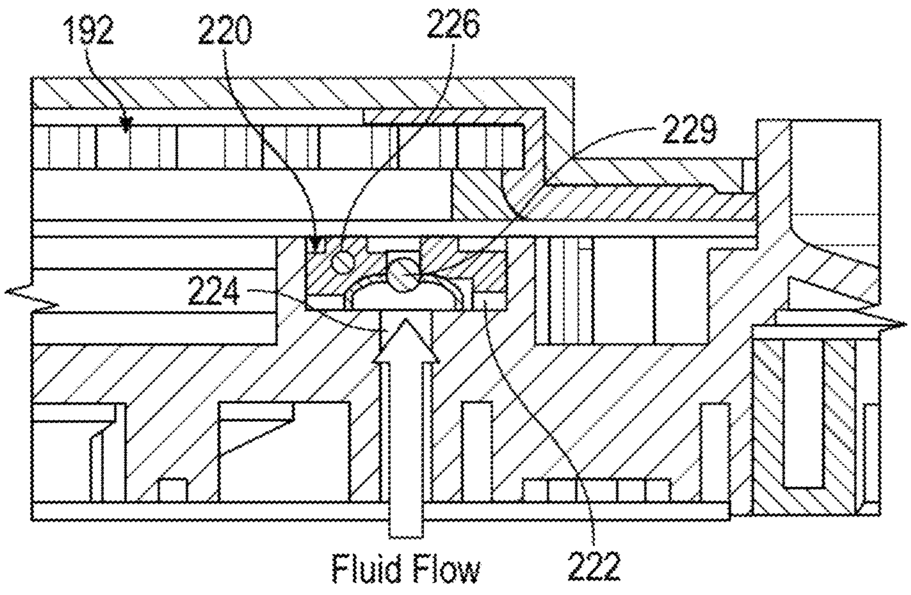
FIG. 11 is a perspective, cross sectional view of the passive valve along the line 11-11 in FIG. 2.
Figure 12:
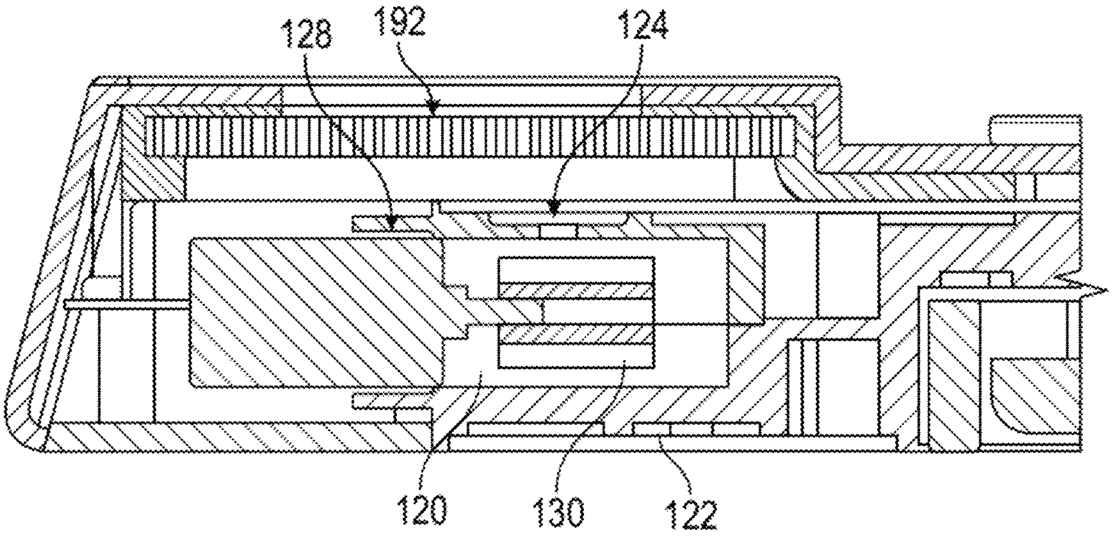
FIG. 12 is a perspective, cross sectional view of a lysis chamber and bead mixer along the line 12-12 in FIG. 2.

Details of the passive valve assembly 220 are shown in FIGS. 10 and 11. The valve assembly 220 comprises a valve cavity 222 formed in the substrate 72 and an inlet 224 formed in the substrate 72 and extending upwardly into the valve cavity 222. A valve 229, which may comprise a Belleville valve, is disposed within the valve cavity 222 over the inlet 224. A retainer 226 is disposed over the valve 229. An outlet 228 extends radially from the valve cavity 222.

In an unpressurized condition, the valve 229 and the retainer 226 are at rest at the bottom of the valve cavity 222, with the valve 229 covering the inlet 224. The retainer 226 may be biased in a down position, e.g., by a suitable spring or the like. Accordingly, fluid flowing from the inlet 224 is not able to pass into and through the valve cavity 222, and thus, fluid is not able to escape the mixing well 90. On the other hand, if fluid in the inlet 224 is sufficiently pressurized to overcome any force (e.g., spring bias) holding the retainer 226 in a down position (e.g., about 3 to 5 psi), the valve 229 and the retainer 226 will be lifted off the bottom of the valve cavity 222 thereby opening the inlet 224 and allowing fluid to flow into the valve cavity 222 and out of the outlet 228.

The sample preparation module 70 may further include a pump port 104 by which an external source of pressure may be coupled to the sample preparation module 70. The pump port 104 is connected, via a pressure conduit 106 to the sample well 78 so that pressure applied at the pump port 104 will pressurize the sample well 78 to motivate the contents of the sample well 78 out of the well.

The sample preparation module 70 may further include a passive valve port 108 is connected, via a valve conduit 110 to the pressure snorkel 94 of the mixing well 90. If the passive valve port 108 is open, pressure will not build up within the mixing well 90, and the passive valve assembly 220 will remain closed. If the passive valve port 108 is closed, pressure will build up within the mixing well 90 and the passive valve assembly 220 will open so that the contents of the mixing well 90 can flow from the well.

Some organisms, such as viruses and many bacteria, can be lysed chemically by the addition of a lysis buffer with or without elevated temperature or proteolytic enzymes. Some organisms are difficult to lyse by chemical and/or enzymatic methods and require mechanical disruption or shearing of the cell membranes. As such, an optional component of the multiplex cartridge 10 is an impeller component, wherein the impeller is activated to grind or break up solid components such that individual cells are more accessible to lysis buffer and so that more target analytes are released. The impeller imparts turbulent action to the fluid in which lysis beads are contained. The primary lysis action is due to bead collisions with target organisms, which are thereby lysed, breaking them open and exposing the target nucleic acids. The presence of the lysis buffer inhibits the Dnases or Rnases which may destroy the RNA or DNA targets once the cells are disrupted. In various embodiments, the impeller is like a paddle wheel that rotates very fast.

Thus, in various embodiments, the sample preparation module 70 further includes a lysis chamber 120 with a driven agitator, such as a motorized bead mixer mechanism, disposed therein. The driven agitator is disposed at least partially within the lysis chamber 120 and is constructed and arranged to agitate fluid flowing through the processing chamber. The fluid flowing through the lysis chamber may comprise a mixture of sample material, lysis buffer, and lysis beads. The lysis beads may comprise silica (ceramic) beads (of, e.g., 100 μm diameter) that are dispensed into the lysis chamber 120 during assembly of the multiplex cartridge 10. The bead mixer comprises motor 128 with an impeller 130 mounted on an output shaft of the motor (see FIG. 2). Fluid flows into the lysis chamber 120 through an inlet 122 and flows out of the lysis chamber 120 through an outlet 124. A mesh filter may be provided in front of the inlet 122 and/or the outlet 124. The mesh filter(s) have a pore size configured to retain the lysis beads within the lysis chamber 120 while allowing sample fluid to flow into and out of the lysis chamber 120. In operation, the motor 128 rotates the impeller 130 at a high rate of rotation (e.g., about 5,000 to about 100,000 rpm, preferably about 10,000 to about 50,000 rpm, more preferably about 20,000 to about 30,000 rpm), so that fluid within the lysis chamber 120, which may include sample material and lysis beads, is vigorously agitated by the rotating impellor, thereby assisting the lysis beads in disrupting the molecular structure of the sample material. Thus, the sample mixture flowing out of the lysis chamber 120 is more completely lysed than it would be without the bead mixer.

A suitable motor 128 of the bead mixer includes Feiying, Model FY0610-Q-04170Y from Jinlong Machinery. The motor may be powered by a temporary connection of the multiplex cartridge 10 to an external power source of an instrument in which the cartridge 10 is being processed. Control of the motor 128 may be implemented by means of logic elements provided externally and/or internally of the cartridge 10. In one embodiment, a mixer printed circuit board ("PCB") is provided within the lower shroud 30 that controls operation of the bead mixer motor 128. The mixer motor 128 is ideally only operated when fluid is flowing through the lysis chamber 120. Fluid flowing into the lysis chamber 120 can be detected by an optical sensor through the inlet optical port 14 formed in the upper shroud 12 (see FIG. 2), which is aligned with an inlet optical sensing chamber 154 (see, e.g., FIG. 15), so that the bead mixer motor 128 can be activated, for example, upon detection of the forward end of a fluid stream flowing through the inlet optical sensing chamber 154 toward the lysis chamber 120. Similarly, fluid flowing out of the lysis chamber 120 can be detected by an optical sensor through the outlet optical port 16 (see FIG. 2), which is aligned with the outlet optical sensing chamber 158 (see FIG. 15), so that the bead mixer motor 128 can be deactivated, for example, upon detection of the trailing end of a fluid stream flowing through the outlet optical sensing chamber 158.

The sample preparation module 70 further includes two active valve assemblies 204, 219. The valve assembly 204 is known as the sample valve assembly and is positioned at the junction of the tenth fluid channel 172, the thirteenth fluid channel 178, and the fourteenth fluid channel 180 and controls flow from the thirteenth fluid channel 178 into the fourteenth fluid channel 180. Valve assembly 219 is known as the waste valve assembly and is positioned at the junction of the tenth fluid channel 172 and the eleventh fluid channel 174 and controls flow from the tenth fluid channel 172 to the eleventh fluid channel 174 and the waste chamber 102.

Figure 13:
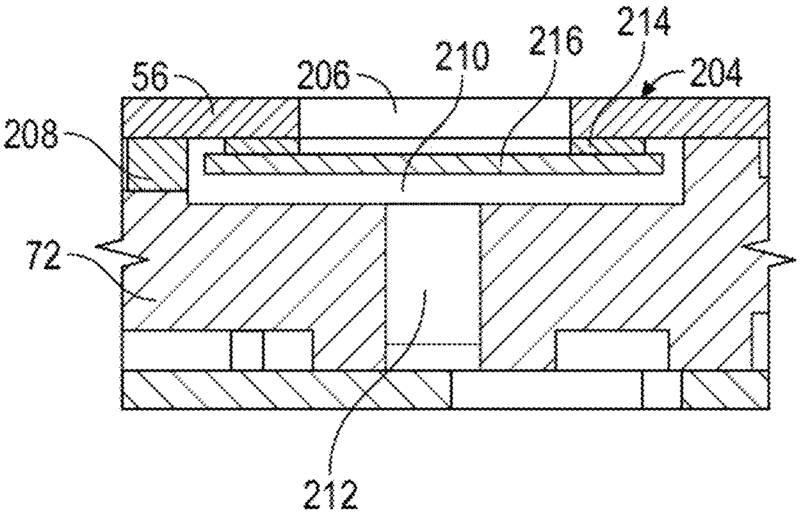
FIG. 13 is a perspective, cross sectional view of an active valve assembly along the line 13-13 in FIG. 2.
Figure 14:
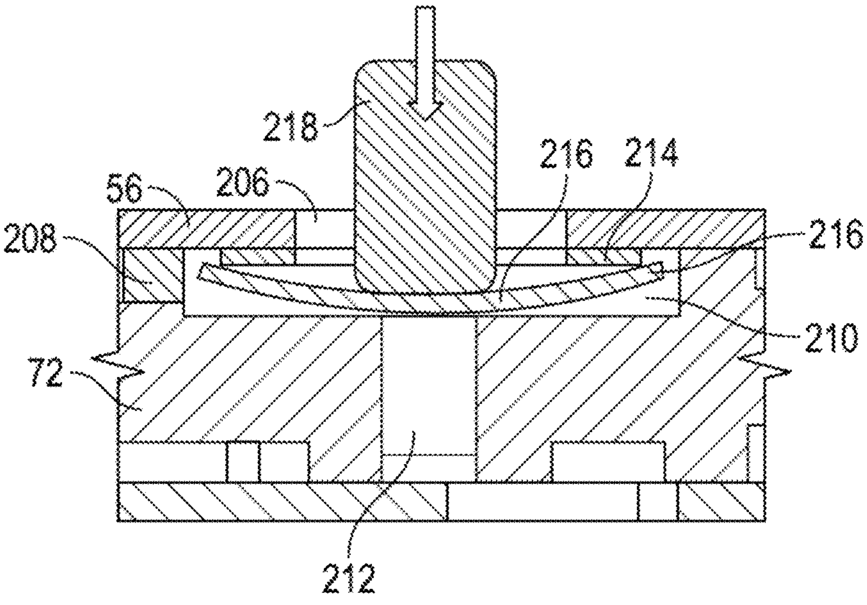
FIG. 14 is a perspective, cross sectional view of the active valve, wherein the valve is actuated by an external valve actuator.

Details of an active valve assembly, e.g., the valve assembly 204, are shown in FIGS. 13 and 14. The valve assembly 204 comprises a valve cavity 210 formed in the substrate 72. An inlet conduit 208 leads into the valve cavity 210, and an outlet channel 212 extends out of the cavity 210. An access opening 206 is formed in the top seal 56 disposed atop the substrate 72. A flexible valve membrane 216 is secured to an underside of the top seal 56 beneath the access opening 206 by means of an adhesive 214 surrounding the access opening 206. In the undeflected, or unactuated, position, a. shown in FIG. 13, fluid may flow into the valve cavity 210 through the inlet 208 and flow out of the valve cavity 210 through the outlet 212. Accordingly, fluid flow through the valve assembly 204 is unimpeded. As shown in FIG. 14, when an external valve actuator 218 presses down through the access opening 206 to deflect the valve membrane 216 over the outlet 212, fluid flow through the valve assembly 204 is blocked. The valve actuator 218 may comprise an actuator post 26 of the actuator tab 20 formed in the upper shroud 12 (see FIG. 1). Specifically, valve actuator tab 18 is aligned with the active valve assembly 204, and valve actuator tab 20 is aligned with the active valve assembly 219.

In various embodiments, the sample preparation module 70 further includes a waste chamber 102 (or more than one waste chamber) configured to receive and container excess or used fluids.

The invention can be further understood by the following numbered paragraphs:

Paragraph 1: A sample preparation module comprising a mixing well containing magnetic beads.

Paragraph 2: A microfluidic device comprising a reaction module, a sample preparation; module and an external housing wherein the sample preparation module comprises a mixing well containing magnetic beads.

Paragraph 3: A method for preparing a sample for target analyte detection comprising loading a sample into a sample preparation module and exposing the sample to magnetic beads in a mixing well thereby preparing the sample.

Paragraph 4: The method of paragraph 3, wherein the target analyte is nucleic acid from a respiratory virus selected from the group consisting of, Influenza A, Adenovirus, Influenza A H1 subtype, Human Bocavirus, Influenza A H3, Human Rhinovirus/Enterovirus, Influenza A 2009 H1N1 subtype, Coronavirus 229E, Influenza B, Coronavirus HKU1, Respiratory Syncytial Virus A, Coronavirus NL63, Respiratory Syncytial Virus B, Coronavirus OC43, Parainfluenza Virus 1, Coronavirus MERS, Parainfluenza Virus 2, *Bordetella pertussis*, Parainfluenza Virus 3, *Chlamydophila pneumoniae*, Parainfluenza Virus 4, *Mycoplasma pneumoniae*, Human Metapneumovirus, *Legionella pneumophila* and combinations thereof; wherein the target analyte is nucleic acid from a gram-positive bacteria, a gram-negative bacteria or a fungal infection and wherein the gram-positive bacteria is selected from the group consisting of *Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group, *Enterococcus faecium, Streptococcus pneumonia, Lactobacillus, Streptococcus pyogenes, Listeria* and combinations thereof and wherein the gram-negative bacteria is selected from the group consisting of *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca* and combinations thereof and wherein the fungus is selected from the group consisting of *Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon* and combinations thereof.

Reaction Module—Top Plate

Figure 24:
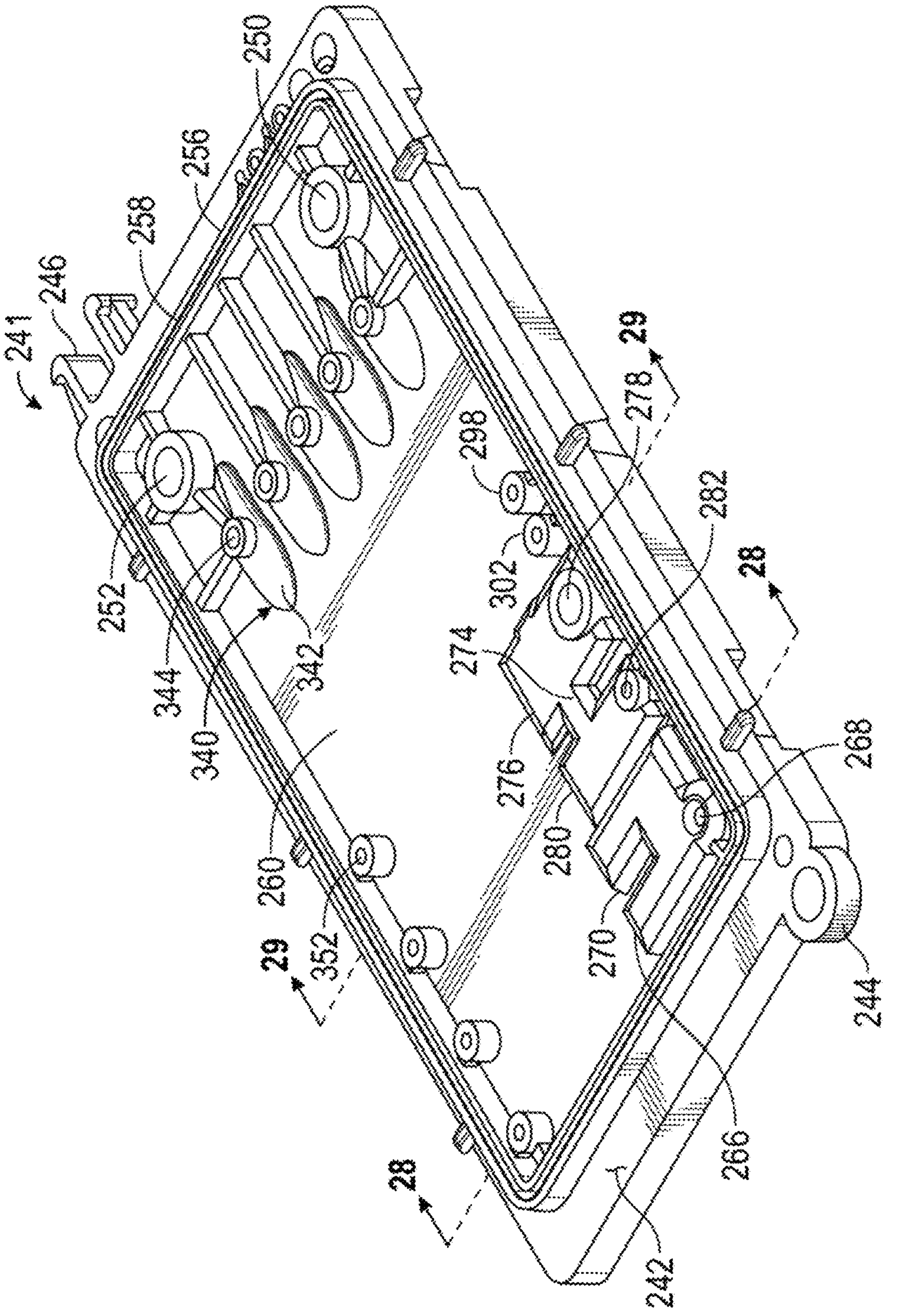
FIG. 24 is a top perspective view of a top plate of a reaction module of the multiplex cartridge.
Figure 25:
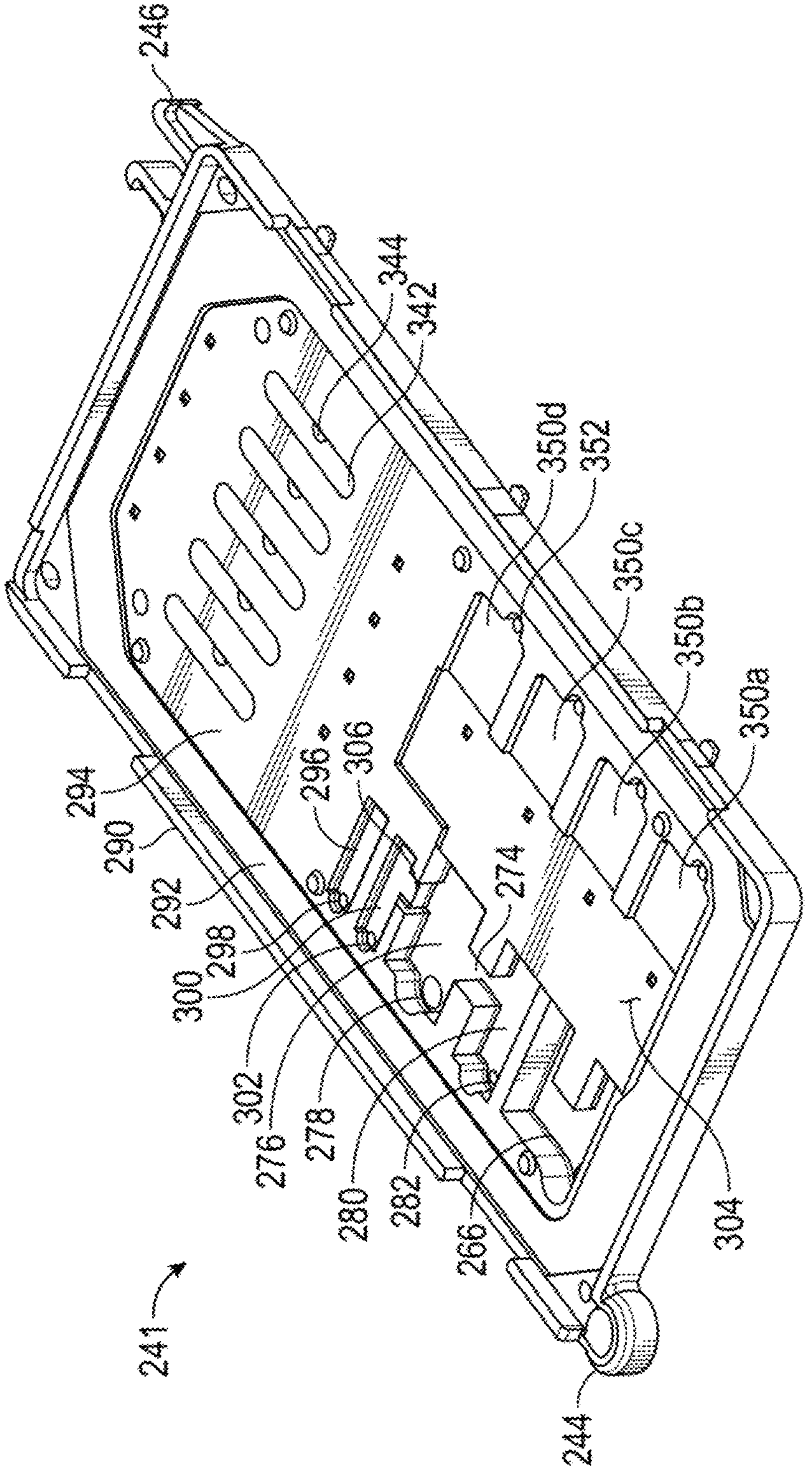
FIG. 25 is a bottom perspective view of the top plate.
Figure 26:
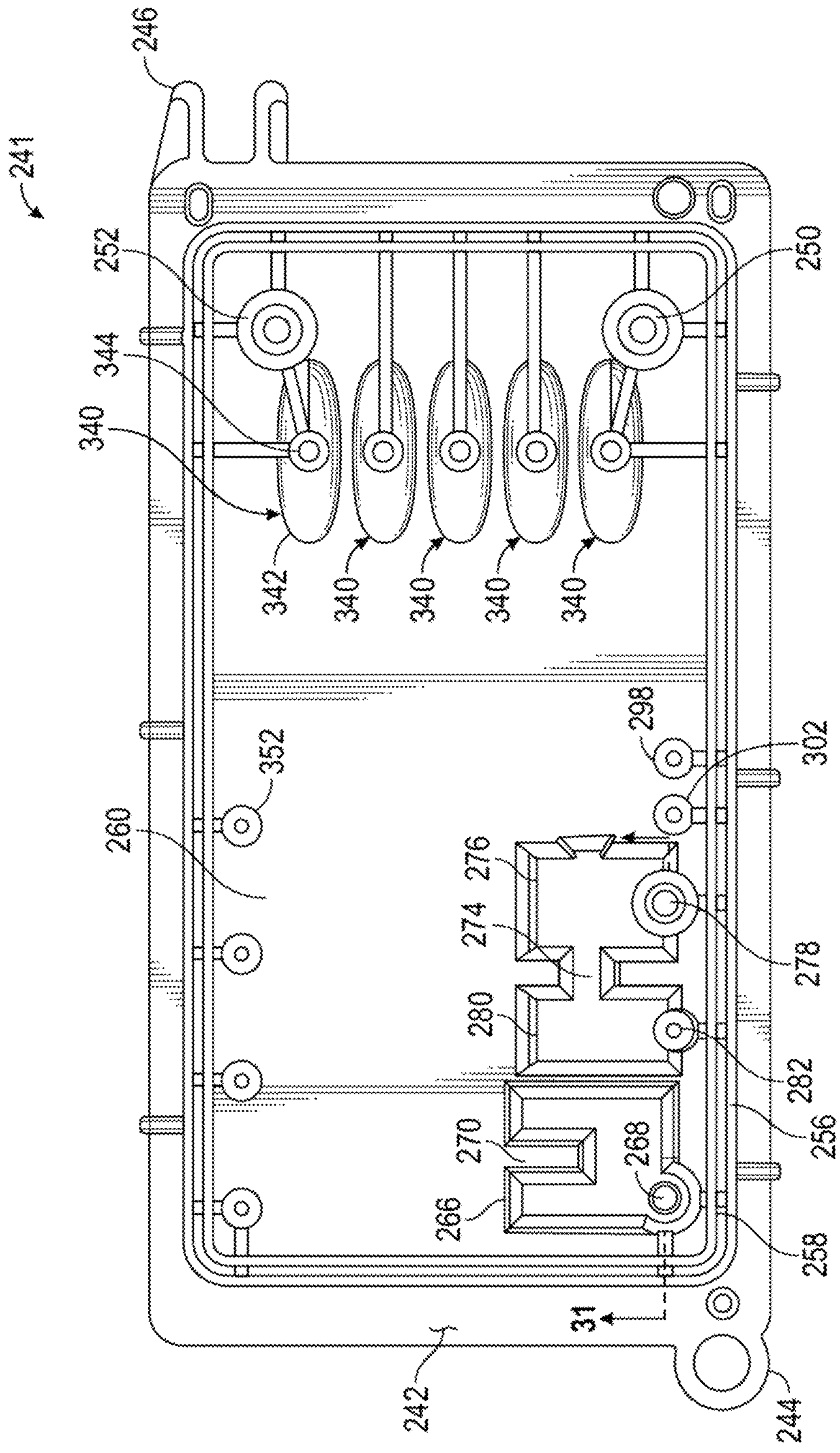
FIG. 26 is a top plan view of the top plate.

Details of the reaction module 240, and the top plate 241 in particular, are shown in FIGS. 24-31. Referring to FIGS. 24 and 26, which show a top perspective view and a top plan view, respectively, of the top plate 241, the top plate 241 includes an upper perimeter wall 256 projecting straight up above a top surface 242 of the top plate 241 and at least partially circumscribing the top surface 240 at a location offset inwardly from the outer edges of the top plate 241. The upper perimeter wall 256 has a continuous open channel or groove 258 formed along its top edge which provides a seat for the adhesive gasket 232 securing the reaction module 240 to the sample preparation module 70. See FIG. 4. The upper perimeter wall 256 forms a recessed area 260 surrounded by the upper perimeter wall 256 on the top surface 242. See also FIGS. 28 and 29.

Top plate 241 can take on a number of configurations and can be made of a variety of materials. Suitable materials include, but are not limited to, fiberglass, TEFLON®, ceramics, glass, silicon, mica, plastic (including acrylics, polystyrene and copolymers of styrene and other materials, polypropylene, polyethylene, polybutylene, polycarbonate, polyurethanes, and derivatives thereof, etc.), etc. A particularly preferred top plate material is polycarbonate.

An alignment fork 246 extends from one end of the top plate 241, and an alignment loop 244 extends from an opposite end of the top plate 241. The alignment fork 246 and alignment loop 244 are configured to receive alignment pins in an instrument for processing the multiplex cartridge 10 to ensure proper alignment of the cartridge 10, as described in more detail below.

The top plate 241 further includes a sample compartment 266 with an inlet port 268 that is in fluid communication with the third outlet port 190 of the sample preparation module 70.

The top plate 241 further includes a rehydration (elution) buffer compartment 276 having an inlet port 278 that is in fluid communication with the second outlet port 188 of the sample preparation module 70. A detection buffer compartment 280 contains an initially-dried detection buffer (applied to a portion of the top plate 241 forming the detection buffer compartment 280 or a portion of the fluidic processing panel 354 covering the detection buffer compartment 280) that is reconstituted with an amount of the reconstitution buffer dispensed into the rehydration buffer compartment 276 and transferred to the detection buffer compartment 280. In one embodiment, the detection buffer compartment 280 has a capacity of 120-160 µl. In various embodiments, top plate 241 includes a connecting passage 274 between the detection buffer compartment 280 and the rehydration buffer compartment 276. The detection buffer compartment 280 may further include a port 282 for injecting a buffer into the compartment 280 during a manufacturing process and/or for venting the compartment 280.

Figure 27:
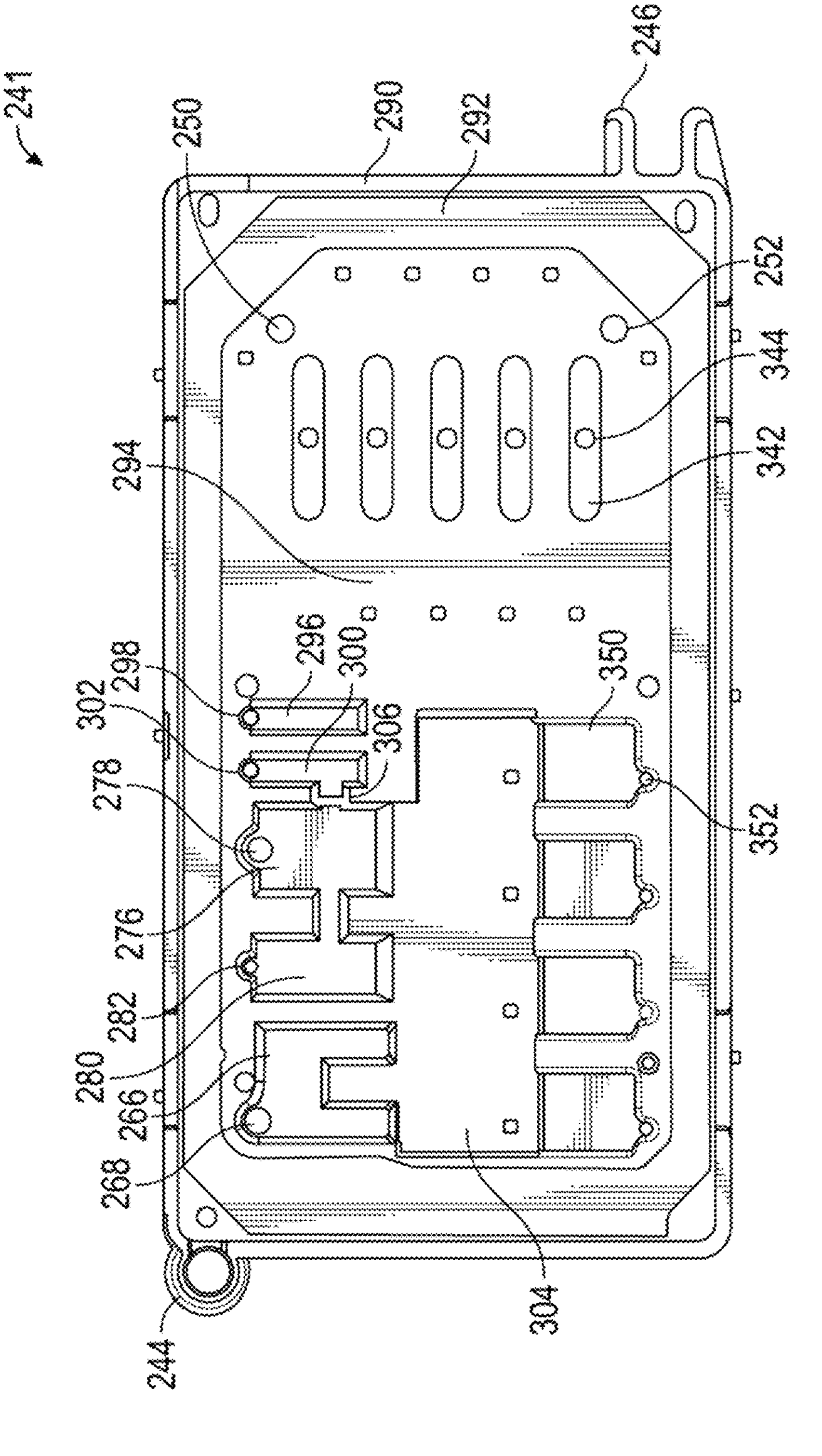
FIG. 27 is a bottom plan view of the top plate.
Figure 28:
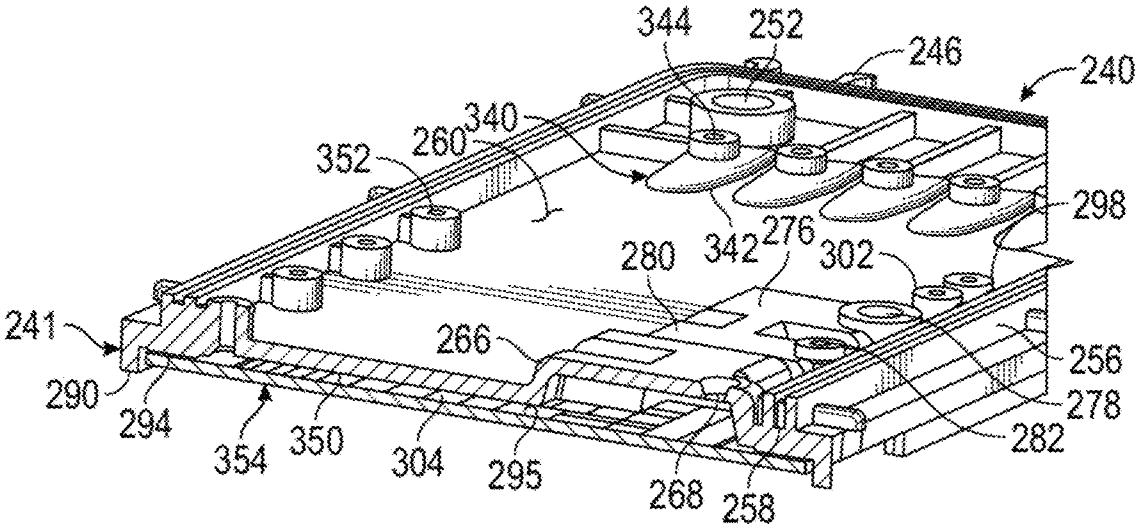
FIG. 28 is a perspective, cross sectional view of the reaction module along the line 28-28 in FIG. 24.
Figure 29:
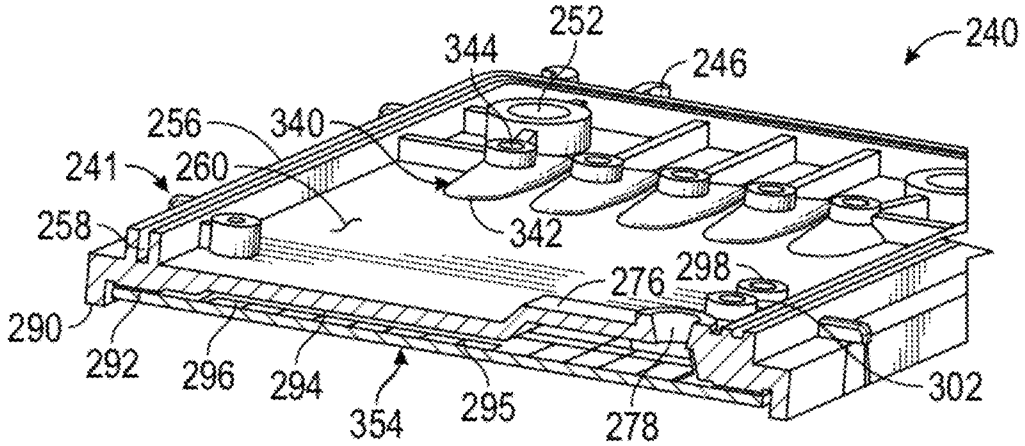
FIG. 29 is a perspective, cross sectional view of the reaction module along the line 29-29 in FIG. 24.

FIGS. 25 and 27 show a bottom perspective view and a bottom plan view, respectively, of the top plate 241. Referring to FIGS. 25 and 27, in addition to FIGS. 24 and 26, the top plate 241 further includes a buffer compartment 296, which, in one embodiment, contains a PCR buffer/enzyme in a dried form (applied to a portion of the top plate 241 forming the buffer compartment 296 or to a portion of the fluidic processing panel 354 (see FIGS. 4 and 58) covering the buffer compartment 296), to be later reconstituted (rehydrated) by an amount of rehydration buffer from the rehydration buffer compartment 276. In one embodiment, the buffer compartment 296 has a capacity of about 20 µl. A port 298 is provided for injecting the PCR buffer/enzyme into the compartment during the manufacturing process and/or for venting the buffer compartment 296.

The top plate 241 further includes a second buffer compartment 300 which may contain an exonuclease reagent in a dried form (applied to a portion of the top plate 241 forming the second buffer compartment 300 or to a portion of the fluidic processing panel 354 covering the second buffer compartment 300), to be later reconstituted by an amount of rehydration buffer from the rehydration buffer compartment 276. In one embodiment, the second buffer compartment 300 has a capacity of about 20 µl. A port 302 may be provided for injecting buffer into the second buffer compartment 300 during a manufacturing process and/or for venting the compartment 300. A weir 306 may be provide, between the rehydration buffer compartment 276 and the second buffer compartment 300 to permit fluid flow from the rehydration buffer compartment 276 into the compartment 300.

The top plate 241 further includes a lower perimeter wall 290 circumscribing the bottom of the top plate 241. The lower perimeter wall 290 defines a recess surrounded by the perimeter wall 290 configured to receive a panel, such as the fluidic processing panel 354, to enclose the lower half of the top plate 241. A raised panel support 290 surrounds the outer periphery of the lower surface of the top plate 241 just inside the perimeter wall 290. Area 294 inside the panel support 292 is slightly recessed with respect to the panel support 292, so that a panel inserted within the perimeter wall 290 is supported on the panel support surface 292, and the recess 294 defines a gap 295 (see FIGS. 28, 29) between the panel and the top plate 241.

The top plate 241 may further include fluid inlet ports 250, 252, at least one of which is in fluid communication with the first outlet port 182 of the sample preparation module 70. The inlet ports 250, 252 provide a fluid communication with the gap 295 between the bottom surface of the reaction top plate 241, e.g., at the area 294, and the fluidic processing panel 354 enclosing the bottom surface of the top plate 241.

The top plate 241 further includes detection compartments 350*a*, 350*b*, 350*c*, and 350*d* each with an inlet port or venting port 352. The illustrated embodiment includes four detection compartments 350*a-d*, though one can easily envision alternative configurations of the top plate 241 comprising a smaller or larger number of the detection compartments 350.

Area 304 on the lower surface comprises a processing area that is slightly recessed relative to the area 294, thereby forming a larger gap between the top plate 241 and a lower panel in the area 304 than in the area 294.

The reaction module 240 may further include one or more bubble traps 340 that are formed in the top plate 241. Each bubble trap 340 includes a bubble capture hood 342 formed in the top plate 241 which slopes upwardly toward a vent opening 344. In one embodiment, rising air bubbles generated by fluid movement beneath the bubble trap are captured in the capture hood 344 and released through the vent opening 344. The capture hood may be shaped as to conform to a fluid movement path beneath or adjacent to the bubble trap. In the illustrated embodiment, five bubble traps 340 having elongated capture hoods 342 are positioned above four fluid movement paths, each located below and between two adjacent bubble traps 340, as will be described in further detail below.

Figure 30:
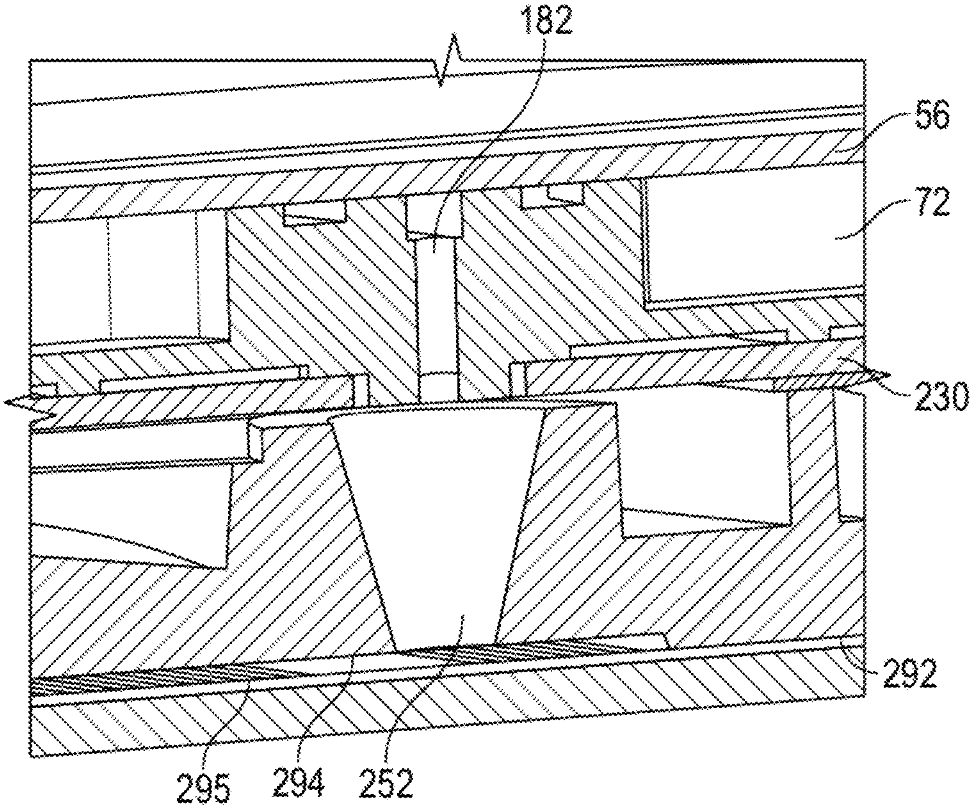
FIG. 30 is a perspective detail of a fluid inlet of the reaction module.

Details of the fluid inlet 252 are shown in FIG. 30. As noted, the fluid inlet 252 may be aligned with first fluid outlet 182 of the sample preparation module 70. The fluid inlet 252 may have an inwardly tapered, frustoconical shape, wherein the size of the outlet 182 above the inlet 252 is narrower than the upper end of the inlet 252. This helps ensure that fluid dispensed through the outlet 182 is captured by the inlet 252.

Figure 31:
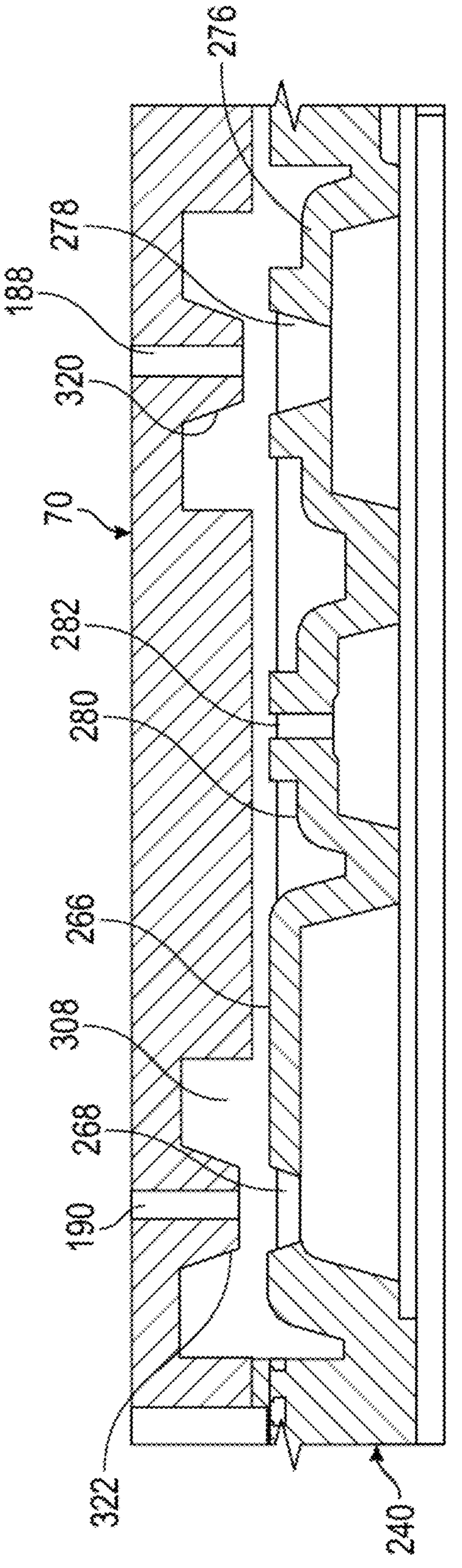
FIG. 31 is a partial cross sectional view along the line 31-31 in FIG. 26.

Details of the sample compartment 266, the rehydration buffer compartment 276, and the detection buffer compartment 280 are shown in FIG. 31. The sample compartment 266 is configured to receive an amount (e.g., 200 μl) of magnetic beads with bound target analyte (e.g., DNA, nucleic acid) from the sample preparation module 270 through the inlet port 268. The inlet port 268 of the sample compartment 266 preferably has a conical shape and is aligned with the third outlet 190 of the sample preparation module 70. In various embodiments, the third outlet 190 passes through a tapered nipple 322 to minimize hanging droplets from the end the outlet 190. The inlet port 268 is also preferably tapered with its widest end at the top to thereby ensure that fluid dispensed through the outlet 190 is captured in the inlet port 268. The outlet 190 and the inlet port 268 are configured such that there is a small gap therebetween. This gap comprises part of an interstitial space 308 between the top of the top plate 241 of the reaction module 240 and the bottom of the sample preparation module 70. This gap provides a trap for collecting any air bubbles contained in fluids within the reaction module 240, especially air bubbles that may be generated when dispensing fluid from the outlet 190 into the inlet port 268.

The rehydration buffer compartment 276 is configured to receive an amount (e.g., 200 μl) of a buffer solution that is suitable for rehydration of dried reagents and elution of nucleic acid from beads from the sample preparation module 270 through the inlet port 278. The inlet port 278 of the rehydration buffer compartment 276 is aligned with the second outlet 188 of the sample preparation module 70. Again, the outlet 188 preferably flows through a tapered nipple 320, the end of which is spaced apart from the inlet port 278, which is also tapered. Again, the space between the end of the nipple 320 and the inlet port 278 allows gas bubbles within the fluid flowing between the outlet 188 and the inlet port 278 to escape into the interstitial space 308.

Wide Vent Top Plate

Also provided herein are systems and methods to prevent/reduce bubble entrapment without reagent washout.

The concept of having air bubbles escape via vents is known. Air bubbles typically form in three situations (1) during mixing of biological samples, foam and bubbles may form that negatively impact the assay performance of the device; (2) during initial wetting of the channels and chambers in the reaction module 240 (FIG. 31) while rehydrating dried reagents. Initial wetting can be uneven such that air pockets form; (3) during heating of a sample. The problem of bubble formation is described in U.S. Pat. No. 9,132,423 and US Patent Application Nos. 2005/0136552 and 2004/024051 (which are herein incorporated by reference in their entirety).

The presence of a bubble may impair the reaction efficiency, and thus sensitivity of the device. For example, the entrapment of one or more bubbles in the reaction module after filling the reaction module with the sample may result in an incomplete mixing of the reagent and the sample, thereby impairing the reaction efficiency and sensitivity of the test.

Bubbles may also interfere with biochemical reactions by altering solute concentrations at bubble interfaces, by denaturing protein structure, and by impacting bulk heating rate and the homogeneity of temperature in a liquid. For example, in the PCR reaction, in which a thermostable polymerase is used to amplify copies of a target nucleic acid, heating and cooling is uneven in the presence of bubbles in the fluid, reducing the efficiency of the process and limiting sensitivity. The presence of bubbles also reduces the volume of fluid in the reaction chambers, and in assays which rely on detecting analyte in volumes of 10-50 uL or less, the presence of a large trapped bubble in a reaction chamber can effectively terminate the run.

In some conventional devices, surface treatments, such as, for example, the application of surfactants or plasma processes, have been used on portions of the device which are filled with a substance. Such surface treatments chemically alter the surface and may be used, for example, to increase the hydrophilicity (wettability) of the portions and thereby reduce beading of the substance and subsequent bubble entrapment. The application of such surface treatments, however, may be difficult to control and may result in non-uniform wettability of the portions being coated. This may lead to non-uniformities in the movement of the substance during filling of the portions and consequent trapping of gas bubbles. Also, the application of these surface treatments may increase the cost and complexity of manufacturing microfluidic devices. Moreover, in some cases, such surface treatments that chemically alter the chamber surface may degrade and/or become ineffective after a time period.

Reduction in bubble formation is focused on initial wetting and detection See e.g. U.S. Pat. No. 9,132,423 (which is herein incorporated by reference in its entirety). But, as far as applicant is aware, the only method to eliminate/prevent bubble formation during the amplification phase is to include passage-defining structures as part of the vent assembly called bubble traps or bubble hoods. See U.S. Pat. No. 9,598,722 and U.S. patent application Ser. No. 14/062,860 (U.S., Publication No. 2014-0322706). Specifically, in the embodiment described in U.S. Pat. No. 9,598,722 (FIG. 26) which is herein incorporate by reference in its entirety, the reaction module 240 includes one or more bubble traps 340 that are formed in the top plate 241. Each bubble trap 340 includes a bubble capture hood 342 formed in the top plate 241 which slopes upwardly toward a vent opening 344. In one embodiment, rising air bubbles generated by fluid movement beneath the bubble trap are captured in the capture hood 344 and released through the vent hole opening. The capture hood may be shaped as to conform to a fluid movement path beneath or adjacent to the bubble trap. In. the illustrated embodiment in U.S. Pat. No. 9,598,722 (FIG. 26), five bubble traps 340 having elongated capture hoods 342 are positioned above four fluid movement paths, each located below and between two adjacent bubble traps 340. It is these components (bubble trap, bubble capture hood) that are omitted in the current assembly and the vent has an open configuration.

These vent assemblies described above which have bubble traps/bubble hoods have electrowetting failures in the PCR region termed pinning. It is hypothesized that pinning is caused, in large part, by bubbles formed during PCR.

Applicant surprisingly found that samples run in a cartridge assembly (i.e., when a sample is run in a cartridge with a sample preparation module 70 and shroud 12, 30) have much higher pinning rates than open bay runs (i.e., when a sample is run with just a top plate and bottom substrate). Further, Applicant discovered that greater than 80% of in-lane pinning (pinning occurring over heaters 1 and 3 during annealing wherein the drop is split but stays in the lane) are reproduced when rerun on open bays. But, >90% of pinning caused by deflection (pinning over heater 2 during denaturation when the drop exits the reaction module via the vent) cannot be reproduced when rerun on open bays. Thus, the current system identifies a problem that was not previously recognized. Without being limited to a single theory, deflection may be the result of the LRM occluding the top plate vent. In the cartridge assembly, the space above the vent is reduced compared to open bay systems which may prevent bubbles from escaping the vent. When blisters in the LRM are pierced and fluid pushed out, the LRM may deflect down further reducing the interstitial space 308 between the top of the top plate 241 of the reaction module 240 and the bottom of the sample preparation module 70. As the interstitial space 308 between the top plate and sample preparation module 70 becomes smaller, surface tension increases and may be sufficient for oil to wick up into the vent blocking the vent. Oil may also wick up into the interstitial space 308 between the top plate and sample preparation module 70 blocking the vent or blocking bubble escape. Thus the current system is less complex than prior art methods which must carefully control the interstitial space 308 between the sample preparation module 70 (especially after the blister is deformed) and the top plate. As such the current design allows for more variability in manufacturing and assembly.

The bubble problem can be overcome by, reducing bubble formation by reducing Oxygen content in oil or by changing the voltage and/or electrowetting movement to reduce bubble formation. The bubble problem can also be overcome by, venting bubbles more efficiently using an alternative top plate design.

Applicants surprisingly discovered that removal or omission of these passage-defining structures as part of the vent assembly significantly reduced pinning and increased reliability.

In some embodiments when a wide vent is used, invalid runs are reduced by 10%, 9%, 8%, 7%, 6%, 5%, 4%, 3%, 2% or 1%. In some embodiments when a wide vent is used, invalid runs are reduced by 1-10% preferably, 5-10%, preferably 7-9%. In some embodiments when a wide vent is used, valid runs are increased by 10%, 9%, 8%, 7%, 6%, 5%, 4%, 3%, 2% or 1%. In some embodiments when a wide vent is used, valid runs are increased by 1-10% preferably, 5-10%, preferably 7-9%. In some embodiments when a wide vent is used, electrowetting failures are reduced by 10%, 9%, 8%, 7%, 6%, 5%, 4%, 3%, 2% or 1%. In some embodiments when a wide vent is used, electrowetting failures are reduced by 1-10% preferably, 5-10%, preferably 7-9%. In some embodiments when a wide vent is used, pinning is reduced by 10%, 9%, 8%, 7%, 6%, 5%, 4%, 3%, 2% or 1%. In some embodiments when a wide vent is used, pinning is reduced by 1-10% preferably, 5-10%, preferably 7-9%.

When validity is high i.e., over 80% or over 85% or over 90% or over 95%, identifying structural features to increase validity further is difficult. This is true in part because many tests must be run in order to see if a design change has an impact and whether that impact is positive or negative Thus, a small increase in validity or decrease in invalidity when run results are already high represents a significant improvement. In some embodiments when overall validity is greater than 90%, use of a wide vent top plate decreases invalid runs by 10%, 9%, 8%, 7%, 6%, 5%, 4%, 3%, 2% or 1%. In some embodiments when overall validity is greater than 90%, use of a wide vent top plate decreases invalid runs by 1-10% preferably, 5-10%, preferably 7-9%. In some embodiments when overall validity is greater than 90%, use of a wide vent top plate increases valid runs by 10%, 9%, 8%, 7%, 6%, 5%, 4%, 3%, 2% or 1%. In some embodiments when overall validity is greater than 90%, use of a wide vent top plate increases valid runs by 1-10% preferably, 5-10%, preferably 7-9%. In some embodiments when overall validity is greater than 90%, use of a wide vent top plate decreases electrowetting failures by 10%, 9%, 8%, 7%, 6%, 5%, 4%, 3%, 2% or 1%. In some embodiments when overall validity is greater than 90%, use of a wide vent top plate decreases electrowetting failures by 1-10% preferably, 5-10%, preferably 7-9%. In some embodiments when overall validity is greater than 90%, use of a wide vent top plate decreases pinning by 10%, 9%, 8%, 7%, 6%, 5%, 4%, 3%, 2% or 1%. In some embodiments when overall validity is greater than 90%, use of a wide vent top plate decreases pinning by 1-10% preferably, 5-10%, preferably 7-9%.

A wide vent top plate also reduces variability in pinning errors. As shown in example below and FIG. 71A, the pinning rate can be highly variable across lots when a standard vent is used. In contrast, when a wide vent top plate is used, pinning rates do not exceed 6%, preferably 5%, preferably 4%, preferably 3%, preferably 3%, preferably 2%, preferably 1%. In a preferred embodiment, pinning rates do not exceed 2% across lots when a wide vent top plate is used. In a preferred embodiment there are no pinning errors (0%) when a wide vent top plate is used.

Omission of these passage-defining structures increased sample seepage, i.e., the drawing up of oil out of the amplification zone and into the interstitial space 308 (i.e. the thermocycling pathways and the thermocycling regions) which negatively impact electrowetting and could result in droplets mixing. Applicants surprisingly discovered that a rib surrounding each vent or a rib around a plurality of vents in the amplification zone is sufficient to retain the sample in place.

Removal or omission of these passage-defining structures as part of the vent assembly also caused thermodynamic problems associated with heating and cooling the sample during PCR, i.e. a change in the temperature profile during reverse transcriptase and PCR. Specifically, the wide vent is parallel to the thermocycling pathways 364 and is open across heater 1, heater 2 and heater 3.

Figure 66:
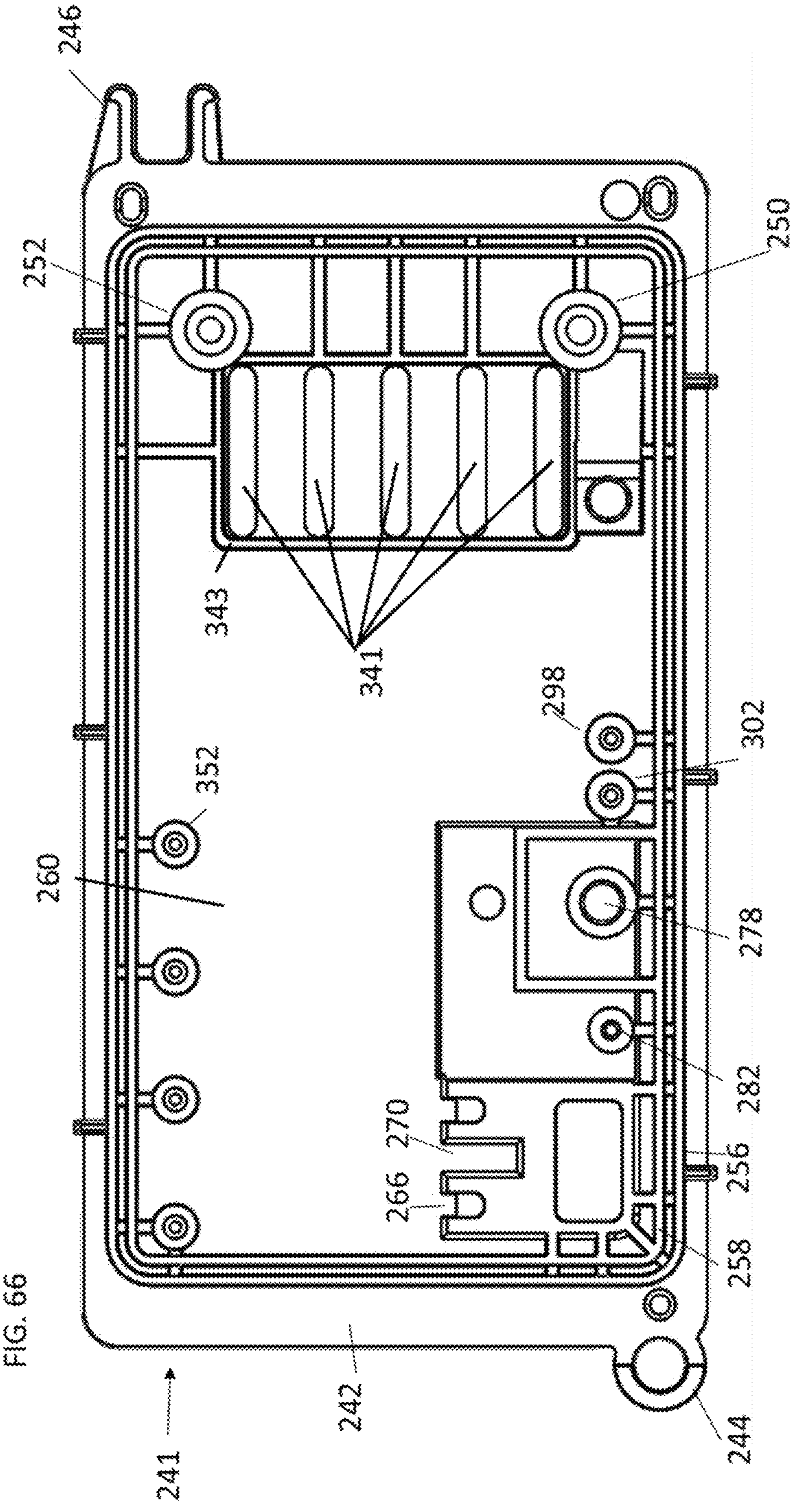
FIG. 66 is a top plan view of the top plate showing a wide vent.
Figure 67:
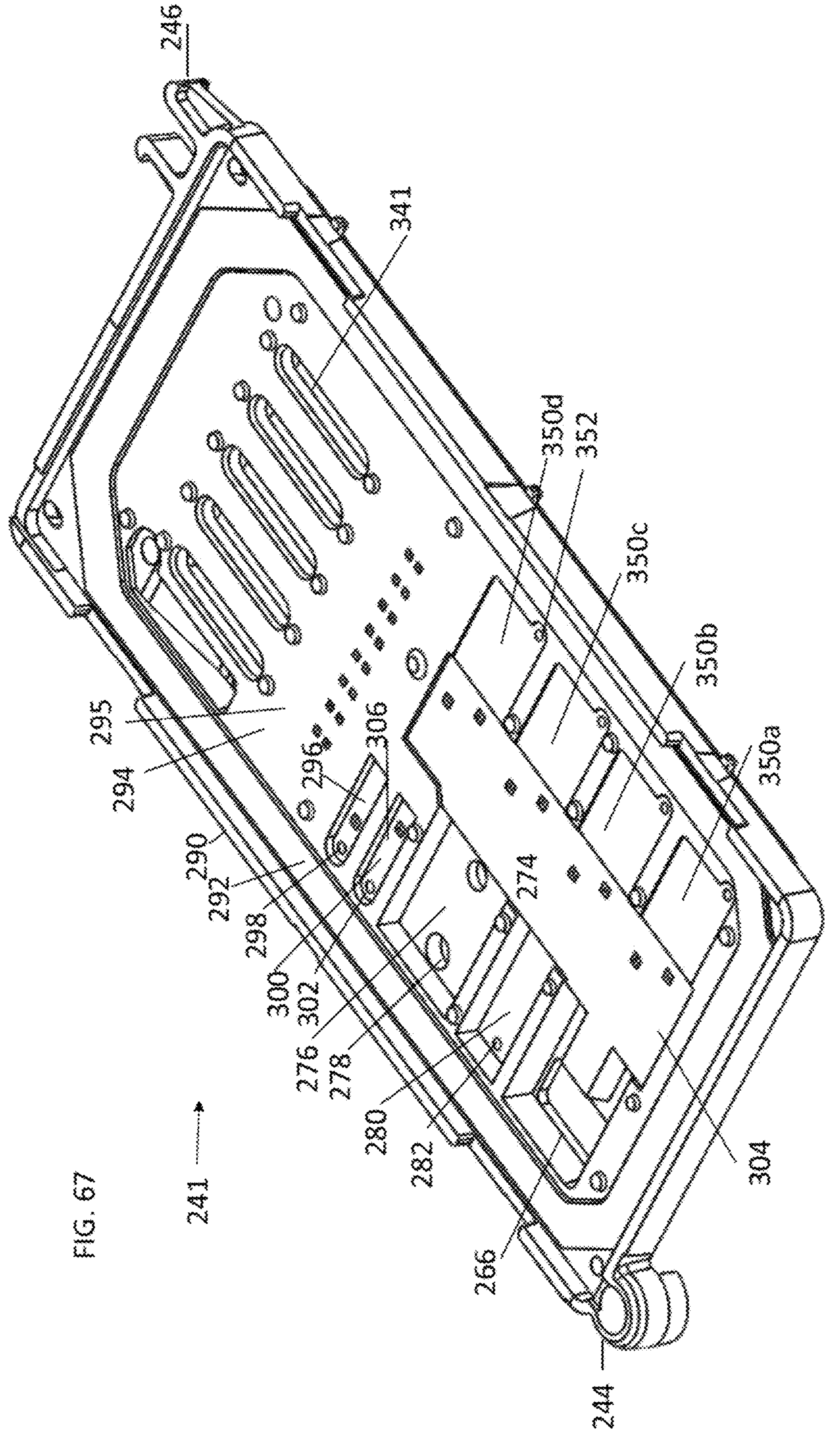
FIG. 67 is a bottom perspective view of the top plate showing a wide vent.

Referring to FIGS. 66 and 67, which show a top and bottom view of the top plate 241, the top plate 241 includes an upper perimeter wall 256 projecting above a top surface 242 of the top plate 241 and at least partially circumscribing the top surface at a location offset inwardly from the outer edges of the top plate 241. The upper perimeter wall 256 has a continuous open channel or groove 258 formed along its top edge. The upper perimeter wall 256 forms a recessed area 260 surrounded by the upper perimeter wall 256 on the top surface 242.

The top plate 241 further includes detection compartments 350 *a*, 350*b*, 350*c*, and 350*d*, each with an inlet port or venting port 352. The illustrated embodiment includes four detection compartments 350 *a-d*, though one can easily envision alternative configurations of the top plate 241 comprising a smaller or larger number of the detection compartments 350.

The top plate 241 excludes one or more bubble traps described in U.S. Pat. No. 9,598,722 (e.g., bubble traps 340 shown in FIGS. 24 and 26). Instead the top plate has a whole or cutout 341 and includes a raised rib 343 projecting above a top surface 242 of the top plate 241. FIG. 66. In the illustrated embodiment, five holes 341 are positioned adjacent to four fluid movement paths (thermocycling pathways or PCR Lanes in FIGS. 70A-C). Also shown in FIG. 66 are the top surface 242 of the top plate 241, fluid inlet 252, alignment fork 246, fluid inlet ports 250, 252, 298, 302, 278, 282, venting port 352, upper perimeter wall 256 has a continuous open channel or groove 258, alignment loop 244, sample compartment 266, sample preparation module 270 the details of which are described and shown in FIGS. 24-29 above as well as in FIG. 30 of U.S. Pat. No. 9,598,722 which is incorporated by reference. The top plate 241 further includes a lower perimeter wall 290, a panel support surface 292, and the recess 294 defines a gap 295 between the panel and the top plate 241, the details of which are shown in FIGS. 28 and 29 described above as well as FIGS. 28 and 29 of U.S. Pat. No. 9,598,722. The top plate 241 further includes detection compartments 350*a*, 350*b*, 350*c*, and 350*d*, venting port 352, sample compartment 266, port 282, compartment 280, compartment 276, port 278, compartment 300, port 302, compartment 296, port 298, a weir 306 the details of which are shown in FIG. 27 described above as well as in FIG. 27 described above as well as in FIGS. 24-27 of U.S. Pat. No. 9,598,722. Area 304 on the lower surface comprises a processing area that is slightly recessed relative to the area 294, thereby forming a larger gap between the top plate 241 and a lower panel in the area 304 than in the area 294 the details of which are further described and shown in FIG. 28 above as well as in FIGS. 24-27 of U.S. Pat. No. 9,598,722 which it incorporated by reference.

In the current embodiment, the vent is adjacent to the thermodynamic cycling pathway 364. There are clear functional advantages to drop movement by having the thermodynamic cycling pathway 364 in the amplification zone covered by the top plate. Specifically, the system allows for tight control over droplet movement. In the current embodiment, droplets are moved using coplanar movement; the top plate does not have a conductive surface. Because there is a cover over the thermodynamic cycling pathway 364 smaller volumes of liquid can be moved in a controlled manner. Indeed the drop tends to have near-zero curvature at the apex i.e., to adopt a flattened pancake shape having a 2D appearance. If the top plate were not present over the thermodynamic cycling pathway 364 the drop would be larger and have a more ball or 3D shape. Such a drop is harder to control/move/split during amplification.

The top plate with a vent adjacent to the thermodynamic cycling pathway 364 helps facilitate thermal management within the amplification zone. Indeed, as demonstrated in Example 2 below, the thermal profile of the heaters changed when the wide vent was used. But, because the vent in the top plate includes some covering over the amplification region, heat control can be achieved.

The invention can be further understood by the following numbered paragraphs:

Paragraph 1: An analytical cartridge for use in electrochemical analysis of fluids, said cartridge comprising: a bottom substrate, a top plate comprising at least one vent spanning at least two thermal zones.

Paragraph 2: The analytical cartridge of paragraph 1, wherein the at least one vent is adjacent to at least one thermocycling pathway.

Paragraph 3: The analytical cartridge of paragraph 1, wherein the at least one vent excludes bubble trap structures.

Paragraph 4: An analytical cartridge for use in electrochemical analysis of fluids, said cartridge comprising: a bottom substrate, a top plate comprising at least one vent spanning at least two thermal zones wherein the at least one vent is adjacent to at least one thermocycling pathways and wherein the at least one vent excludes bubble trap structures.

Paragraph 5: An analytical cartridge for use in electrochemical analysis of fluids, said cartridge comprising: a bottom substrate, a top plate comprising a plurality of vents having a single rib surrounding the plurality of vents.

Paragraph 6: The analytical cartridge of paragraph 5, wherein the plurality of vents is adjacent to a plurality of thermocycling pathways.

Paragraph 7: The analytical cartridge of paragraph 5, wherein the plurality of vents exclude bubble trap structures.

Paragraph 8: An analytical cartridge for use in electrochemical analysis of fluids, said cartridge comprising: a bottom substrate, a top plate comprising a plurality of vents having a single rib surrounding the plurality of vents, wherein the plurality of vents is adjacent to a plurality of thermocycling pathways, wherein the plurality of vents exclude bubble trap structures.

Paragraph 9: An analytical cartridge for use in electrochemical analysis of fluids, said cartridge comprising: a bottom substrate, a top plate comprising a plurality of vents each vent spanning at least two thermal zones and a single rib surrounding the plurality of vents.

Paragraph 10: The analytical cartridge of paragraph 9, wherein the plurality of vents is adjacent to a plurality of thermocycling pathways.

Paragraph 11: The analytical cartridge of paragraph 8, wherein the plurality of vents exclude bubble trap structures.

Paragraph 12: An analytical cartridge for use in electrochemical analysis of fluids, said cartridge comprising: a bottom substrate, a top plate comprising a plurality of vents each vent spanning at least two thermal zones and a single rib surrounding the plurality of vents, wherein the plurality of vents is adjacent to a plurality of thermocycling pathways, wherein the plurality of vents exclude bubble trap structures.

Paragraph 13: An analytical cartridge for use in electrochemical analysis of fluids, said cartridge comprising: a bottom substrate, a top plate comprising five vents each vent spanning three thermal zones and a single rib surrounding the five vents.

Paragraph 14: The analytical cartridge of paragraph 13, wherein each of the five vents is adjacent to five thermocycling pathways.

Paragraph 15: The analytical cartridge of paragraph 13, wherein each of the five vents exclude bubble trap structures.

Paragraph 16: An analytical cartridge for use in electrochemical analysis of fluids, said cartridge comprising: a bottom substrate, a top plate comprising five vents each vent spanning three thermal zones and a single rib surrounding the five vents, wherein each of the five vents is adjacent to five thermocycling pathways, and wherein each of the five vents exclude bubble trap structures.

Paragraph 17: A top plate comprising at least one vent spanning at least two thermal zones.

Paragraph 18: The top plate according to Paragraph 17, wherein the at least one vent is adjacent to at least one thermocycling pathways.

Paragraph 19: The top plate according to Paragraph 17, wherein the at least one vent excludes bubble trap structures.

Paragraph 20: A top plate comprising at least one vent spanning at least one thermal zones wherein the at least one vent is adjacent to at least one thermocycling pathways and wherein the at least one vent excludes bubble trap structures.

Paragraph 21: A top plate comprising a plurality of vents having a single rib surrounding the plurality of vents.

Paragraph 22: A top plate comprising a plurality of vents each vent spanning at least two thermal zones and a single rib surrounding the plurality of vents.

Paragraph 23: A top plate comprising five vents each vent spanning three thermal zone and a single rib surrounding the five vents.

Paragraph 24: A method for amplifying DNA in a microfluidic cartridge comprising loading a sample into the cartridge; amplifying the sample in the cartridge; during said amplification allowing gas to escape through a vent spanning at least two thermal zones; detecting said analyte.

Paragraph 25: The method of paragraph 24, wherein temperature of the denature heater is 95° C.

Paragraph 26: A processing board wherein there is one vent spanning at least two thermal zones above the amplification zone.

Paragraph 27: A processing board wherein there is a plurality of vents having a single rib surrounding the plurality of vents above the amplification zone.

Paragraph 28: A processing board wherein there is a plurality of vents each vent spanning at least two thermal zones and a single rib surrounding the plurality of vents above the amplification zone.

Paragraph 29: A processing board wherein there are five vents each vent spanning three thermal zones and a single rib surrounding the five vents above the amplification zone.

Paragraph 30: A method for reducing invalid runs comprising loading a sample into the cartridge comprising a wide vent top plate thereby reducing invalid runs.

Paragraph 31: The method of Paragraph 30, wherein the invalid runs are reduced by 1-10%.

Paragraph 32: The method of Paragraph 30, wherein the denature heater temperature is 95° C.

Paragraph 33: A method for reducing electrowetting failures comprising loading a sample into the cartridge comprising a wide vent top plate thereby reducing electrowetting failures.

Paragraph 34: The method of Paragraph 31, wherein the electrowetting failures are reduced by 1-10%.

Paragraph 35: The method of Paragraph 34, wherein the denature heater temperature is 95° C.

Paragraph 36: A method for reducing pinning comprising loading a sample into the cartridge comprising a wide vent top plate thereby reducing pinning.

Paragraph 37: The method of Paragraph 36, wherein pinning is reduced by 1-10%.

Paragraph 38: The method of Paragraph 37, wherein the denature heater temperature is 95° C.

Paragraph 39: An analytical cartridge for use in electrochemical analysis of fluids, said. cartridge comprising: a bottom substrate, a top plate comprising at least one vent spanning at least two thermal zones wherein the cartridge has 95%-100% validity.

Paragraph 40: An analytical cartridge for use in electrochemical analysis of fluids, said cartridge comprising: a bottom substrate, a top plate comprising at least one vent spanning at least two thermal zones wherein the cartridge has 95%-98% validity.

Paragraph 41: An analytical cartridge for use in electrochemical analysis of fluids, said cartridge comprising: a bottom substrate, a top plate comprising at least one vent spanning at least two thermal zones wherein the cartridge has 95%-98% validity and wherein electrowetting failures are less than 10%.

Paragraph 42: An analytical cartridge for use in electrochemical analysis of fluids, said cartridge comprising: a bottom substrate, a top plate comprising at least one vent spanning at least two thermal zones wherein the cartridge has 95%-98% validity and wherein pinning failures are less than 6%.

Paragraph 43: An in vitro method for the detection and/or identification of a hybridization complex comprising a human pathogen and/or genetic material thereof hybridized to a signal probe and a capture probe comprising: loading a sample into the cartridge comprising a wide vent top plate; subjecting a sample comprising or suspected of comprising a human pathogen and/or genetic material thereof to amplification and detecting the binding between the human pathogen and/or genetic material thereof and the signal probe and a capture probe.

Paragraph 44: The method of Paragraph 43, wherein the human pathogen is selected from the group consisting of Influenza A, Adenovirus, Influenza A H1 subtype, Human Bocavirus, Influenza A H3, Human Rhinovirus/Enterovirus, Influenza A 2009 H1N1 subtype, Coronavirus 229E. Influenza B, Coronavirus HKU1, Respiratory Syncytial Virus A, Coronavirus NL63, Respiratory Syncytial Virus B, Coronavirus OC43, Parainfluenza Virus 1, Coronavirus MERS, Parainfluenza Virus 2, *Bordetella pertussis*, Parainfluenza Virus 3, *Chlamydophila pneumoniae*, Parainfluenza Virus 4, *Mycoplasma pneumoniae*, Human Metapneumovirus, *Legionella pneumophila, Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group, *Enterococcus faecium, Streptococcus pneumonia, Lactobacillus, Streptococcus pyogenes, Listeria, Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca, Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon* and combinations thereof.

Paragraph 45: A microfluidic device comprising a wide vent top plate for detecting a human pathogen and/or genetic material thereof comprising: a mixture of oligonucleotides and reagents for carrying out a nucleic acid amplification reaction to detect the human pathogen selected from the group consisting of Influenza A, Adenovirus, Influenza A H1 subtype, Human Bocavirus, Influenza A H3, Human Rhinovirus/Enterovirus, Influenza A 2009 H1N1 subtype, Coronavirus 229E Influenza B, Coronavirus HKU1, Respiratory Syncytial Virus A, Coronavirus NL63, Respiratory Syncytial Virus B, Coronavirus OC43, Parainfluenza Virus 1, Coronavirus MERS, Parainfluenza Virus 2, *Bordetella pertussis*, Parainfluenza Virus 3, *Chlamydophila pneumoniae*, Parainfluenza Virus 4, *Mycoplasma pneumoniae*, Human Metapneumovirus, *Legionella pneumophila, Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group: *Enterococcus faecium, Streptococcus pneumonia, Lactobacillus, Streptococcus pyogenes, Listeria, Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca, Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon* or combinations thereof.

EXAMPLES

Example 1: Comparison of Validity and Signal Sensitivity Between Standard and Wide Vent Top Plates Run at Standard PCR Conditions, i.e., Absolute Temperature During PCR of 95.9 C All clinical NPS samples were pre-screened and shown to be negative for any of the analytes outlined in Table 1, bacterial and viral organisms are identified using the GenMark RP Panel.

WV-TABLE 1

List of Analytes for the RP Panel (for Example 1 and 3)
List of Analytes for the RP Panel

| | |
|---|---|
| Influenza A | Adenovirus |
| Influenza A H1 subtype | Human Bocavirus |
| Influenza A H3 | Human Rhinovirus/Enterovirus |
| Influenza A 2009 H1N1 subtype | Coronavirus 229E |
| Influenza B | Coronavirus HKU1 |
| Respiratory Syncytial Virus A | Coronavirus NL63 |
| Respiratory Syncytial Virus B | Coronavirus OC43 |
| Parainfluenza Virus 1 | Coronavirus MERS |
| Parainfluenza Virus 2 | *Bordetella pertussis* |
| Parainfluenza Virus 3 | *Chlamydophila pneumoniae* |
| Parainfluenza Virus 4 | *Mycoplasma pneumoniae* |
| Human Metapneumovirus | *Legionella pneumophila* |

Eight different sample mixes will be tested that contain all targets of the Respiratory Pathogen Panel. The eight different sample mixes are listed in Table 2.

WV-TABLE 2

Targets and Strains of the 8 Sample Mixes (For Examples 1 and 3)

| Analyte | Strain | Supplier |
|---|---|---|
| | Mix 1 | |
| Human Metapneumovirus | B2 Peru1-2002 | ZeptoMetrix |
| Parainfluenza Virus 2 | Type 2 | ZeptoMetrix |
| Adenovirus C | Type 1 | ZeptoMetrix |
| Coronavirus OC43 | OC43 | ZeptoMetrix |
| *Bordetella pertussis* | 18323 | GenMark Diagnostics |
| | Mix 2 | |
| Human Rhinovirus | 1A | ZeptoMetrix |
| Influenza A H1 subtype | Brisbane/59/07 | ZeptoMetrix |
| Adenovirus E | Type 4 | ZeptoMetrix |
| Parainfluenza Virus 3 | Type 3 | ZeptoMetrix |
| Coronavirus NL63 | NL63 | ZeptoMetrix |
| | Mix 3 | |
| Human Enterovirus | Type 68 | ZeptoMetrix |
| *Chlamydophila pneumoniae* | AR-39, TWAR 2023 | ATCC |
| Influenza A H3 subtype | A/Texas/50/2012 | ZeptoMetrix |
| Adenovirus B | Type 7A | ZeptoMetrix |
| Coronavirus 229E | 229E | ZeptoMetrix |
| | Mix 4 | |
| Parainfluenza Virus 4 | Type 4a | ZeptoMetrix |
| *Mycoplasma pneumoniae* | FH strain of Eaton Agent | ATCC/GNMK |
| Influenza B | Florida/02/06 | ZeptoMetrix |
| Respiratory Syncytial Virus B | CH93(18)-18 | ZeptoMetrix |
| | Mix 5 | |
| Parainfluenza Virus 1 | Type 1 | ZeptoMetrix |
| *Legionella pneumophila* | Philadelphia-1 | ATCC/GNMK |

WV-TABLE 2-continued

Targets and Strains of the 8 Sample Mixes (For Examples 1 and 3)

| Analyte | Strain | Supplier |
|---|---|---|
| Influenza A 2009 H1N1 subtype | NY/01/2009 | ZeptoMetrix |
| Respiratory Syncytial Virus A | 2006 | ZeptoMetrix |
| Mix 6 | | |
| Human Bocavirus | Bocavirus (Plasmid) | Blue Heron |
| Coronavirus MERS | MERS (IVT) | bioSynthesis |
| Mix 7 | | |
| Coronavirus HKU1 | HKU1 (IVT) | bioSynthesis |
| 7-fold Mix | | |
| Influenza A H3 Subtype | H3N2 Brisbane/10/07 | ZeptoMetrix |
| Respiratory Syncytial Virus A | 2006 Isolate | ZeptoMetrix |
| Parainfluenza Virus 1 | Clinical Isolate | ZeptoMetrix |
| Human Metapneumovirus | B2 Peru1-2002 | ZeptoMetrix |
| Coronavirus | OC43 | ZeptoMetrix |
| Adenovirus B | Type 7 | ZeptoMetrix |
| *Bordetella pertussis* | 18323 [NCTC 10739] | GenMark Diagnostics |

Each target was tested at a final concentration of approximately 1-10×LoD.

Three lots of consumables were tested, with each lot produced with half of the consumables containing the standard design top plates and half containing the wide vent top plate design.

Each lot of consumables was tested with a subset of the eight sample mixes, with either twenty or forty replicates each as outlined in Table 3. All targets in the 7-fold mix are present at 1×LoD, and this mix was used for analytical studies to demonstrate assay performance under various conditions; this mix was tested with 20 or 40 replicates. A total of 140 tests was run on each lot with each top plate design. Each of the eight sample mixes was tested on at least two lots of consumables for both top plate designs.

The first-pass validity rate of 89.7% (10.3% invalid) and 92.8% (7.2% invalid) for standard design top plates and wide vent top plates, respectively (data not shown). The final validity rate (excluding cartridges which had DNF, detection, LRM or SEF failures) was 92.4% (7.6% invalid) and 96.5% (3.5% invalid), for standard top plates and wide vent top plates, respectively (FIG. 71A-C).

Figure 71D:
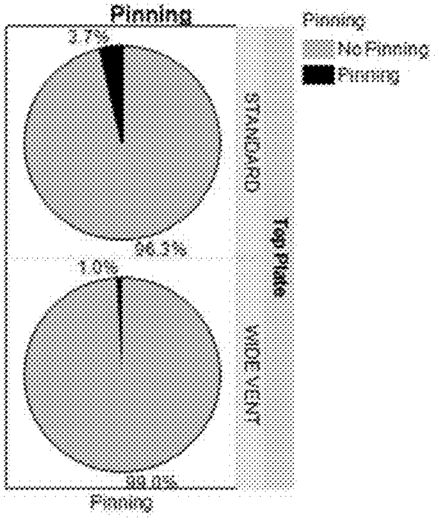
FIGS. 71D-F.
Figure 71E:
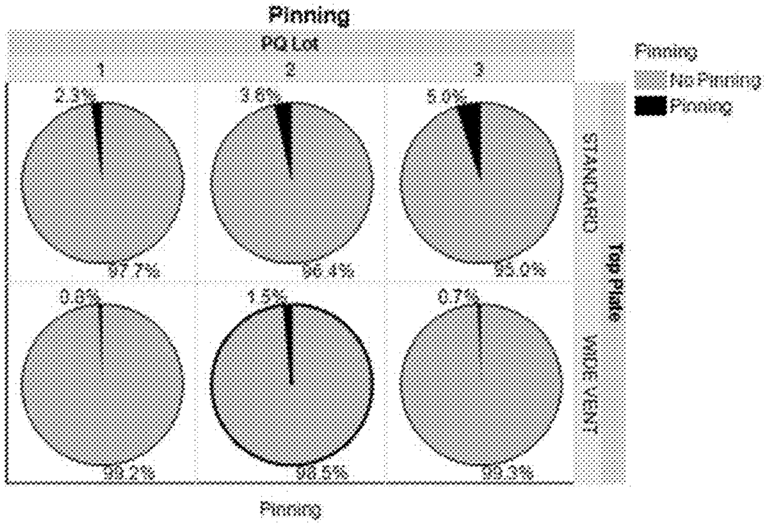
Figure 71F:
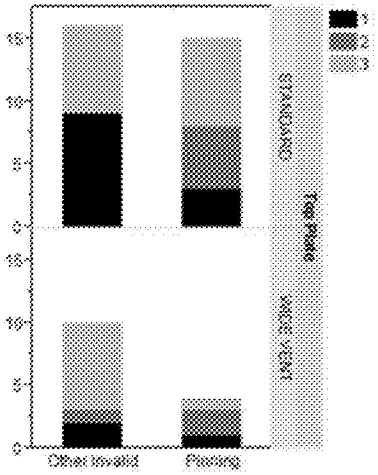
Figure 71G:
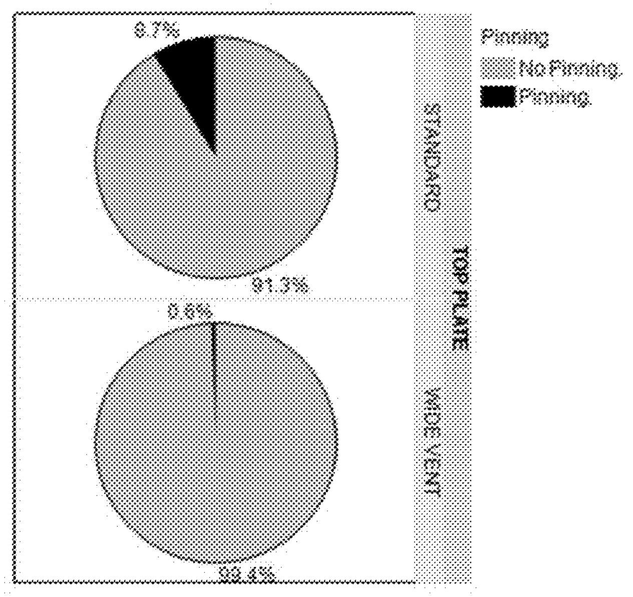
FIGS. 71G-H.
Figure 71H:
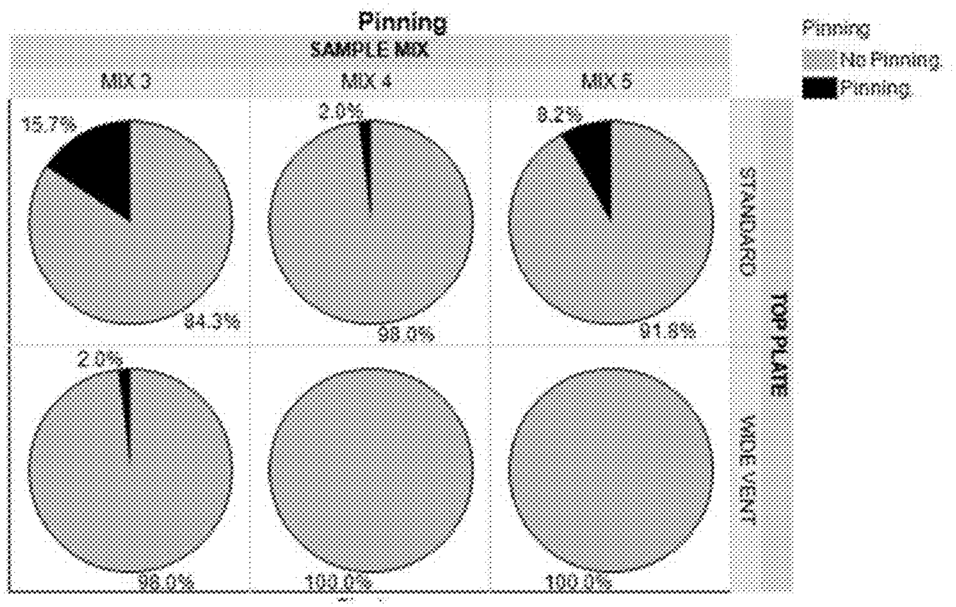

There was no significant decrease in the positivity rate for each analyte for the wide vent compared to the standard top plate when analyzed in each of the three lots. There is no clinically relevant effect on the nA signal for the wide vent compared to the standard top plate when analyzed in each of the three lots. There was no significant decrease in the accuracy rate for wide vent compared to standard top plate consumables. However, pinning rate is reduced in wide vent top plate consumables compared to standard design top plate consumables (3.7% and 1%, respectively) (FIG. 71D-F). The rates for other failure modes are comparable in wide vent top plate consumables and standard design top plate consumables (FIG. 71F). Moreover, across experiments there is more variability in pinning rates with rates being as high as 15%. The wide rent top plate reduces the variability in pinning rates across lots. See FIGS. 71G-H wherein pinning rates are always 2% or less when a wide vent top plate is used but are variable for the standard top plate.

Example 2: Optimizing Assay Performance on Wide Vent Top Plate

Change in the top plate design caused a reduction in reliability. It was hypothesized that this change was caused by a change in the temperature profile during reverse transcriptase and PCR. As such, the temperature profile for standard vs wide vent top plates was compared during PCR. Temperature was compared in three ways (1) Thermistor temperature profile (2) liquid crystals and (3 Oil temperature assessed by thermocouples.

Temperature Profile During PCR

A comparison of the Temperature Profile during PCR was assessed. FIGS. 71A-H show the temperature of each heater (heater 1, 2 and 3) at standard PCR set points. Heater 2 had the largest temperature change (delta+1.78° C.). The temperature change for heater 1 and 3 were minor.

Droplet Temperature is 1-2° C. Higher in Wide Vent than in Standard Top Plate Cartridges Next, droplet temperature was assessed by liquid crystals on PCR lanes. Red indicates a starting temperature of 93.6° C., green represents a starting temperature of 94.3° C., and blue represents a starting temperature of 97.8° C.

WV-TABLE 4

| Ink L/N | Red Starts | Green Starts | Blue Starts | Clearing Point |
|---|---|---|---|---|
| 150324-4 | 93.6 | 94.3 | 97.8 | 125 |

The PCR heaters were programmed to increase temperature by 1° C. increment at 1 min interval. Liquid crystals were distributed across PCR lanes on cartridge as indicated in the top right figure. Open bays runs were carried out in the environmental chamber set to 40° C. mimicking internal temperature of system instruments. Pictures of the cartridge were taken at 1 min intervals before every temperature change. See FIGS. 72A-C. The temperature set points at which liquid crystal changed color over heater 2 were recorded. As assessed by droplet color change, droplet temperature is 1-2° C. higher in wide vent than in standard top plate cartridges.

Oil Temperature Assessed by Thermocouples Placed on Top Plate Inside Cartridge

Thermocouples were placed inside the cartridge on the top plate surface on OCR lanes 1 and 4 at heater 2 area. Open bays runs were carried out in the environmental chamber set to 40° C. mimicking internal temperature of system instruments. Temperatures during PCR cycle time as logged by the thermocouple were analyzed.

Results: The mean of the "stabilized temperature" across 4 independent runs in standard or wide vent top plate were compared. FIGS. 73A-C demonstrates that the wide vet top plate had a mean temperature of 93.4° C. whereas the standard top plate had a mean temperature of 91.7° C. representing a 1.7° C. increase in the wide vent top plate. Thus, cartridges with wide vent top plate are hotter in heater 2 area than those with standard top plate.

FIGS. 73A-C shows a test set up and results for a comparison of heater 2 temperatures for standard vent and wide vent top plates. Droplet temperatures in the PCR lanes are assessed by liquid crystals placed on the lanes. The locations of the liquid crystals are shown in FIG. 73A, and the local heat is assessed by a droplet color change in response to changing heater set points. The results of the test show that the droplet temperature is 1 to 2° C. higher in a cartridge with a wide vent top plate then in a cartridge with a standard vent top plate.

Impact of Heater2 Temperature on Assay Performance

Next, the impact of heater 2 temperature on assay performance in consumables with standard top plate was assessed.

Three different protocols that differ only by H2 temperature set during PCR

Control: H2 at 95.9° C.

H2+1 C: H2 at 96.9° C.

H2−1 C: H2 at 95° C.

Negative NPS samples spiked with organisms at 1×LoD. Most targets tolerate the temperature change with minimal change in signal level. See FIGS. 74A-C. M.pneumo had higher signal when H2 is set to 1° C. hotter. This is in line with the higher signal observed in wide vent consumables, suggesting droplets in wide vent consumables likely have higher H2 temperature at standard PCR parameter setting.

FIGS. 74A-C show results of PCR temperature assessment on heater 2. In the experiment setup, thermocouples were placed inside the cartridge on the top plate surface on PCR lanes 1 and at heater 2 area (See FIG. 74A, and open bays runs were carried out in the environmental chamber set to 40° C. mimicking internal temperature of an instrument in which the cartridge is processed. Temperatures during PCI. cycle time as logged by the thermocouple were analyzed (See FIG. 74B). The mean of the "stabilized temperature" across 4 independent runs in standard or wide vent top plate were compared, and the mean temperature for the wide vent configuration was 93.4° C. and for the standard configuration was 91.7° C., for a difference of 1.7° C. From these results, it can be concluded that cartridges with a wide vent top plate is hotter in heater 2 area than those with standard vent top plate.

Decrease heater 2 to 95° C.

Next, the impact of decreasing heater 2's temperature was assessed.

Negative NPS samples were spiked with organisms at 1×LoD and run at the following conditions:

Standard top plate consumables running with standard PCR condition (STANDARD CONTROL)

Wide vent top plate consumables running with standard PCR condition (WIDE VENT CONTROL)

Wide vent top plate consumables running with the new PCR condition with H2 temperature set to 95° C. (WIDE VENT H2−1 C)

Lowering PCR heater2 temperature on wide vent top plate consumables improved signal in some targets, although no impact on positivity rates in the test set (n=−200). FIGS. 75A-D.

Example 3: Higher Reliability and Lower Pinning in Wide Vent TP at Improved PCR Conditions, i.e., Absolute Temperature During PCR of 95.0 C A natural clinical matrix (negative pooled NPS) was used as sample matrix. Two residual NPS samples and/or presumed negative NPS samples were pooled. These pools were screened to verify that the pooled samples were negative. It is recognized that targets present at low levels (i.e., concentrations at or below the target's LoD) could be missed in this screening process. The pools that tested negative were then combined to generate the material used for this study. Indeed, when this material was later used, a low level of positivity for several targets was sometimes detected, consistent with presence of the targets at levels below LoD.

Dilutions of quantified viral and bacterial analytes were prepared for testing by combining into seven sample mixes. Each analyte was combined to an intermediate concentration of 100×LoD. This intermediate aliquot was used to prepare the sample mix at the final testing concentration of approximately 2×LoD. The strain information for the analytes is listed in WV-Table 2 of Example 1.

Mixes 6 and 7 consist of plasmid and/or in vitro transcripts, and were diluted in PBS rather than NPS due to the instability of naked nucleic acid in NPS.

Three lots of consumables were tested, with each lot produced with half of the consumables containing the standard top plate and half containing the wide vent top plate design.

Each lot of consumables was tested with each of the seven sample mixes, with thirty replicates each for both top plate designs. An additional 98 consumables were repeated to replace the invalid consumables. In total, 1360 consumables were tested as outlined in WV-Table 2 (from Example 1), with 3 consumables that failed to start (DNS), and another 7 that failed to complete (DNF). A total number of 1350 consumable runs completed.

WV-TABLE 5

Summary of tested consumables for 3 lots of standard and wide vent top plates.

| | Lot | | | | | |
|---|---|---|---|---|---|---|
| | 1 | | 2 | | 3 | |
| Top Plate | STANDARD | WIDE VENT | STANDARD | WIDE VENT | STANDARD | WIDE VENT |
| Mix-1 | N = 32 | N = 32 | N = 31 | N = 32 | N = 34 | N = 34 |
| Mix-2 | N = 33 | N = 31 | N = 33 | N = 31 | N = 33 | N = 31 |
| Mix-3 | N = 31 | N = 31 | N = 31 | N = 30 | N = 32 | N = 36 |
| Mix-4 | N = 32 | N = 31 | N = 33 | N = 31 | N = 39 | N = 31 |
| Mix-5 | N = 34 | N = 30 | N = 32 | N = 31 | N = 34 | N = 32 |
| Mix-6 | N = 35 | N = 30 | N = 32 | N = 33 | N = 32 | N = 33 |
| Mix-7 | N = 36 | N = 33 | N = 32 | N = 32 | N = 33 | N = 31 |

N denotes the number of replicates tested

Figures 77A, 77B:
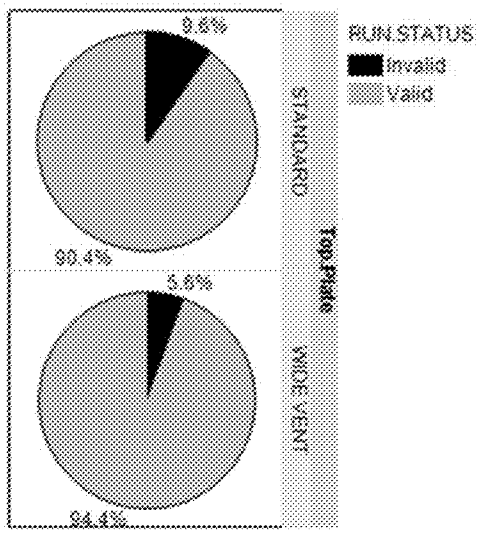
FIGS. 77A-B: 77A shows the validity between standard and Wide Vent top plate at new PCR conditions. 77A shows that the overall validity is over 94% when a wide vent top plate is used. Example 3. 77B shows the pinning rate compared to other electrowetting errors across all of the lots.

Results: There were 1260 first-pass runs performed. Ninety four (94) of the first-pass runs were invalid, and there were 5 DNF and 3 DNS, resulting in a first-pass validity rate of 90.0% and 93.8% for standard design top plates and wide vent top plates, respectively (FIG. 77A). Additional runs were repeated to replace the invalid runs. In total, 1360 consumables were run, of which 1350 completed. The final validity rate for completed runs is 90.8% and 94.4%, for standard to plates and wide vent top plates, respectively. One-tailed Fisher's exact test confirms that the wide vent top plate consumables had higher validity than the standard design top plate consumables (p=0.038). See FIGS. 76A-B.

There was no significant decrease in the positivity rate for each analyte for the wide vent compared to the standard top plate when analyzed in each of the three lots.

Comparison of the positivity rate between the two top plate designs in each analyte and each consumable lot There was no significant decrease in the positivity rate for each analyte for the wide vent compared to the standard top plate when analyzed in the combined three lots.

WV-TABLE 6

| Sample 1 | Target | Lot | Top Plate | Detected | Not Detected | Positivity Rate |
|---|---|---|---|---|---|---|
| | | | Mix-1 | | | |
| Mix-1 | AdvC | 1 | STANDARD | 28 | 2 | 93.3% |
| Mix-1 | AdvC | 1 | WIDE VENT | 30 | | 100.0% |
| Mix-1 | AdvC | 2 | STANDARD | 30 | | 100.0% |
| Mix-1 | AdvC | 2 | WIDE VENT | 30 | | 100.0% |
| Mix-1 | AdvC | 3 | STANDARD | 29 | 1 | 96.7% |
| Mix-1 | AdvC | 3 | WIDE VENT | 29 | | 100.0% |
| Mix-1 | AdvC.Pen | 1 | STANDARD | 29 | 1 | 96.7% |
| Mix-1 | AdvC.Pen | 1 | WIDE VENT | 29 | 1 | 96.7% |
| Mix-1 | AdvC.Pen | 2 | STANDARD | 30 | | 100.0% |
| Mix-1 | AdvC.Pen | 2 | WIDE VENT | 30 | | 100.0% |
| Mix-1 | AdvC.Pen | 3 | STANDARD | 28 | 2 | 93.3% |
| Mix-1 | AdvC.Pen | 3 | WIDE VENT | 29 | | 100.0% |
| Mix-1 | B.pert | 1 | STANDARD | 30 | | 100.0% |
| Mix-1 | B.pert | 1 | WIDE VENT | 30 | | 100.0% |
| Mix-1 | B.pert | 2 | STANDARD | 30 | | 100.0% |
| Mix-1 | B.pert | 2 | WIDE VENT | 30 | | 100.0% |
| Mix-1 | B.pert | 3 | STANDARD | 29 | 1 | 96.7% |
| Mix-1 | B.pert | 3 | WIDE VENT | 29 | | 100.0% |
| Mix-1 | hMPV | 1 | STANDARD | 30 | | 100.0% |
| Mix-1 | hMPV | 1 | WIDE VENT | 30 | | 100.0% |
| Mix-1 | hMPV | 2 | STANDARD | 30 | | 100.0% |
| Mix-1 | hMPV | 2 | WIDE VENT | 30 | | 100.0% |
| Mix-1 | hMPV | 3 | STANDARD | 29 | 1 | 96.7% |
| Mix-1 | hMPV | 3 | WIDE VENT | 29 | | 100.0% |
| Mix-1 | OC43 | 1 | STANDARD | 30 | | 100.0% |
| Mix-1 | OC43 | 1 | WIDE VENT | 30 | | 100.0% |
| Mix-1 | OC43 | 2 | STANDARD | 30 | | 100.0% |
| Mix-1 | OC43 | 2 | WIDE VENT | 30 | | 100.0% |
| Mix-1 | OC43 | 3 | STANDARD | 27 | 3 | 90.0% |
| Mix-1 | OC43 | 3 | WIDE VENT | 29 | | 100.0% |
| Mix-1 | Pan.Adv | 1 | STANDARD | 30 | | 100.0% |
| Mix-1 | Pan.Adv | 1 | WIDE VENT | 30 | | 100.0% |
| Mix-1 | Pan.Adv | 2 | STANDARD | 30 | | 100.0% |
| Mix-1 | Pan.Adv | 2 | WIDE VENT | 29 | 1 | 96.7% |
| Mix-1 | Pan.Adv | 3 | STANDARD | 29 | 1 | 96.7% |
| Mix-1 | Pan.Adv | 3 | WIDE VENT | 29 | | 100.0% |
| Mix-1 | PIV-2 | 1 | STANDARD | 30 | | 100.0% |
| Mix-1 | PIV-2 | 1 | WIDE VENT | 30 | | 100.0% |
| Mix-1 | PIV-2 | 2 | STANDARD | 29 | 1 | 96.7% |
| Mix-1 | PIV-2 | 2 | WIDE VENT | 30 | | 100.0% |
| Mix-1 | PIV-2 | 3 | STANDARD | 29 | 1 | 96.7% |
| Mix-1 | PIV-2 | 3 | WIDE VENT | 29 | | 100.0% |
| | | | Mix-2 | | | |
| Mix-2 | AdvE | 1 | STANDARD | 29 | | 100.0% |
| Mix-2 | AdvE | 1 | WIDE VENT | 30 | | 100.0% |
| Mix-2 | AdvE | 2 | STANDARD | 30 | | 100.0% |
| Mix-2 | AdvE | 2 | WIDE VENT | 30 | | 100.0% |
| Mix-2 | AdvE | 3 | STANDARD | 31 | | 100.0% |
| Mix-2 | AdvE | 3 | WIDE VENT | 29 | | 100.0% |
| Mix-2 | Flu A | 1 | STANDARD | 29 | | 100.0% |
| Mix-2 | Flu A | 1 | WIDE VENT | 30 | | 100.0% |
| Mix-2 | Flu A | 2 | STANDARD | 30 | | 100.0% |
| Mix-2 | Flu A | 2 | WIDE VENT | 30 | | 100.0% |
| Mix-2 | Flu A | 3 | STANDARD | 31 | | 100.0% |
| Mix-2 | Flu A | 3 | WIDE VENT | 29 | | 100.0% |
| Mix-2 | H1 | 1 | STANDARD | 28 | 1 | 96.6% |
| Mix-2 | H1 | 1 | WIDE VENT | 30 | | 100.0% |
| Mix-2 | H1 | 2 | STANDARD | 29 | 1 | 96.7% |
| Mix-2 | H1 | 2 | WIDE VENT | 28 | 2 | 93.3% |
| Mix-2 | H1 | 3 | STANDARD | 31 | | 100.0% |
| Mix-2 | H1 | 3 | WIDE VENT | 29 | | 100.0% |
| Mix-2 | HRV/EV | 1 | STANDARD | 29 | | 100.0% |
| Mix-2 | HRV/EV | 1 | WIDE VENT | 30 | | 100.0% |
| Mix-2 | HRV/EV | 2 | STANDARD | 30 | | 100.0% |
| Mix-2 | HRV/EV | 2 | WIDE VENT | 30 | | 100.0% |
| Mix-2 | HRV/EV | 3 | STANDARD | 31 | | 100.0% |
| Mix-2 | HRV/EV | 3 | WIDE VENT | 29 | | 100.0% |
| Mix-2 | NL63 | 1 | STANDARD | 29 | | 100.0% |
| Mix-2 | NL63 | 1 | WIDE VENT | 29 | 1 | 96.7% |
| Mix-2 | NL63 | 2 | STANDARD | 29 | 1 | 96.7% |
| Mix-2 | NL63 | 2 | WIDE VENT | 28 | 2 | 93.3% |
| Mix-2 | NL63 | 3 | STANDARD | 31 | | 100.0% |
| Mix-2 | NL63 | 3 | WIDE VENT | 29 | | 100.0% |
| Mix-2 | Pan.Adv | 1 | STANDARD | 29 | | 100.0% |

WV-TABLE 6-continued

| Sample 1 | Target | Lot | Top Plate | Detected | Not Detected | Positivity Rate |
|---|---|---|---|---|---|---|
| Mix-2 | Pan.Adv | 1 | WIDE VENT | 30 | | 100.0% |
| Mix-2 | Pan.Adv | 2 | STANDARD | 30 | | 100.0% |
| Mix-2 | Pan.Adv | 2 | WIDE VENT | 30 | | 100.0% |
| Mix-2 | Pan.Adv | 3 | STANDARD | 31 | | 100.0% |
| Mix-2 | Pan.Adv | 3 | WIDE VENT | 29 | | 100.0% |
| Mix-2 | PIV-3 | 1 | STANDARD | 29 | | 100.0% |
| Mix-2 | PIV-3 | 1 | WIDE VENT | 30 | | 100.0% |
| Mix-2 | PIV-3 | 2 | STANDARD | 30 | | 100.0% |
| Mix-2 | PIV-3 | 2 | WIDE VENT | 30 | | 100.0% |
| Mix-2 | PIV-3 | 3 | STANDARD | 31 | | 100.0% |
| Mix-2 | PIV-3 | 3 | WIDE VENT | 29 | | 100.0% |
| | | | Mix-3 | | | |
| Mix-3 | 229E | 1 | STANDARD | 28 | 1 | 96.6% |
| Mix-3 | 229E | 1 | WIDE VENT | 30 | | 100.0% |
| Mix-3 | 229E | 2 | STANDARD | 27 | 3 | 90.0% |
| Mix-3 | 229E | 2 | WIDE VENT | 28 | 1 | 96.6% |
| Mix-3 | 229E | 3 | STANDARD | 26 | 5 | 83.9% |
| Mix-3 | 229E | 3 | WIDE VENT | 28 | 1 | 96.6% |
| Mix-3 | AdvB | 1 | STANDARD | 29 | | 100.0% |
| Mix-3 | AdvB | 1 | WIDE VENT | 30 | | 100.0% |
| Mix-3 | AdvB | 2 | STANDARD | 30 | | 100.0% |
| Mix-3 | AdvB | 2 | WIDE VENT | 29 | | 100.0% |
| Mix-3 | AdvB | 3 | STANDARD | 31 | | 100.0% |
| Mix-3 | AdvB | 3 | WIDE VENT | 29 | | 100.0% |
| Mix-3 | C.pneu | 1 | STANDARD | 29 | | 100.0% |
| Mix-3 | C.pneu | 1 | WIDE VENT | 30 | | 100.0% |
| Mix-3 | C.pneu | 2 | STANDARD | 30 | | 100.0% |
| Mix-3 | C.pneu | 2 | WIDE VENT | 29 | | 100.0% |
| Mix-3 | C.pneu | 3 | STANDARD | 31 | | 100.0% |
| Mix-3 | C.pneu | 3 | WIDE VENT | 29 | | 100.0% |
| Mix-3 | Flu A | 1 | STANDARD | 29 | | 100.0% |
| Mix-3 | Flu A | 1 | WIDE VENT | 30 | | 100.0% |
| Mix-3 | Flu A | 2 | STANDARD | 30 | | 100.0% |
| Mix-3 | Flu A | 2 | WIDE VENT | 29 | | 100.0% |
| Mix-3 | Flu A | 3 | STANDARD | 31 | | 100.0% |
| Mix-3 | Flu A | 3 | WIDE VENT | 29 | | 100.0% |
| Mix-3 | H3 | 1 | STANDARD | 28 | 1 | 96.6% |
| Mix-3 | H3 | 1 | WIDE VENT | 30 | | 100.0% |
| Mix-3 | H3 | 2 | STANDARD | 29 | 1 | 96.7% |
| Mix-3 | H3 | 2 | WIDE VENT | 29 | | 100.0% |
| Mix-3 | H3 | 3 | STANDARD | 31 | | 100.0% |
| Mix-3 | H3 | 3 | WIDE VENT | 29 | | 100.0% |
| Mix-3 | HRV/EV | 1 | STANDARD | 24 | 5 | 82.8% |
| Mix-3 | HRV/EV | 1 | WIDE VENT | 29 | 1 | 96.7% |
| Mix-3 | HRV/EV | 2 | STANDARD | 24 | 6 | 80.0% |
| Mix-3 | HRV/EV | 2 | WIDE VENT | 26 | 3 | 89.7% |
| Mix-3 | HRV/EV | 3 | STANDARD | 28 | 3 | 90.3% |
| Mix-3 | HRV/EV | 3 | WIDE VENT | 27 | 2 | 93.1% |
| Mix-3 | Pan.Adv | 1 | STANDARD | 29 | | 100.0% |
| Mix-3 | Pan.Adv | 1 | WIDE VENT | 30 | | 100.0% |
| Mix-3 | Pan.Adv | 2 | STANDARD | 30 | | 100.0% |
| Mix-3 | Pan.Adv | 2 | WIDE VENT | 29 | | 100.0% |
| Mix-3 | Pan.Adv | 3 | STANDARD | 31 | | 100.0% |
| Mix-3 | Pan.Adv | 3 | WIDE VENT | 29 | | 100.0% |
| | | | Mix-4 | | | |
| Mix-4 | Flu B | 1 | STANDARD | 29 | | 100.0% |
| Mix-4 | Flu B | 1 | WIDE VENT | 30 | | 100.0% |
| Mix-4 | Flu B | 2 | STANDARD | 29 | 1 | 96.7% |
| Mix-4 | Flu B | 2 | WIDE VENT | 30 | | 100.0% |
| Mix-4 | Flu B | 3 | STANDARD | 30 | | 100.0% |
| Mix-4 | Flu B | 3 | WIDE VENT | 29 | 1 | 96.7% |
| Mix-4 | M.pneu | 1 | STANDARD | 27 | 2 | 93.1% |
| Mix-4 | M.pneu | 1 | WIDE VENT | 29 | 1 | 96.7% |
| Mix-4 | M.pneu | 2 | STANDARD | 30 | | 100.0% |
| Mix-4 | M.pneu | 2 | WIDE VENT | 29 | 1 | 96.7% |
| Mix-4 | M.pneu | 3 | STANDARD | 27 | 3 | 90.0% |
| Mix-4 | M.pneu | 3 | WIDE VENT | 29 | 1 | 96.7% |
| Mix-4 | PIV-4 | 1 | STANDARD | 29 | | 100.0% |
| Mix-4 | PIV-4 | 1 | WIDE VENT | 30 | | 100.0% |
| Mix-4 | PIV-4 | 2 | STANDARD | 30 | | 100.0% |
| Mix-4 | PIV-4 | 2 | WIDE VENT | 30 | | 100.0% |
| Mix-4 | PIV-4 | 3 | STANDARD | 30 | | 100.0% |
| Mix-4 | PIV-4 | 3 | WIDE VENT | 29 | 1 | 96.7% |
| Mix-4 | RSV-B | 1 | STANDARD | 29 | | 100.0% |
| Mix-4 | RSV-B | 1 | WIDE VENT | 30 | | 100.0% |

WV-TABLE 6-continued

| Sample 1 | Target | Lot | Top Plate | Detected | Not Detected | Positivity Rate |
|---|---|---|---|---|---|---|
| Mix-4 | RSV-B | 2 | STANDARD | 29 | 1 | 96.7% |
| Mix-4 | RSV-B | 2 | WIDE VENT | 30 | | 100.0% |
| Mix-4 | RSV-B | 3 | STANDARD | 30 | | 100.0% |
| Mix-4 | RSV-B | 3 | WIDE VENT | 29 | 1 | 96.7% |
| Mix-5 | | | | | | |
| Mix-5 | Flu A | 1 | STANDARD | 28 | | 100.0% |
| Mix-5 | Flu A | 1 | WIDE VENT | 30 | | 100.0% |
| Mix-5 | Flu A | 2 | STANDARD | 30 | | 100.0% |
| Mix-5 | Flu A | 2 | WIDE VENT | 30 | | 100.0% |
| Mix-5 | Flu A | 3 | STANDARD | 27 | 1 | 96.4% |
| Mix-5 | Flu A | 3 | WIDE VENT | 30 | | 100.0% |
| Mix-5 | H1N1 | 1 | STANDARD | 27 | 1 | 96.4% |
| Mix-5 | H1N1 | 1 | WIDE VENT | 30 | | 100.0% |
| Mix-5 | H1N1 | 2 | STANDARD | 29 | 1 | 96.7% |
| Mix-5 | H1N1 | 2 | WIDE VENT | 30 | | 100.0% |
| Mix-5 | H1N1 | 3 | STANDARD | 26 | 2 | 92.9% |
| Mix-5 | H1N1 | 3 | WIDE VENT | 30 | | 100.0% |
| Mix-5 | L.pneu | 1 | STANDARD | 28 | | 100.0% |
| Mix-5 | L.pneu | 1 | WIDE VENT | 30 | | 100.0% |
| Mix-5 | L.pneu | 2 | STANDARD | 30 | | 100.0% |
| Mix-5 | L.pneu | 2 | WIDE VENT | 30 | | 100.0% |
| Mix-5 | L.pneu | 3 | STANDARD | 25 | 3 | 89.3% |
| Mix-5 | L.pneu | 3 | WIDE VENT | 30 | | 100.0% |
| Mix-5 | PIV-1 | 1 | STANDARD | 28 | | 100.0% |
| Mix-5 | PIV-1 | 1 | WIDE VENT | 30 | | 100.0% |
| Mix-5 | PIV-1 | 2 | STANDARD | 30 | | 100.0% |
| Mix-5 | PIV-1 | 2 | WIDE VENT | 29 | 1 | 96.7% |
| Mix-5 | PIV-1 | 3 | STANDARD | 28 | | 100.0% |
| Mix-5 | PIV-1 | 3 | WIDE VENT | 30 | | 100.0% |
| Mix-5 | RSV-A | 1 | STANDARD | 28 | | 100.0% |
| Mix-5 | RSV-A | 1 | WIDE VENT | 30 | | 100.0% |
| Mix-5 | RSV-A | 2 | STANDARD | 30 | | 100.0% |
| Mix-5 | RSV-A | 2 | WIDE VENT | 30 | | 100.0% |
| Mix-5 | RSV-A | 3 | STANDARD | 28 | | 100.0% |
| Mix-5 | RSV-A | 3 | WIDE VENT | 30 | | 100.0% |
| Mix-6 | | | | | | |
| Mix-6 | Boca | 1 | STANDARD | 28 | | 100.0% |
| Mix-6 | Boca | 1 | WIDE VENT | 29 | | 100.0% |
| Mix-6 | Boca | 2 | STANDARD | 30 | | 100.0% |
| Mix-6 | Boca | 2 | WIDE VENT | 29 | 1 | 96.7% |
| Mix-6 | Boca | 3 | STANDARD | 29 | | 100.0% |
| Mix-6 | Boca | 3 | WIDE VENT | 29 | | 100.0% |
| Mix-6 | MERS | 1 | STANDARD | 28 | | 100.0% |
| Mix-6 | MERS | 1 | WIDE VENT | 29 | | 100.0% |
| Mix-6 | MERS | 2 | STANDARD | 30 | | 100.0% |
| Mix-6 | MERS | 2 | WIDE VENT | 30 | | 100.0% |
| Mix-6 | MERS | 3 | STANDARD | 29 | | 100.0% |
| Mix-6 | MERS | 3 | WIDE VENT | 29 | | 100.0% |
| Mix-7 | | | | | | |
| Mix-7 | HKU1 | 1 | STANDARD | 29 | 1 | 96.7% |
| Mix-7 | HKU1 | 1 | WIDE VENT | 29 | 1 | 96.7% |
| Mix-7 | HKU1 | 2 | STANDARD | 31 | | 100.0% |
| Mix-7 | HKU1 | 2 | WIDE VENT | 30 | | 100.0% |
| Mix-7 | HKU1 | 3 | STANDARD | 30 | | 100.0% |
| Mix-7 | HKU1 | 3 | WIDE VENT | 30 | | 100.0% |

The positivity rate for each target for the three consumable lots combined in each sample mix are calculated in valid runs performed on the wide vent consumables and compared to the standard top plate consumables. One-tailed Fisher's exact test indicates there is no significant decrease in the positivity rate for each target for the wide vent compared to the standard top plate consumables. The results are listed in WV-Table 7.

WV-TABLE 7

| Positivity rates for each target in the three consumable lots combined | | | | | | |
|---|---|---|---|---|---|---|
| Sample.1 | Target | Top.Plate | Detected | Not Detected | Positive Rate | p-value |
| Mix-1 | AdvC | STANDARD | 87 | 3 | 96.7% | NC |
| Mix-1 | AdvC | WIDE VENT | 89 | | 100.0% | |

WV-TABLE 7-continued

Positivity rates for each target in the three consumable lots combined

| Sample.1 | Target | Top.Plate | Detected | Not Detected | Positive Rate | p-value |
|---|---|---|---|---|---|---|
| Mix-1 | AdvC.Pen | STANDARD | 87 | 3 | 96.7% | 0.938 |
| Mix-1 | AdvC.Pen | WIDE VENT | 88 | 1 | 98.9% | |
| Mix-1 | B.pert | STANDARD | 89 | 1 | 98.9% | NC |
| Mix-1 | B.pert | WIDE VENT | 89 | | 100.0% | |
| Mix-1 | hMPV | STANDARD | 89 | 1 | 98.9% | NC |
| Mix-1 | hMPV | WIDE VENT | 89 | | 100.0% | |
| Mix-1 | OC43 | STANDARD | 87 | 3 | 96.7% | NC |
| Mix-1 | OC43 | WIDE VENT | 89 | | 100.0% | |
| Mix-1 | Pan.Adv | STANDARD | 89 | 1 | 98.9% | 0.749 |
| Mix-1 | Pan.Adv | WIDE VENT | 88 | 1 | 98.9% | |
| Mix-1 | PIV-2 | STANDARD | 88 | 2 | 97.8% | NC |
| Mix-1 | PIV-2 | WIDE VENT | 89 | | 100.0% | |
| Mix-2 | AdvE | STANDARD | 90 | | 100.0% | NC |
| Mix-2 | AdvE | WIDE VENT | 89 | | 100.0% | |
| Mix-2 | Flu A | STANDARD | 90 | | 100.0% | NC |
| Mix-2 | Flu A | WIDE VENT | 89 | | 100.0% | |
| Mix-2 | H1 | STANDARD | 88 | 2 | 97.8% | 0.685 |
| Mix-2 | H1 | WIDE VENT | 87 | 2 | 97.8% | |
| Mix-2 | HRV/EV | STANDARD | 90 | | 100.0% | NC |
| Mix-2 | HRV/EV | WIDE VENT | 89 | | 100.0% | |
| Mix-2 | NL63 | STANDARD | 89 | 1 | 98.9% | 0.306 |
| Mix-2 | NL63 | WIDE VENT | 86 | 3 | 96.6% | |
| Mix-2 | Pan.Adv | STANDARD | 90 | | 100.0% | NC |
| Mix-2 | Pan.Adv | WIDE VENT | 89 | | 100.0% | |
| Mix-2 | PIV-3 | STANDARD | 90 | | 100.0% | NC |
| Mix-2 | PIV-3 | WIDE VENT | 89 | | 100.0% | |
| Mix-3 | 229E | STANDARD | 81 | 9 | 90.0% | 0.995 |
| Mix-3 | 229E | WIDE VENT | 86 | 2 | 97.7% | |
| Mix-3 | AdvB | STANDARD | 90 | | 100.0% | NC |
| Mix-3 | AdvB | WIDE VENT | 88 | | 100.0% | |
| Mix-3 | C.pneu | STANDARD | 90 | | 100.0% | NC |
| Mix-3 | C.pneu | WIDE VENT | 88 | | 100.0% | |
| Mix-3 | Flu A | STANDARD | 90 | | 100.0% | NC |
| Mix-3 | Flu A | WIDE VENT | 88 | | 100.0% | |
| Mix-3 | H3 | STANDARD | 88 | 2 | 97.8% | NC |
| Mix-3 | H3 | WIDE VENT | 88 | | 100.0% | |
| Mix-3 | HRV/EV | STANDARD | 76 | 14 | 84.4% | 0.982 |
| Mix-3 | HRV/EV | WIDE VENT | 82 | 6 | 93.2% | |
| Mix-3 | Pan.Adv | STANDARD | 90 | | 100.0% | NC |
| Mix-3 | Pan.Adv | WIDE VENT | 88 | | 100.0% | |
| Mix-4 | Flu B | STANDARD | 88 | 1 | 98.9% | 0.754 |
| Mix-4 | Flu B | WIDE VENT | 89 | 1 | 98.9% | |
| Mix-4 | M.pneu | STANDARD | 84 | 5 | 94.4% | 0.865 |
| Mix-4 | M.pneu | WIDE VENT | 87 | 3 | 96.7% | |
| Mix-4 | PIV-4 | STANDARD | 89 | | 100.0% | 0.503 |
| Mix-4 | PIV-4 | WIDE VENT | 89 | 1 | 98.9% | |
| Mix-4 | RSV-B | STANDARD | 88 | 1 | 98.9% | 0.754 |
| Mix-4 | RSV-B | WIDE VENT | 89 | 1 | 98.9% | |
| Mix-5 | Flu A | STANDARD | 85 | 1 | 98.8% | NC |
| Mix-5 | Flu A | WIDE VENT | 90 | | 100.0% | |
| Mix-5 | H1N1 | STANDARD | 82 | 4 | 95.3% | NC |
| Mix-5 | H1N1 | WIDE VENT | 90 | | 100.0% | |
| Mix-5 | L.pneu | STANDARD | 83 | 3 | 96.5% | NC |
| Mix-5 | L.pneu | WIDE VENT | 90 | | 100.0% | |
| Mix-5 | PIV-1 | STANDARD | 86 | | 100.0% | 0.508 |
| Mix-5 | PIV-1 | WIDE VENT | 89 | 1 | 98.9% | |
| Mix-5 | RSV-A | STANDARD | 86 | | 100.0% | NC |
| Mix-5 | RSV-A | WIDE VENT | 90 | | 100.0% | |
| Mix-6 | Boca | STANDARD | 87 | | 100.0% | 0.503 |
| Mix-6 | Boca | WIDE VENT | 87 | 1 | 98.9% | |
| Mix-6 | MERS | STANDARD | 87 | | 100.0% | NC |
| Mix-6 | MERS | WIDE VENT | 88 | | 100.0% | |
| Mix-7 | HKU1 | STANDARD | 90 | 1 | 98.9% | 0.749 |
| Mix-7 | HKU1 | WIDE VENT | 89 | 1 | 98.9% | |

* NC = Not calculable; p-value cannot be calculated due to all zeros in a column. Results will be evaluated as not statistically different.

The positivity rate for each target in each sample mix was also calculated for each consumable lot performed on the wide vent consumables and the standard top plate consumables. Comparison of the positivity rates between the two top plate designs are listed below in WV-Table 8:

WV-TABLE 8

Analysis of analyte signal

| Sample Mix | PCR Drop | Target | Top Plate | Mean | SD | Mean-2xSD | Threshold nA | Above Threshold |
|---|---|---|---|---|---|---|---|---|
| Mix-1 | 1 | hMPV | standard | 305.6 | 93.0 | 119.5 | 5 | Yes |
| Mix-1 | 1 | hMPV | wide vent | 293.0 | 92.6 | 107.7 | 5 | Yes |
| Mix-1 | 2 | PIV-2 | standard | 810.2 | 212.5 | 385.2 | 10 | Yes |
| Mix-1 | 2 | PIV-2 | wide vent | 823.1 | 159.7 | 503.7 | 10 | Yes |
| Mix-1 | 3 | B.pert | standard | 687.2 | 175.8 | 335.7 | 10 | Yes |
| Mix-1 | 3 | B.pert | wide vent | 671.8 | 162.8 | 346.3 | 10 | Yes |
| Mix-1 | 4 | IC-4 | standard | 651.3 | 153.9 | 343.5 | 20 | Yes |
| Mix-1 | 4 | IC-4 | wide vent | 652.1 | 136.3 | 379.4 | 20 | Yes |
| Mix-1 | 5 | AdvC | standard | 629.8 | 258.4 | 113.1 | 10 | Yes |
| Mix-1 | 5 | AdvC | wide vent | 561.7 | 175.0 | 211.6 | 10 | Yes |
| Mix-1 | 6 | AdvC.Pen | standard | 344.4 | 144.1 | 56.3 | 14 | Yes |
| Mix-1 | 6 | AdvC.Pen | wide vent | 282.1 | 122.5 | 37.1 | 14 | Yes |
| Mix-1 | 7 | Pan.Adv | standard | 164.4 | 58.7 | 47.0 | 10 | Yes |
| Mix-1 | 7 | Pan.Adv | wide vent | 138.1 | 47.8 | 42.4 | 10 | Yes |
| Mix-1 | 8 | OC43 | standard | 512.2 | 208.6 | 95.0 | 10 | Yes |
| Mix-1 | 8 | OC43 | wide vent | 447.8 | 150.1 | 147.6 | 10 | Yes |
| Mix-2 | 1 | HRV/EV | standard | 326.5 | 114.8 | 96.9 | 15 | Yes |
| Mix-2 | 1 | HRV/EV | wide vent | 295.7 | 103.1 | 89.5 | 15 | Yes |
| Mix-2 | 2 | IC-2 | standard | 431.4 | 171.4 | 88.5 | 5 | Yes |
| Mix-2 | 2 | IC-2 | wide vent | 426.5 | 138.6 | 149.4 | 5 | Yes |
| Mix-2 | 3 | IC-3 | standard | 667.4 | 115.1 | 437.3 | 20 | Yes |
| Mix-2 | 3 | IC-3 | wide vent | 664.9 | 103.9 | 457.0 | 20 | Yes |
| Mix-2 | 4 | H1 | standard | 354.2 | 139.3 | 75.6 | 10 | Yes |
| Mix-2 | 4 | H1 | wide vent | 352.9 | 131.3 | 90.4 | 10 | Yes |
| Mix-2 | 5 | AdvE | standard | 834.8 | 296.5 | 241.8 | 15 | Yes |
| Mix-2 | 5 | AdvE | wide vent | 834.6 | 279.5 | 275.6 | 15 | Yes |
| Mix-2 | 6 | Flu A | wide vent | 751.8 | 136.4 | 479.0 | 20 | Yes |
| Mix-2 | 6 | Flu A | standard | 746.0 | 139.9 | 466.1 | 20 | Yes |
| Mix-2 | 7 | NL63 | standard | 527.5 | 114.5 | 298.4 | 10 | Yes |
| Mix-2 | 7 | NL63 | wide vent | 531.1 | 150.4 | 230.3 | 10 | Yes |
| Mix-2 | 7 | Pan.Adv | standard | 281.6 | 71.7 | 138.2 | 10 | Yes |
| Mix-2 | 7 | Pan.Adv | wide vent | 261.7 | 70.8 | 120.1 | 10 | Yes |
| Mix-2 | 8 | PIV-3 | standard | 326.8 | 131.3 | 64.3 | 10 | Yes |
| Mix-2 | 8 | PIV-3 | wide vent | 348.8 | 114.5 | 119.9 | 10 | Yes |
| Mix-3 | 1 | HRV/EV | standard | 123.9 | 74.0 | −24.1 | 15 | No |
| Mix-3 | 1 | HRV/EV | wide vent | 130.0 | 66.0 | −2.1 | 15 | No |
| Mix-3 | 2 | IC-2 | standard | 473.3 | 129.9 | 213.5 | 5 | Yes |
| Mix-3 | 2 | IC-2 | wide vent | 479.3 | 137.3 | 204.8 | 5 | Yes |
| Mix-3 | 3 | C.pneu | standard | 716.7 | 149.8 | 417.2 | 10 | Yes |
| Mix-3 | 3 | C.pneu | wide vent | 727.9 | 112.3 | 503.4 | 10 | Yes |
| Mix-3 | 4 | H3 | standard | 308.9 | 83.9 | 141.2 | 5 | Yes |
| Mix-3 | 4 | H3 | wide vent | 321.8 | 62.4 | 196.9 | 5 | Yes |
| Mix-3 | 5 | AdvB | standard | 278.3 | 45.7 | 186.9 | 10 | Yes |
| Mix-3 | 5 | AdvB | wide vent | 264.4 | 35.6 | 193.1 | 10 | Yes |
| Mix-3 | 6 | Flu A | wide vent | 767.8 | 125.5 | 516.8 | 20 | Yes |
| Mix-3 | 6 | Flu A | standard | 785.6 | 145.2 | 495.2 | 20 | Yes |
| Mix-3 | 7 | 229E | standard | 122.2 | 78.9 | −35.7 | 10 | No |
| Mix-3 | 7 | 229E | wide vent | 165.3 | 77.2 | 10.8 | 10 | Yes |
| Mix-3 | 7 | Pan.Adv | standard | 253.0 | 67.9 | 117.2 | 10 | Yes |
| Mix-3 | 7 | Pan.Adv | wide vent | 265.8 | 63.1 | 139.5 | 10 | Yes |
| Mix-3 | 8 | IC-8 | standard | 573.7 | 68.7 | 436.3 | 20 | Yes |
| Mix-3 | 8 | IC-8 | wide vent | 573.4 | 78.3 | 416.8 | 20 | Yes |
| Mix-4 | 1 | IC-1 | standard | 646.7 | 150.5 | 345.8 | 20 | Yes |
| Mix-4 | 1 | IC-1 | wide vent | 618.3 | 128.2 | 361.8 | 20 | Yes |
| Mix-4 | 2 | PIV-4 | standard | 166.6 | 111.8 | −57.0 | 5 | No |
| Mix-4 | 2 | PIV-4 | wide vent | 205.6 | 120.0 | −34.3 | 5 | No |
| Mix-4 | 3 | M.pneu | standard | 261.6 | 147.4 | −33.2 | 5 | No |
| Mix-4 | 3 | M.pneu | wide vent | 290.5 | 128.4 | 33.7 | 5 | Yes |
| Mix-4 | 4 | IC-4 | standard | 580.5 | 150.1 | 280.3 | 20 | Yes |
| Mix-4 | 4 | IC-4 | wide vent | 662.1 | 88.8 | 484.5 | 20 | Yes |
| Mix-4 | 5 | IC-5 | standard | 371.8 | 69.3 | 233.2 | 20 | Yes |
| Mix-4 | 5 | IC-5 | wide vent | 378.4 | 67.0 | 244.4 | 20 | Yes |
| Mix-4 | 6 | Flu B | standard | 545.7 | 145.1 | 255.4 | 10 | Yes |
| Mix-4 | 6 | Flu B | wide vent | 553.4 | 139.8 | 273.8 | 10 | Yes |
| Mix-4 | 7 | IC-7 | standard | 554.2 | 155.6 | 243.1 | 10 | Yes |
| Mix-4 | 7 | IC-7 | wide vent | 480.2 | 135.3 | 209.6 | 10 | Yes |
| Mix-4 | 8 | RSV-B | standard | 531.6 | 97.8 | 335.9 | 20 | Yes |
| Mix-4 | 8 | RSV-B | wide vent | 521.6 | 88.9 | 343.8 | 20 | Yes |

WV-TABLE 8-continued

Analysis of analyte signal

| Sample Mix | PCR Drop | Target | Top Plate | Mean | SD | Mean-2xSD | Threshold nA | Above Threshold |
|---|---|---|---|---|---|---|---|---|
| Mix-5 | 1 | IC-1 | standard | 654.8 | 161.6 | 331.7 | 20 | Yes |
| Mix-5 | 1 | IC-1 | wide vent | 636.5 | 122.0 | 392.5 | 20 | Yes |
| Mix-5 | 2 | PIV-1 | standard | 536.5 | 90.2 | 356.2 | 10 | Yes |
| Mix-5 | 2 | PIV-1 | wide vent | 552.0 | 96.0 | 360.0 | 10 | Yes |
| Mix-5 | 3 | L.pneu | standard | 325.9 | 110.2 | 105.4 | 20 | Yes |
| Mix-5 | 3 | L.pneu | wide vent | 310.2 | 77.9 | 154.3 | 20 | Yes |
| Mix-5 | 4 | H1N1 | standard | 551.6 | 189.4 | 172.8 | 10 | Yes |
| Mix-5 | 4 | H1N1 | wide vent | 590.3 | 154.2 | 282.0 | 10 | Yes |
| Mix-5 | 5 | IC-5 | standard | 339.5 | 75.2 | 189.1 | 20 | Yes |
| Mix-5 | 5 | IC-5 | wide vent | 390.2 | 65.0 | 260.1 | 20 | Yes |
| Mix-5 | 6 | Flu A | standard | 420.0 | 181.9 | 56.1 | 20 | Yes |
| Mix-5 | 6 | Flu A | wide vent | 478.6 | 178.0 | 122.7 | 20 | Yes |
| Mix-5 | 7 | IC-7 | standard | 502.1 | 147.7 | 206.7 | 10 | Yes |
| Mix-5 | 7 | IC-7 | wide vent | 408.7 | 120.3 | 168.1 | 10 | Yes |
| Mix-5 | 8 | RSV-A | standard | 630.6 | 109.5 | 411.5 | 10 | Yes |
| Mix-5 | 8 | RSV-A | wide vent | 626.5 | 90.6 | 445.2 | 10 | Yes |
| Mix-6 | 1 | IC-1 | standard | 708.8 | 153.6 | 401.5 | 20 | Yes |
| Mix-6 | 1 | IC-1 | wide vent | 586.7 | 171.5 | 243.7 | 20 | Yes |
| Mix-6 | 2 | IC-2 | standard | 512.6 | 121.7 | 269.3 | 5 | Yes |
| Mix-6 | 2 | IC-2 | wide vent | 425.1 | 157.5 | 110.1 | 5 | Yes |
| Mix-6 | 3 | IC-3 | standard | 670.8 | 102.8 | 465.3 | 20 | Yes |
| Mix-6 | 3 | IC-3 | wide vent | 678.9 | 113.0 | 452.9 | 20 | Yes |
| Mix-6 | 4 | IC-4 | standard | 639.2 | 143.1 | 353.0 | 20 | Yes |
| Mix-6 | 4 | IC-4 | wide vent | 621.4 | 130.6 | 360.1 | 20 | Yes |
| Mix-6 | 5 | Boca | standard | 430.7 | 105.0 | 220.6 | 20 | Yes |
| Mix-6 | 5 | Boca | wide vent | 406.1 | 178.8 | 48.4 | 20 | Yes |
| Mix-6 | 6 | IC-6 | standard | 667.7 | 155.1 | 357.4 | 5 | Yes |
| Mix-6 | 6 | IC-6 | wide vent | 530.2 | 196.6 | 137.0 | 5 | Yes |
| Mix-6 | 7 | MERS | standard | 185.4 | 26.3 | 132.8 | 10 | Yes |
| Mix-6 | 7 | MERS | wide vent | 174.4 | 39.6 | 95.2 | 10 | Yes |
| Mix-6 | 8 | IC-8 | standard | 559.0 | 61.5 | 436.1 | 20 | Yes |
| Mix-6 | 8 | IC-8 | wide vent | 507.7 | 81.9 | 344.0 | 20 | Yes |
| Mix-7 | 1 | IC-1 | standard | 682.9 | 145.5 | 391.8 | 20 | Yes |
| Mix-7 | 1 | IC-1 | wide vent | 566.9 | 152.3 | 262.4 | 20 | Yes |
| Mix-7 | 2 | IC-2 | standard | 500.5 | 156.7 | 187.2 | 5 | Yes |
| Mix-7 | 2 | IC-2 | wide vent | 417.5 | 104.3 | 208.9 | 5 | Yes |
| Mix-7 | 3 | IC-3 | standard | 664.4 | 111.1 | 442.2 | 20 | Yes |
| Mix-7 | 3 | IC-3 | wide vent | 653.9 | 85.4 | 483.1 | 20 | Yes |
| Mix-7 | 4 | IC-4 | standard | 636.6 | 124.7 | 387.2 | 20 | Yes |
| Mix-7 | 4 | IC-4 | wide vent | 647.2 | 130.0 | 387.2 | 20 | Yes |
| Mix-7 | 5 | IC-5 | standard | 379.8 | 69.6 | 240.6 | 20 | Yes |
| Mix-7 | 5 | IC-5 | wide vent | 375.5 | 54.4 | 266.6 | 20 | Yes |
| Mix-7 | 6 | IC-6 | standard | 620.6 | 176.1 | 268.5 | 5 | Yes |
| Mix-7 | 6 | IC-6 | wide vent | 557.2 | 141.6 | 274.0 | 5 | Yes |
| Mix-7 | 7 | HKU1 | standard | 582.7 | 125.3 | 332.1 | 10 | Yes |
| Mix-7 | 7 | HKU1 | wide vent | 551.6 | 118.8 | 314.0 | 10 | Yes |
| Mix-7 | 8 | IC-8 | standard | 549.8 | 80.1 | 389.6 | 20 | Yes |
| Mix-7 | 8 | IC-8 | wide vent | 510.9 | 65.6 | 379.7 | 20 | Yes |

Analysis of nA Signal

For the nA signal of each RP Panel target: the mean, the standard deviation (SD), and the mean minus 2 SD were calculated for each test condition. The mean minus 2 SD was compared to the target cutoff. All but two targets had mean minus 2 SD above the cutoff, demonstrating there is no clinically relevant effect on the nA signal. Two targets, Enterovirus in Mix-3 and PIV-4 in Mix-4, had lower than the cutoff in both standard and wide vent top plate consumables, indicating no difference between the top plate versions. Additionally, 229E and *M. pneumoniae* had had lower than the cutoff in standard top plate consumables, indicating that wide vent consumables were not worse than the standard consumables (WV-Table 8). These targets had overall lower signal and higher variable signal ranges, thus making the 2×SD calculation irrelevant. However, the mean minus 1 SD were above the target cutoff (WV-Table 9).

WV-TABLE 9

Additional analysis of analyte signal

| Sample Mix | PCR Drop | Target | Top Plate | Mean | SD | Mean-1xSD | Threshold nA | Above Threshold |
|---|---|---|---|---|---|---|---|---|
| Mix-3 | 7 | 229E | STANDARD | 122.2 | 78.9 | 43.3 | 10 | Yes |
| Mix-3 | 1 | HRV/EV | STANDARD | 123.9 | 74.0 | 49.9 | 15 | Yes |
| Mix-3 | 1 | HRV/EV | WIDE VENT | 130.0 | 66.0 | 64.0 | 15 | Yes |

WV-TABLE 9-continued

| Additional analysis of analyte signal | | | | | | | | |
|---|---|---|---|---|---|---|---|---|
| Sample Mix | PCR Drop | Target | Top Plate | Mean | SD | Mean-1xSD | Threshold nA | Above Threshold |
| Mix-4 | 3 | M.pneu | STANDARD | 261.6 | 147.4 | 114.2 | 5 | Yes |
| Mix-4 | 2 | PIV-4 | STANDARD | 166.6 | 111.8 | 54.8 | 5 | Yes |
| Mix-4 | 2 | PIV-4 | WIDE VENT | 205.6 | 120.0 | 85.6 | 5 | Yes |

For the nA signal of each RP Panel control in a PCR drop where the control is the only target amplifying: the mean, the standard deviation (SD), and the mean minus 2 SD were calculated for each test condition. All ICs had mean minus 2 SD above the cutoff (WV-Table 8).

There was no significant decrease in the accuracy rate for wide vent compared to standard top plate consumables.

The accuracy rate for all testing performed on the wide vent consumables was calculated and compared to the accuracy rate for all testing performed on the standard top plate consumables. A consumable is evaluated as accurate if all targets that are expected to be detected are detected. Consumable accuracy in the wide vent consumables (96.6%) is no worse than the standard top plate consumables (93.2%), p=0.997 by one tailed Fisher's exact test (see WV-Table 10).

WV-TABLE 10

| Comparison of Consumable Accuracy in Wide Vent and Standard Top Plate Consumables from the three lots combined | | | | |
|---|---|---|---|---|
| Top Plate | Total Samples Tested | True Positives | Observed False Negative | % Accuracy |
| STANDARD | 623 | 582 | 41 | 93.42% |
| WIDE VENT | 624 | 603 | 21 | 96.63% |

The accuracy rate for all testing performed on the wide vent consumables was calculated and compared to the accuracy rate for all testing performed on the standard top plate consumables, in each of the three consumable lots. A comparison of the accuracy in each lot between the two top plate designs is listed in WV-Table 11.

WV-TABLE 11

| Comparison of Consumable Accuracy in Wide Vent and Standard Top Plate Consumables in Each of the Three Lots | | | | | |
|---|---|---|---|---|---|
| Lot | Top Plate | Total Samples Tested | True Positives | Observed False Negative | % Accuracy |
| 1 | STANDARD | 203 | 190 | 13 | 93.60% |
| | WIDE VENT | 209 | 204 | 5 | 97.61% |
| 2 | STANDARD | 211 | 199 | 12 | 94.31% |
| | WIDE VENT | 209 | 197 | 12 | 94.26% |
| 3 | STANDARD | 209 | 193 | 16 | 92.34% |
| | WIDE VENT | 206 | 202 | 4 | 98.06% |

Figures 77C, 77D, 77E:
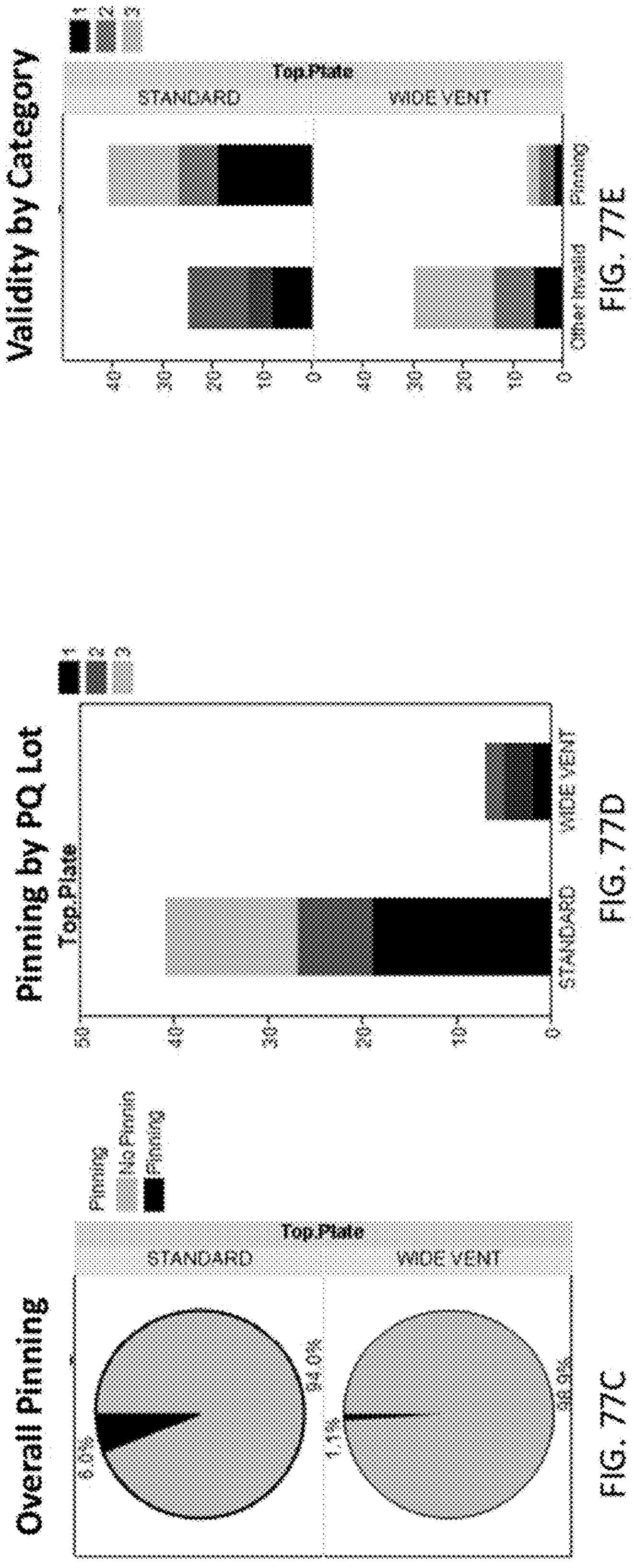
FIGS. 77C-E: 77C shows that pinning is reduced from 6.0% when a standard top plate is used to 1.1% when a wide vent top plate is used. 77D shows the pinning by PQ lot. Also, the variability in pinning in the standard top plate can also be seen. 77E shows the pinning rate compared to other electrowetting errors across all of the lots. Example 3.

Summary of completed invalid runs are listed in WV-Table 12. Pinning rate is greatly reduced in wide vent top plate consumables compared to standard design top plate consumables (1.1% and 6.0%, respectively; P<0.0001, one-tailed Fisher's exact test) (FIGS. 77C-E). The rates for other failure modes are comparable in wide vent top plate consumables and standard design top plate consumables.

WV-TABLE 12

| Summary Invalid Runs (excluding incomplete runs) | | |
|---|---|---|
| Validity Category | STANDARD | WIDE VENT |
| Other | 25 | 30 |
| Pinning | 41 | 7 |
| Valid | 623 | 624 |
| Total Completed Runs | 689 | 661 |

Reaction Module—Fluidic Processing Panel

Figure 58:
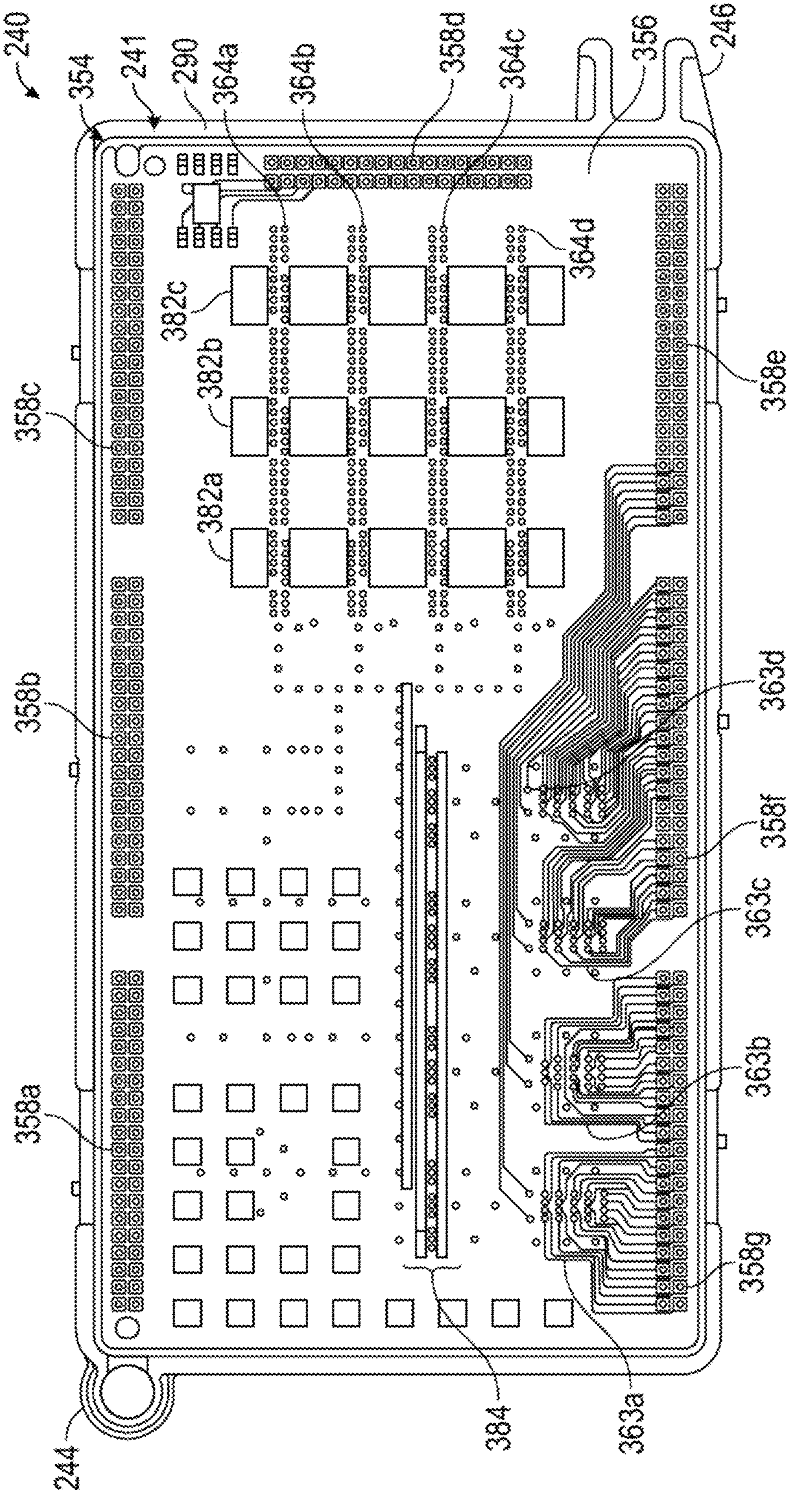
FIG. 58 is a bottom plan view of a fluidic processing panel of the reaction module.
Figure 59:
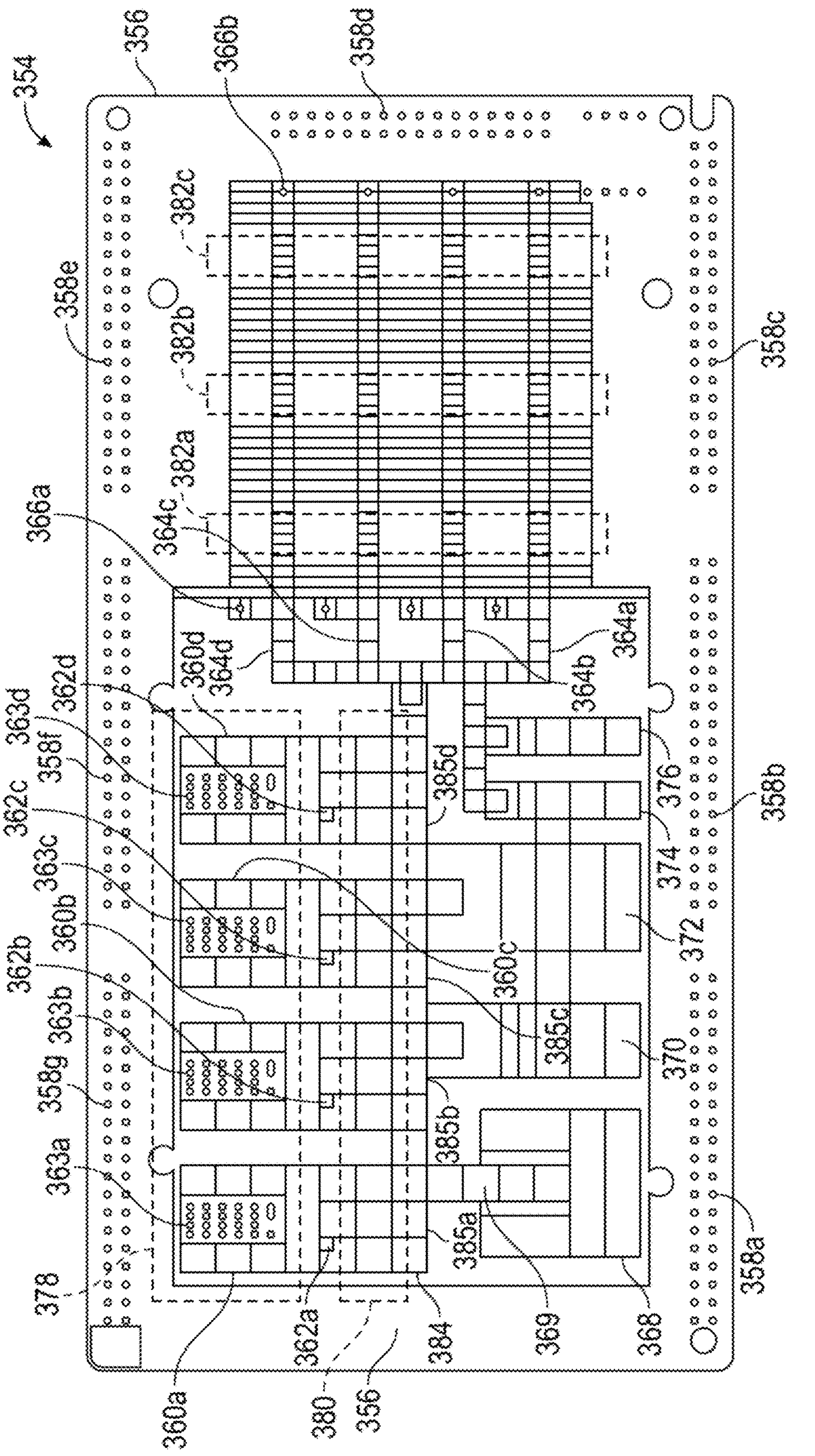
FIG. 59 is a top plan view of an electrical block diagram of an exemplary system according to the present invention.

Referring to FIGS. 58, 59, in various embodiments, the reaction module 240 of the multiplex cartridge 10 includes a fluidic processing panel 354, secured to the bottom of the top plate 241. The fluidic processing panel 354 is surrounded peripherally by the perimeter wall 290 and is support on and secured to the panel support 292, for example by an oil and temperature-resistant adhesive. The fluidic processing panel 354 facilitates a number of functionalities of the multiplex cartridge 10, such as fluid movement and analyte detection. Such fluid movements may include transporting one or more droplets of fluid along fluid transport pathways, mixing fluids by moving one or more droplets in an oscillatory fashion (e.g., linearly back and forth or in a continuous (e.g., circular, oval, rectangular) path), combining fluid droplets that may contain different materials, splitting droplets into two or more smaller droplets, etc.

The fluidic processing panel 354 includes a substrate 356. Suitable substrates include metal surfaces such as gold, electrodes as defined below, glass and modified or functionalized glass, fiberglass, ceramics, mica, plastic (including acrylics, polystyrene and copolymers of styrene and other materials, polypropylene, polyethylene, polybutylene, polyimide, polycarbonate, polyurethanes, TEFLON®, and derivatives thereof, etc.), GETEK® (a blend of polypropylene oxide and fiberglass), etc., polysaccharides, nylon or nitrocellulose, resins, silica or silica-based materials including silicon and modified silicon, carbon, metals, inorganic glasses and a variety of other polymers, with printed circuit board (PCB) materials being particularly preferred.

In various embodiments, the fluidic processing panel 354 may divided into a number of distinct functional areas or processing zones, which can be spatially overlapping or spatially distinct or partially spatially separate and partially spatially distinct.

In various embodiments, fluid reaction processing within the reaction module 240 is at least partially based on microfluidic fluid manipulation using so-called electrowetting techniques to form microdroplets that can be manipulated both spatially and biochemically.

In general, electrowetting is the modification of the wetting properties of a hydrophobic surface (such as PCB) with an applied electric field. In an electrowetting system, the change in the substrate-electrolyte contact angle due to an applied potential difference results in the ability to move the electrolyte on a surface. Essentially, as described in U.S. Pat. No. 6,565,727, the disclosure of which is hereby expressly incorporated by reference, by applying an electric potential to an electrode (or group of electrodes) adjacent to a drop of polar liquid (e.g., one containing a target analyte), the surface on these electrodes becomes more hydrophilic and the drop is pulled by a surface tension gradient to increase the area overlap with the charged electrodes. This causes the drop to spread on the surface, and, by subsequently removing the potential or activating different electrodes, the substrate returns to a hydrophobic state, resulting in the drop moving to a new hydrophilic area on the substrate. In this way, the drops can be physically and discretely moved on the planar surface of the substrate to different processing zones, for processing, handling, and detection. The drops can be moved at varied speeds, split (e.g. a single drop can be split into two or more drops), pulsed and/or mixed (two or more drops merged onto the same location and then either split or moved as one). In addition, electrowetting can instigate mixing within a single droplet. As described in more detail below, drops can also be used to rehydrate dry reagents stored at different locations on the PCB substrate. One typical characteristic of electrowetting is precise manipulation of very small fluid volumes. For example, isolated target nucleic acid can be eluted at a very high concentration in less than 10 μl prior to PCR amplification, compared to 100 μl elution volumes and much lower target analyte concentrations featured in other systems. In addition, electrowetting allows fluid paths to be altered in development and in the product via software, without the need to make any changes to the physical interface (e.g., new valves, fluid paths, etc.).

Exemplary microfluidic systems utilizing electrowetting techniques are described in U.S. Patent Pub. Nos. 2013/0252262, 2013/0233712, 2013/0233425, 2013/0230875, 2013/0225452, 2013/0225450, 2013/0217113, 2013/0217103, 2013/0203606, 2013/0178968, 2013/0178374, 2013/0164742,2013/0146461,2013/0130936,2013/01 18901,2013/0059366,2013/0018611, 2013/0017544, 2012/0261264, 2012/0165238, 2012/0132528, 2012/0044299, 2012/0018306, 2011/0311980, 2011/0303542, 2011/0209998, 2011/0203930, 2011/0186433, 2011/0180571, 2011/01 14490, 2011/0104816, 2011/0104747, 2011/0104725, 2011/0097763, 2011/0091989, 2011/0086377, 2011/0076692, 2010/0323405, 2010/0307917, 2010/0291578, 2010/0282608, 2010/0279374, 2010/0270156, 2010/0236929, 2010/0236928, 2010/0206094, 2010/0194408, 2010/0190263, 2010/0130369, 2010/0120130, 2010/0116640, 2010/0087012, 2010/0068764, 2010/0048410, 2010/0032293, 2010/0025250, 2009/0304944, 2009/0263834, 2009/0155902, 2008/0274513, 2008/0230386, 2007/0275415, 2007/0242105, 2007/0241068, U.S. Pat. Nos. 8,541,176, 8,492,168, 8,481,125, 8,470,606, 8,460,528, 8,454,905, 8,440,392, 8,426,213, 8,394,641, 8,389,297, 8,388,909, 8,364,315, 8,349,276, 8,317,990, 8,313,895, 8,313,698, 8,304,253, 8,268,246, 8,208,146, 8,202,686, 8,137,917, 8,093,062, 8,088,578, 8,048,628, 8,041,463, 8,007,739, 7,998,436, 7,943,030, 7,939,021, 7,919,330, 7,901,947, 7,851,184, 7,822,510, 7,816,121, 7,815,871, 7,763,471, 7,727,723, 7,439,014, 7,255,780, 6,773,566, and 6,565,727, the respective disclosures of which are hereby incorporated by reference.

Thus, in various embodiments, the fluidic processing panel 354 comprises a grid of electrodes which form and define discrete processing zones, including pathways, for fluid droplets as appropriate for the assays or other process (es) being performed in the reaction module 240. In general, a "spot" or "location" or "pad" (sometimes referred to as an "electrowetting pad" or "EWP") is generally depicted in the figures as a rectangle wherein the lines forming the sides of the rectangle represent electrodes, such that a droplet moves along a path in discrete steps, from pad to pad. By manipulating the electrode grid, the droplets can be selectively moved in any of four directions as needed: forward, backward, left, or right, relative to a current position. Thus, in various embodiments the fluidic processing panel 354 includes a grid of etched electrodes forming a network of pads for moving sample droplets from sample preparation through detection of target analytes.

In the illustrated embodiment, the electrodes formed on the substrate 356 of the fluidic processing panel 354 define a number of discrete, functional regions that provide for movement and/o collection of fluid droplets. As shown in FIGS. 26, 27, and 59, these zones include a sample bead zone 368 spatially corresponding to the sample compartment 266 of the top plate 241, a hybridization zone 370 spatially corresponding to the detection buffer compartment 280 of the top plate 241, a rehydration buffer zone 372 spatially corresponding to the rehydration (elution) buffer compartment 276 of the top plate 241, an exonuclease reagent zone 374 spatially corresponding to the second buffe compartment 300 of the top plate 241, and a PCR reagent zone 376 spatially corresponding to the buffer compartment 296 of the top plate 241. Other zones defined on the fluidic processing panel 354 include electrosensor zones 360*a*, 360*b*, 360*c*, and 360*d* corresponding spatially to detection compartments 350*a*, 350*b*, 350*c*, and 350*d*, respectively, and which further include electrosensor arrays 363*a*, 363*b*, 363*c*, and 363*d*, respectively. Still other pathways defined on the fluidic processing panel 354 include thermocycling, or PCR, pathways 364*a*, 364*b*, 364*c*, and 364*d*, each being located spatially below and between two adjacent bubble traps 340 of the top plate 241.

Electrodes of the fluidic processing panel 354 may further define an exonuclease zone 384.

Electrodes of the fluidic processing panel 354 may further define detection mixing zones, which, in the illustrated embodiment comprise four groups of nine electrode pads indicated by reference numbers 385*a*, 385*b*, 385*c*, and 385*d*.

The fluidic processing panel may further include a number of connector pad arrays configured to contact and make electrical connections with connector pins (e.g., pogo pins) located within the processing instrument, as will be described in further detail below. The illustrated embodiment includes seven connector pad arrays: 358*a*, 358*b*, 358*c*, 358*d*, 358*e*, 358*f*, and 358*g*.

As will be appreciated by those in the art, there are a wide number of electrode grid configurations that can be employed in the multiplex cartridge 10, including, without limitation, configurations described herein. Exemplary electrowetting electrode configurations for different utilities are shown in previously-incorporated U.S. Pat. No. 8,541,176.

In general, preferred materials for the fluidic processing panel 354 include printed circuit board materials. In various embodiments, circuit board materials are those that comprise an insulating substrate (e.g., the substrate 356) that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" boards (e.g., all electrodes and interconnections in a plane, "edge card connectors") or "three dimensional" boards (wherein the electrodes are on one surface and the interconnects may go through the board to the other side or wherein electrodes are on a plurality of surfaces). Three dimensional systems frequently rely on the use of drilling or etching to form holes, or vias, through the substrate, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

In one embodiment, electrical connections from both the electrowetting electrode grids and detection electrodes, i.e., the connector pad arrays 360*a-g*, extend through the panel to produce a so-called land grid array that can interface to a pogo pin or like connector to make connections from the chip to a processing instrument. In various embodiments, the surface of the fluidic processing panel 354 (e.g., the PCB with the electrode grids) is coated with a film of a substance to facilitate the electrowetting mechanism and clean transport from pad to pad. In various embodiments, the surface is coated with a polyimide film, such as KAPTON® from DuPont (e.g., black or yellow KAPTON®), which forms a dielectric layer. The surface properties of the dielectric layer are important to facilitate electrowetting and to attenuate the voltage being used in order to prevent electrolysis in the aqueous droplet. In addition, the Kapton® or similar surface, such as a solder mask, must be coated with a hydrophobic coating, such as Paralyene, TEFLON® (polytetrafluoroethylene), CYTOP® fluoropolymers, to name a few, to render the surface hydrophobic, which is required for electrowetting. to function.

As will be appreciated by those in the art, the form of the reagent provided in the reaction module 240 will depend on the reagent. Some reagents can be dried or in solid form (for example, when particular buffers are to be used), others can be lyophilized, etc. Particularly useful embodiments utilize dried reagents with added stabilizers, such as salts, sugars, polysaccharides, polymers or proteins such as gelatins, etc. as will be appreciated by those in the art. For example, Biomatrica produces commercial stabilizers for use in the present system.

As will be appreciated by those in the art, if used, the dried reagents can be rehydrated in one of two general ways. Either liquid from the sample preparation module 70 is introduced at the appropriate pad (or zone) or the sample itself serves as an aqueous solvent to put the solid reagents into solution. For example, the appropriate resuspension buffer (which can be water, in some cases) can be added through the top plate 241 from the sample preparation module 70 to a particular pad to rehydrate the reagent(s), and then the reagent droplet can be merged with the sample droplet.

Alternatively, the drops containing the target analyte (for example, in elution buffer used to liberate the target analytes from the capture beads) may be transported to a pad containing the dried reagent(s), which are then suspended in the drop itself. One benefit of this embodiment is that the ultimate volume of a droplet does not increase significantly, as it does when a drop of reagent is merged with a drop of sample. This may be particularly useful in situations where multiple reagent additions are required.

The number, type and quantity of the different reagents will depend on sample, the target analyte and the desired reaction. For example, for nucleic acid target sequences in a standard PCR reaction, when the starting sample is DNA, the on-board dried reagents include RT-PCR buffer, PCR enzyme (e.g. a Taq polymerase), dNTPs, PCR primers, exonuclease, signal probes, signal buffer and detection buffers (with the lysis buffer, the binding buffer, the elution buffer, the (optional) reconstitution buffer(s), and magnetic bead suspension all being contained in the sample preparation module 70, rather than dried on the fluidic processing panel 354). Exemplary embodiments are outlined herein. However, as will be appreciated by those in the art, any number of configurations of dried reagents and liquid reagents in the sample preparation module 70 can be used.

The compartment within the reactor module 240 formed between the fluidic processing panel 354 and top plate 241 described above, is generally filled with a fluid in which the target analyte droplets (usually aqueous solutions) are immiscible, and this immiscible fluid is generally less polar than the solution of the drop. As described in U.S. Pat. No. 8,541,177, the disclosure of which is hereby incorporated by reference, there are two general ways of isolating drops on pads including filling the compartment with an immiscible fluid including immiscible liquids and immiscible gases, or by using the immiscible liquid as a droplet encapsulant, for example giving the droplet a shell of oil by passing the droplet through an air/oil interface.

Particularly suitable immiscible fluids for use in the nucleic acid detection assays described herein include, but are not limited to, silicone oils, mineral oil, fluorosilicone oils; hydrocarbons, including for example, alkanes, such as decane, undecane, dodecane, tridecane, tetradecane, pentadecane, hexadecane; aliphatic and aromatic alkanes such as dodecane, hexadecane, and cyclohexane, hydrocarbon oils, mineral oils, paraffin oils; halogenated oils, such as fluorocarbons and perfluorocarbons (e.g. 3M Fluorinert liquids) as well as mixtures of the above. Examples of suitable gas filler fluids include, without limitation, air, argon, nitrogen, carbon dioxide, oxygen, humidified air, any inert gases. In one embodiment, the primary phase is an aqueous solution, and the secondary phase is air or oil, which is relatively immiscible with water. In another embodiment, the filler fluid includes a gas that fills the space between the plates surrounding the droplets. A preferred filler fluid is low-viscosity oil, such as silicone oil. Other suitable fluids are described in U.S. Patent Application No. 60/736,399, entitled "Filler Fluids for Droplet-Based Microfluidics" filed on Nov. 14 2005, the entire disclosure of which is incorporated herein by reference. The fluid may be selected to prevent any significant evaporation of the droplets.

As will be understood by those in the art, the movement of droplets from pad to pad, with the addition of reagents as needed, can be used for any number of sample manipulations. In the case of the nucleic acid manipulations for nucleic acid detection, these manipulations generally include the addition of reagents, such as PCR enzymes, PCR buffer, primers, exonuclease, reverse transcriptase (RT) enzymes, RT-PCR buffers, signal buffers, signal probes, etc.

In various embodiments, one or more portions, or sections, of the electrode grid pathway of pads is/are exposed to heat within discrete thermal zones for, e.g., amplification, exonuclease digestion, reverse transcription, target elution, and electrochemical detection. Such thermal zones may comprise a detection region 378, an exonuclease region 380, and a thermocycling (PCR) regions (also referred to as thermal zones) 382*a*, 382*b*, 382*c*.

As will be appreciated by those in the art, some manipulations, such as PCR amplification, require the thermocycling between 2 to 3 different temperatures (primer binding, extension and denaturation), while others require a uniform temperature for best results, e.g., enzymatic processes such as the use of exonuclease and reverse transcriptase, specific temperature(s) for improved elution and/or reagent resuspension, or binding/assay temperatures in the case of the electrochemical detection. Isothermal amplification techniques and other PCR alternatives typically require precise temperature control.

In various embodiments, heat applied to different portions of the fluidic processing panel 354 is generated by thermal components, such as resistive heaters or thermoelectric (Peltier) chips and are found off-cartridge in the processing bays of the instrument into which the cartridge 10 is placed. Examples of such thermal components are described below.

In one embodiment, the sample manipulation zones on the reactor panel 354 can optionally include sensors, for example, to monitor and control thermal zone temperatures, particularly in the case where specific temperatures are desirable. These sensors can include, but are not limited to, thermocouples and resistance temperature detectors (RTDs). Alternatively, such sensors can also be "off cartridge" in the bays.

In various embodiments for detecting nucleic acid targets, the fluidic processing panel 354 comprises one or more thermocycling, or PCR or amplification, pathways 364*a*, 364*b*, 364*c*, and 364*d*. The fluidic processing panel 354 can contain 1, 2, 3 or more thermocycling pathways of pads. These can be used for individual PCR reactions (e.g., one droplet is moved up and down a pathway or up one pathway and down another, etc.) or for multiplexing (e.g. for multiple pathways, multiple different droplets can be moved up and down each pathway).

As will be appreciated by those in the art, each PCR reaction can additionally be multiplexed. That is, for target-specific amplification, the use of multiple primer sets in a single PCR reaction can be unwieldy, and thus the present invention allows multiple reactions to achieve higher levels of multiplexing. For example, for the evaluation of 21 different target sequences (for example, in screening of respiratory viruses), it may be desirable to run 3 different reactions of seven primer sets; e.g. a first PCR sample droplet in a first pathway picks up a first set of 7 primer pairs (e.g., "Primer Mix A"), a second droplet picks in a second pathway up a second set of 7 primer pairs ("Primer Mix B"), and a third droplet in a third pathway pick up a third set ("Primer Mix C"). In some embodiments, more than one droplet can be processed in each pathway, so each pathway may include more than one primer set. In some embodiments, the primers will be completely different in each set; in others, redundancy and/or internal controls are built into the system by adding the same primer sets to different pathways. The number of multiplexes can vary easily through software without the need to modify any physical components of the system.

In general, amplification reactions suitable for use in the present systems use sets of primers wherein one primer of each set has a blocked end that is impervious to standard exonucleases. That is, it is desirable to remove one strand of the double stranded amplicons that are generated in the PCR reaction, so as to simplify the detection reactions and remove background signal. Thus, by running a first PCR reaction and then adding exonuclease, one strand of the double stranded amplicon is digested, leaving only the detection strand.

The use of multiple heating zones along the thermocycling pathways 364*a-d*, as generally depicted in FIG. 59, allows the droplets to travel through the appropriate thermal zones. As shown in FIG. 59, the four thermocycling pathways 364*a*, 364*b*, 364*c*, and 364*d* are shown that extend through the three thermal zones 382*a*, 382*b*, and 382*c*. Thermal elements, e.g., resistive heaters, corresponding to the thermal zones, 382*a*, 382*b*, and 382*c* zones are off-cartridge heater elements and may be maintained at temperatures of 95° C., 72° C., and 64° C. for use in PCR thermocycling. In some embodiments, two different temperature zones (e.g., about 95° C. for denaturation and about 60° C. for annealing and extension) can be used for a two-step PCR reaction. In other embodiments, a three-zone, two-temperature configuration may be employed, wherein a middle heater corresponding to middle thermal zone 382*b* controls the denaturation temperature (e.g., about 95° C.), and additional heaters corresponding to the thermal zones 382*a*, 382*c* on each side of the denaturation heater provide substantially the same annealing and extension temperature (e.g., about 60° C.). In this configuration, two-step amplification cycles can be performed with more than one droplet in each thermocycling pathway 364*a-d*. For example, two droplets may be positioned in each thermocycling pathway and spaced in such a way that when one droplet is in the denaturation zone 382*b*, the other is in one of the combined annealing and extension zones 382*a* or 382*b*, and vice versa. Each droplet may pick up amplification reagents (e.g., a primer cocktail) at locations, for example, at each end of a thermocycling pathway, such as locations 366*a*, 366*b* of each of the thermocycling pathways 364*a-d*. As shown in FIGS. 68A-B, up to eight primer cocktails may be placed at the PCR staging area 364.1. By shuttling the droplets in tandem back and forth between the denaturation and annealing/extension zones, one can amplify both of them in the same amount of time it would normally take to amplify a single droplet. In a four pathway configuration as shown, this means that eight droplet can be amplified simultaneously instead of three.

In various embodiments, the multiplex cartridge 10 of the present invention relies on the use of electrodes and electrochemical labels for the detection of target analytes. Generally, the surface of electrodes within each electrosensor array 363*a*, 363*b*, 363*c*, and 363*d* (optionally coated with a self-assembled monolayer (SAM)) has capture ligands which bind the target. A second label ligand, which also binds to the target, is included, such that in the presence of the target, the label ligand is bound near the surface of the electrode, and can be detected electronically.

Thus, the detection zone of the fluidic processing panel 354 comprises one or more separate arrays of detection electrodes 363*a*, 363*b*, 363*c*, and 363*d* within the respective electrosensor zones 360*a*, 360*b*, 360*c* and 360*d*. By "electrode" herein is meant a composition, which, when connected to an electronic device, is able to sense a current or charge and convert it to a signal. Alternatively, an electrode can be defined as a composition which can apply a potential to and/or pass electrons to or from species in the solution. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred. In a particularly useful embodiment, both the electrowetting electrode grid and the detection electrodes are gold, and are fabricated simultaneously on the fluidic processing panel 354.

The present system finds particular utility in array formats, i.e., wherein there is a matrix of addressable detection electrodes. By "array" herein is meant a plurality of capture ligands on electrodes in an array format; the size of the array will depend on the composition and end use of the array. Arrays containing from about two different capture ligands to about 50 to 100 can be made. In some preferred embodiments, 80 or 100 working detection electrodes are split into four or five distinct zones of twenty, with each zone having up to sixty capture probes (three different capture probes per electrode).

The detection zone of the fluidic processing panel 354 comprises one or more arrays of detection electrodes 363*a-d*, each of which is within an electrosensor zone 360*a-d* that is in fluid communication with the droplet pathway of an associated one of the detection mixing zones 385*a-d*. That is, the droplets containing the amplicons will pick up necessary detection reagent such as label probe (e.g., a signal probe cocktail which may be in dry form, e.g., at locations 362*a*, 362*b*, 362*c*, and 362*d*) adjacent to the electrosensor detection zones 360*a*, 360*b*, 360*c*, and 360*d*, respectively, and then be dispersed on the associated electrosensor detection zones 360*a*, 360*b*, 360*c*, and 360*d*. The signal probe cocktails may be applied to a portion of the top plate 241 forming the locations 362*a*, 362*b*, 362*c*, and 362*d* or a portion of the fluidic processing panel 354 covering the locations 362*a*, 362*b*, 362*c*, and 362*d*. In general, each detection zone receives one or more sample droplets which are generally dispersed on the array of electrodes, which is considered one larger "pad".

In one embodiment, the reaction module 240 includes four (4) electrosensor detection zones, and each electrosensor array includes 20 working electrodes (which may include one reference electrode and one auxiliary electrode). Each detection electrode of each electrosensor array 363*a-d* comprises an independent lead (interconnect) to transmit input and electronic response signals for each electrode of the array such that both input and electronic response signals are independently monitorable for each electrode. That is, each electrode is independently addressable. Moreover, the reaction module is preferably configured for independent control of electrowetting pads surrounding each electrode of each electrosensor array 363*a*, 363*b*, 363*c*, and 363*d*.

In addition to the components of the fluidic processing panel 354 described above, the fluidic processing panel 354 can also optionally comprise an EPROM, EEPROM or RFID to identify the cartridge, for example containing information about the batch, treatment or contents of the multiplex cartridge 10. This can include information about the identification of the assay, for example.

The reaction module can be further understood by the following numbered paragraphs:

Paragraph 1: A reaction module comprising a processing panel with 1-8 primer cocktails located at the PCR staging area.

Paragraph 2: A reaction module comprising a processing panel with 1-8 primer cocktails located at each end of four thermocycling pathways.

Paragraph 3: A sample preparation module comprising a mixing well containing magnetic beads connected to a reaction module comprising a processing panel with 1-8 primer cocktails located at the PCR staging area.

Paragraph 4: A sample preparation module comprising a mixing well containing magnetic beads connected to a reaction module comprising a wide vent top plate and a processing panel with 1-8 primer cocktails located at the PCR staging area.

Paragraph 5: A microfluidic device comprising a reaction module comprising a processing panel with 1-8 primer cocktails located at the PCR staging area; a sample preparation module comprising a mixing well containing magnetic beads; and an external housing.

Paragraph 6: A microfluidic device comprising a reaction module comprising a wide vent top plate and a processing panel with 1-8 primer cocktails located at the PCR staging area; and a sample preparation module comprising a mixing well containing magnetic beads; and an external housing.

Paragraph 7: A method for preparing a sample for analyte detection comprising loading a sample into a sample preparation module and exposing the sample to magnetic beads in a mixing well thereby preparing the sample and preparing the sample for amplification by moving the sample across 1-8 primer cocktails located at the PCR staging area.

Paragraph 8: A method for preparing a sample for analyte detection comprising loading a sample into a reaction module and preparing the sample for amplification by moving the sample across 1-8 primer cocktails located at the PCR staging area.

Paragraph 9: the method of paragraph 8, wherein the primer cocktail amplify target nucleic acid wherein the target nucleic acid is nucleic acid from a gram-positive bacteria wherein the gram-positive bacteria is selected from the group consisting of *Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group, *Enterococcus faecium, Streptococcus pneumonia, Lactobacillus, Streptococcus pyogenes, Listeria* and combinations thereof.

Paragraph 10: the method of paragraph 8, wherein the primer cocktail amplify target nucleic acid wherein the target nucleic acid is nucleic acid from a gram-negative bacteria wherein the gram-negative bacteria is selected from the group consisting of *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-cloacae complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca* and combinations thereof.

Paragraph 11: the method of paragraph 8, wherein the primer cocktail amplify target nucleic acid wherein the target nucleic acid is nucleic acid from a fungus wherein the fungus is selected from the group consisting of *Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon* and combinations thereof.

Paragraph 12: the method of paragraph 8, wherein the primer cocktail amplify target nucleic acid wherein the target nucleic acid is nucleic acid from a respiratory virus selected from the group consisting of, Influenza A, Adenovirus, Influenza A H1 subtype, Human Bocavirus, Influenza P H3, Human Rhinovirus/Enterovirus, Influenza A 2009 H1N1 subtype, Coronavirus 229E, Influenza B, Coronavirus HKU1, Respiratory Syncytial Virus A, Coronavirus NL63, Respiratory Syncytial Virus B, Coronavirus OC43, Parainfluenza Virus 1, Coronavirus MERS, Parainfluenza Virus 2, *Bordetella pertussis*, Parainfluenza Virus 3, *Chlamydophila pneumoniae*, Parainfluenza Virus 4, *Mycoplasma pneumoniae*, Human Metapneumovirus, *Legionella pneumophila* and combinations thereof.

Instrument Overview

Figure 32:
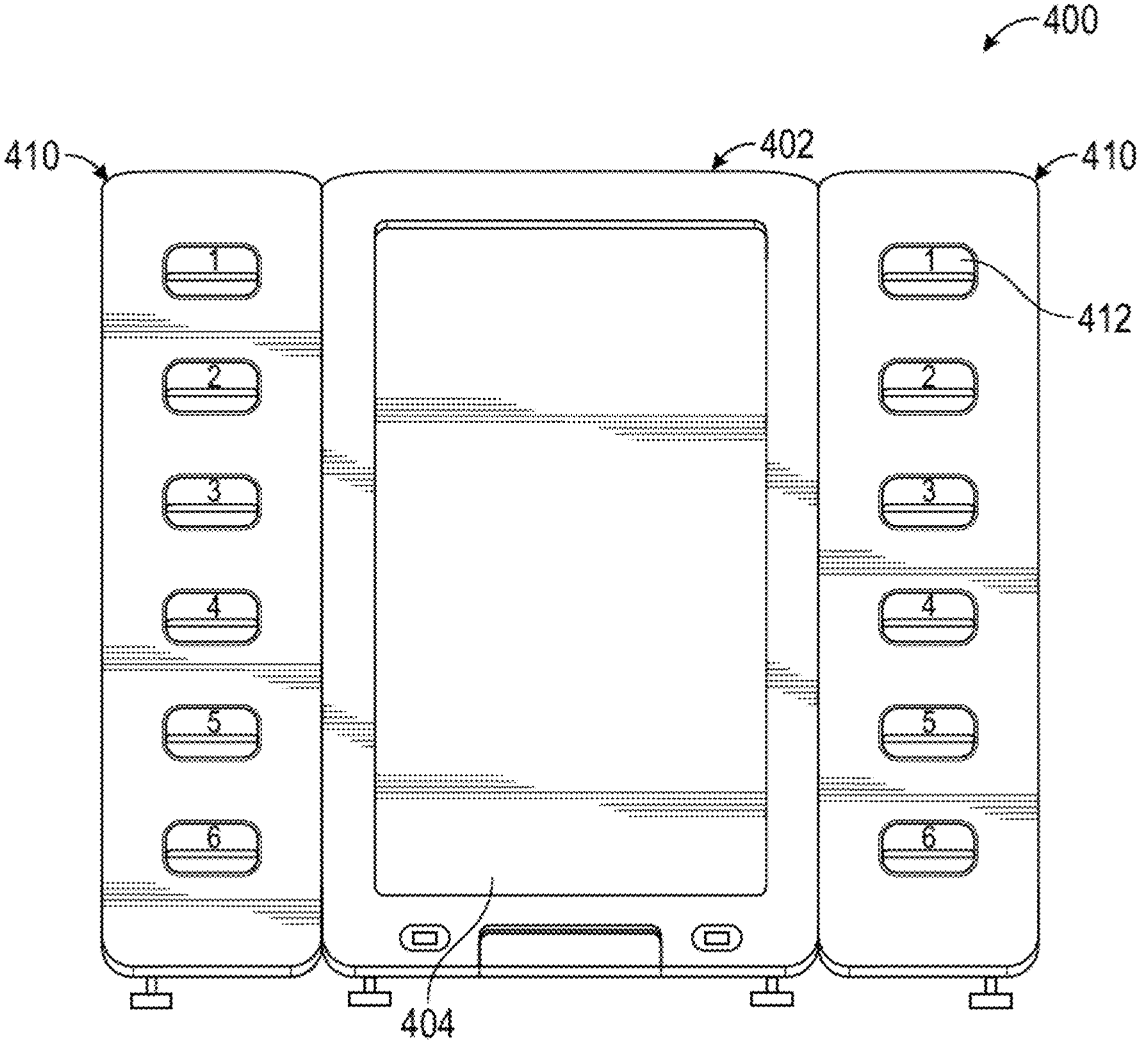
FIG. 32. is a front view of an instrument embodying aspects of the invention.
Figure 33:
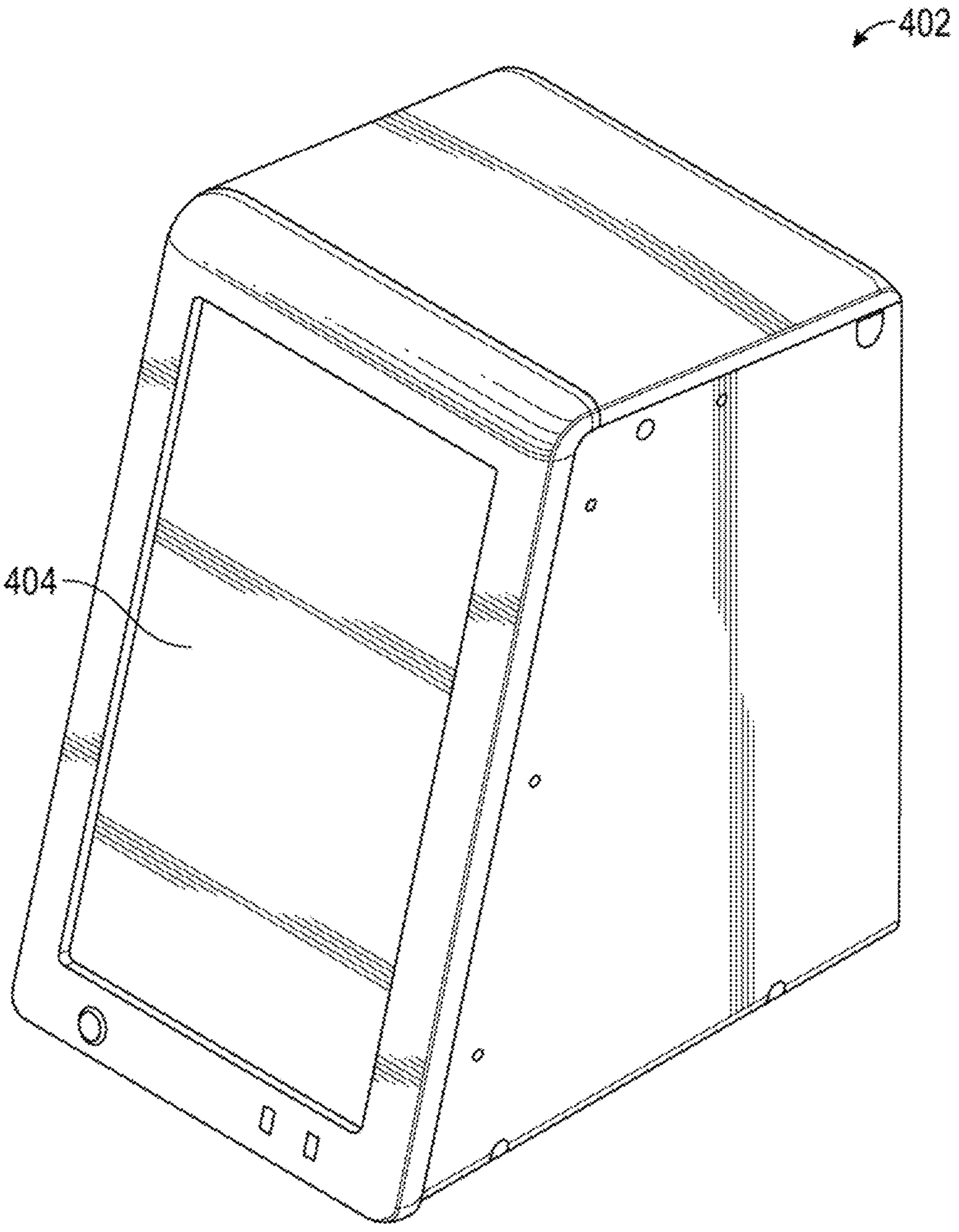
FIG. 33 is a front perspective view of a control console of the instrument.

An instrument configured for processing the multiplex cartridge 10 and embodying aspects of the present invention is indicated by reference number 400 in FIG. 32. The instrument comprises a control console 402, one or more processing modules 410 operatively coupled to the control console 402, processing bays within each processing module 410, each of which is configured to receive a multiplex cartridge and process the multiplex cartridge independently of the other bays, and instrument software (ISW). In various embodiments, the instrument comprises one control console 402 and up to four processing modules 410, with each processing module including six processing bays. Each processing module 410 is operatively coupled to the control console 402, e.g., to exchange power, input and output data, and control signal transmissions with the control console 402 and may be physically connected to the control console 402 as well. Each processing bay with the processing module 410 is configured to accept one multiplex cartridge 10 at a time and to process the cartridge independently of other processing bays processing other multiplex cartridges. In various embodiments, the instrument is configured for each processing bay to complete processing of a cartridge in 60 minutes or less.

The ISW provides the graphical user interface for the user to start runs, receive results, and provide inputs that at least partially control operation of the instrument. In various embodiments, the ISW is configured to run on a Windows® computer with a touchscreen 404 located on the control console 402 providing the primary functionality for user input. In various embodiments, the instrument is configured to provide connectivity to a local area network ("LAN") and a laboratory information system ("LIS"). The instrument may also include a barcode scanner (not shown) that facilitates logging in to the ISW, tracking samples, and positive 1D features of the instrument.

The control console 402 of the instrument includes a touchscreen panel 404, a system computer, a power supply, connectivity to external data systems, and connectivity for the processing module(s) and processing bay(s). In various embodiments, a power supply in the control console powers the entire instrument. Cabling from the control console provides power transmission and provides for data flow to and from the processing bays. In various embodiments, the control console also has provision for physically attaching the one or more processing modules to the control console Each processing bay includes hardware, firmware, and electronics that run an assay on a multiplex cartridge 10. Each processing bay may include a bay PCB. In various embodiments, the bay PCB includes the electronics and firmware of the processing bay (such as, microprocessors and firmware on the microprocessors), circuitry that supplies power (e.g., up to 300 V to the electrowetting pads) in the multiplex cartridge, circuitry that performs electronic sensing of reaction products on the multiplex cartridge, circuitry that controls heaters in the processing bay that interact with the multiplex cartridge, circuitry that measures and controls temperatures in the multiplex cartridge, circuitry that controls motion of various moving components of the processing bay, and circuitry that controls a pump of the processing bay.

Each processing bay may also include a connector PCB. In various embodiments, the connector PCB includes pogo pins configured to make contact with the multiplex cartridge and transmit data, control signals, and power between the multiplex cartridge and the processing bay PCB and pogo pins configured to make electrical contact with heater elements within the processing bay.

Each processing bay further includes stepper motors. In various embodiments, the processing bay comprises two stepper motors: one stepper motor that controls positioning of magnets, heaters, and pogo pins, or other connector elements, relative to the multiplex cartridge, and one stepper motor controls a cam follower plate within the processing bay that compresses blisters on the multiplex cartridge and causes the blisters to dispense their contents in a predefined sequence.

Each processing bay also includes a blister compression assembly configured to compress the blisters of the multiplex cartridge 10 in a specified sequence and actuate the active valves of the multiplex cartridge 10, thereby dispensing the contents of the cartridge's blisters in the specified sequence. In various embodiments, the blister compression mechanism assembly comprises an array of blister-compressing actuators, or compression mechanisms, each comprising a cam arm configured to push a compression pad onto a blister. The blister compression mechanism assembly further includes a cam arm plate within which the cam arms and compression pads of the compression mechanisms are operatively mounted above the blisters for movement between a retracted position and an extended, blister-compressing position, a cam follower plate that is movable with respect to the cam arm plate and includes grooves with ridges (or other cam follow elements) located and sequence (to engage cam arms of the actuator array as the cam follower plate moves with respect to the cam arm plate to actuate the cam arms to compress the blisters in a sequence determined by the relative locations of the compression mechanisms in the cam arm plate and the grooves and ridges of the cam follower plate.

Each processing bay may also include a pump coupled to the multiplex cartridge 10 via pump port 104 and configured to provide a motivating force for reagents and sample in sample preparation module of the multiplex cartridge.

Each processing bay may also include an LED PCB 466 (see FIGS. 38-41) that provides LED indicators of the processing bay status and optical sensors that detect conditions within the multiplex cartridge, for example, through inlet optical port 14 and outlet optical port 16.

Each processing bay may also include mounting hardware configured to attach the processing bay into the processing module and electrical connectors configured to transmit power and data between the processing bay and the processing module.

Each processing bay may also include a multiplex cartridge carrier configured to provide a physical connection and alignment between the top bay, comprising the blister compression mechanism assembly, and a multiplex cartridge processing assembly, or bottom bay, comprising a cartridge carriage assembly, a heating and control assembly, and a cam frame assembly configured to effect movement of the heating and control assembly with respect to a multiplex cartridge held in the cartridge carriage assembly.

The Instrument can be further understood by the following numbered paragraphs:

Paragraph 1: A system comprising an instrument software module coupled to a processing bay module.

Paragraph 2: The system of Paragraph 1, wherein the ISW communicates the OPUS portion of the ADF to the processing bay module Paragraph 3: The system of Paragraph 2, wherein the processing bay module generates sensor scan data.

Paragraph 4: The system of Paragraph 3, wherein the processing bay module communicates sensor scan data to the ISW Paragraph 5: The system of Paragraph 4, wherein the ISW then communicates the sensor scan data to the AAM module.

Paragraph 6: The system of Paragraph 5, wherein the AAM module applies the AAM file to the sensor scan data and generates a detection report based on the analysis.

Paragraph 7: The system of Paragraph 6, wherein the AAM module communicates the detection report to the ISW.

Paragraph 8: The system of Paragraph 7, wherein the ISW communicates the detection report to the hospital LIS Paragraph 9: The system of Paragraph 8, wherein analyzing the scan data by the AAM module comprises applying a digital filter to the scan data.

Paragraph 10: The system of Paragraph 9, wherein analyzing the scan data by the AAM module comprises applying a classifier to the scan data.

Control Console

A processing instrument embodying aspects of the present invention and configured to process the multiplex cartridge 10 described above is indicated by reference number 400 in FIG. 32. As noted above, the instrument 400 includes the control console 402 and one or more processing modules 410 operatively associated with the control console 402. The control console 402, in one embodiment, includes a display panel 404 presenting a graphical user interface and comprising a touchscreen by which a user may input information to the control console 402 and/or by which information can be presented to the user. In various embodiments, the control console 402 may comprise additional or alternate means for inputting data, such as keyboards, microphones, switches, manually-operated scanners, voice-activated input, etc. As further noted above, the instrument may include a barcode scanner for reading barcodes, for example, one-dimensional or two-dimensional barcodes, or other types of scanners for reading machine-readable code, such as an RFID scanner. In various embodiments, the control console 402 may comprise additional or alternate means for outputting data (i.e., information and/or results), including hard drives or other storage media, monitors, printers, indicator lights, or audible signal elements (e.g., buzzer, horn, bell, etc.), email, text message, etc.

Processing Module

Figure 34:
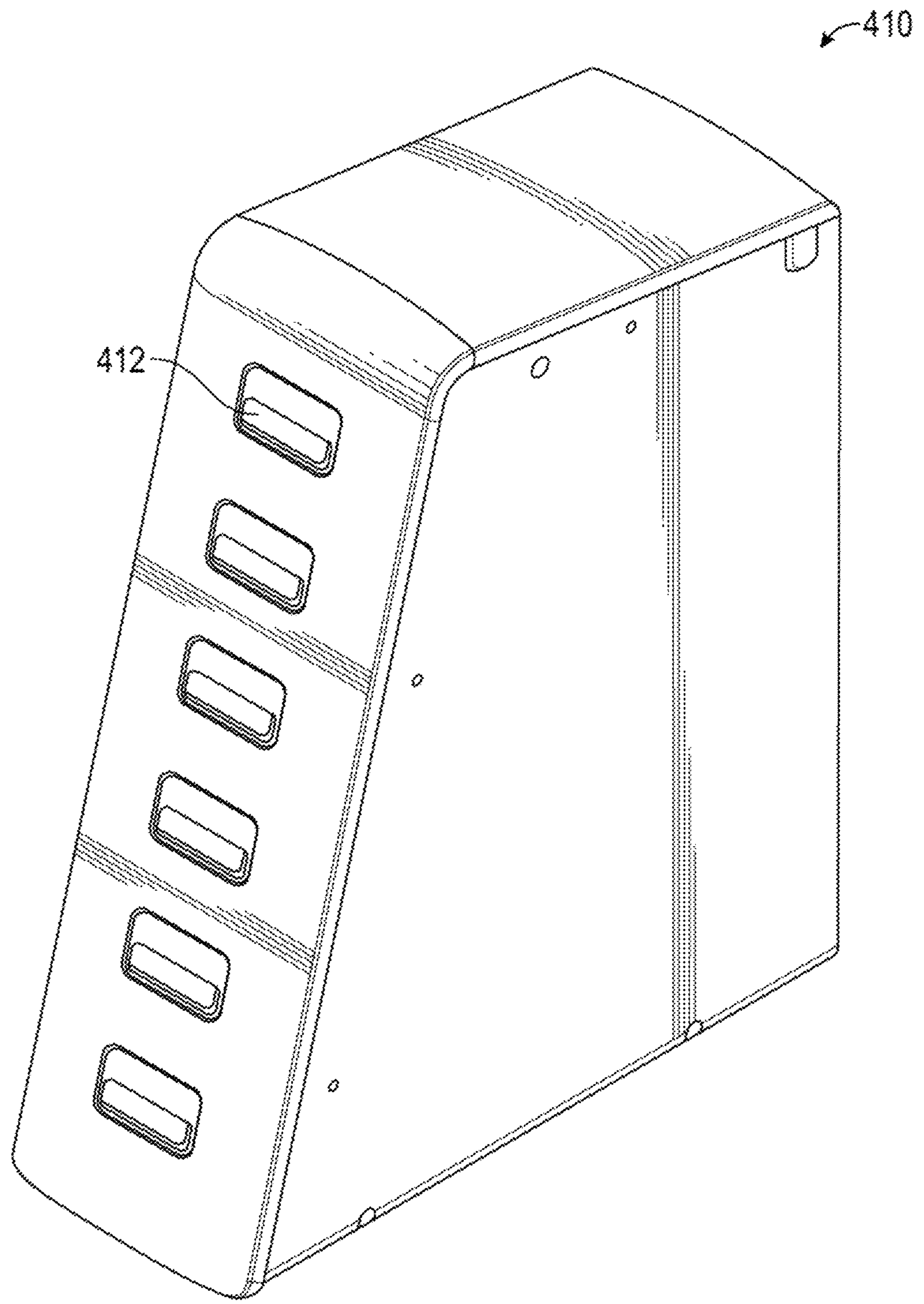
FIG. 34 is a front perspective view of a processing module of the instrument.

As shown in FIGS. 32 and 34, each processing module 410 includes one or more cartridge doors 412, each cartridge door 412 being associated with a processing bay (described below) within which a cartridge 10 may be processed. In the illustrated embodiment, each processing module 410 includes six (6) cartridge doors 412 and associated processing bays. Each cartridge door 412 is configured to accept a multiplex cartridge 10, preferably in a single, preferred orientation. Each cartridge door also preferably includes a closeable door (e.g., a pivoting door panel) that is biased, e.g., by a spring or the like, in a closed position but can be pushed open when a cartridge is inserted therein.

In various embodiments, each processing module 410 is operatively coupled to the control console 402. The processing module 410 may be electronically coupled to the control console 402 so as to enable electronic transmissions between the control console 402 and the processing module 410. Such electronic transmissions may comprise power transmissions from the control console to the processing module for powering various electronic components within the processing module, control signals, input data, output data, etc.

Each processing module 410 may also be physically connected, e.g., in a side-by-side relationship as shown in FIG. 32, with the control console 402. As in the illustrated embodiment, the instrument 400 may include one or more processing modules 410 secured to one or both sides of the control console 402. Additional processing modules maybe secured to other processing modules in a side-by-side relationship on one or both sides of the control console 402. In one preferred arrangement, the instrument 400 includes up to 2 processing modules 410 secured to each side of the control console 402, each processing module 410 comprising six (6) cartridge doors 412 and associated processing bays for processing up to six multiplex cartridges 10 per processing module.

It is preferred that the control console 402 and the processing module 410 be provided in a modular manner as shown. so as to facilitate scalability of the instrument, e.g., by adding one or more processing modules 410 to or subtracting one or more processing modules 410 from a single control console 402, and also to facilitate instrument trouble-shooting whereby a processing module 410 having one or more malfunctioning processing bays can be removed from the instrument for repair or replacement, and the instrument may still be useable with the remaining, operative processing modules 410.

In an alternate embodiment, however, a control console and associated input screen—and/or other input means—and one or more—preferably a plurality of—cartridge doors and associate processing bays may be provided in a single, integral instrument having a single housing.

Figure 35:
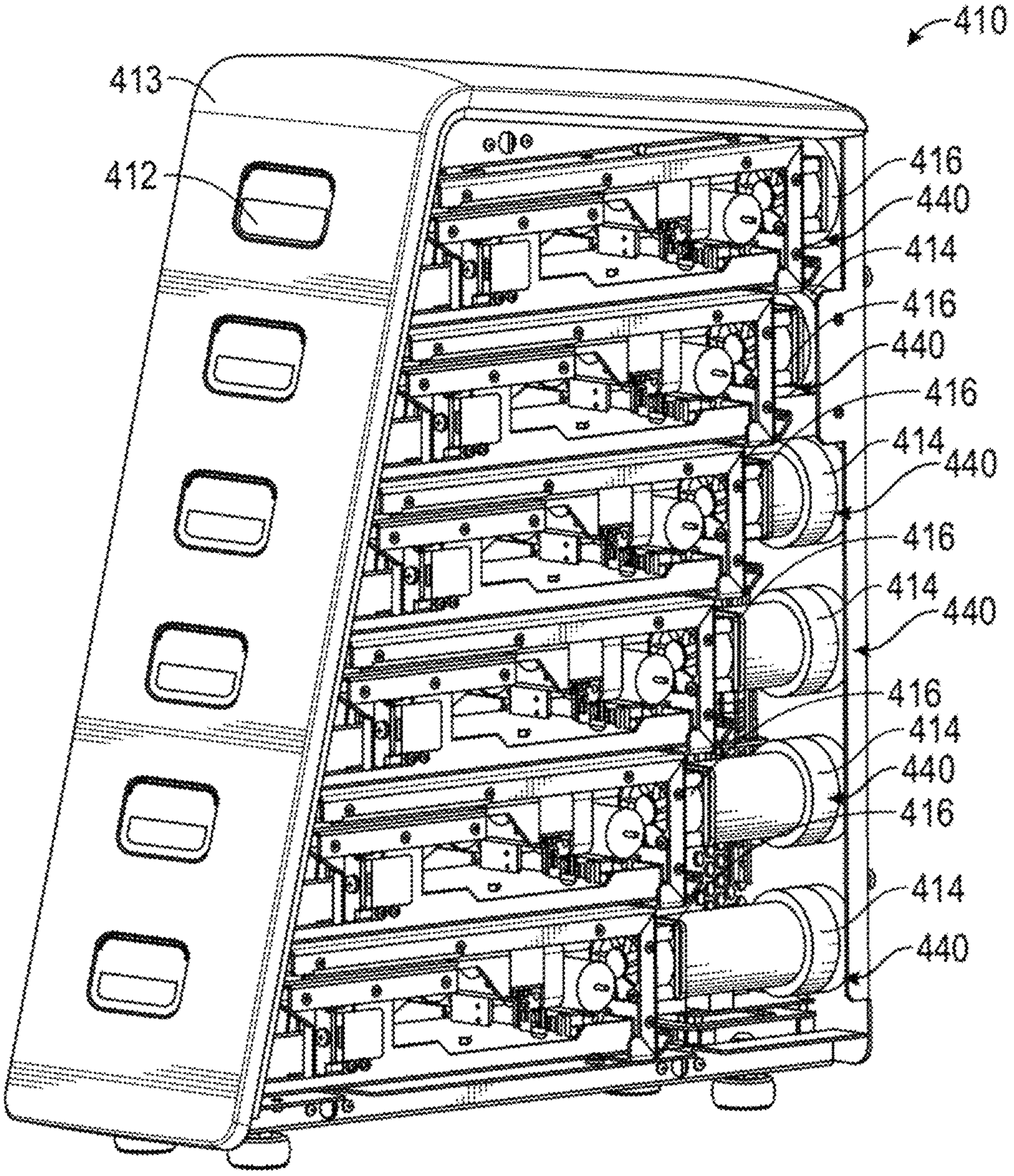
FIG. 35 is a front perspective view of the processing module with one side wall of the module removed to show internal components of the processing module.
Figure 36:
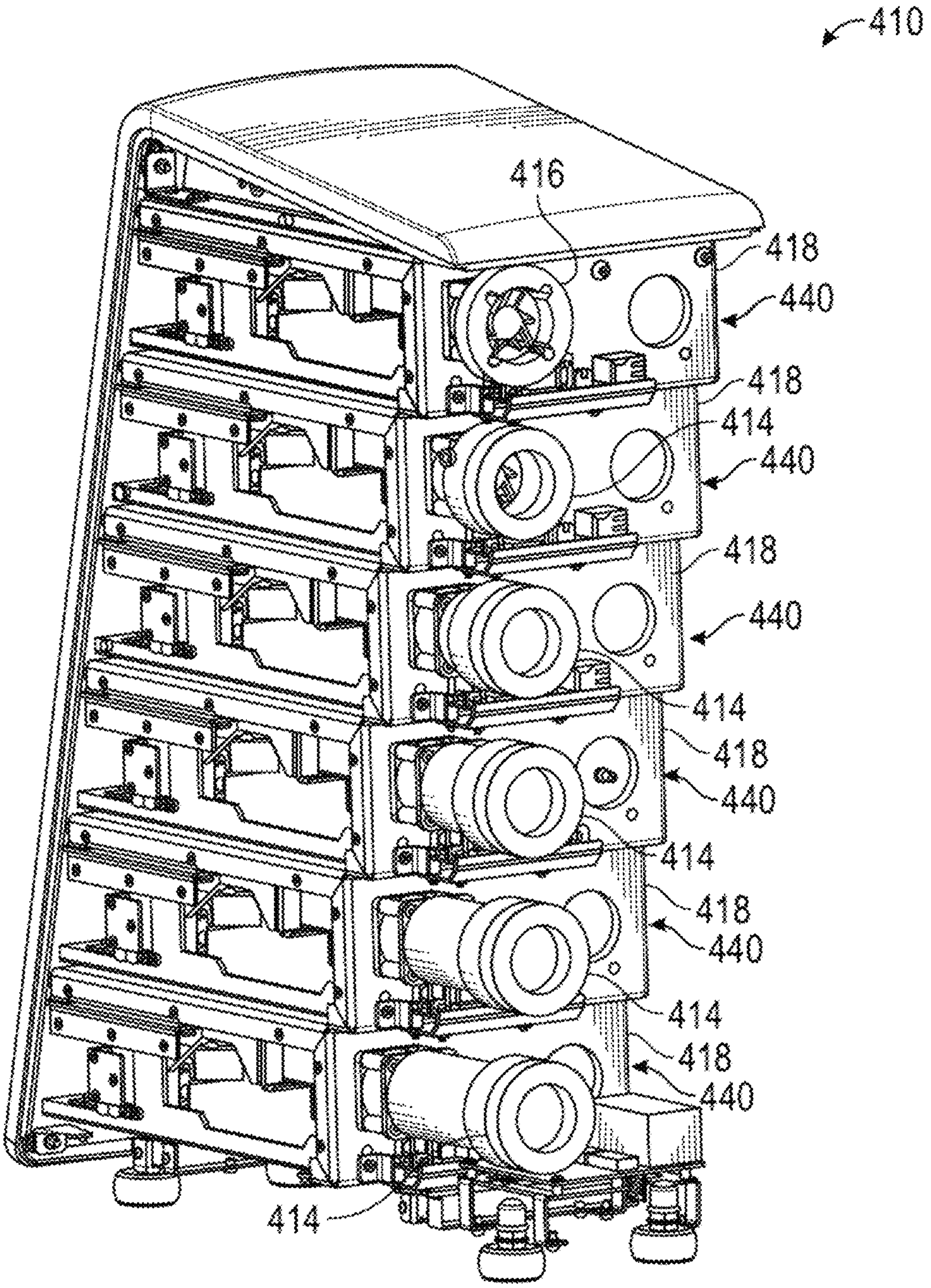
FIG. 36 is a rear perspective view of the processing module with one side wall and the rear wall of the module removed to show internal components of the processing module.
Figure 37:
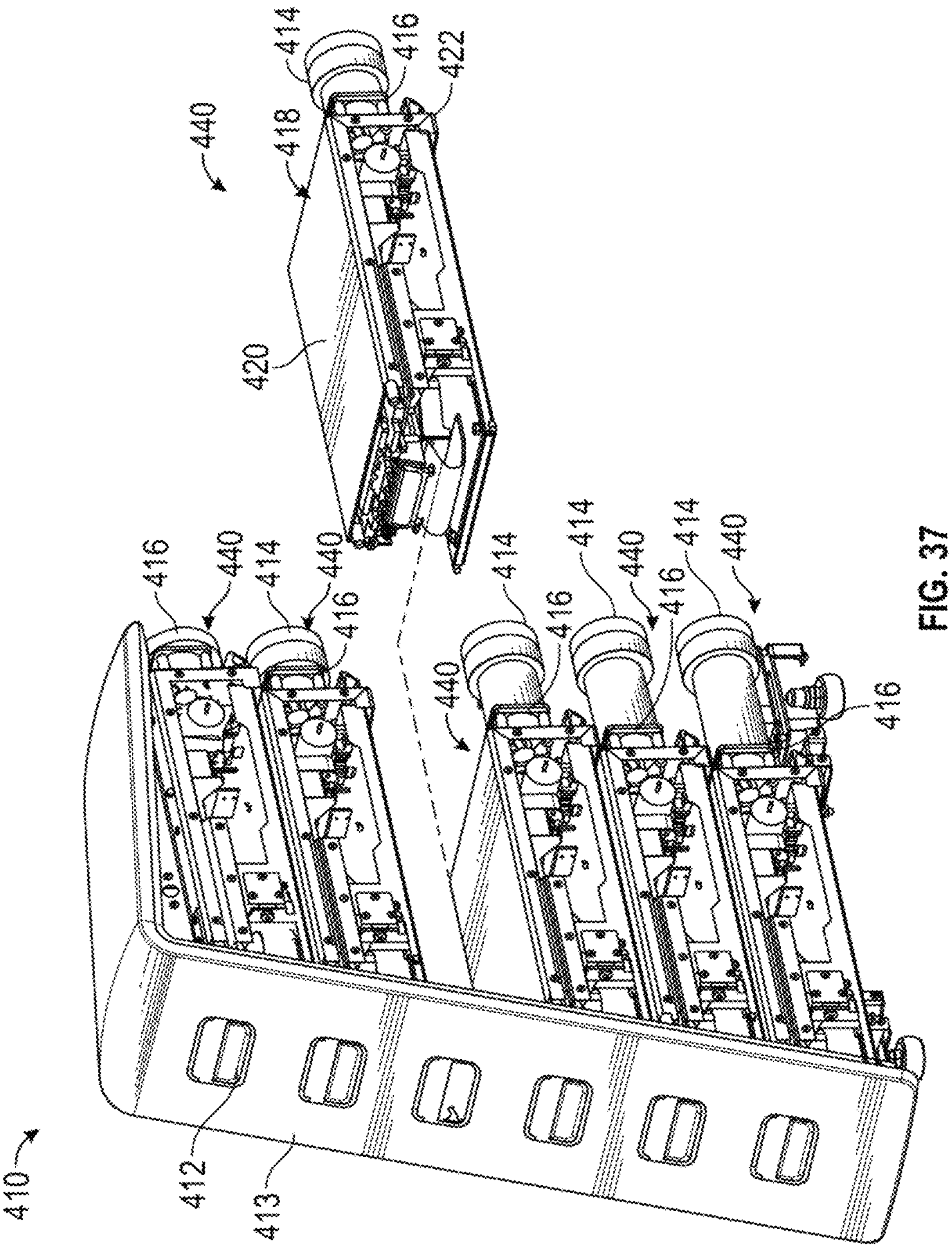
FIG. 37 is a front perspective view of the processing module with one side wall and one rear wall of the module removed and with one processing bay of the processing module exploded from the module.

Further details of the processing module 410 are shown in FIGS. 35, 36, and 37. Each processing module 410 includes a plurality of cartridge doors 412 and associated processing bays 440. The processing module can include 1, preferably 2, preferably 3, preferably 4, preferably 5, preferably 6, preferably 7, preferably 8, preferably 9, preferably 10 processing bays 440. The processing module can include 1-10, preferably 1-6 processing bays 440. The illustrated embodiment includes six (6) processing bays 440. The processing bays 440 are arranged in a stacked arrangement within a housing of the processing module 410. Each processing bay 440 has associated therewith a frame 418 partially surrounding the processing bay with a horizontal top panel 420 and a vertical rear panel 422 (See FIG. 37). As shown in the figures, a front panel 413 of the processing module 410 within which the cartridge doors 412 are positioned is oriented at an angle tilted back from the bottom of the processing module 410 to the top of the processing module 410. This may be for ergonomic and/or esthetic reasons. In other embodiments, a front panel of the processing module may be vertical. Because of the angle of the front panel 413 of the processing module 410, each processing bay 440 is offset horizontally (i.e., rearwardly) relative to the processing bay immediately below it.

In various embodiments, each processing bay 440 has associated therewith a ventilation fan 416 secured to the vertical panel 422 of the housing 418 and a ventilation duct 414 extending from the fan 416 to a rear wall of the housing of the processing module 410. As shown in the figures, due to the tilt of the front panel 413 and the horizontal offset of the processing bays 440, the ventilation ducts 414 have decreasing lengths progressing from the bottom-most processing bay 440 to the top-most processing bay.

The processing module 410 may further include additional structural elements for securing each of the processing bays 440 within the housing of the processing module. The processing bays 440 and processing module 410 are preferably configured so that each bay 440 may be independently removed from the processing module 410 and replaced to facilitate instrument repair if one or more processing bays 440 malfunctions or is otherwise in need of maintenance or repair.

Processing Bay

Figure 38:
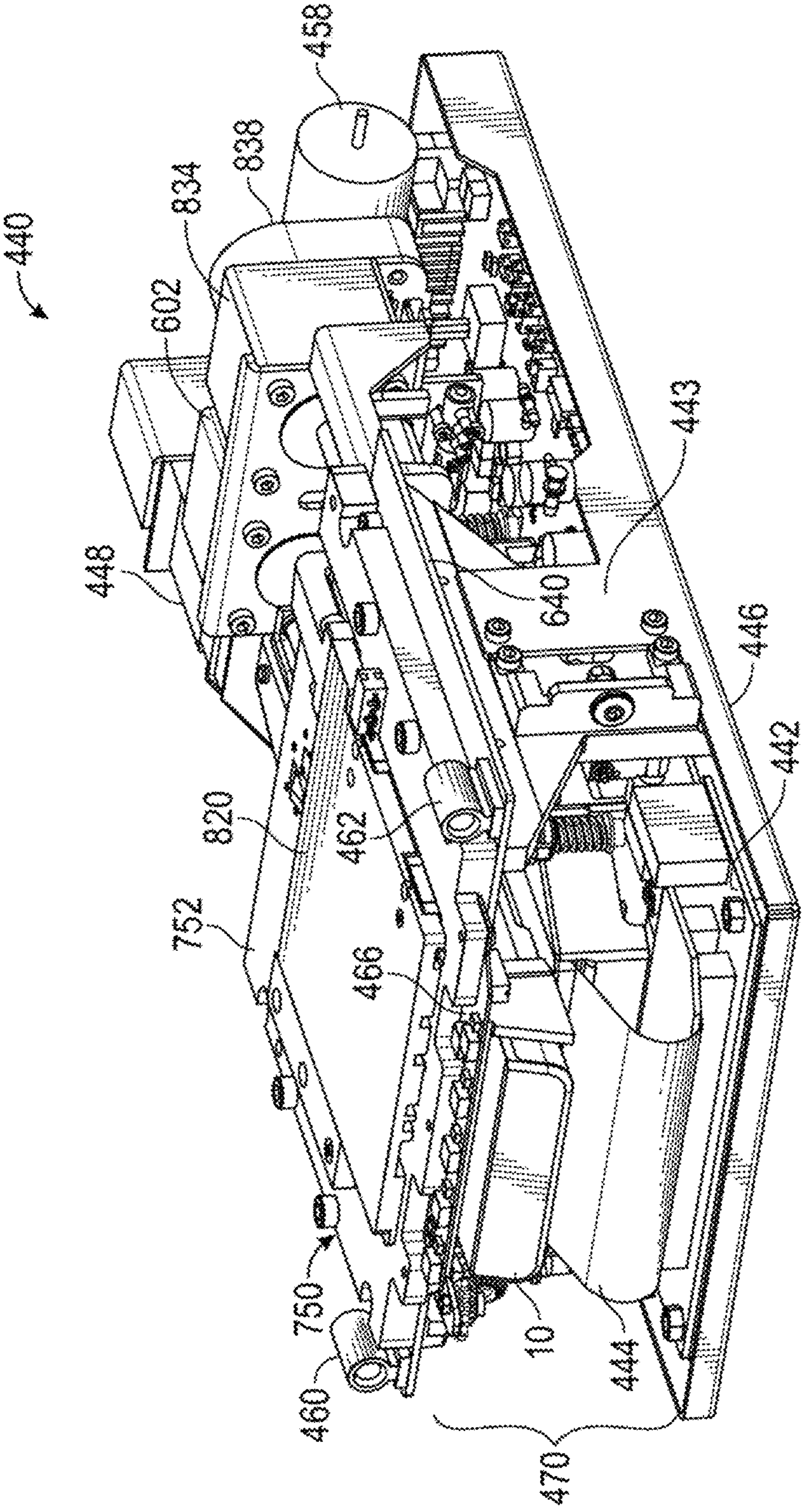
FIG. 38 is a front, right-side perspective view of a processing bay embodying aspects of the present invention.
Figure 39:
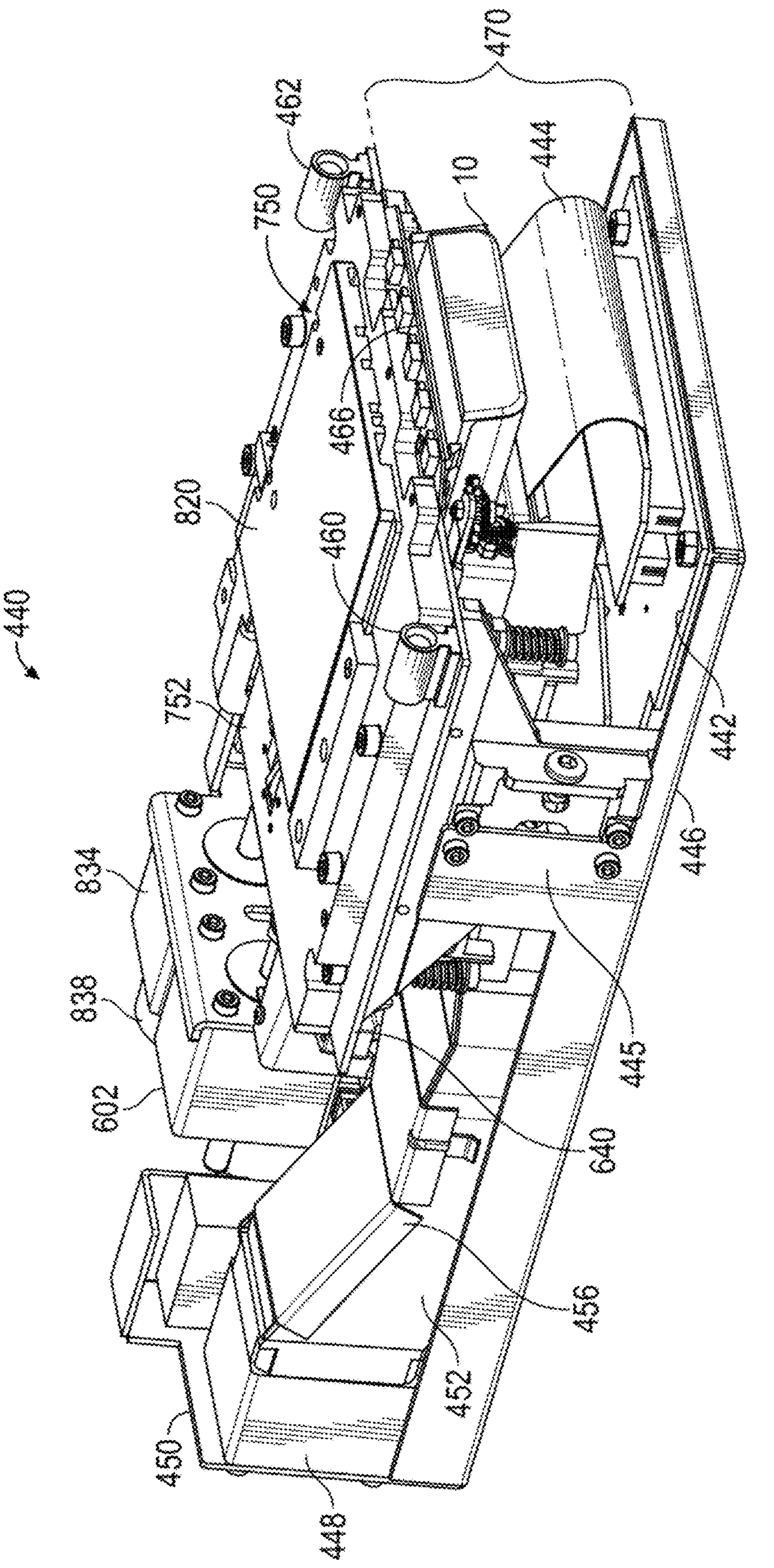
FIG. 39 is a front, left-side perspective view of the processing bay.
Figure 40:
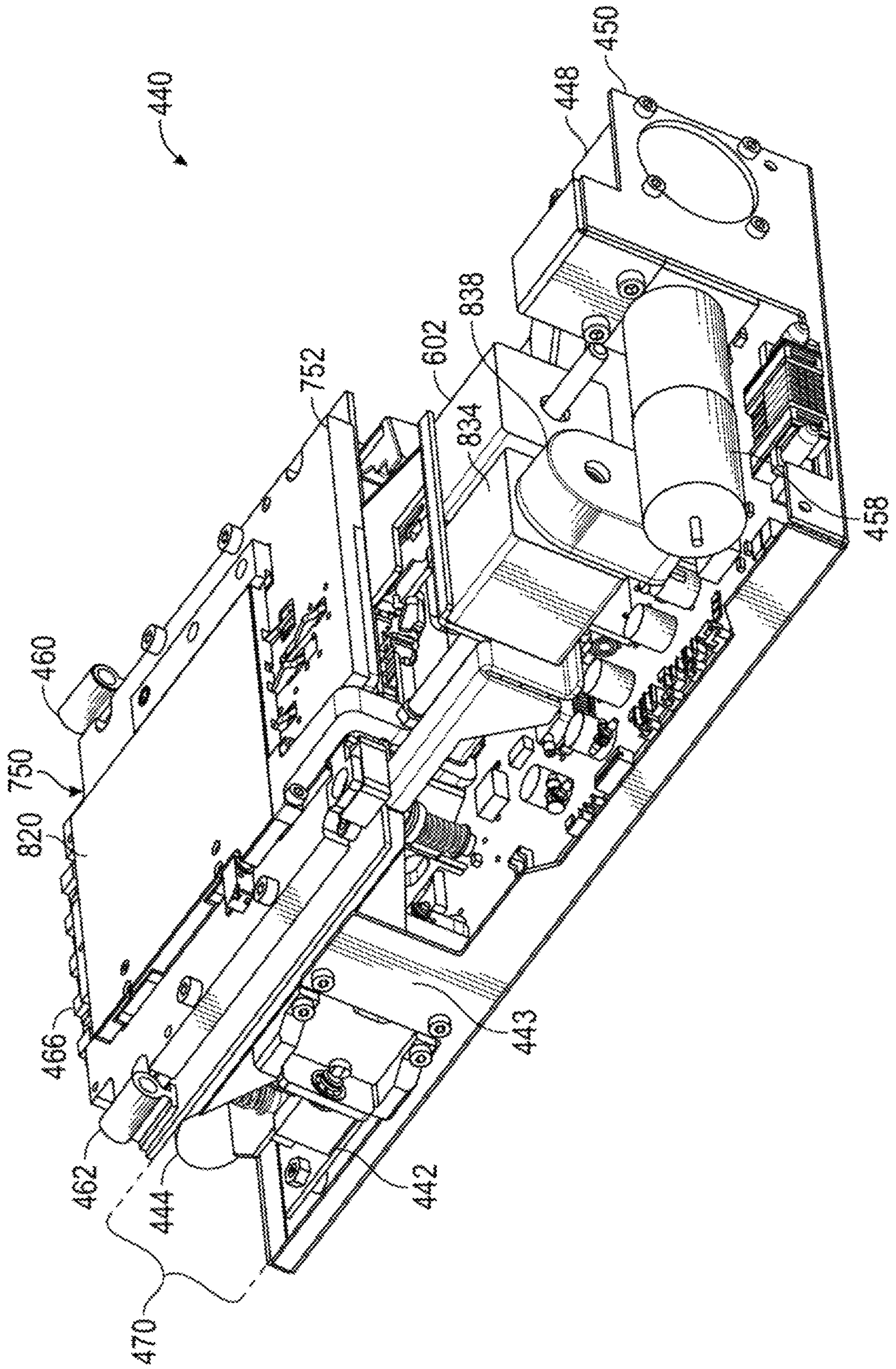
FIG. 40 is a rear, right-side perspective view of the processing bay.
Figure 41:
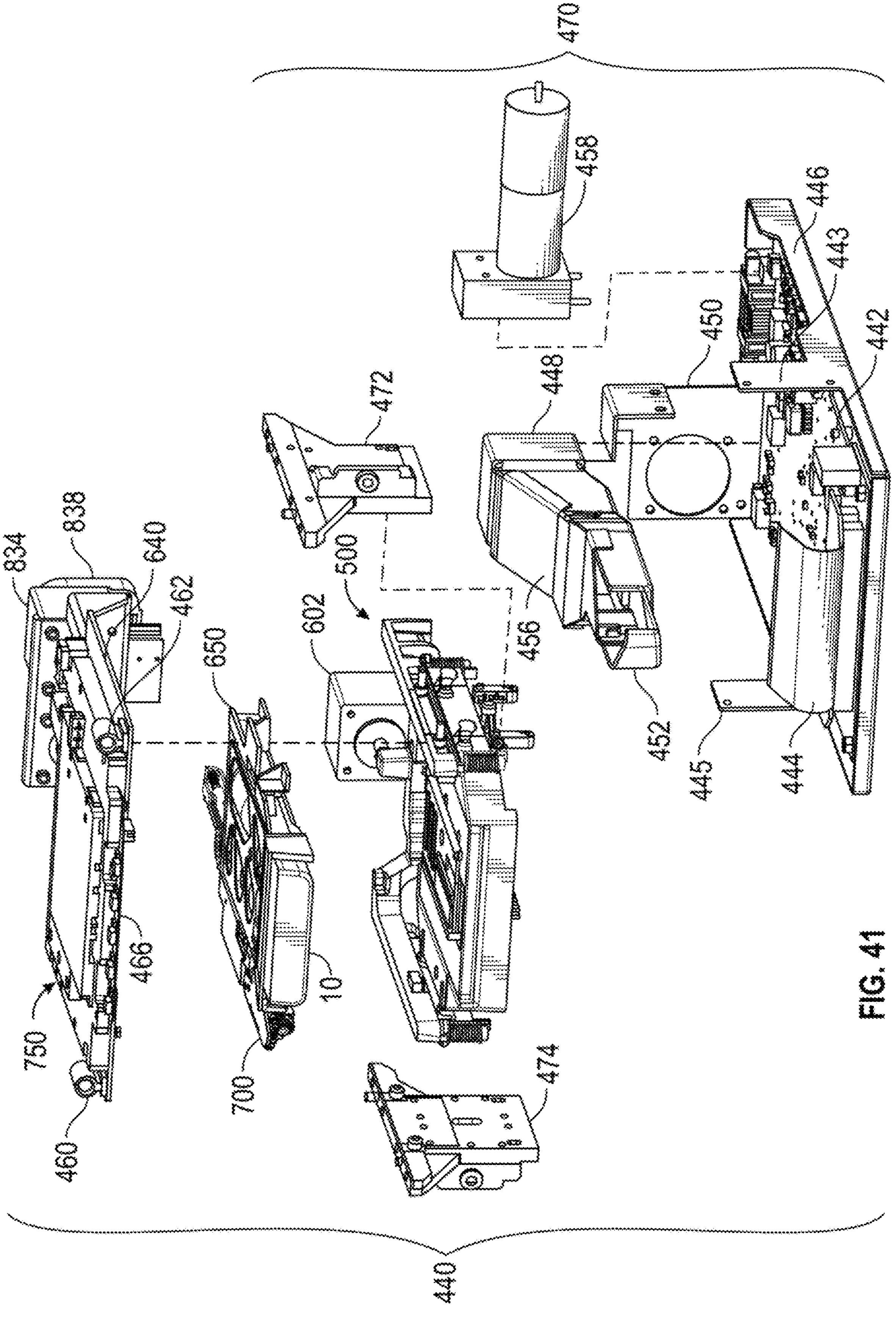
FIG. 41 is a front, right-side, exploded perspective view of the processing bay.

A processing bay 440 is shown in various views in FIGS. 38, 39, 40, and 41. In each of FIGS. 38-41, the frame 418 of the processing bay 440 is omitted from the figure. FIG. 38 is a front, right-side perspective view of the processing module 440 with a multiplex cartridge 10 inserted therein. FIG. 39 is a front, left-side perspective view of the processing module 440 with a multiplex cartridge 10 inserted therein. FIG. 40 is a rear, right-side perspective view of the processing module 440. FIG. 41 is a front, right-side, exploded perspective view of the processing module 440 with a multiplex cartridge 10 inserted therein.

Each processing bay 440 has a drip tray 446 forming a lower floor of the processing bay 440 and constructed and arranged to contain fluid leaks that may occur from the multiplex cartridge 10 and to provide a support and mounting structure for various components of the processing bay 440. A main PCB (printed circuit board) 442, also referred to as the bay PCB, provides primary control of the processing bay 440 as well as data and power distribution and transmission. A flexible connector 444 connects the bay PCB 442 with a connector PCB (described below, not visible in FIGS. 38-41) within the processing bay 440, as will be described in further detail below. The processing bay 440 may further include alignment elements, such as two (2) tubular female alignment elements 460, 462, that receive male alignment elements disposed within the processing module 410 for properly aligning and positioning the processing bay 440 in a bay mounting location within the processing module 410.

The processing bay 440 may be conceptually divided along functional lines between a cartridge processing assembly 470 (also known as the lower bay) and a blister (or deformable chamber) compression mechanism assembly 750 (also known as the upper bay). The primary function of the cartridge processing assembly 470 is to receive the cartridge 10, secure the cartridge within the bay 440, apply heat and magnetic forces to the processing module 240 of the multiplex cartridge 10, apply controlled power to the multiplex cartridge 10, engage the rotary mixer 192 of the cartridge 10 and effect powered rotation of the rotary mixer 192, and eject the cartridge 10 from the processing bay 440 at the conclusion of an assay or other process performed within the bay 440. The primary function of the blister compression mechanism assembly 750 is to collapse the various deformable chambers of the multiplex cartridge 10 in a proper sequence. Each of these various components will be discussed in further detail below.

Processing bay 440 further includes an LED PCB 466 for controlling one or more LEDs that provide information to a user, such as indicating the status of the processing bay 440 and/or whether a cartridge is located within the processing bay 440. The status LEDs may be visible via a light pipe or other optical transmitter that provides an optical indication signal adjacent to the cartridge door 412 associated with the bay 440 on the front panel 413 of the processing module 410. The LED PCB 466 may also control optical sensors constructed and arranged to detect (e.g., generate a signal), through the inlet and outlet optical ports 14, 16, fluid flow through the inlet optical sensing chamber 154 and the outlet optical sensing chamber 158 of the sample preparation module 70.

Sidewalls 472, 474 extend upwardly along opposite sides of the processing bay 440 and may be secured to upwardly extending elements 443 445 of the drip tray 446. A mounting plate 640 includes a generally horizontal blister plate 644 (see FIG. 42) secured to the top edges of the sidewalls 472, 474 and which generally separates the cartridge processing assembly 470 from the blister compression assembly 750.

In various embodiments, each processing bay 440 further includes a cam follower motor 834 and an associated encoder 838 and a cam frame motor 602. The cam plate motor 834 and the cam frame motor 602 are secured to a motor mount 642 of the mounting plate 640 (see FIG. 42).

A pump 458 provides the pressure that is applied to the multiplex cartridge 10 via the pump port 104.

As will be described in further detail below, the cartridge processing assembly 470 includes a Peltier heater assembly for effecting thermal processes within the processing bay 440. To ventilate the processing bay 440 and dissipate excess heat generated at the Peltier heater, the processing bay 440 may include a peltier ventilation assembly. The ventilation assembly comprises a cooling fan 448 attached to a fan mount 450 of the drip tray 446 and positioned in front of an airflow duct extending between the cooling fan 448 and the Peltier heating assembly within the processing bay 440. In various embodiments, the airflow duct may comprise a cooling duct 452 and a duct cover 456 extending between the cooling fan 448 and the beginning of the cooling duct 452. (See FIGS. 39 and 41).

Cartridge Processing Assembly (Lower Bay)

Figure 42:
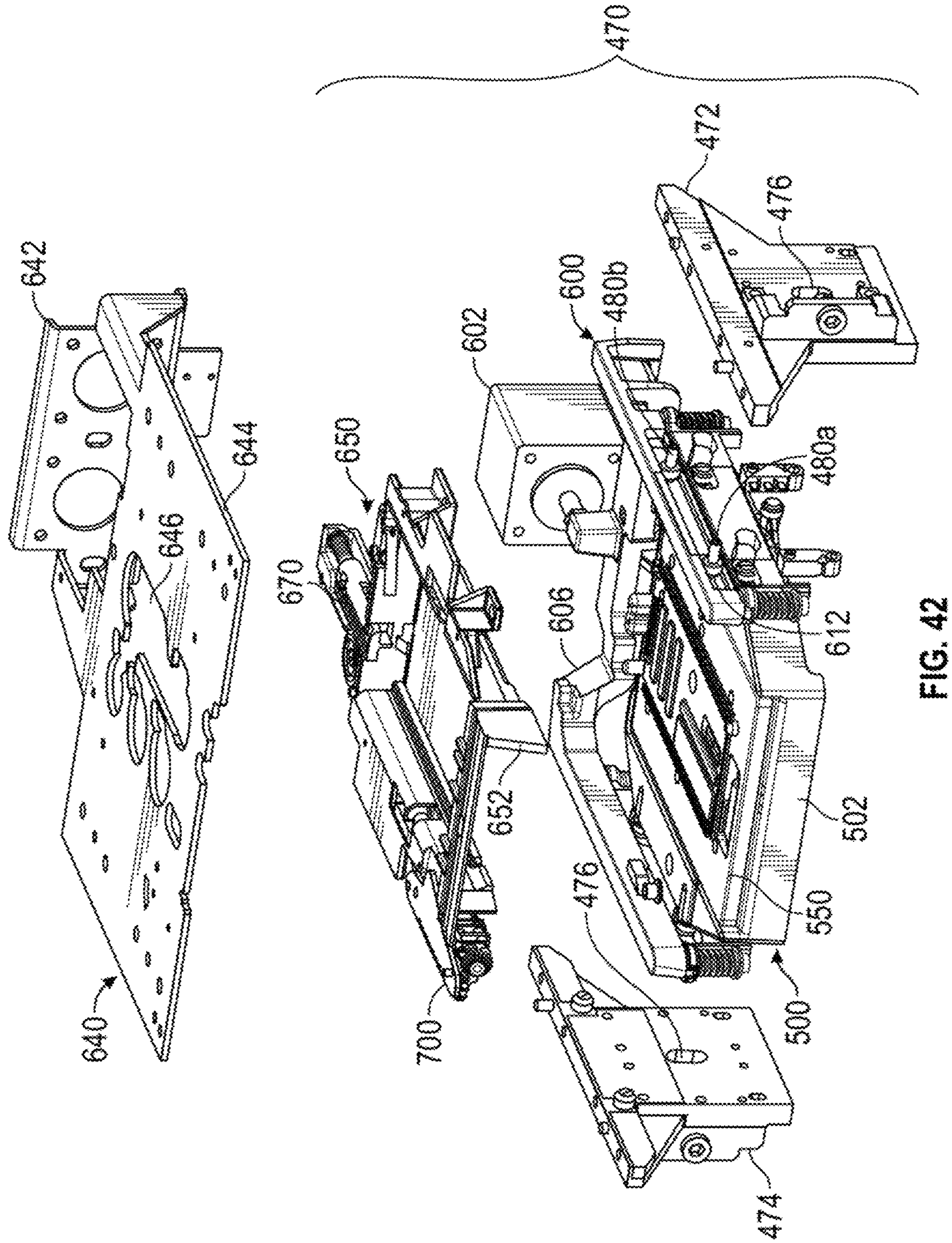
FIG. 42 is an exploded perspective view of the cartridge processing assembly of the processing bay.

Aspects of the cartridge processing assembly 470 are shown in FIGS. 41 and 42. As noted above, most features of the cartridge processing assembly 470 are located beneath the blister plate 644 of the motor mount 642. The cartridge processing assembly 470 includes a cartridge carriage assembly 650 configured to receive and hold, and later eject, a multiplex cartridge 10. The cartridge carriage assembly 650 is secured to a bottom surface of the blister plate 644 of the mounting plate 640.

A cam block assembly 600 includes a cam frame 606 that surrounds the cartridge carriage assembly 650 on three sides and is mounted for linear fore and aft movement within the processing bay 440 where it is supported on linear cam followers 480*a*, 480*b* extending from each of the sidewalls 472, 474 into a follower slot 612 formed on each side of the cam frame 606.

A mixing motor assembly 700 is pivotally connected to the blister plate 644 beneath the blister plate and is configured to pivot into and out of an operative engagement with the rotary mixer 192 of the multiplex cartridge 10 disposed within the cartridge carriage assembly 650.

A heating and control assembly 500 is positioned beneath the cartridge carriage assembly 650 and is operatively coupled to the cam frame 606 and the cam block assembly 600 for converting the longitudinal, fore and aft movement of the cam frame 606 into vertical movement of the heating and control assembly 500 for selectively bringing the heating and control assembly 500 into contact with a bottom surface of the multiplex cartridge 10 when a cartridge is inserted into the cartridge carriage assembly 650.

Cartridge Carriage Assembly

Figure 46:
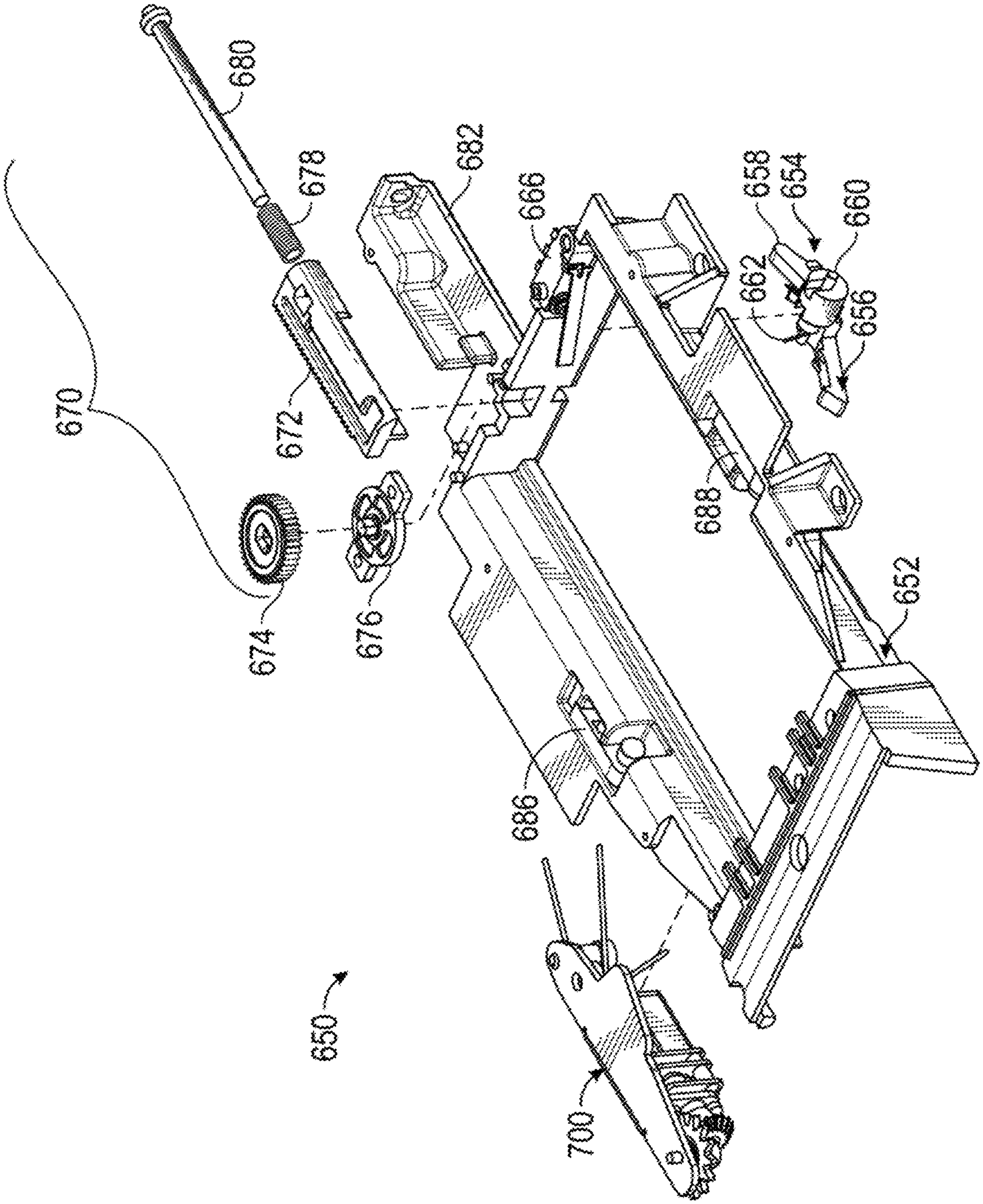
FIG. 46 is an exploded perspective view of a cartridge carriage assembly of the cartridge processing assembly.

Further details of the cartridge carriage assembly 650 are shown in FIG. 46, which is an exploded perspective view of the cartridge carriage assembly 650 with other components of the cartridge processing assembly 470 omitted. The cartridge carriage assembly 650 includes a carriage holder 652 comprising a generally rectangular frame which is secured to the underside of the blister plate 644 of the mounting plate 640. A detector may be provided for detecting when a multiplex cartridge 10 (not shown in FIG. 46) is inserted into the cartridge holder 652. In various embodiments, the detector comprises an optical detector comprising an emitter 686 and detector 688 each disposed within a respective pocket on opposite sides of the cartridge holder 652. An optical beam from the emitter 686 to the detector 688 is broken when a multiplex cartridge is inserted into the cartridge holder 652, thereby generating a signal indicating the presence of the cartridge.

A cartridge latch 654 is mounted for pivotal movement at a closed end of the cartridge holder 652. The cartridge latch 654 is pivotally mounted on a latch pin 660 for rotation about a horizontal axis of rotation. The cartridge latch 654 further includes a forward hook 656 and a trailing lever 658. A torsion spring 662 rotationally biases the latch 654 so that the hook 656 is in an upward position. When a cartridge 10 is inserted into the cartridge holder 652, the cartridge pushes the hook down until the hook 656 of the cartridge latch 654 engages a recess in a bottom portion of the lower shroud 30 of the cartridge 10. The bias of the torsion spring 662 holds the hook 656 into that recess to retain the cartridge within the cartridge holder 652.

A cartridge ejector assembly 670 includes an ejector rack 672 that is positioned within an ejector bracket 682 extending off a rear end of the cartridge holder 652. The linear gear-teeth of the ejector rack 672 engage a damper pinion gear 674 that is coupled to a rotary damper 676 and is mounted for rotation on the ejector bracket 682 adjacent the ejector rack 672. A spring capture pin 680 extends through the ejector rack 672 and is supported at an end thereof by an end wall of the ejector bracket 682. A compression spring 678 is disposed between an end of the ejector rack 672 and the end of the spring capture pin 680. Accordingly, the ejector rack 672 is biased longitudinally toward the open end of the cartridge holder 652. A limit stop element may be provided to prevent the cartridge rack 672 from being pushed too far by the spring 678. The ejector rack 672 initially extends into the cartridge holder 652 and is contacted by the end of a multiplex cartridge 10 inserted into the cartridge holder 652. As the cartridge is further inserted into the cartridge holder 652, the ejector rack 672 is pushed back, thereby compressing the spring 678 and generating a bias force urging the cartridge 10 longitudinally toward the open end of the cartridge holder 652 and out of the processing bay 440. Because the cartridge latch 654 captures the fully-inserted multiplex cartridge, the ejector assembly 670 is prevented from pushing the cartridge back out of the cartridge holder 652.

A cartridge latch switch 666 is positioned at the closed end of the cartridge holder 652 and is configured to signal when the multiplex cartridge has been inserted to a position within the cartridge holder 652, such that the cartridge will be engaged by the cartridge latch 654. At the conclusion of an assay or other process performed within the processing bay 440 the cartridge latch 654 is pivoted (counterclockwise in the illustrated embodiment) against the bias of the torsion spring 662, in a manner that will be described below, to thereby release the multiplex cartridge held within the cartridge holder 652. Upon release of the cartridge, the cartridge is ejected by the stored energy in the compress spring 678 bearing against the ejector rack 672. The damper pinion 674 and the operatively-associated rotary damper 676 with which the ejector rack 672 is engaged ensures a controlled release of the ejector rack 672 so that the multiplex cartridge 10 is not ejected too abruptly from the cartridge holder 652.

Heating and Control Assembly

Figure 43:
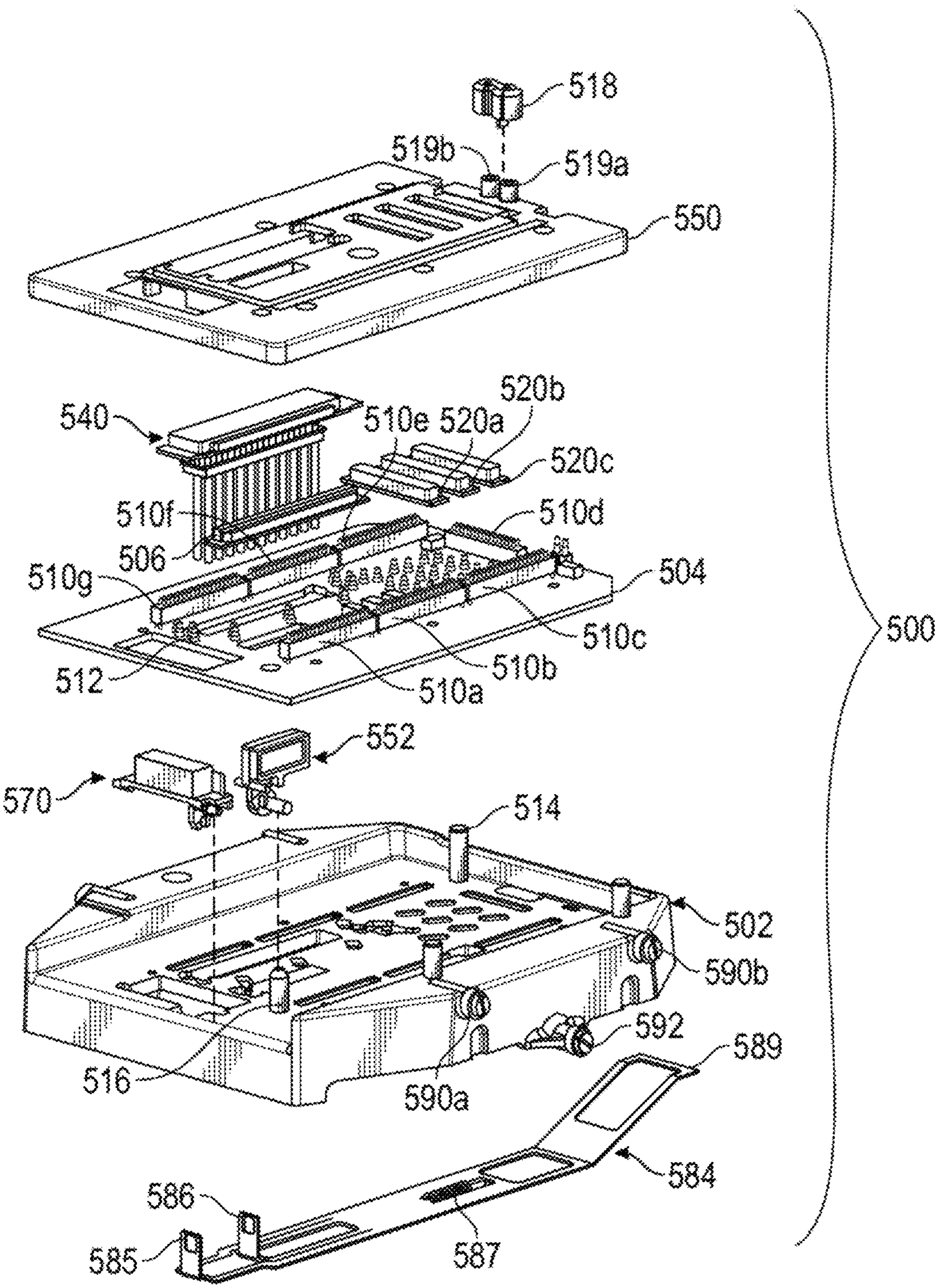
FIG. 43 is an exploded perspective view of a heating and control assembly of the cartridge processing assembly.

Details of the heating and control assembly 500 are shown in FIG. 43, which is an exploded perspective view of the heating and control assembly 500 with other components of the cartridge processing assembly 470 omitted.

The heating and control assembly 500 includes a support plate 502, a connector PCB 504 supported on the support plate 502, a cover plate 550 partially covering the connector PCB 504, a cartridge magnet assembly 552, a sample preparation magnet assembly 570, and a magnet actuator 584 located beneath the support plate 502. A front alignment pin 416 and a rear alignment pin 414 extend upwardly from the support plate 502.

A pneumatic connector 518 is attached to pneumatic ports 519*a*, 519*b* of the cover plate 550. The pneumatic connector 518 provides a connection between the pressure source, e.g., pump 458, and the cartridge 10 via pump port 104 and provides a connection between an external valve within the processing bay 440 and the passive valve assembly 220 of the cartridge 10 via the passive valve port 108 (see FIG. 15).

Figure 44:
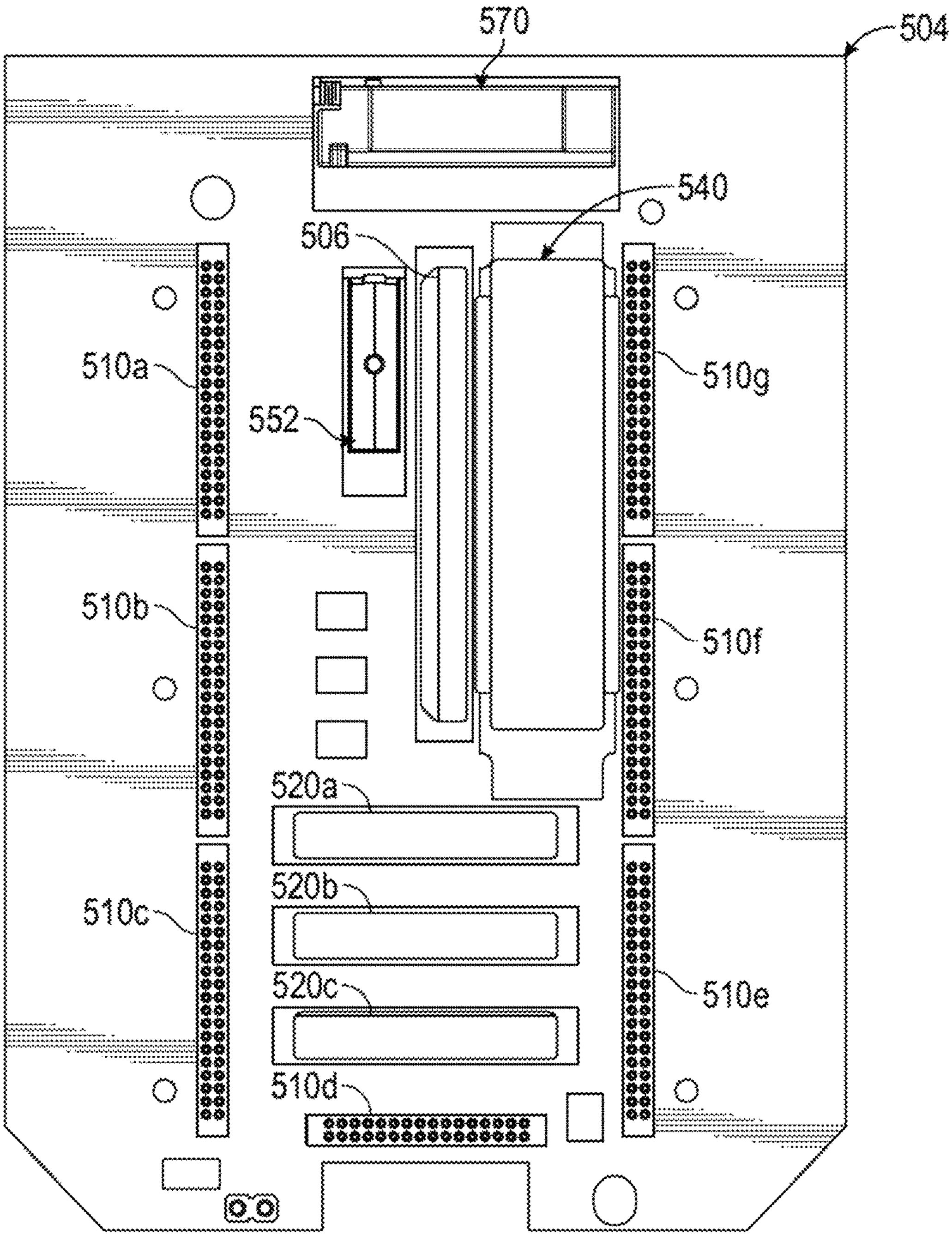
FIG. 44 is a top plan view of a connector PCB and magnets of the heating and control assembly of the cartridge processing assembly.

Referring to FIGS. 43 and 44, which is a top plan view of the connector PCB 504, the connector PCB 504 includes an elution heater assembly 506, a detection Peltier assembly 540, and PCR heater assembly 520*a*, 520*b*, and 520*c*. In various embodiments, the elution heater assembly 506 comprises a resistive heating element attached to a dedicated PCB and a heat spreader comprised of a thermally-conductive material attached or otherwise thermally coupled to the resistive heating element. Similarly, in various embodiments, each element 520*a*, 520*b*, and 520*c* of the PCR heater assembly comprises a resistive heating element attached to a dedicated PCB and a heat spreader comprised of a thermally-conductive material attached or otherwise thermally coupled to the resistive heating element.

Figure 45:
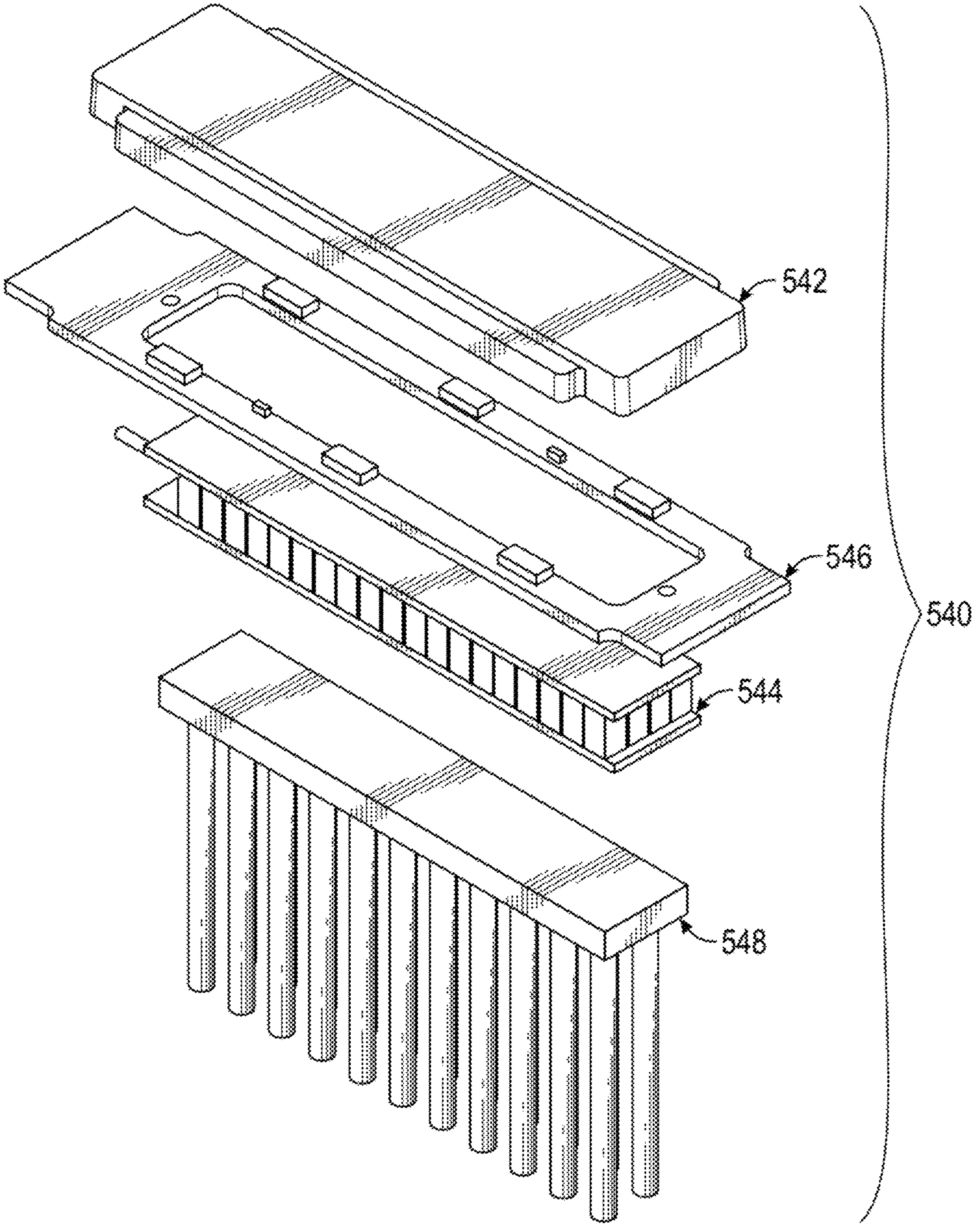
FIG. 45 is an exploded perspective view of a detection Peltier heater assembly of the heating and control assembly.

Details of the detection Peltier assembly 540 are show in FIG. 45, which is an exploded, perspective view of the Peltier assembly 540. The assembly 540 includes a Peltier device 544 (i.e., a thermoelectric element) coupled to a power and control printed circuit board 546. A heat spreader 542, preferably comprised of a thermally conductive material, is disposed above the Peltier device 544. A heat sink 548 is disposed beneath the peltier chip 544. The heat sink 548 may comprise a panel that is in surface-to-surface contact with a surface of the Peltier device 544 with a plurality of heat-dissipating rods (or fins) extending therefrom and formed from a thermally conductive material. The detection Peltier assembly 540 is mounted within, and at least a portion of the heat sink 548 extends through, an associated opening formed in the support plate 542. The heat dissipating rods of the heat sink 548 extend beneath the support plate 502 and are disposed at a terminal end of the Peltier cooling duct 452 (See FIGS. 39 and 41). In one embodiment, the detection Peltier is configured to apply a thermal gradient to, e.g., reduce the temperature of, a detection area, e.g., the detection region 378, of the multiplex cartridge 10.

A plurality of connector pin arrays 510*a*, 510*b*, 510*c*, 510*d*, 510*d*, 510*e*, 510*f*, and 510*g* are disposed around the connector PCB 504 and comprise arrays of connector pogo pins that contact and effect electrical connection between connection pads of associated connector pad arrays 358*a*-358*g* of the fluidic processing panel 354 of the multiplex cartridge 10 (See FIG. 58). Connections between the connector pin arrays 510*a*-510*g* and the connector pad arrays 358*a*-358*g* provides connections between the instrument 400 and the multiplex cartridge 10 for, e.g., power, control signals, and data. For example, the connections between the connector pin arrays 510*a*-510*g* and the connector pad arrays 358*a*-358*g* provides provide power and control from the instrument to the electrowetting grid (e.g., the thermal cycling tracks 364*a*-364*d*, the sample bead zone 368, the hybridization zone 370, the elution buffer zone 372, the exonuclease reagent zone 374, the PCR reagent zone 376, the detection mixing zones 385*a*-385*d*, and the exonuclease zone 384). In addition, connections between the connector pin arrays 510*a*-510*g* and the connector pad arrays 358*a*-358*g* provides power to and receives date from the electrosensor arrays 363*a*-363*d*.

As shown in FIG. 43, the connector PCB 504 further includes a number of heater pins 512—which may comprise pogo pins—that connect to the various heater assemblies 540, 506, and 520*a, b, c*.

The heating and control assembly 500 further includes a cartridge magnet assembly 552 and a sample preparation magnet assembly 570.

Figure 49A:
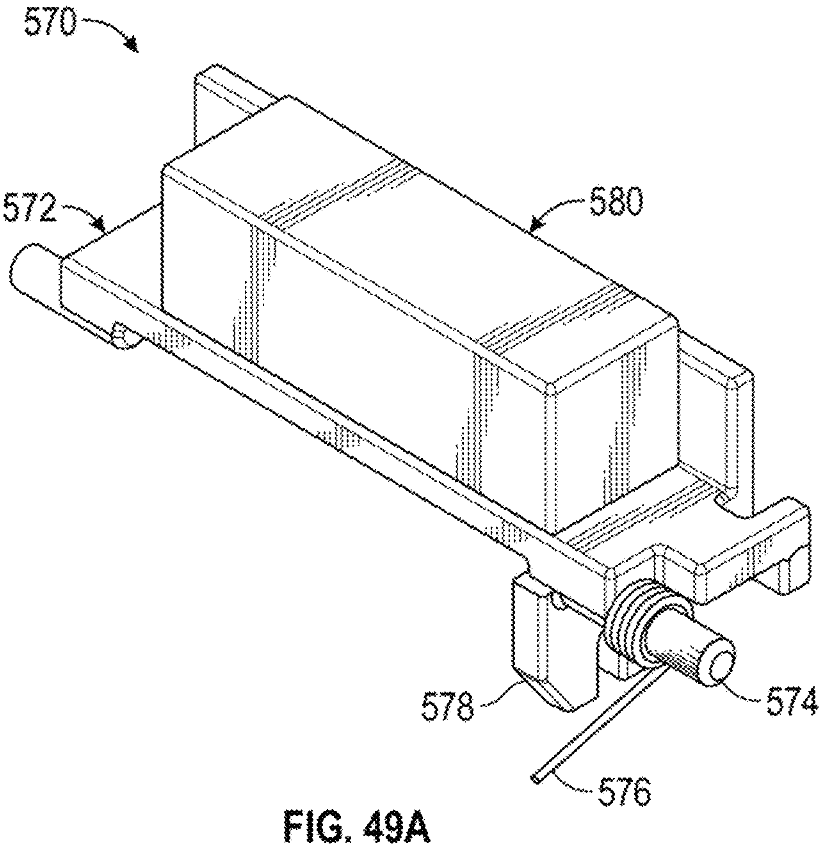
FIG. 49A is a top perspective view of a sample preparation magnet assembly of the cartridge processing assembly.

Details of the sample preparation magnet assembly 570 are shown in FIG. 49A, which is a top perspective view of the sample preparation magnet assembly. The sample preparation magnet assembly 570 comprises a magnet holder 572 mounted on a horizontal spindle 574 so as to be rotatable about the spindle 574 relative to the support plate 502. A torsion spring 576 biases the sample preparation magnet assembly 570 downwardly. An actuator bracket 578 extends beneath the magnet holder 572, and a magnet 580 is supported on top of the magnet holder 572 and is secured thereto, e.g., by a suitable adhesive. When deployed and rotated upwardly against the bias of the torsion spring 576, the magnet 580 extends through aligned openings formed in the support plate 502, the connector PCB 504, and the cover plate 550.

The sample preparation magnet assembly 570, when deployed, is positioned adjacent the capture chamber 100 of the sample preparation module 70 of the multiplex cartridge 10 to thereby apply a magnetic force to fluids contained within and flowing through the capture chamber.

Figure 49B:
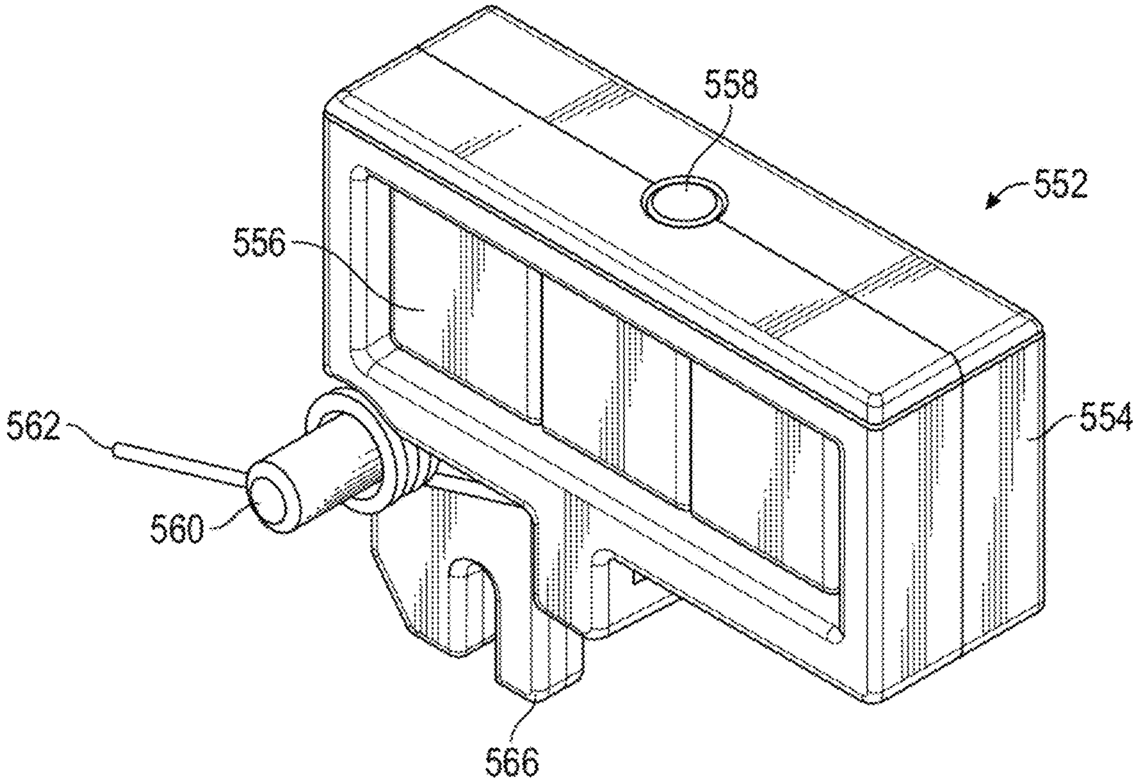
FIG. 49B is a top perspective view of a cartridge magnet assembly of the cartridge processing assembly.

Details of the cartridge magnet assembly 552 are shown in FIG. 49B, which is a top perspective view of the cartridge magnet assembly. The cartridge magnet assembly 552 comprises a magnet holder frame 554 and a magnet array 556 disposed within the magnet holder frame 554. The magnet array 556 may comprise individual magnets (e.g., three), and may be surrounded on four sides by the magnet holder frame 554 to form a frame surrounding the magnet array 556. The magnet array 556 may be secured within the magnet holder frame 554 by, for example, a suitable adhesive. A focusing magnet 558 is disposed within an opening in a top part of the frame of the magnet holder 554. In one embodiment, the focusing magnet 558 is cylindrical and may comprise neodymium N52. The focusing magnet 558 focuses the magnetic forces of the magnet array 556 to a relatively small area for attracting magnetic target capture beads to that small area. The magnet holder 554 is mounted on a horizontal spindle 560 connected to the support plate 502 so that the magnet holder 554 and the magnet array 556 are rotatable about the spindle 560. A torsion spring 562 biases the cartridge magnet assembly 552 downwardly. An actuator bracket 566 extends beneath the magnet holder 554. When the magnet holder 554 is rotated upwardly against the bias of the torsion spring 562, the upper portion of the magnet assembly 552 extends through aligned openings formed in the support plate 502, the connector PCB 504, and the cover plate 550.

The cartridge magnet assembly 552, when deployed, is positioned adjacent to the sample chamber 266 of the reaction module 240, adjacent to a position indicated by reference number 270 (see FIG. 26).

Returning now to FIG. 43, cam followers 590*a* and 590*b* extend from opposite sides of the support plate 502 and a slot follower 592 extends from opposite sides of the support plate 502. The slot followers 592 extend into and are vertically movable within a slot 476 formed in each of the side walls 472, 474 (see FIG. 42) and are configured to enable vertical movement of the support plate 502 relative to the side walls 472, 474 while preventing horizontal movement of the support plate 502 relative to the side walls 472, 474.

Cam Frame Assembly

Figure 47:
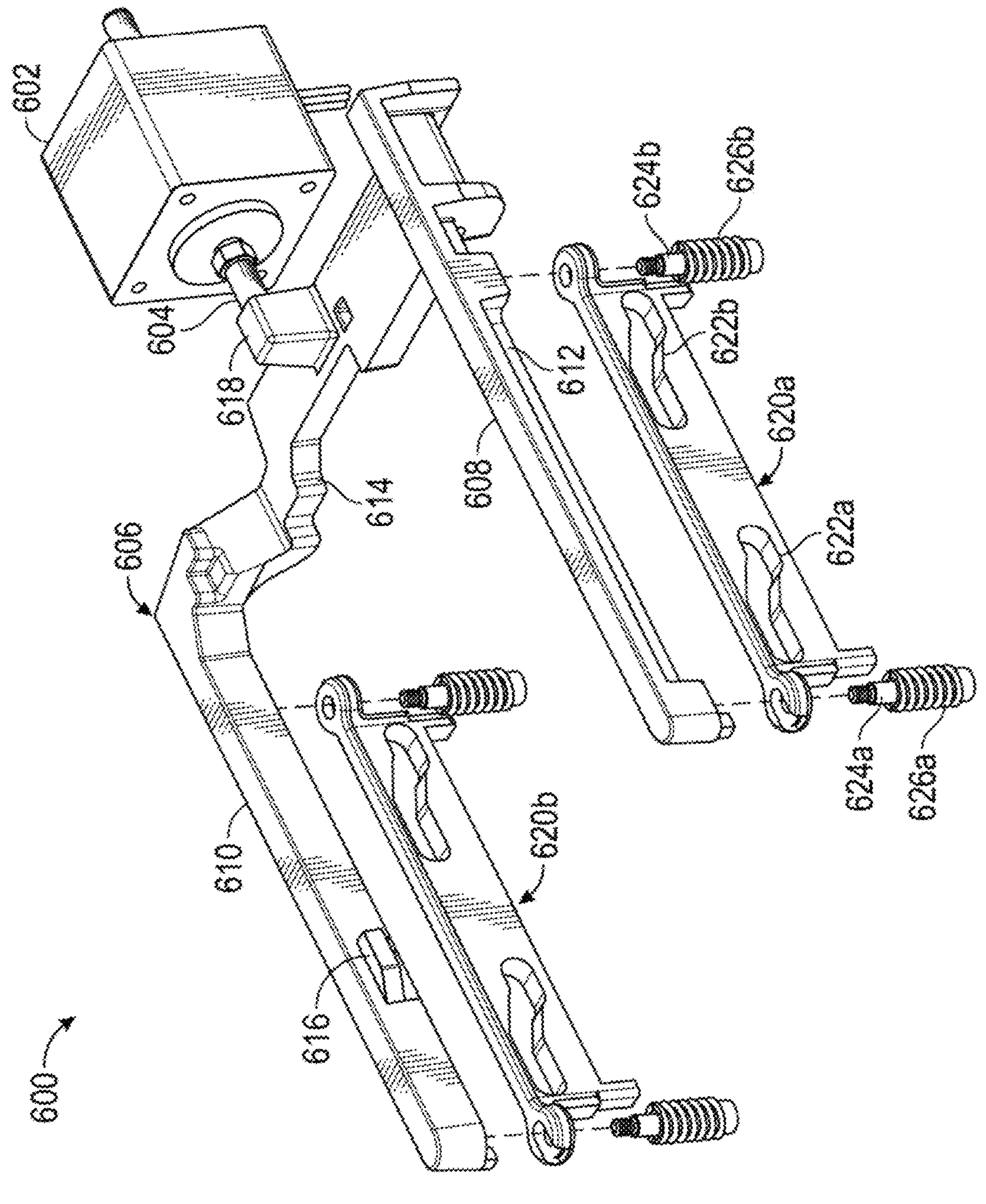
FIG. 47 is an exploded perspective view of the cam frame assembly of the cartridge processing assembly.

Details of a cam frame assembly 600 are shown in FIG. 47, which is an exploded perspective view of the cam frame assembly 600 with other components of the cartridge processing assembly 470 omitted. The cam frame assembly 600 includes the cam frame motor 602 that drives a linear actuator 604. A cam frame 606 includes opposed, generally parallel, longitudinal spars 608, 610 and a cross spar 614 extending between corresponding ends of each of the longitudinal spars 608, 610. The linear actuator 604 is coupled to the cam frame 606 at a motor connector 618 projecting upwardly from the cross spar 614. A follower slot, or channel, 612 is formed along the outer side beneath a top surface of the each of the longitudinal spars 608, 610. Follower elements 480*a*, 480*b* extending from each of the side walls 472, 474 (See FIG. 42) extend into the follower slot 612.

A cam rail 620*a* is secured to the longitudinal spar 608, and a cam rail 620*b* is secured to the longitudinal spar 610. A top edge of the cam rail 620*a* cooperates with the follower slot 612 formed in lower outer edge of the longitudinal spar 608 to form a channel that receives the cam followers 480*a*, 480*b*, which permit longitudinal movement of the cam frame 606 and the cam rails 620*a*, 620*b* with respect to the side walls 472, 474, while preventing vertical movement of the cam frame 606 relative to the side walls 472, 474.

Each cam rail 620*a* and 620*b* includes a forward cam slot 622*a* and a rear cam slot 622*b*. The cam followers 590*a*, 590*b* projecting from the side of the support plate 502 of the heating and control assembly 500 (See FIG. 43) extend into the cam slots 622*a*, 622*b*, respectively. Each cam slot 622*a*, 622*b* has a lower horizontal segment (the right-side segment in FIG. 47), an upper horizontal segment (the left-side segment in FIG. 47), and an angled transition between the lower horizontal segment and the upper horizontal segment.

Before a multiplex cartridge 10 is inserted into the cartridge carriage assembly 650, the cam frame 606 is in a relatively forward position relative to the heating and control assembly 500 so that the cam followers 590*a*, 590*b* extending from the support plate 502 are at the lower horizontal segment (the right side segment as shown in FIG. 47) of each of the cam slots 622*a*, 622*b*. Thus, the support plate 502 and the entire heating and control assembly 500 is in a down position with respect t the cartridge carriage assembly 650. When a multiplex cartridge 10 is inserted into the cartridge carriage assembly 650, the alignment fork 246 of the top plate 241 (see FIG. 24) engages the rear alignment pin 514—which is longer than the front alignment pin 516 and extends up into the cartridge carriage assembly 650 even with the support plate 502 in the down position—to properly position the cartridge within the carriage assembly 650.

After the multiplex cartridge is inserted into the cartridge carriage assembly 650, as indicated, for example, when the cartridge latch switch 666 is triggered by the end of a fully-inserted cartridge, the cam frame motor 602 is activated to retract the linear actuator 604 and the cam frame 606 attached thereto. This causes movement of cam rails 620*a*, 620*b* relative to the support plate 502, thereby moving the cam followers 590*a*, 590*b* from the lower, right side horizontal segments of the cam slots 622*a*, 622*b*, up the angled transitions, and to the upper, left side horizontal segments of the cam slots 622*a*, 622*b*, thereby raising the support plate 502 and the heating and control assembly 500 into contact with the multiplex cartridge that has been placed into the cartridge carriage assembly 650.

Raising the support plate 502 relative to the cartridge held in the cartridge carriage assembly 650, causes the front alignment pin 516 of the support plate 502 to extend into the alignment loop 244 extending from the top plate 241 (See FIG. 24). With the rear alignment pin 514 engaged by the alignment fork 246 and the front alignment pin 516 extending into the alignment loop 244, the cartridge is substantially immobilized within the cartridge carriage assembly 650.

Raising the heating and control assembly 500 with respect to the cartridge 10 held in the cartridge carriage assembly 650 places the connector pin arrays 510*a*-510*g* of the connector PCB 504 into contact with the respective connector pad arrays 358*a*-358*g* of the fluidic processing panel 354 of the multiplex cartridge 10. In addition, the elution heater assembly 506 of the connector PCB 504 is brought into contact or close proximity (i.e., so as to enable the transfer of thermal energy) with a portion of the fluidic processing panel 354 corresponding to the exonuclease region 380. Similarly, the components of the PCR heater assembly 520*a*, 520*b*, 520*c* of the connector PCB 504 are brought into contact or close proximity (i.e., so as to enable the transfer of thermal energy) with portions of the fluidic processing panel 354 corresponding to the thermocycling regions 382*a*, 382*b*, and 382*c*. The detection Peltier assembly 540 of the connector PCB 504 is brought into contact or close proximity (i.e., so as to enable the transfer of thermal energy) with portions of the fluidic processing panel 354 corresponding to the detection region 378. Also, the pneumatic connector 518 is brought into contact with the pump port 104 and the passive valve port 108 of the sample preparation module 70 of the multiplex cartridge 10.

Each cam rail 620*a*, 620*b* is secured to the respective longitudinal spar 608, 610 of the cam frame 606 by means of two threaded spring capture posts 624*a*, 624*b* with a compression spring 626*a*, 626*b* disposed between the cam rail 620*a* and a head of each of the posts 624*a*, 624*b*. This "shock absorber" configuration permits a certain amount of movement of the cam rails 620*a*, 620*b* relative to the longitudinal spars 608, 610 to thereby prevent the heating and control assembly 500 from being pushed against the bottom of the multiplex cartridge 10 with too great a force. Accordingly, the heating and control assembly 500 will be pushed against the bottom of the multiplex cartridge with a force that is no greater than the compressive force of the springs 626*a*, 626*b*.

Figure 48:
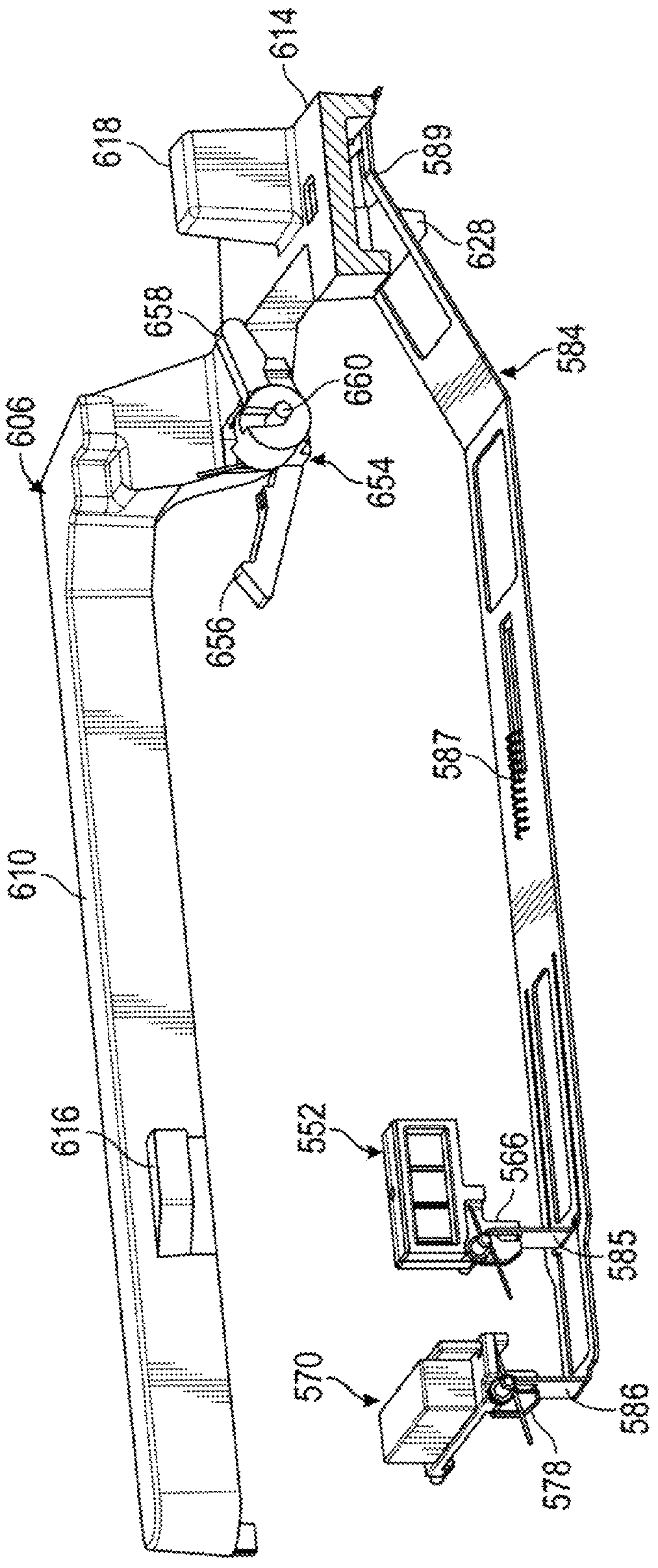
FIG. 48 is a perspective, cross-sectional view of the cam frame and a magnet actuator of the cartridge processing assembly.

Referring to FIGS. 43 and 48, which is a perspective cross-sectional view of the cam frame and a magnet actuator 584 of the cartridge processing assembly 470, a magnet actuator 584 is coupled to the cam frame 606 and is configured to rotate the cartridge magnet assembly 552 and the sample preparation magnet assembly 570 into their respective operative positions with respect to a multiplex cartridge when the cartridge is inserted in the cartridge carriage assembly. The magnet actuator 584 includes a spring 587 that biases the actuator to the left in FIG. 48. The magnet actuator 584 includes a vertical tab 585 configured to engage the actuator bracket 566 of the cartridge magnet assembly 552 and a vertical tab 586 configured to engage the actuator bracket 578 of the sample preparation magnet assembly 570. The magnet actuator 584 is coupled to the cam frame 606 by means of a magnet actuator hook 628 extending below the cross bar 614 and engaging a hook loop 589 formed in an end of the magnet actuator 584.

As noted above, before a multiplex cartridge 10 is inserted into the cartridge carriage assembly 650, the cam frame 606 is in a forward position. The magnet actuator 584 is biased forward (to the left) by the spring 587 so that the cartridge magnet assembly 552 and the sample preparation magnet assembly 570 are rotated clockwise to their retracted positions due to the force of their respective torsion springs 562, 576, respectively. In the present context, the retracted positions of the cartridge magnet assembly 552 and the sample preparation magnet assembly 570 positions in which the cartridge magnet assembly 552 and the sample preparation magnet assembly 570 do not apply a significant magnetic force to any portion of the multiplex cartridge 10. After the multiplex cartridge is inserted into the cartridge carriage assembly 650, the cam frame 606 is retracted by the cam frame motor 602 and the linear actuator 604 (to the right in FIG. 48) as described above. Retraction of the cam frame 606 causes the heating and control assembly 500 to be raised into contact with the multiplex cartridge 10, as the cam followers 590*a*, 590*b* of the support plate 502 move from the lower right side horizontal segments of the cam slots 622*a*, 622*b*, up the angled transitions, and to the upper, left side horizontal segments of the cam slots 622*a*, 622*b*.

The magnet actuator 584 coupled to the cam frame 606 by the magnet actuator hook 628 also moves with the cam frame 606 to pull the magnet actuator 584 to the right in FIG. 48 against the bias of the spring 587. As the actuator bracket 584 is pulled by the moving cam frame 606, the vertical tab 585 engaging the actuator bracket 566 of the cartridge magnet assembly 552 rotates the magnet assembly 552 counterclockwise toward its upward, deployed position as shown in FIG. 48. Similarly, the vertical tab 586 of the actuator bracket 584 engaging the actuator bracket 578 of the cartridge magnet assembly 570 rotates the magnet assembly 570 counterclockwise toward its upward, deployed position as shown in FIG. 48. Due to the longitudinal extent of the upper horizontal segment of each of the cam slots 622*a*, 622*b*, the cam frame 606 and the cam rails 620*a*, 620*b* can move longitudinally with respect to the support plate 502, while the cam followers 590*a*, 590*b* are positioned in the upper horizontal segments, without changing the height position of the support plate 502 and the heating and control assembly 500 with respect to the multiplex cartridge that has been placed into the cartridge carriage assembly 650. In various embodiments, the magnet actuator bracket 584 is configured with respect to the cartridge magnet assembly 552 and the sample preparation magnet assembly 570 so that as the cam frame 606 moves (to the right) to raise the support plate 502 and the heating and control assembly 500, the magnet assemblies 552, 570 are not initially deployed (or are not fully deployed) when the support plate 502 and the heating and control assembly

500 are first raised into contact with the multiplex cartridge (i.e., when the cam followers 590*a*, 590*b* of the support plate 502 first reach the upper horizontal segments of the cam slots 622*a*, 622*b*). Further movement (to the right) of the cam frame 606 (which, due to the longitudinal extent of the upper horizontal segments of the cam slots 622*a*, 622*b*, will not change the position of the support plate 502 and the heating and control assembly 500 with respect to the cartridge carriage assembly 650 and the multiplex cartridge held therein) will further pull the magnet actuator bracket 584 to fully rotate the magnet assemblies 552, 570 (counterclockwise) into their fully deployed positions in contact or close proximity to the multiplex cartridge. Thus, with the support plate 502 and the heating and control assembly 500 maintained at the up position in contact with the multiplex cartridge, the magnet assemblies are configured for movement independently of the rest of the heating and control assembly 500 and the cam frame 606 can move longitudinally to effect selective deployment of the magnet assemblies 552, 570 in support of requirements to selectively apply or remove magnetic forces with respect to the multiplex cartridge held within the cartridge carriage assembly 650.

Also, as can be best seen in FIG. 48, when the cam frame 606 is advanced (to the left it FIG. 48) to lower the heating and control assembly 500 relative to the cartridge, the linear actuator connector 618 extending above the cross bar 614 contacts the lever 658 of the cartridge latch 654, thereby rotating the cartridge latch 654 counterclockwise to lower the hook 656 and disengage the hook 656 from the multiplex cartridge so that the multiplex cartridge can be ejected from the cartridge holder 652 by the cartridge ejector assembly 670.

Mixing Motor Assembly

Figure 50A:
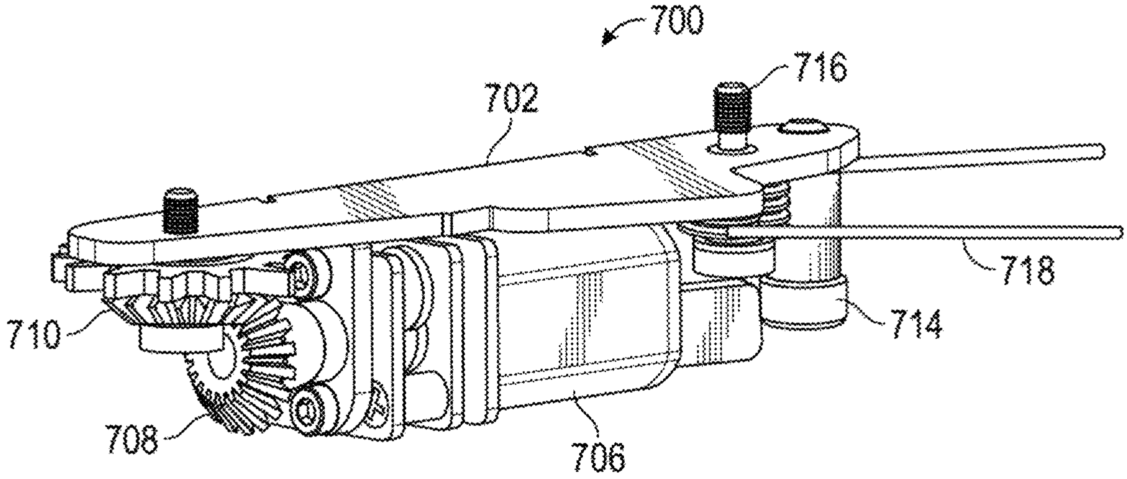
FIG. 50A is a perspective view of a mixing motor assembly of the cartridge processing assembly.
Figure 50B:
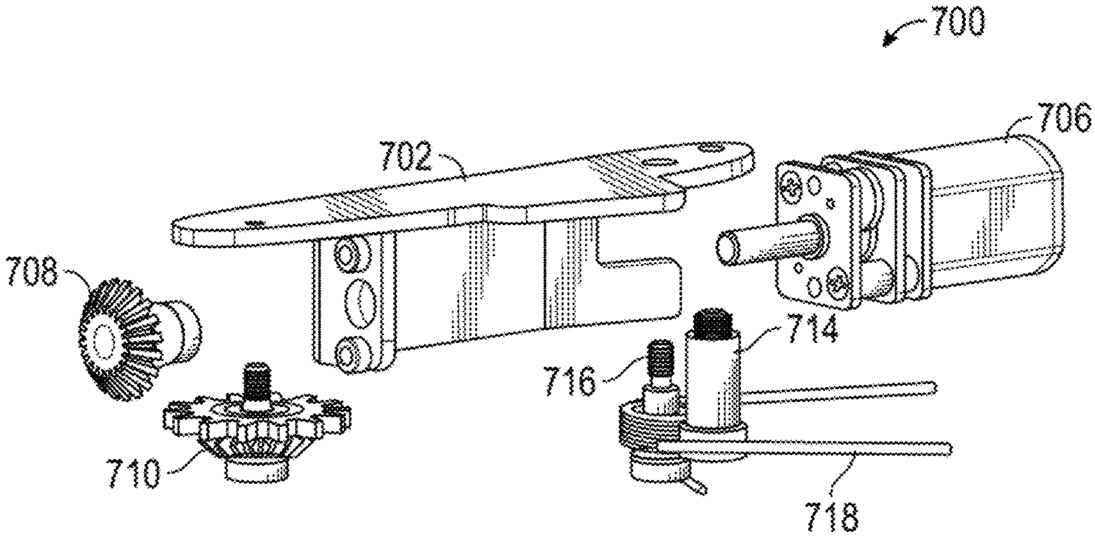
FIG. 50B is an exploded perspective view of the mixing motor assembly.

Details of the mixing motor assembly 700 are shown in FIGS. 50A and 50B. FIG. 50A is a perspective view of the mixing motor assembly 700, and FIG. 50B is an exploded perspective view of the mixing motor assembly 700.

The mixing motor assembly 700 includes a mixing motor bracket 702 to which is mounted a mixing motor 706. Suitable motors include the Pololu Micro Metal Gearmotor with a 150:1 gearbox and the Maxon, model DCX10L EB SL 4.5V with a 64:1 gearbox. Preferred characteristics of the motor include 100 rep at 12 oz-in torque, 3000 hrs. life at 45° C. operating environment and compact size (e.g., 10 mm width (diameter) and less than 25 mm long).

A beveled gear 708 is fixed to an output shaft of the motor 706. A bevel-spur gear 710 rotatably mounted to the mixing motor mounting bracket 702 is operatively coupled to the beveled gear 708 with the beveled gear teeth of the bevel-spur gear 706 engaged with the beveled gear teeth of the beveled gear 708. Thus, powered rotation of the beveled gear 708 about a horizontal axis of rotation corresponding to the output shaft of the motor 706 is converted to a rotation of the bevel-spur gear 710 about a vertical axis of rotation.

The mixing motor assembly 700 is pivotally connected to an underside of the blister plate 644 of the mounting plate 640 by means of a pivot screw 716 extending through the mixing motor bracket 702. A standoff 714 (comprising a threaded screw and a cylindrical sleeve disposed over a portion of the screw shaft) is attached to one end of the mounting bracket 702. A torsion spring 718 is coupled to the pivot screw 716 and biases the mixing motor assembly 700 inwardly relative to the sidewall 474 (see FIG. 42) so that the bevel-spur gear 710 engages the peripheral gear teeth 198 of the rotary mixer 192 (see FIG. 8) of the multiplex cartridge 10.

As shown in FIG. 48, the longitudinal spar 610 of the cam frame 606 includes a beveled block 616 extending inwardly from the longitudinal spar 610. As noted above, the mixing motor assembly 700 is biased to pivot inwardly relative to the side wall 474 and the longitudinal spar 610 due to the torsion spring 718. The beveled block 616 is positioned so as to engage the mixing motor assembly 700 when the cam frame 606 is in the forward position. Thus, when the cam frame 606 is in the retracted position to raise the heating and control assembly 500 into engagement with the multiplex cartridge 10 held in the cartridge carriage assembly 650, the mixing motor assembly 700 pivots inwardly under the force of the torsion spring 718 into engagement with the multiplex cartridge, As the cam frame 606 moves forwardly (to the left in FIG. 48) to lower the heating and control assembly 500 away from the multiplex cartridge held in the cartridge carriage assembly 650, the beveled block 616 contacts the standoff 714 of the mixing motor assembly 700 and pivots the mixing motor assembly outwardly (toward the longitudinal spar 610) against the bias of the torsion spring 718 to disengage the bevel spur gear 710 from the rotary mixer 192 of the multiplex cartridge 10. In one embodiment, the beveled block 616 contacts the standoff 714 to pivot the mixing motor assembly 700 out of engagement with the rotary mixer 192 before the actuator connector 618 of the cam frame 606 contacts the lever 658 of the cartridge latch 654 to lower the hook 656 and release the cartridge to be ejected by the cartridge ejector assembly 670.

Thus, when the cam frame 606 is in the forward position, the heating and control panel 500 is in the lowered position out of contact with the multiplex cartridge, the magnet assemblies 552, 570 rotate downwardly to their retracted positions away from the multiplex cartridge, the mixing motor assembly 700 is pivoted outwardly out of an engagement with the multiplex cartridge, and the multiplex cartridge latch 654 is pivoted so that the hook 656 disengages from the multiplex cartridge. Therefore, the multiplex cartridge is not contacted or otherwise engaged by any of the components of the multiplex cartridge processing assembly 470, and the multiplex cartridge 10 can be ejected by the cartridge ejector assembly 670.

Blister Compression Mechanism Assembly (Top Bay)

Figure 51:
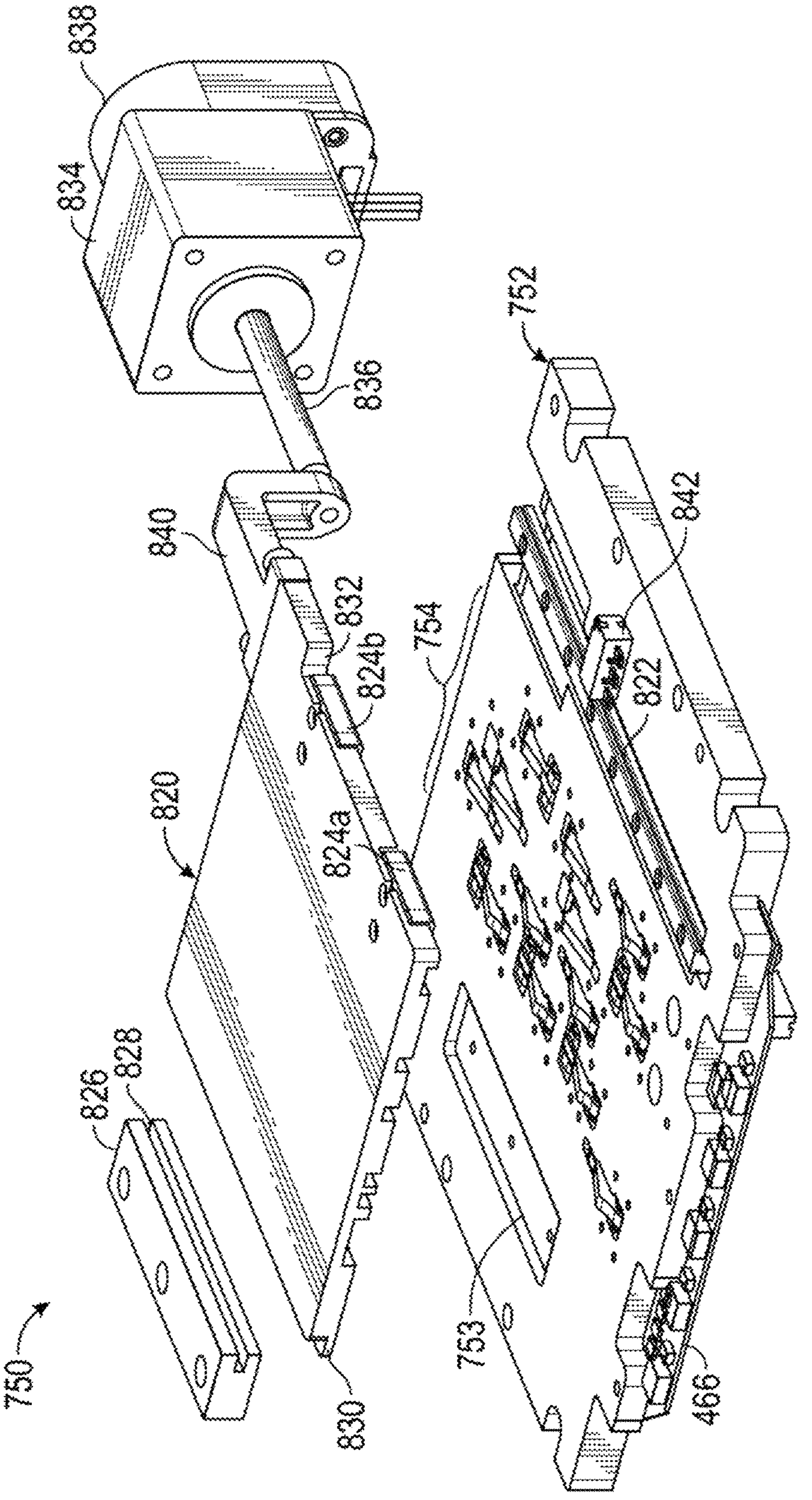
FIG. 51 is an exploded prospective view of a blister compression mechanism assembly of the processing bay.

Details of a blister compression mechanism assembly 750 are shown in FIG. 51; which is an exploded prospective view of the blister compression mechanism assembly 750. The assembly 750 comprises a cam arm plate 752 and an array 754 of cam arm-operative compression mechanisms operatively mounted within the cam arm plate 752. The cam arm plate 752 is mounted on top of the blister plate 644 of the mounting plate 640. The compression mechanisms of the array 754 comprise compression mechanisms configured to compress collapsible fluid compartments or blisters of the multiplex cartridge 10, compression mechanisms configured to compress lance blisters of the cartridge, and compression mechanisms configured to press down on and close active valve assemblies of the cartridge. The various compression mechanisms of the array 754 are aligned with blister holes 646 formed in the blister plate 644 so that the compression mechanisms of the array 754 can access the blisters and active valves of the multiplex cartridge 10 positioned below the blister plate 644 within the processing bay 440.

In various embodiments, the LED PCB 466 is attached to the cam arm plate 752.

The blister compression mechanism assembly 750 further includes a cam follower plate 820 mounted to the cam arm plate 752 for linear movement with respect to the cam arm plate. In various embodiments, one edge of the cam follower plate 820 is secured to a linear guide rail 822 attached to a top surface of the cam arm plate 752 by means of linear guide carriages 824*a* and 824*b* attached to the cam follower plate 820. An opposite edge of the cam follower plate 820 is secured against vertical movement by a hold down element 826 (or Z-axis constraint) mounted within a recess 753 formed in the cam arm plate 752, e.g., by suitable fasteners, and including a longitudinal slot 828 along one edge thereof which receives a stepped edge 830 of the cam follower plate 820. Suitable materials for construction of the hold down element include Delrin and brass. Accordingly, the cam follower plate 820 is fixed in the Z, or vertical direction or normal direction with respect to the plane of the cam arm plate 752, at a given space from the cam arm plate 752 and is allowed movement in a longitudinal direction corresponding to the longitudinal direction of the linear guide rail 822 and generally parallel to the plane of the cam arm plate 752 but is restricted from movement in any direction transverse to the linear guide rail 822.

Powered movement of the cam follower plate 820 with respect of the cam arm plate 752 is effected by a cam follower plate motor 834 attached by means of a linear actuator 836 to a drive bracket 840 that is attached to an edge of the cam follower plate 820. In various embodiments, the motor 834 further includes a rotary encoder 838 for providing precise control of and feedback from the motor 834. In various embodiments, the drive bracket 840 has an "L" shape with a first portion extending away from an attachment point to the cam follower plate 820 in a plane generally corresponding to the plane of the cam follower plate and a second portion extending downwardly in a direction that is generally normal to the plane of the cam follower plate. The linear actuator 836 is attached to the drive bracket 840 at a lower end of the second, downwardly-extending portion of the drive bracket 840. This configuration of the drive bracket 840 limits the amount by which the cam follower plate motor 834 extends above the cam follower plate 820, to thus maintain a slim profile of the processing bay 440.

In various embodiments, a sensor mechanism is provided for indicating when the cam follower plate 820 is in a particular, pre-defined position with respect to the cam arm plate 752. In on, embodiment, the sensor mechanism may comprise a home switch 842 that is mounted to the cam arm, plate 752 and is contacted by a home switch contact surface 832 of the cam follower plate 820 when the cam follower plate 820 has been moved to a home position relative to the cam arm plate 752.

In various embodiments, cam arm plate 752 includes two optical sensors 810, 812 positioned so as to correspond spatially to the locations of the inlet and outlet optical ports 14, 16, respectively (see FIG. 1). Sensors 810, 812 are constructed and arranged to detect (e.g., generate a signal) fluid flow through inlet optical sensing chamber 154 and outlet optical sensing chamber 158 of the sample preparation module 70 (see, e.g., FIG. 15). Optical sensors 810, 812 may be connected to and at least partially controlled by the LED PCB 466.

Compression Mechanism

Figure 52:
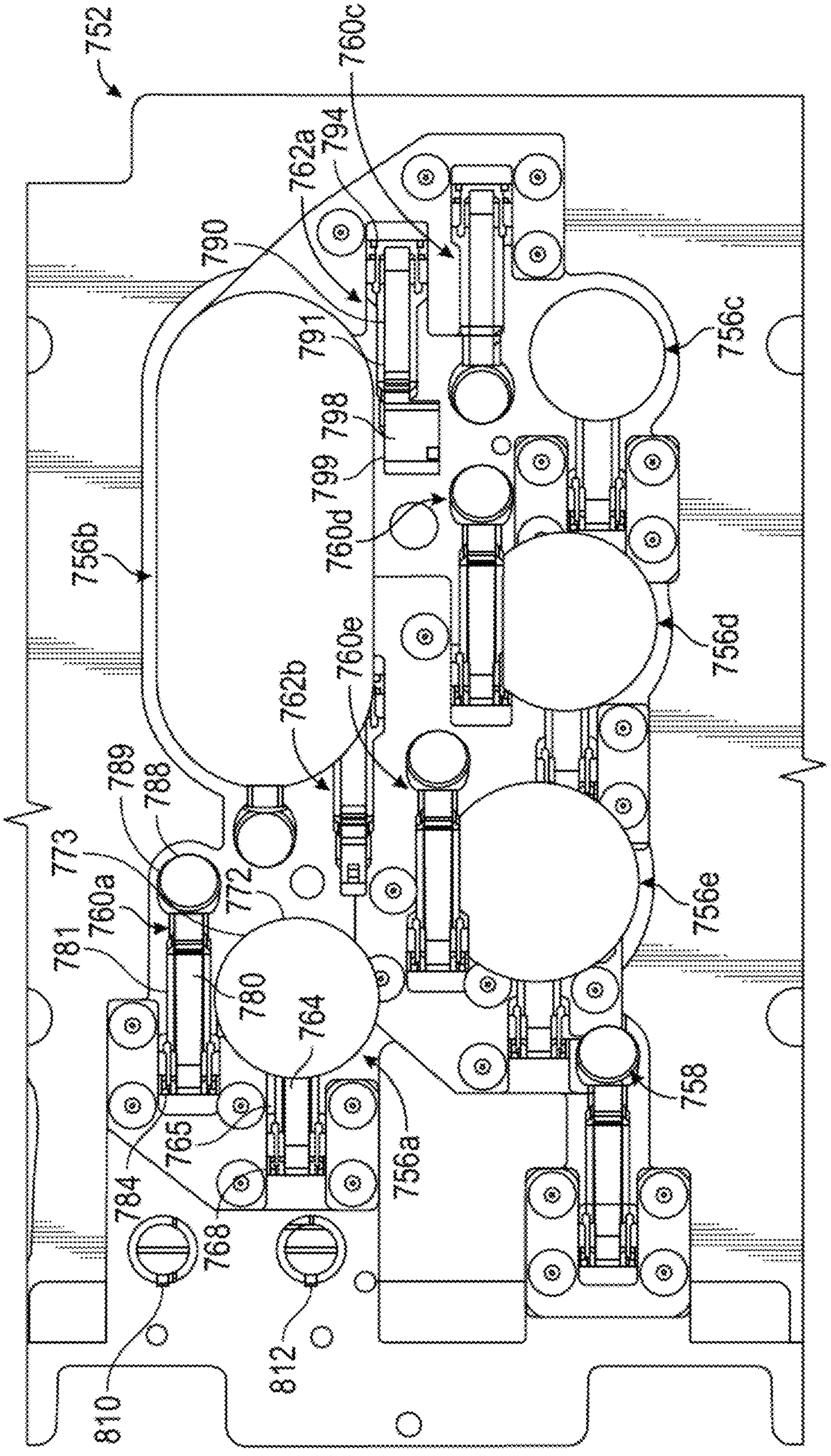
FIG. 52 is a partial bottom plan view of a cam arm plate showing compression pads of an array of compression mechanisms.
Figure 53:
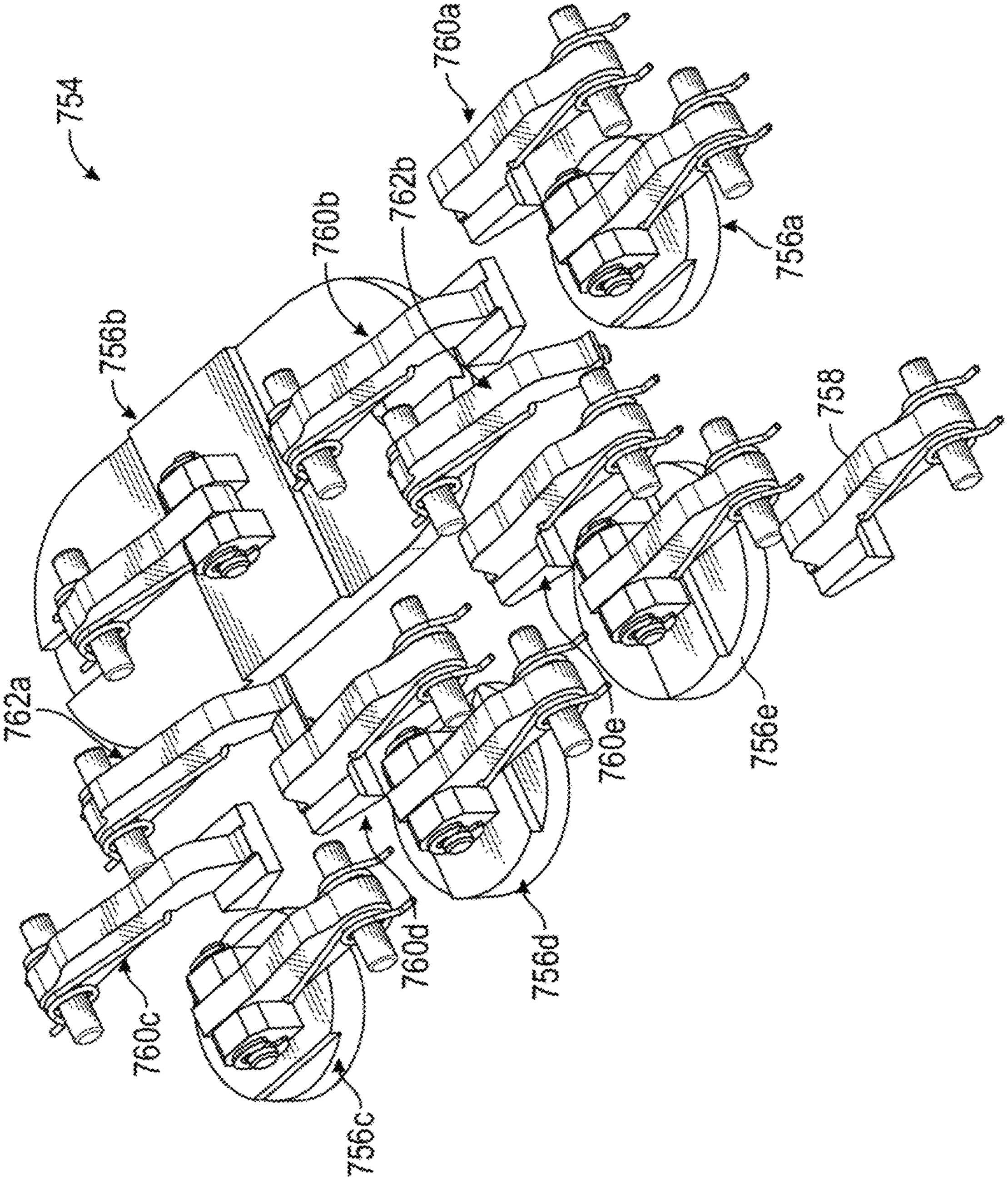
FIG. 53 is a top perspective view of the compression mechanisms of the array isolated from the cam arm plate.
Figure 54:
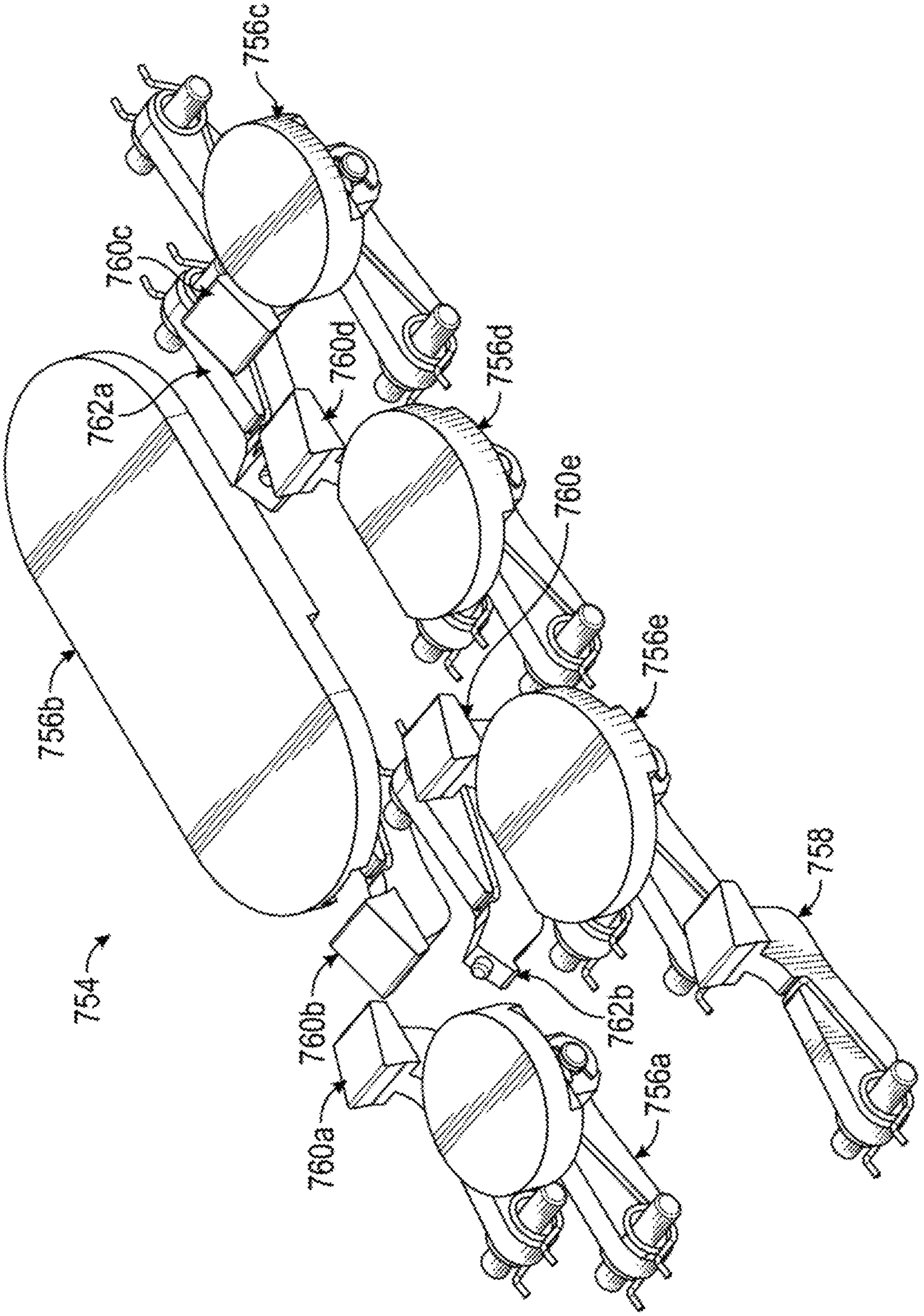
FIG. 54 is a bottom perspective view of the compression mechanisms of the array isolated from the cam arm plate.

Details of the compression mechanisms are shown in FIGS. 52, 53 and 54. FIG. 52 is a bottom partial plan view of the cam arm plate 752 showing compression pads of the array 754 of compression mechanisms. FIG. 53 is a top perspective view of the compression mechanisms of the array 754 isolated from the cam arm plate 752. FIG. 54 is a bottom perspective view of the compression mechanisms of the array 754 isolated from the cam arm plate 752.

The array 754 comprises a plurality of fluid blister compression mechanisms, each configured to, when actuated, apply a compressive force onto an associated deformable fluid blister and thereby compress the deformable blister. In the illustrated embodiment, there are five fluid blister compression mechanisms 756*a*, 756*b*, 756*c*, 756*d*, and 756*e* corresponding to the deformable fluid chambers 34*a*, 36*a*, 38*a*, 40*a*, and 42*a*, respectively, of the multiplex cartridge.

The array 754 further includes a plurality of lance blister compression mechanisms, each configured to, when actuated, apply a compressive force onto an associated lance blister that is associated with one of the deformable fluid blister and thereby compress the lance blister and lance the fluid seal within the lance blister. In the illustrated embodiment, there are five lance blister compression mechanisms 760*a*, 760*b*, 760*c*, 760*d*, and 760*e* corresponding to the lance blisters 34*b*, 36*b*, 38*b*, 40*b*, and 42*b*, respectively, of the multiplex cartridge.

The array 754 further includes a compression mechanism 758 having substantially the same configuration as a lance blister compression mechanism 760*a-e* and corresponding to blister 44 of the multiplex cartridge.

Figure 15:
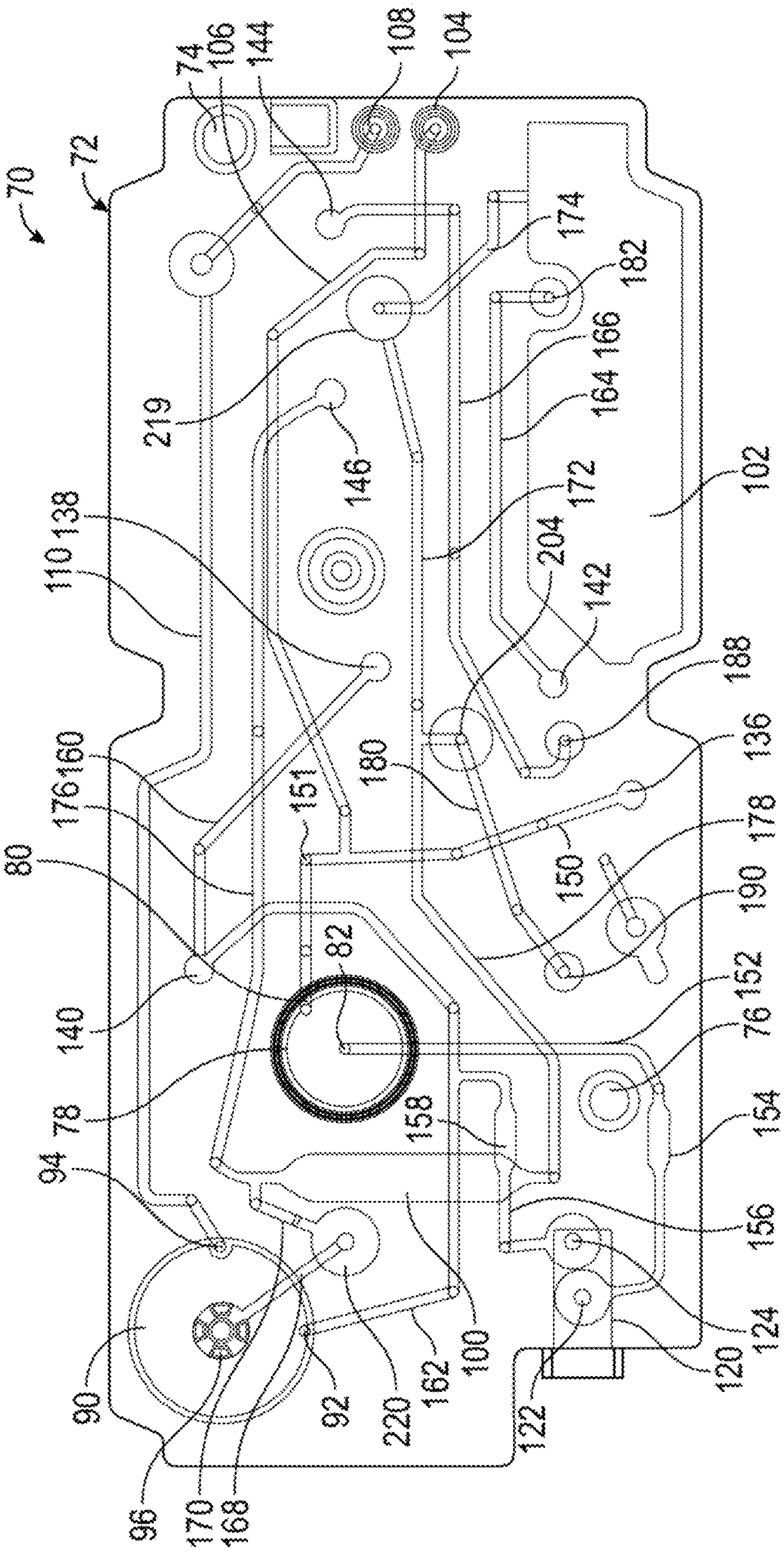
FIG. 15 is a top plan view of a sample preparation module of the multiplex cartridge.

The array 754 includes two valve actuator compression mechanisms 762*a*, 762*b* associated with sample valve assembly 204 and waste valve assembly 219, respectively (see FIG. 15). Each of the valve actuator compression mechanisms 762*a*, 762*b* is configured to, when actuated, apply a compressive force on the valve actuator tabs 20, 18 (see FIG. 1), respectively, and thus to actuate, and close, the active valves 219 and 204.

Figure 55A:
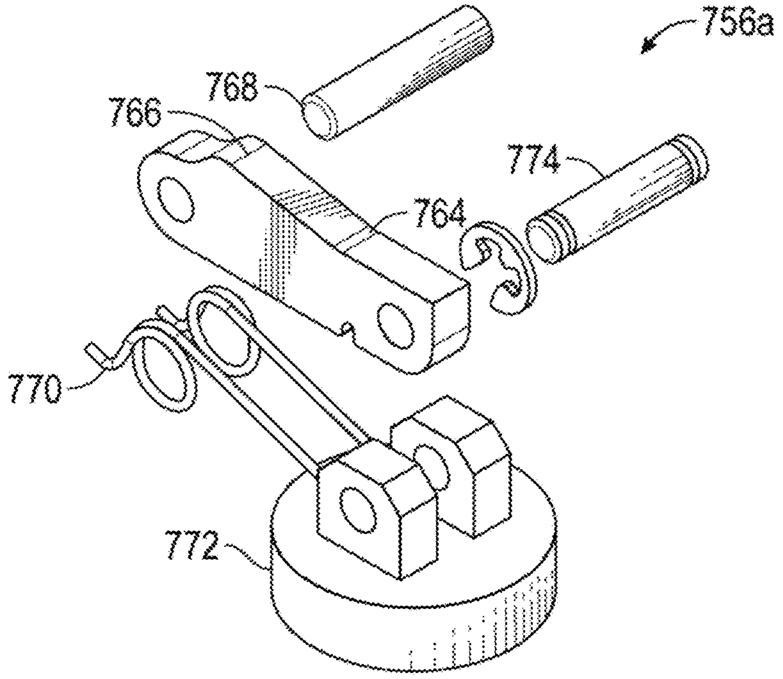
FIG. 55A is an exploded perspective view of a single fluid blister compression mechanism.
Figure 55B:
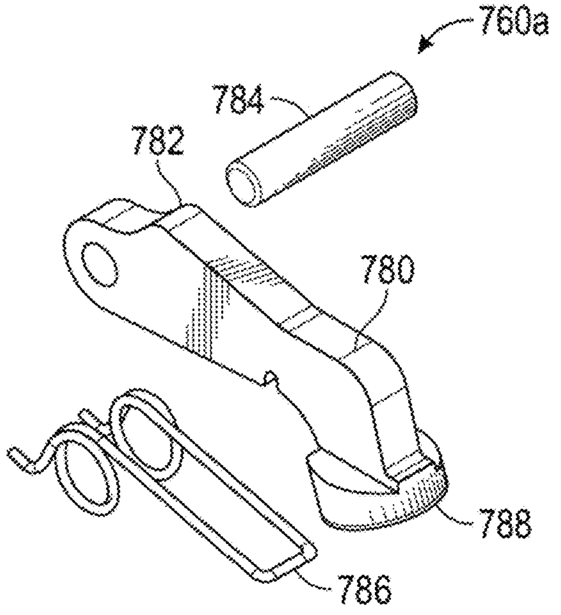
FIG. 55B is an exploded prospective view of a single lance blister compression mechanism.
Figure 55C:
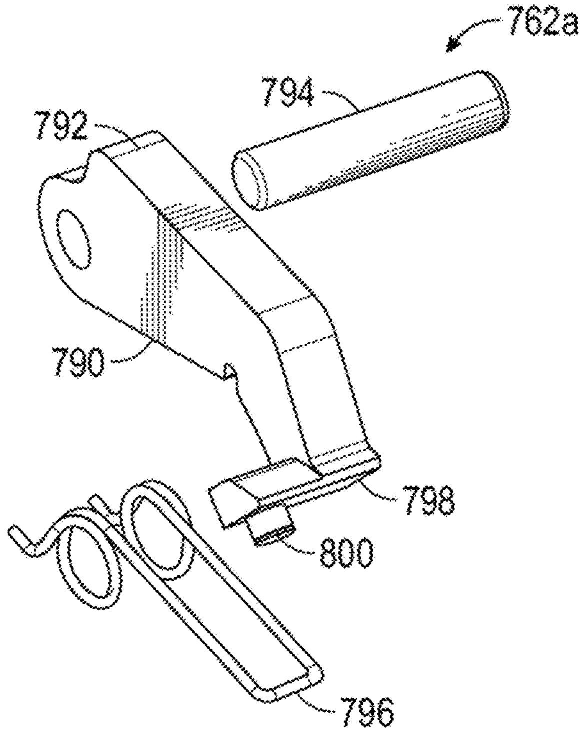
FIG. 55C is an exploded perspective view a single valve actuator compression mechanism.

Details of the constructions of each of the various compression mechanisms are shown in FIGS. 53 and 54, as well as in FIGS. 55A, 55B, and 55C. FIG. 55A is an exploded perspective view of a single fluid blister compression mechanism. FIG. 55B is an exploded prospective view of a single lance blister compression mechanism. FIG. 55C is an exploded perspective view a valve actuator compression mechanism.

The blister compression mechanism assembly employs principles and concepts described in U.S. patent application Ser. No. 14/206,817 entitled "Apparatus and Methods for manipulating deformable fluid vessels" the contents of which are hereby incorporated by reference. In particular, the blister compression mechanism assembly is constructed and arranged to convert the horizontal movement of cam follower pate 820 into vertical, or partially vertical, movement of the compression mechanisms to compress a fluid blister, a lance blister, and a valve assembly without requiring pneumatic, electromechanical, or other components at larger distances above and/or below the multiplex cartridge 10 to thus maintain a slim profile of the processing bay 440.

Referring to FIG. 55A, each fluid blister compression mechanism, such as the fluid blister compression mechanism 756*a*, includes a cam arm 764 with a cam surface 766 formed along a top edge thereof. The cam arm 764 is mounted within the cam arm plate 752 for pivoting movement about an arm pivot pin 768 extending through a hole formed in one end of the cam arm 764. The cam arm 764 is disposed within a slot 765 formed in the cam arm plate 752, and the arm pivot pin 768 is mounted within the cam arm plate 752 transversely to that slot (see FIG. 52). A compression pad 772 is pivotally mounted to an opposite end of the cam arm 764 for pivoting movement about a pad pivot pin 774 extending through a hole formed in the opposite end of the cam arm 764. In various embodiments, the compression pad 772 is disposed within a blind recess 773 formed in a bottom surface of the cam arm plate 752 in a shape generally conforming to the shape of the compression pad 772 (see FIG. 52).

The fluid blister compression mechanism 756*a* is configured to pivot with respect to the cam arm plate 752 about the arm pivot pin 768 between a retracted position in which the compression mechanism is not applying pressure to the associated fluid blister and an extended, or deployed, position in which the compression mechanism is applying a compressive force onto the fluid blister. A torsion spring 770 biases the compression mechanism 756*a* into the retracted position. In the retracted position, the cam arm 764 is substantially disposed within the corresponding slot 765 formed in the cam arm plate 752 and the compression pad 772 is disposed within the pad recess 773 formed in the cam arm plate 752 so that the blister-contacting surface of the compression pad 772 is substantially flush with a surface of the cam arm plate 752. In the extended position, the cam arm 756 is rotated about the cam arm pivot pin 768 so that the compression pad 772 is extended beneath the cam arm plate 752 to compress and collapse the reagent blister disposed beneath the compression pad 772.

The cam surface 766 may include a convex bulge, or other feature, that, in various embodiments, extends above a top surface of the cam arm plate 752 (see FIG. 51, showing cam features of the cam arms of the array 754 of compression mechanisms extending above cam arm plate 752). When the cam surface 766 is engaged by a cam follower element moving relative to the cam arm 764 over the cam surface 766, the cam arm 764 is caused to pivot from the retracted position to the extended position as the cam follower moves over the convex bulge of the cam surface 766. As the cam follower element moves off the cam surface 766, the cam arm 764 returns to the retracted position under the force of the torsion spring 770.

The cam arm 764 is preferably made from a material having sufficient strength to withstand forces applied to it by a cam follower element pushing the cam arm 764 against a collapsible fluid blister and having suitable machinability. Suitable materials include steel for applications in which the cam follower element comprises a roller that rolls over the cam surface 766. For applications in which the cam follower element comprises a sliding (i.e., non-rolling) element that slides over the cam surface 766, suitable materials include low friction, low abrasion materials, such a nylon or a lubricant-impregnated material, such as oil-impregnated bronze.

In various embodiments, the construction and operation of the other fluid blister compression mechanisms, 756*b*, 756*c*, 756*d*, and 756*e* are substantially the same as that of the fluid blister compression mechanism 756*a*, although the size and shape of the compression pads (e.g., compression pad 772) may vary from one fluid blister compression mechanism to the next according to the size and shape of the fluid blister that is to be compressed by the compression mechanism.

Referring to FIG. 55B, each lance blister compression mechanism, such as the lance blister compression mechanism 760*a*, includes a cam arm 780 with a cam surface 782 formed along a top edge thereof. The cam arm 780 is mounted within the cam arm plate 752 for pivoting movement about an arm pivot pin 784 extending through a hole formed in one end of the cam arm 780. The cam arm 780 is disposed within a slot 781 formed in the cam arm plate 752, and the arm pivot pin 784 is mounted within the cam arm plate 752 transversely to that slot (see FIG. 52). A compression pad 788 is formed or positioned on an opposite end of the cam arm 780. In various embodiments, the compression pad 788 is disposed within a blind recess 789 formed in a bottom surface of the cam arm plate 752 in a shape generally conforming to the shape of the compression pad 788 (see FIG. 52).

The lance blister compression mechanism 760*a* is configured to pivot with respect to the cam arm plate 752 about the arm pivot pin 784 between a retracted position in which the compression mechanism is not applying pressure to the associated lance blister and an extended, or deployed, position in which the compression mechanism is applying a compressive force onto the lance blister. A torsion spring 786 biases the compression mechanism 760*a* into the retracted position. In the retracted position, the cam arm 780 is substantially disposed within the corresponding slot 781 formed in the cam arm plate 752 and the compression pad 788 is disposed within the pad recess 789 formed in the cam arm plate 752 so that the blister-contacting surface of the compression pad 788 is substantially flush with a surface of the cam arm plate 752. In the extended position, the cam arm 78G is rotated about the cam arm pivot pin 784 so that the compression pad 788 is extended beneath the cam arm plate 752 to compress and collapse the lance blister disposed beneath the compression pad 788.

The cam surface 782 may include a convex bulge, or other feature, that, in various embodiments, extends above a top surface of the cam arm plate 752 (see FIG. 51, showing cam features of the cam arms of the array 754 of compression mechanisms extending above the cam arm plate 752). When the cam surface 782 is engaged by a cam follower element moving relative to the cam arm 780 over the cam surface 782, the cam arm 780 is caused to pivot from the retracted position to the extended position as the cam follower moves over the convex bulge of the cam surface 782. As the cam follower element moves off the cam surface 782, the cam arm 780 returns to the retracted position under the force of the torsional spring 786.

The cam arm 780 is preferably made from a material having sufficient strength to withstand forces applied to it by a cam follower element pushing the cam arm 780 against a collapsible lance blister and having suitable machinability. Suitable materials include steel for applications in which the cam follower element comprises a roller that rolls over the cam surface 782. For applications in which the cam follower element comprises a sliding (i.e., non-rolling) element that slides over the cam surface 782, suitable materials include low friction, low abrasion materials, such as nylon or a lubricant-impregnated material, such as oil-impregnated bronze.

In various embodiments, the construction and operation of the other lance blister compression mechanisms, 760*b*, 760*c*, 760*d*, and 760*e*, and the compression mechanism 758, are substantially the same as that of the lance blister compression mechanism 760*a*.

Referring to FIG. 55C, each valve actuator compression mechanism, such as valve actuator compression mechanism 762*a*, includes a cam arm 790 with a cam surface 792 formed along a top edge thereof. The cam arm 790 is mounted within the cam arm plate 752 for pivoting movement about an arm pivot pin 794 extending through a hole formed in one end of the cam arm 790. The cam arm 790 is disposed within a slot 791 formed in the cam arm plate 752, and the arm pivot pin 794 is mounted within the cam arm plate 752 transversely to that slot (See FIG. 52). A contact pad 798 is formed or positioned on an opposite end of the cam arm 790. In various embodiments, the contact pad 798 is disposed within a blind recess 799 formed in a bottom surface of the cam arm plate 752 in a shape generally conforming to the shape of the contact pad 798 (see FIG. 52).

In various embodiments, the contact pad 798 may further include a contact pin, or point, 800 projecting from the contact pad 798. The contact point is configured to engage a small dimple or depression formed in the top surface of the valve actuator tab 18 or 20 when the valve actuator compression mechanism is pressing against the tab to prevent the compression mechanism from slipping off the valve actuator tab. Also, in various embodiments, a portion of the contact pad 798, and the contact pin 800, may be offset from the cam arm 690 to accommodate space and orientation limitations within the array 754 of compression mechanisms.

The valve actuator compression mechanism 762*a* is configured to pivot with respect to the cam arm plate 752 about the arm pivot pin 794 between a retracted position in which the compression mechanism is not applying pressure to the associated valve actuator tab and active valve assembly and an extended, or deployed, position in which the compression mechanism is applying a compressive force onto the actuator tab and valve assembly. A torsion spring 796 biases the compression mechanism 762*a* into the retracted position. In the retracted position, the cam arm 790 is substantially disposed within the corresponding slot 791 formed in the cam arm plate 752 and the contact pad 798 is disposed within the pad recess 799 formed in the cam arm plate 752 so that the contact surface of the contact pad 798 is substantially flush with a surface of the cam arm plate 752. In the extended position, the cam arm 790 is rotated about the cam arm pivot pin 794 so that the contact pad 798 is extended beneath the cam arm plate 752 to deflect the valve actuator tab downwardly and close the associated valve assembly disposed beneath the valve actuator tab.

The cam surface 792 may include a convex bulge, or other feature, that, in various embodiments, extends above a top surface of the cam arm plate 752 (see FIG. 51, showing cam features of the cam arms of the array 754 of compression mechanisms extending above the cam arm plate 752). When the cam surface 792 is engaged by a cam follower element moving relative to the cam arm 790 over the cam surface 792, the cam arm 790 is caused to pivot from the retracted position to the extended position as the cam follower moves over the convex bulge of the cam surface 792. A the cam follower element moves off the cam surface 982, the cam arm 790 returns to the retracted position under the force of the torsion spring 796.

The cam arm 790 is preferably made from a material having sufficient strength to withstand forces applied to it by a cam follower element pushing the cam arm 790 against a valve assembly and having suitable machinability. Suitable materials include steel for applications in which the cam follower element comprises a roller that rolls over the cam surface 792. For applications in which the cam follower element comprises a sliding (i.e., non-rolling) element that slides over the can surface 792, suitable materials include low friction, low abrasion materials, such as nylon or a lubricant-impregnated material, such as oil-impregnated bronze.

In various embodiments, the construction and operation of the other valve actuator compression mechanism 762*b* are substantially the same as that of the valve actuator compression mechanism 762*a*.

Figure 56:
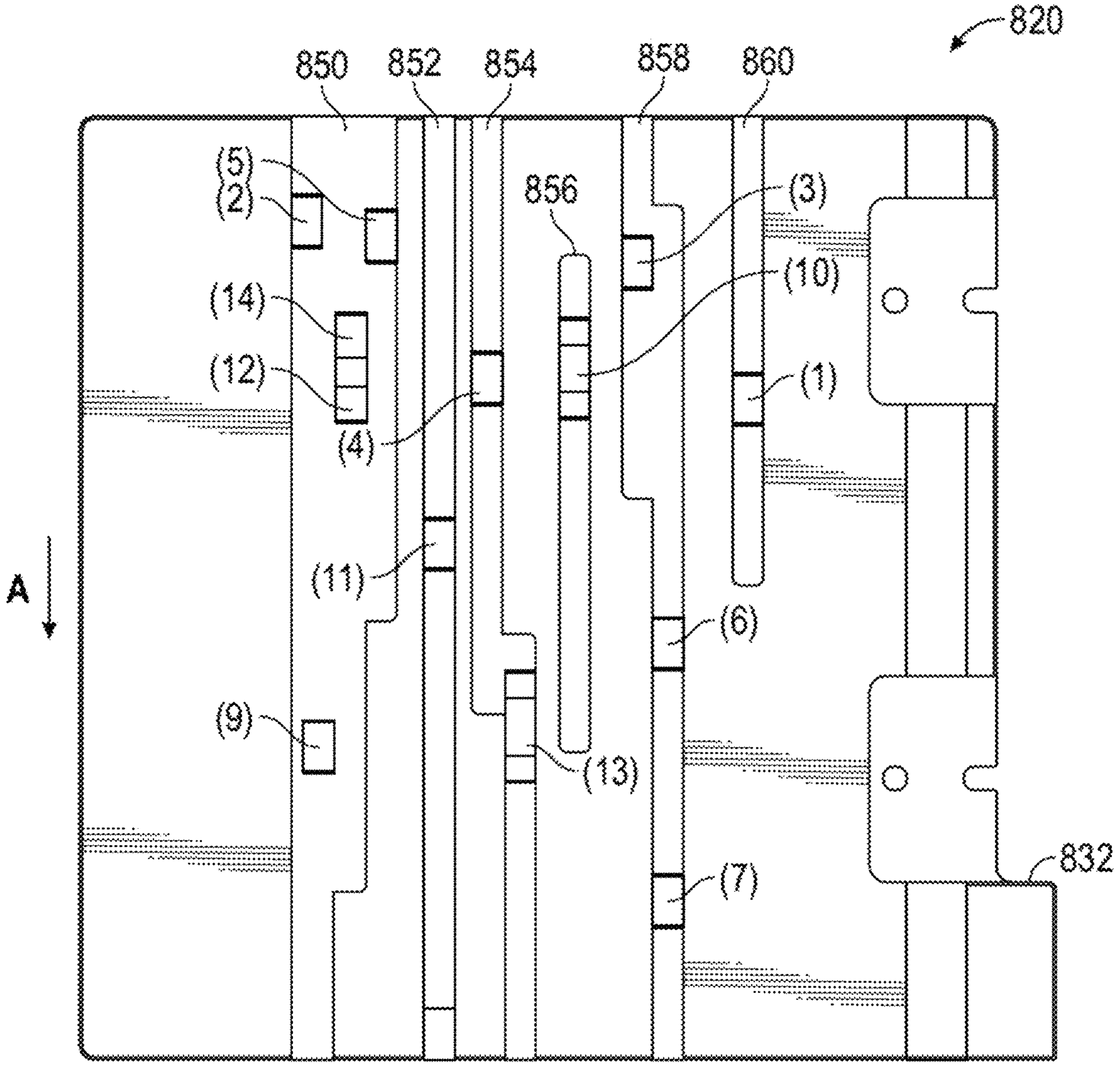
FIG. 56 is a bottom plan view of a cam follower plate of the blister compression mechanism assembly.
Figure 57:
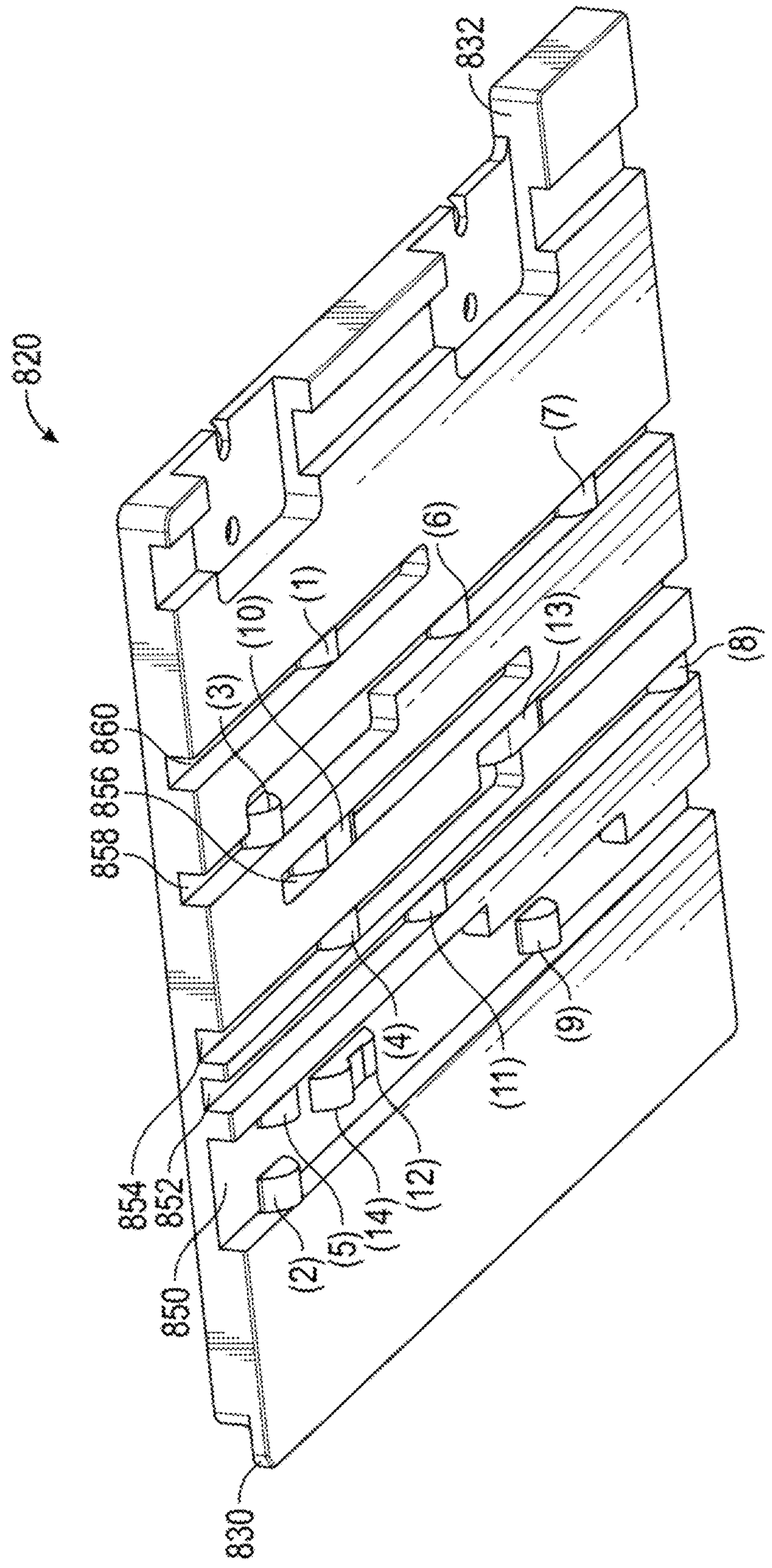
FIG. 57 is a bottom perspective view of the cam follower plate.

Details of the cam follower plate 820 are shown in FIGS. 56 and 57. FIG. 56 is a bottom plain view of the cam follower plate 820, and FIG. 57 is a bottom perspective view of the cam follower plate 820.

The cam follower plate 820 includes a number of generally parallel, longitudinal cam grooves 850, 852, 854, 856, 858 and 860. Each of the grooves 850-860 of the cam follower plate 820 receives a portion of one or more the cam arms 764, 780, 790 of the compression mechanisms of the array 754. In addition, each groove 850-860 includes one or more cam follower elements, e.g., in the form of ribs or rollers formed or positioned at discreet positions along the corresponding groove.

The cam follower plate 820, as noted above, is configured for linear movement relative to the cam arm plate 752 in a plane that is parallel to the cam arm plate 752. As the cam follower plate 820 moves relative to the cam arm plate 752, when a cam follower element within a cam groove encounters the cam surface of the cam arm of the compression mechanism (e.g., cam surface 766, 782, or 792 of cam arms 764, 780, or 790, respectively), the cam arm is pushed downwardly, pivoting about its respective arm pivot pin (e.g., pivot pin 768, 784, or 794) to cause the compression mechanism to compress the blister (e.g., compressible fluid blister or lance blister) or press the active valve assembly disposed beneath that compression mechanism.

During movement of the cam follower plate 820 with respect to the cam arm plate 852, the relative locations of the compression mechanisms of the array 754 of compression mechanisms and the cam follower ribs formed in the grooves 850, 852, 854, 856, 858, and 860 define the sequence in which the compression mechanisms are actuated.

Software and Hardware

As generally and specifically describe above, aspects of the disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such a graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

Sample Preparation Process

An exemplary sample preparation process that may be performed in the sample preparation module 70 is described and illustrated in FIGS. 16-23. Persons of ordinary skill will recognize that sample preparation processes other than that described herein—e.g., reordering of the steps from what is described herein, the omission of certain steps described herein, and/or addition of certain steps—may be performed with the sample preparation module or a modified version of the sample preparation module.

Figure 16:
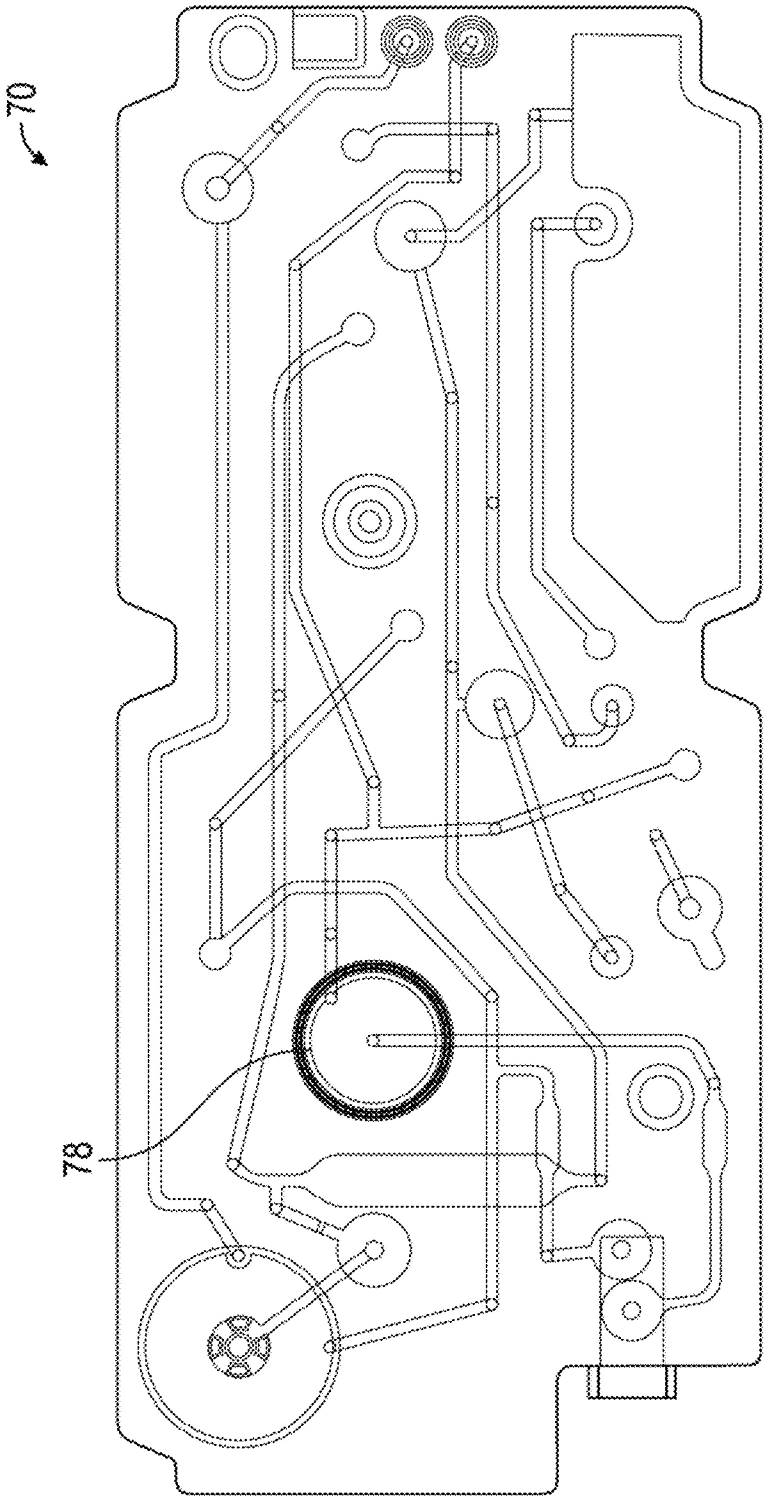
FIGS. 16-23 show top plan views of the sample preparation module, each showing a different step of a sample preparation process performed within the module.

In a first step, illustrated in FIG. 16, a fluid sample specimen is dispensed into the sample well 78. In general, the multiplex cartridge 10 is designed to process liquid or solid samples. Liquid samples may include blood, serum, plasma, urine, saliva, cerebral spinal fluid, lymph, perspiration, semen or epithelial samples such as cheek, nasopharyngeal, anal or vaginal swabs to which lysis buffer has been added to resuspend the cells. Solid samples, such as feces or tissue samples (e.g. tumor biopsies), generally need to be resuspended and diluted in a buffer, e.g., the Cary Blair transport medium. The sample well 78 may then be closed using the sample cap 84 (see FIG. 6). and the multiplex cartridge 10 is then placed in a processing instrument (e.g., into the processing bay 440 of the processing module 410 of the instrument 400).

Figure 17:
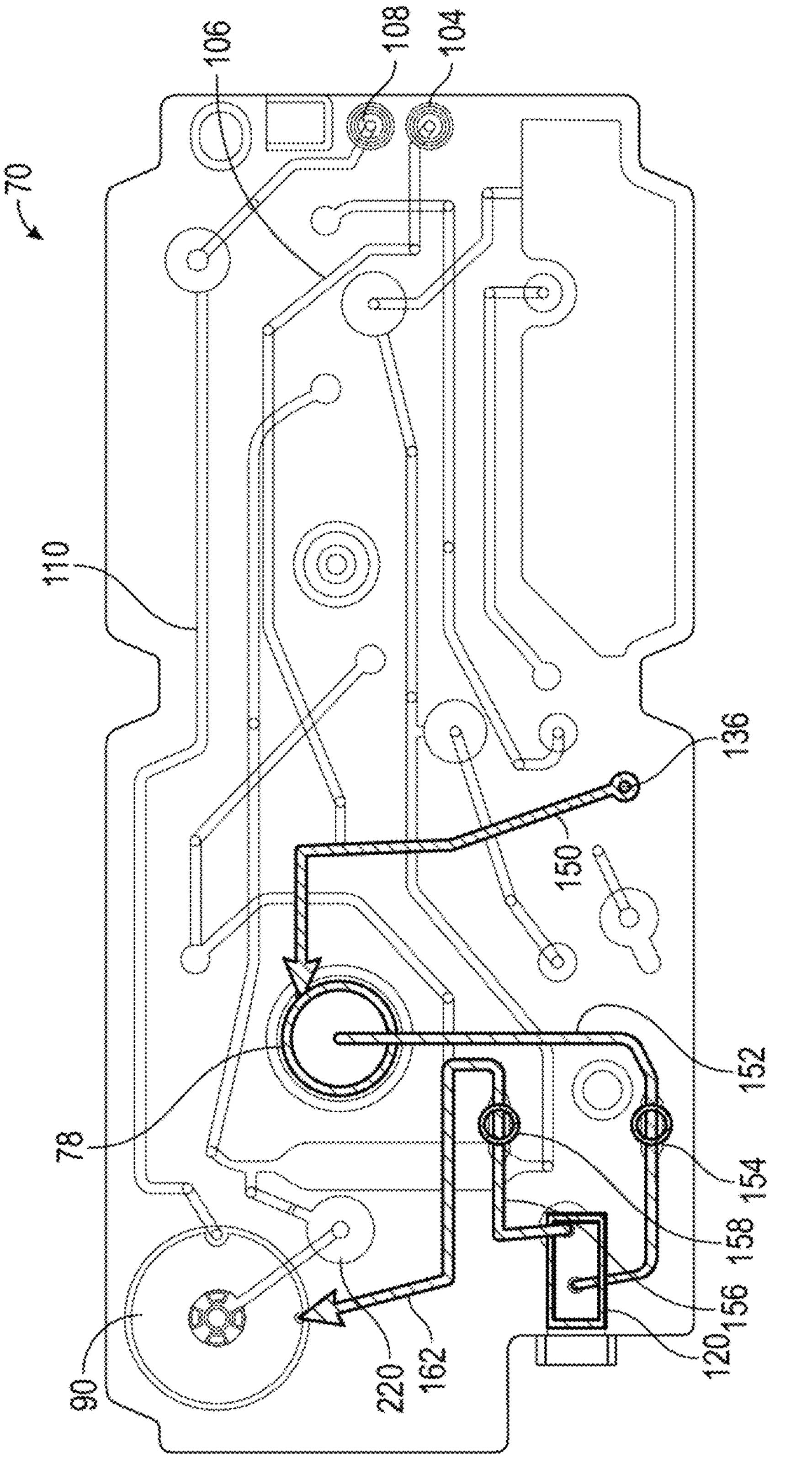

In a first step performed within the instrument, as illustrated in FIG. 17, the lance blister 34*b* associated with the deformable compartment 34*a* is compressed by an external actuator (e.g., the compression mechanism 760*a*) to press a bead or other opening device through a closing seal (i.e., lance the seal with the bead or other device), and then the deformable compartment 34*a* is compressed by an external actuator (e.g., the compression mechanism 756*a*) to force a process fluid contained therein into the first inlet port 136 formed in the substrate 72. In one embodiment, the process fluid contained in the deformable compartment 34*a* is a lysis buffer. The fluid is directed by the first fluid channel 150 from the inlet port 136 to the sample well 78, where the fluid enters the sample well 78 through the inlet snorkel 80. In addition, an external pump (e.g., pump 458) connected to the sample preparation module 70 at the pump port 104 generates pressure that is applied to the contents of the sample well 78 via the pressure conduit 106.

The pressure generated by compressing the deformable compartment 34*a* and the pressure applied at pressure conduit 106 pushes the fluid contents—comprising the fluid sample and the contents of the deformable compartment 34*a*—from the sample well 78 through the second fluid channel 152 to the lysis chamber inlet 122. The fluid continues to flow through the lysis chamber, exiting the outlet 124, where it is directed by the third fluid channel 156 and a portion of the fifth fluid channel 162 into the mixing well 90. As the fluid stream first enters or exits the lysis chamber 120 and passes through the inlet optical sensing chamber 154 or the outlet optical sensor chamber 158, it is detected through the associated optical port 14 or 16 formed in the upper shroud 12 (see FIG. 1) by an optical detector (e.g., optical detector(s) mounted in LED PCB 466). A signal from the optical detector indicating fluid flow (e.g., an air-fluid interface) through the inlet or outlet optical sensing chamber 154 or 158 activates the motor 128 of the lysis chamber mixer to disrupt the fluid flowing through the lysis chamber 120 with lysis beads contained within the lysis chamber 120. The motor 128 continues to operate until a signal from an optical detector indicating the end fluid flow through the inlet or outlet optical sensing chamber 154 or 158—and thus the end of flow through the lysis chamber 120, deactivates the motor 128.

As the fluid mixture is flowing into the mix compartment 90, the passive valve port 108 remains open so that pressure within the mixing well 90 does not rise to a level that will open the passive valve assembly 220. Thus, at the conclusion of the step illustrated in FIG. 17, the mixing well 90 will contain a mixture of fluid sample and the contents of the deformable compartment 34*a* (e.g., a lysis buffer) which has been physically lysed by the lysis mixer and lysis beads contained in the lysis chamber 120.

Figure 18:
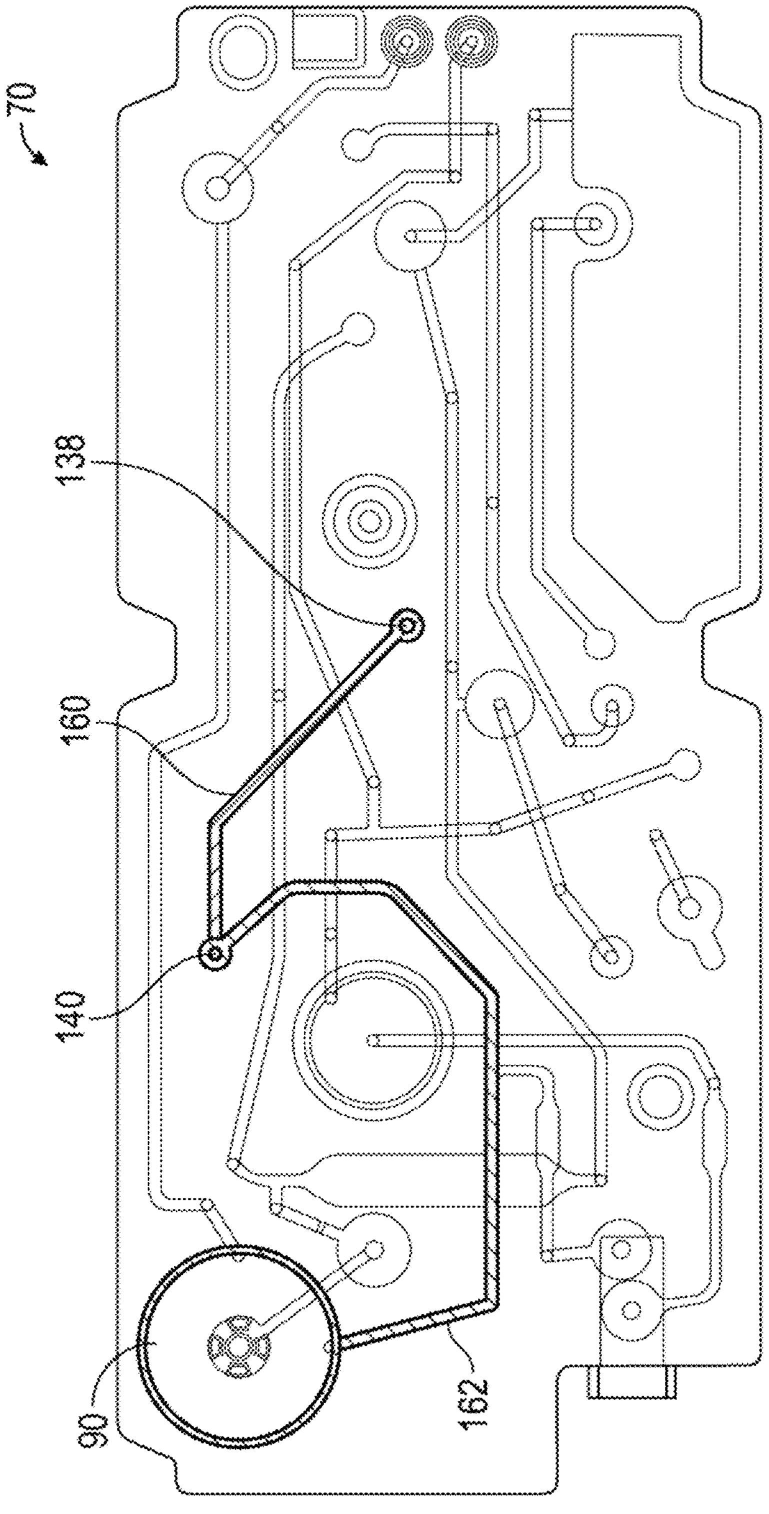

Referring now to FIG. 18, after the step shown in FIG. 17, the pneumatic pump applying pressure at pressure port 104 is turned off, e.g., after a prescribed period of operation, and the third deformable compartment 44 is compressed by an external actuator (e.g., the compression mechanism 758) to force the contents of the deformable compartment 44 into the third inlet port 140. In one embodiment, the contents of the deformable compartment 44 comprise magnetic target capture beads.

Next, the lance blister 36*b* associated with the deformable compartment 36*a* is compressed by an external actuator (e.g., the compression mechanism 760*e*) to press a bead or other opening device through a closing seal (i.e., lance the seal with the bead or other device), and then the deformable compartment 36*a* is compressed by an external actuator (e.g., the compression mechanism 756*e*) to force a process fluid contained therein into the second inlet port 138 formed in the substrate 72. The process fluid then flows through the fourth fluid channel 160 and the fifth fluid channel 162 to the mixing well 90. The contents of the deformable compartment 36*a* may comprise a binding buffer for facilitating the binding of the target capture beads to the target analyte(s). The flowing fluid past the third inlet port 140, under the pressure generated by the compression of the deformable compartment 36*a*, transports the fluid contents of the deformable compartment 36*a* and the contents of the deformable compartment 44 through the fifth fluid channel 162 to the mixing well 90.

As noted above, in an alternate embodiment, the magnetic beads may be provided in the form of a lyophilized pellet contained within the mixing well 90, and the deformable compartment 44, the associated external actuator (e.g., the compression mechanism 758), and the step of bursting the deformable compartment 44 may be omitted.

After the step illustrated in FIG. 18 is completed, the rotary mixer 192 within the mixing well 90 may be activated (e.g., by the mixing motor assembly 700) to stir the contents of the mixing well 90. In various embodiments, a lyophilized or other dried reagent form may be pre-positioned in the mixing well 90 and is dissolved or reconstituted by the fluids transported into the mixing well 90. The rotary mixer 192 helps facilitate the dissolution or reconstitution of the dried reagent and mixes all the materials contained in the mixing well to form a homogeneous fluid mixture.

Figure 19:
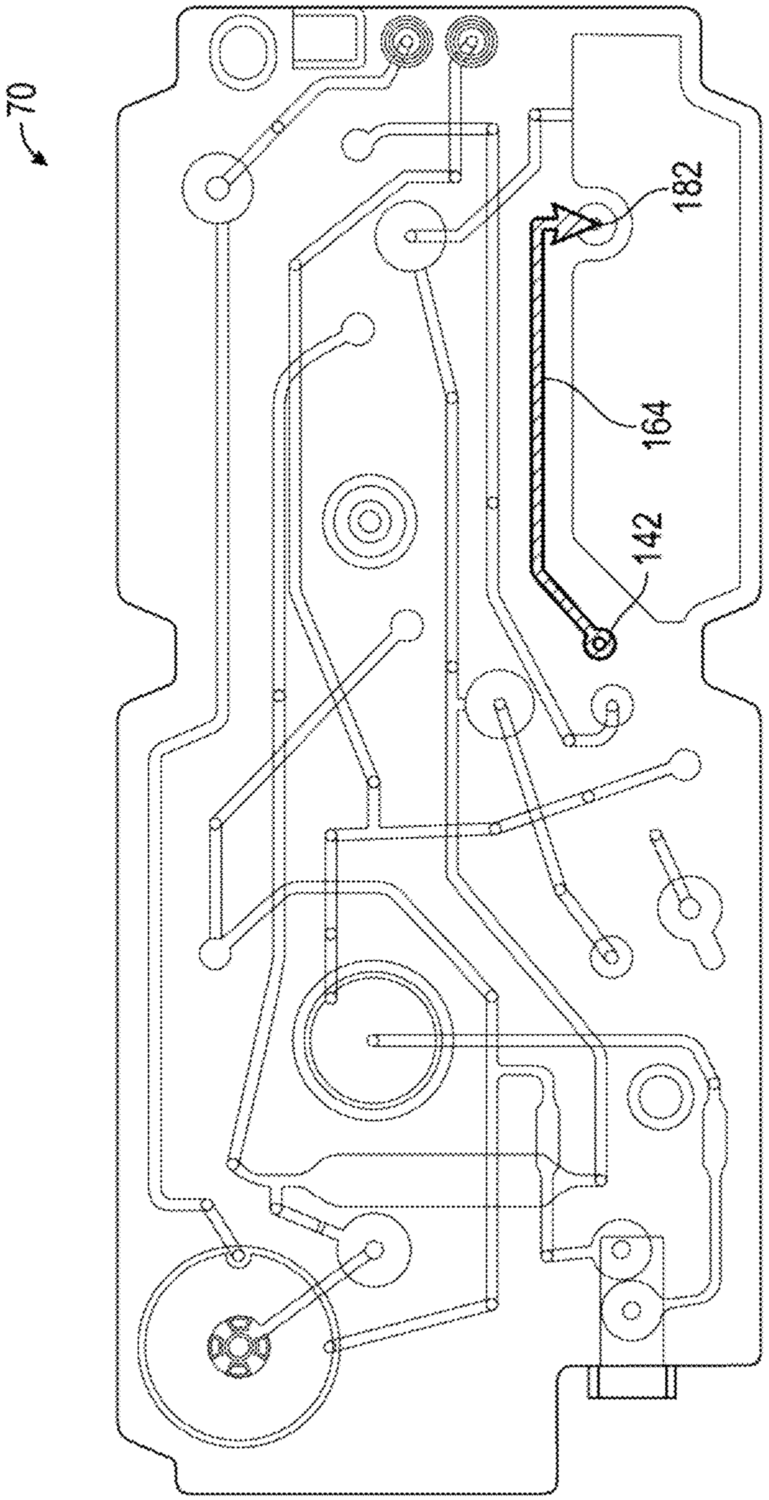

Referring to FIG. 19, a next step comprises collapsing the lance blister 38*b* (e.g., with the compression mechanism 760*b*) associated with the deformable compartment 38*a* to thereby open the compartment to the fourth inlet port 142. The deformable compartment 38*a* is then collapsed (e.g., with the compression mechanism 756*b* to direct the fluid contents thereof into the fourth inlet port 142, through the sixth fluid channel 164 and to the first outlet port 182, where the fluid exits the sample preparation module 70. The first outlet port 182 is in communication with the inlet port 252 of the reaction module 240 as explained above. The fluid contained in the deformable compartment 38*a* may comprise an immiscible fluid, e.g., an oil, which is used to fill a reaction space 295 within the reaction module 240 between the top plate 241 and the fluidic processing panel 354, as shown in FIG. 30.

Figure 20:
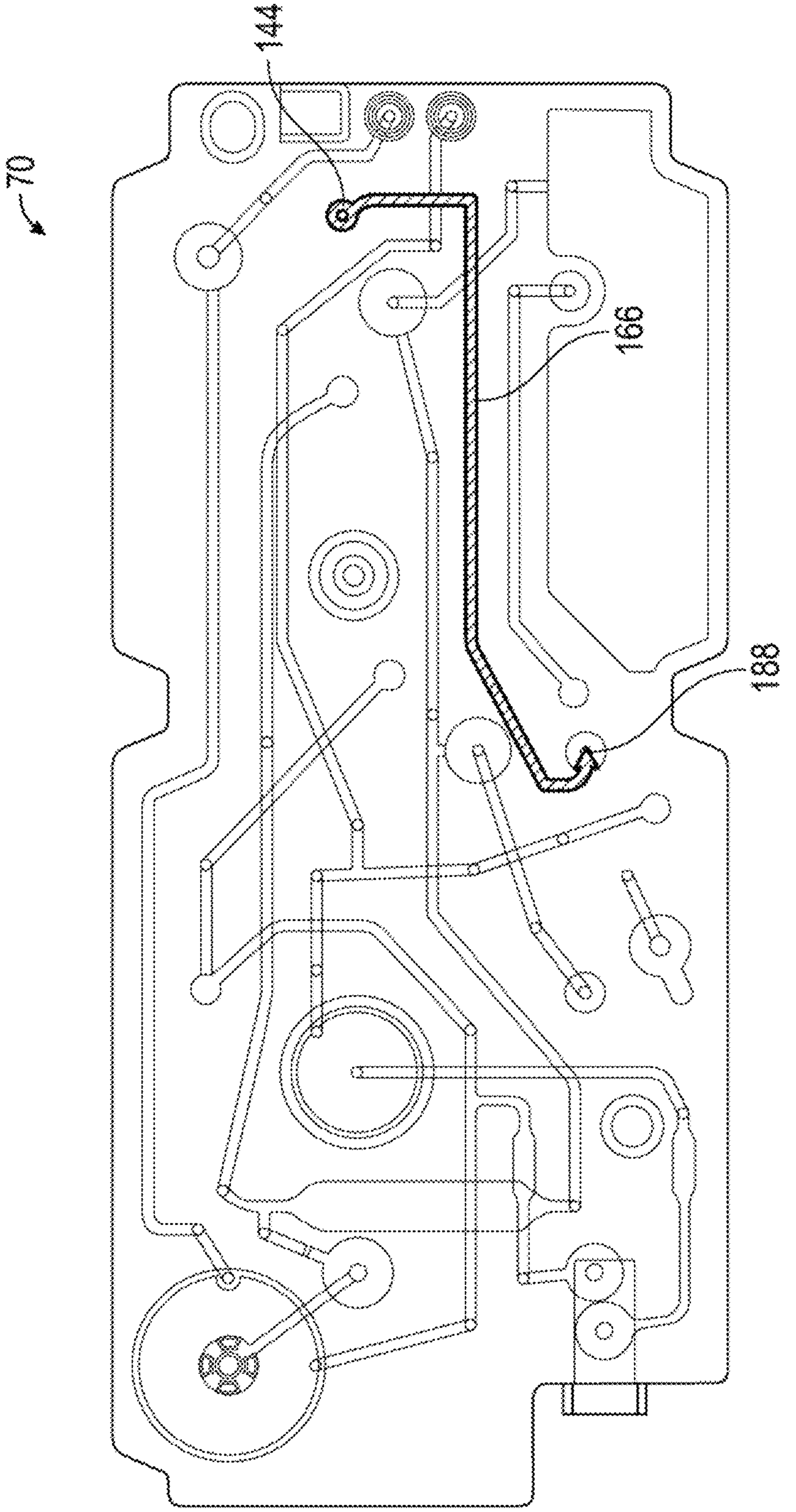

Referring now to FIG. 20, the lance blister 40*b* associated with the deformable compartment 40*a* is collapsed by an external actuator (e.g., the compression mechanism 760*c*) to open the compartment to the fifth inlet port 144, and then the deformable compartment 40*a* is collapsed by an external actuator (e.g., the compression mechanism 756*c*) to force the fluid contents thereof into the fifth inlet port 144. The fluid contents flow from the fifth inlet port 144 to a second outlet 188 via a seventh channel fluid 166. In one embodiment, the fluid content of the deformable compartment 40*a* comprises a rehydration or elution buffer that flows from the second exit port 188 into the rehydration buffer compartment 276 of the reaction module 240 via inlet 278, as shown in FIG. 31 and described above. The same buffer solution contained in the deformable compartment 40*a* may be used for both rehydration of dried or lyophilized reagents or other substances or for elution of nucleic acid or other target analyte from a substrate with which it is bound.

Figure 21:
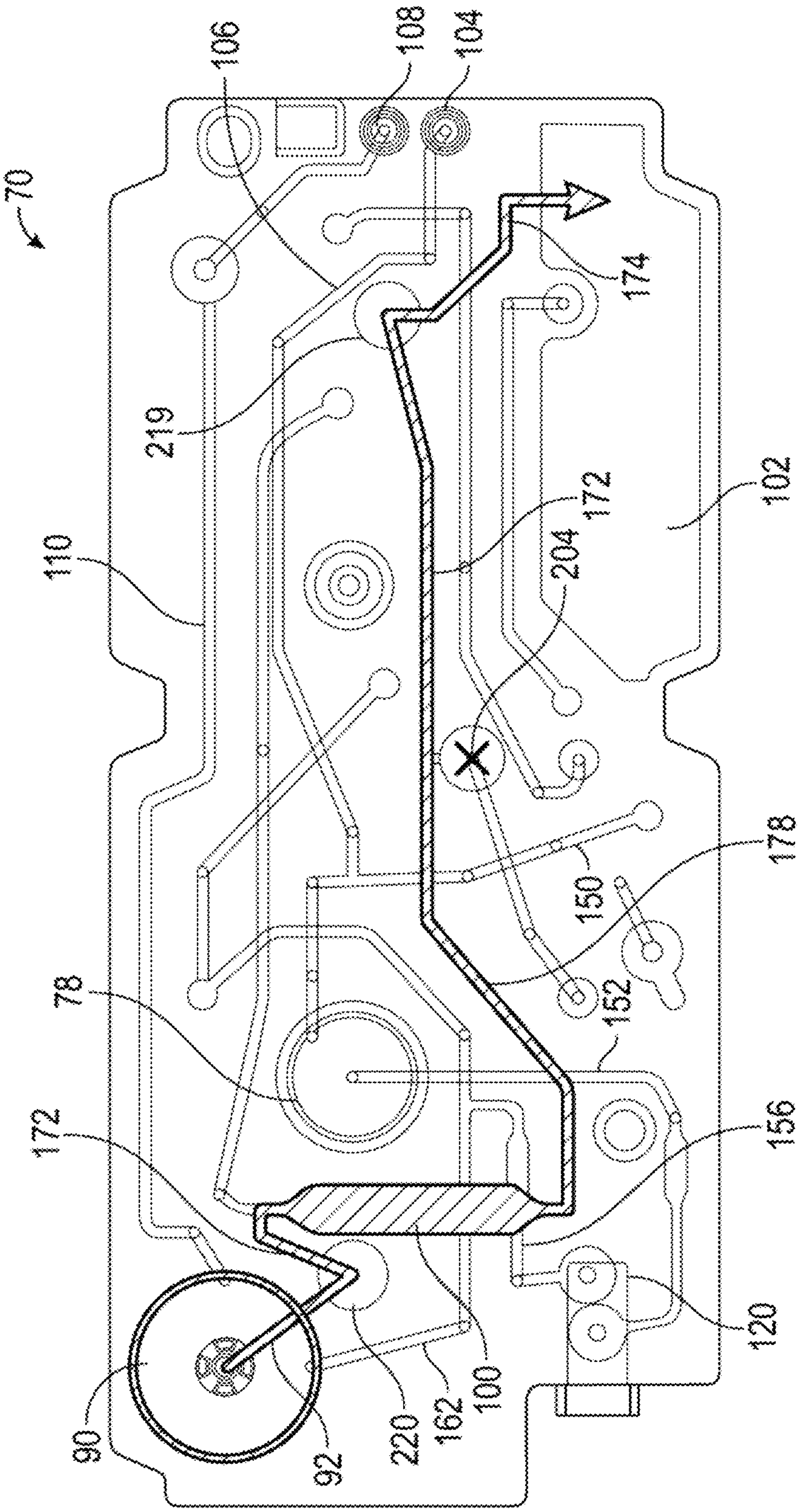

Referring now to FIG. 21, in a next step, the active valve assembly 204 is closed by an external actuator (e.g., the valve actuator 762*b*) pressing down on the valve. The pneumatic pump coupled to the pump port 104 is activated to pressurize the mixing well 90 via the pressure conduit 106, a portion of the first fluid channel 150, the second fluid channel 152, the third fluid channel 156, and a portion of the fifth fluid channel 162. At the same time, the passive valve port 108 is closed to allow a pressure buildup in the mixing well 90 that will actuate the passive valve assembly 220, thereby opening the passive valve 220 to allow fluid contents of the mixing well 90 to flow, via the channels 92 and 172, through the capture compartment 100. Fluid flowing through the capture compartment 100 flows through the thirteenth fluid channel 178, but is prevented by the closed active valve assembly 204 from flowing into the fourteenth fluid channel 180. The active valve assembly 219 remains open so that fluid within the thirteenth fluid channel 178 flows into the tenth fluid channel 172 and into the waste chamber 102. While the fluid is flowing through the capture compartment 100, the contents are subjected to a magnetic force, for example, by placement of an external magnet (e.g., by deploying the sample preparation magnet assembly 570) in proximity to the capture compartment 100. The magnetic force retains magnetic target capture beads and target analyte(s) (e.g., nucleic acid(s)) bound thereto within the capture compartment 100 while the remainder of the contents of the mixing well 90 flows through the capture compartment 100 and into the waste chamber 102.

Figure 22:
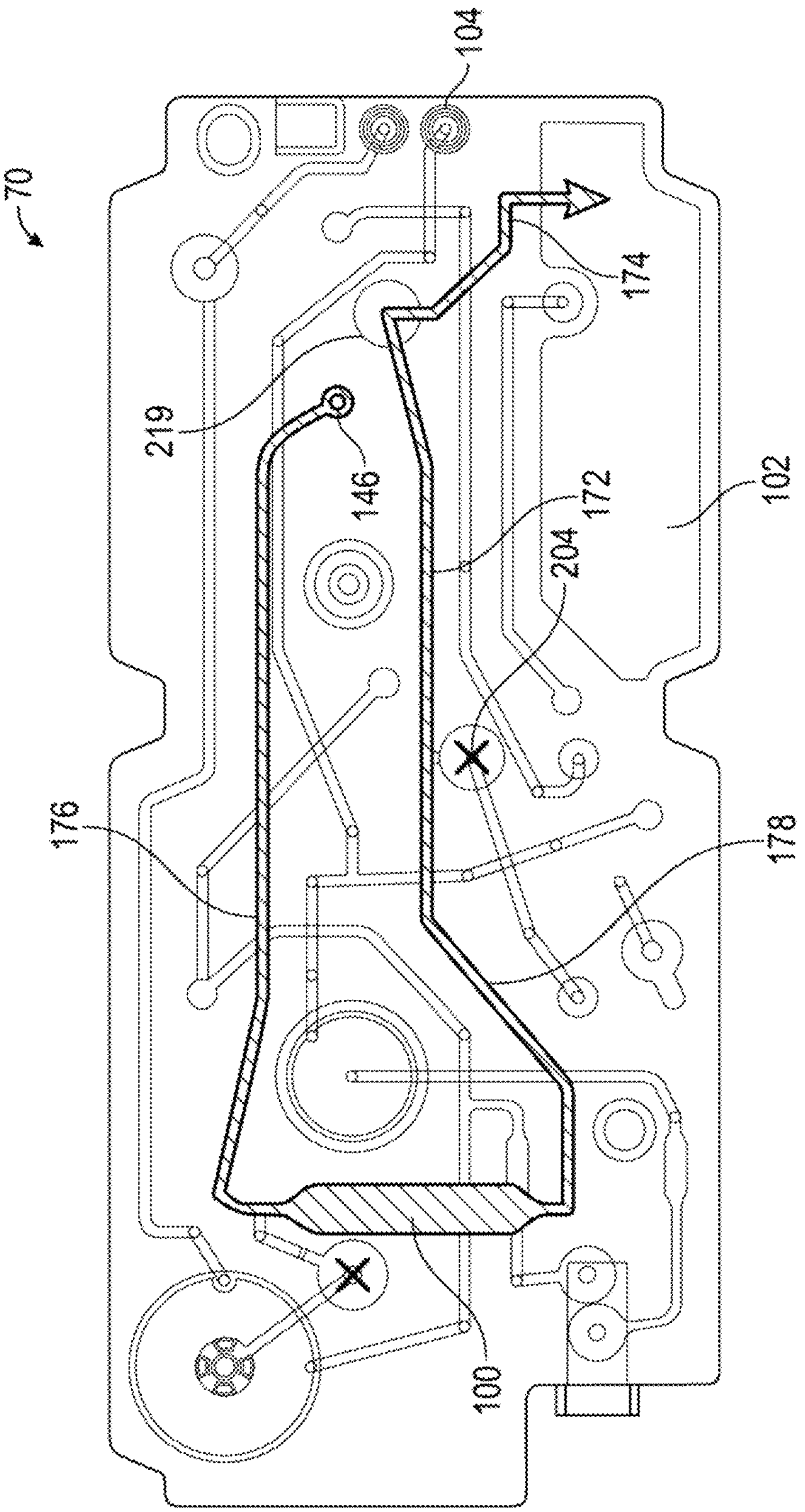

Referring now to FIG. 22, in a next step, the valve assembly 204 remains closed and the valve assembly 219 remains open, and the lance blister 42*b* associated with the deformable compartment 42*a* is collapsed (e.g., with compression mechanism 760*d*) to thereby open the compartment to the sixth inlet port 146. The deformable compartment 42*a* is then partially collapsed (e.g., with the compression mechanism 756*d*) to dispense a portion (e.g., approximately 50%) of its contents into the sixth inlet port 146. In one embodiment, the fluid contents of the deformable compartment 42*a* comprise a wash buffer which flows from the sixth inlet port 146 via the twelfth fluid channel 176 to the capture compartment 100. The wash fluid flows over the capture beads that are immobilized (e.g., by a magnet) within the capture compartment 100 and flows through the channels 178, 172, and 174 to the waste chamber 102 to thereby carry unbound material and other debris into the waste chamber 102.

Figure 23:
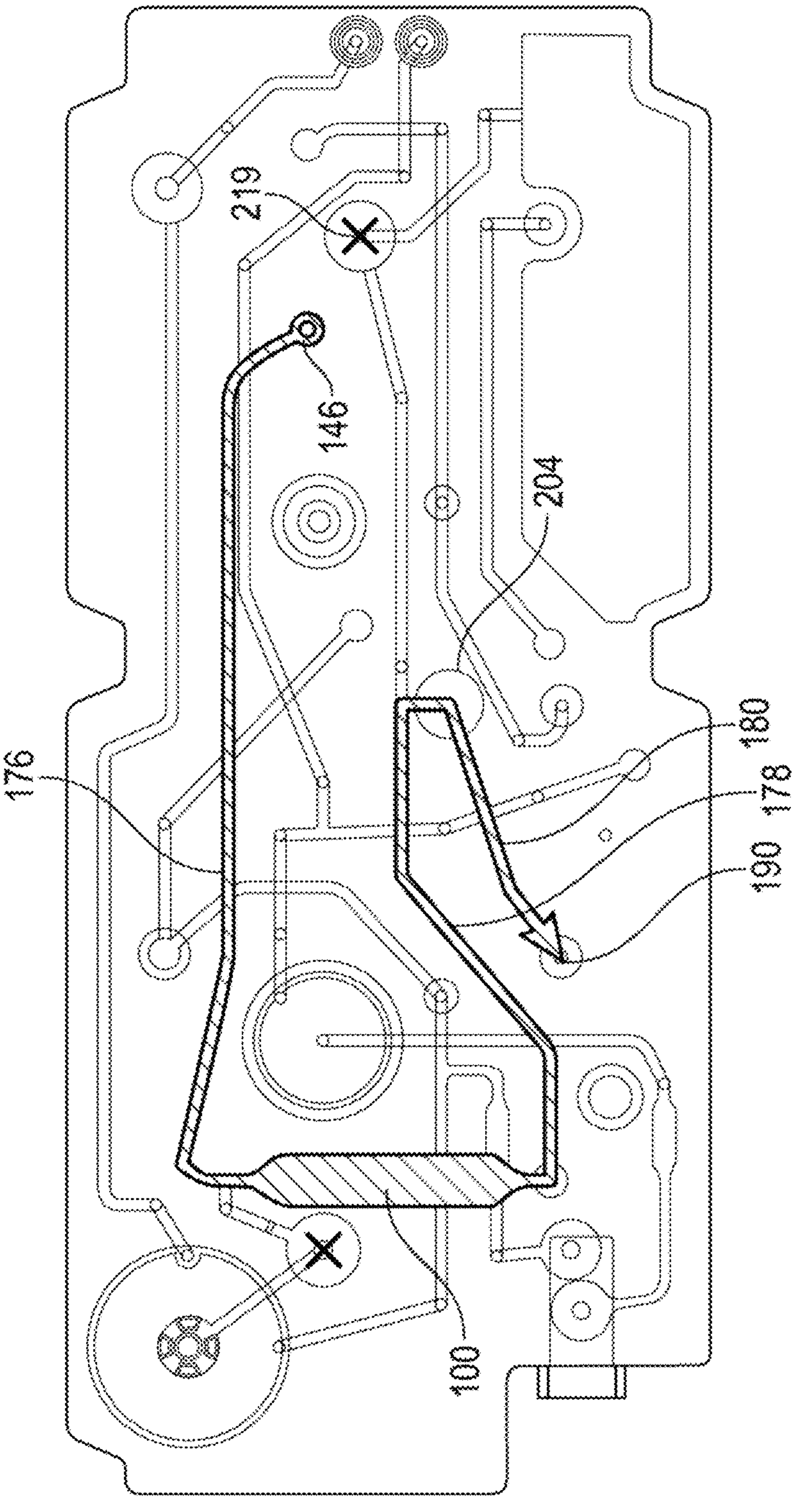

Referring now to FIG. 23, in a next step, the waste valve assembly 219 is closed by an external actuator (e.g., the valve actuator 762*a*), and the sample valve assembly 204 is opened by removing the external actuator. Next, the remainder of the deformable compartment 42*a* is collapsed by the external actuator (e.g., the compression mechanism 756*d*), thereby forcing the remainder of the fluid (e.g., a wash buffer) through the twelfth fluid channel 176 into the capture compartment 100. The magnetic force is removed from the capture compartment 100 (e.g., by retracting the sample preparation magnet assembly 570) so that the magnetic beads within the capture compartment 100 are released and can be carried by the fluid flowing through the capture compartment 100 through the thirteenth fluid channel 178 through the sample valve assembly 204 and the fourteenth fluid channel 180 to a third outlet 190. The fluid flowing from the third outlet 190, which now comprises an at least partially purified target analyte carried on the magnetic beads, is dispensed into the sample compartment 266 of the reaction module 240 via the inlet 268, as shown in FIG. 31 and described above.

In FIGS. 56 and 57, each of the cam follower ribs formed in the cam grooves 850-860 of the cam follower plate 820 is indicated by a unique parenthetical number (1)-(14). As the cam follower plate 820 is moved relative to the cam arm plate 852 in the direction "A," the cam follower ribs formed in various cam grooves 850-860 contact the compression mechanisms of the actuator array 754 in a predetermined sequence so as to open the various reagent chambers and dispense their contents and actuate the various active values in a specified sequence. The parenthetical numbers assigned to the cam follower ribs in FIGS. 56, 57 indicates the sequence in which each rib contacts an associated cam arm of the compression mechanisms of the array 754 to actuate the compression mechanisms in a sequence corresponding to the sample preparation process performed in the sample preparation module 70 as described above and shown in FIGS. 16-23. The table below shows correspondence between each cam follower rib of the cam follower plate 820, the process step, the corresponding compression mechanism, and compressing collapsible chamber or active valve of the multiplex cartridge 10 for the process shown in FIGS. 16-23.

| Follower Element | Process Step | Compression Mechanism/Valve Actuator | Compressible Chamber/ Active Valve |
|---|---|---|---|
| (1) | Open Lysis Lance Blister | 760a | 34b |
| (2)* | Open and dispense magnetic beads | 758 | 44 |
| (3) | Dispense Lysis buffer | 756a | 34a |
| (4) | Open Binding Buffer Lance Blister | 760e | 36b |
| (5) | Dispense Binding Buffer | 756e | 36a |
| (6) | Open Oil Lance Blister | 760b | 38b |
| (7) | Dispense Oil | 756b | 38a |
| (8) | Open Elution/Reconstitution Lance Blister | 760c | 40b |
| (9) | Dispense Elution/ Reconstitution Buffer | 756c | 40a |
| (10) | Close sample Valve assembly | 762b | 204 |
| (11) | Open Wash Buffer Lance Blister | 760d | 42b |
| (12) | Dispense 50% wash buffer | 756d | 42a |
| (13) | Close waste valve assembly | 762a | 219 |
| (14) | Dispense 100% wash buffer | 756d | 42a |

*step (2) is optional and may be omitted if magnetic beads are provided directly, e.g., by a lyophilized pellet, in the mixing well 90.

Sample Reaction Process

The sample material that is dispensed from the sample processing module 70 into the sample compartment 266 of the reaction module 268 is subjected to a reaction process with the reaction module 240. In one exemplary embodiment, that reaction process includes PCR amplification and analyte detection.

Figure 60:
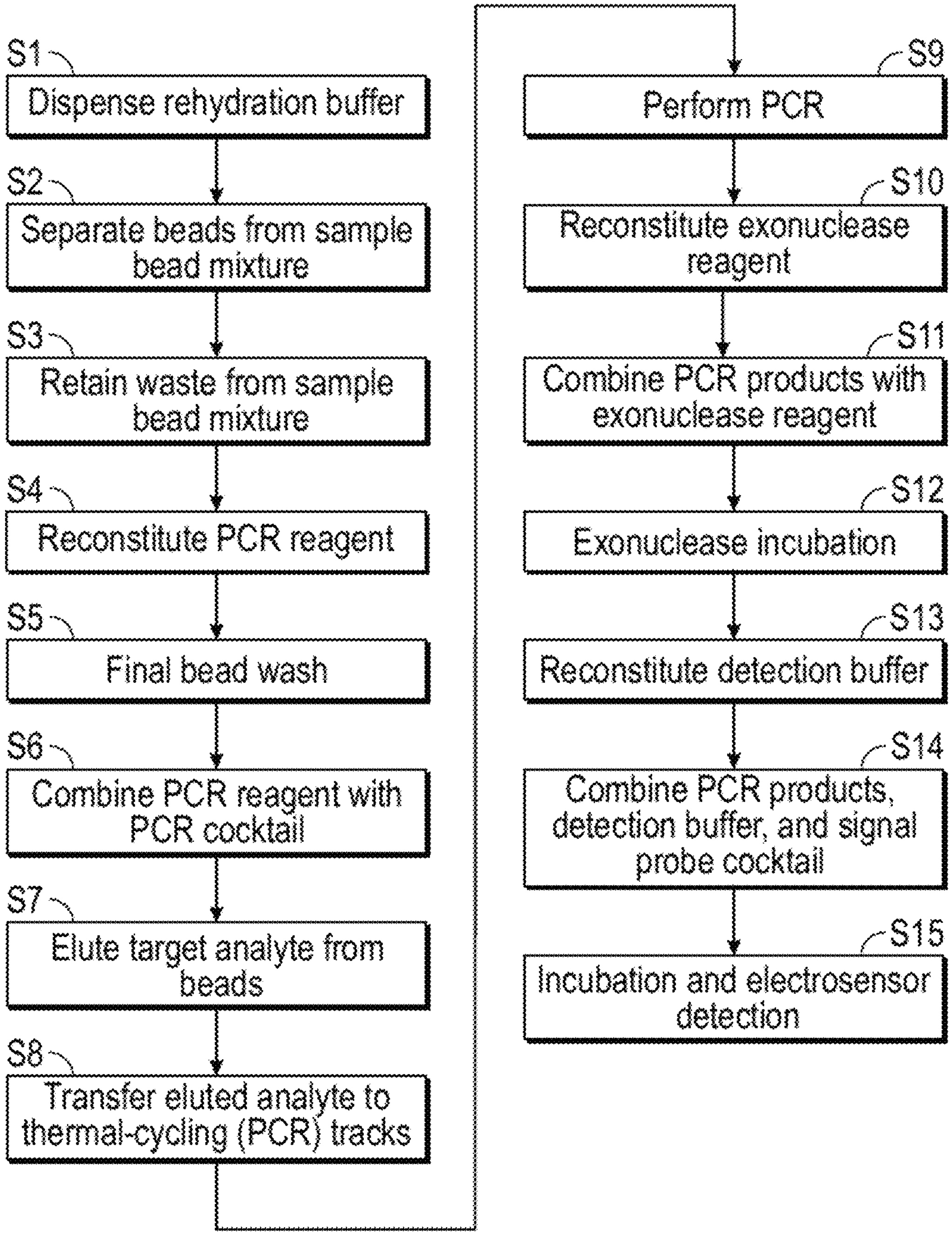
FIG. 60 is a flow chart illustrating an exemplary process that can be performed in the fluidic processing panel.

An exemplary process will be described with reference to flow chart 900 in FIG. 60. Although the various elements (steps) of flow chart 900 in FIG. 60 are shown as sequential steps having a prescribed order, it should be understood that the process 900 as illustrated is exemplary and not intended to be limiting. Persons of ordinary skill will recognize that many of the various element (steps) of the process 900 can be performed in different orders than are shown and described herein, can be performed simultaneously or substantially simultaneously with other elements (steps), or can b omitted altogether. Thus, the order of the elements (steps) as shown in FIG. 60 should not be viewed as limiting unless a specific order for two or more elements (steps) is specifically prescribed or otherwise suggested by the context of the description (e.g., a mixture must first be formed before that mixture can be incubated or otherwise manipulated).

In step S1, an aliquot of the elution/reconstitution buffer (e.g., 15 μl) is dispensed by electrowetting droplet manipulation from the rehydration buffer zone 372 (FIG. 59) (and rehydration buffer compartment 376 of top plate 241 (FIGS. 26, 27)) to an electrowetting pathway defining the exonuclease zone 384 (FIG. 59).

As noted above, in an embodiment of the invention, the region of the reaction module 240 between the top plate 241 and the fluidic processing panel 354 may be filled with a process fluid, such as an immiscible fluid such as oil, and the droplets are manipulated through the oil.

In step S2, an aliquot of the sample mixture (comprising magnetic beads with DNA material bound thereto and wash solution from the sample preparation module 70) is retained by electrowetting manipulation within the sample bead zone 368 (FIG. 59) (and the sample compartment 266 of the top plate 241 (FIGS. 26, 27)), while the magnetic beads are pulled out of the aqueous solution held within the sample bead zone 368 by a magnet that is focused on position 369 (referred to as the bead collection area). The bead collection area 369 corresponds to the position of the focusing magnet 558 of the cartridge magnet assembly 552 (See FIG. 49B) adjacent to the fluid processing panel 554 of the multiplex cartridge 10 when the cartridge magnet assembly 552 is in the deployed position. During the process of collecting the magnetic beads at the bead collection area 369, the aqueous solution may be moved throughout the sample bead zone 368 by selective activation of different electrowetting pads to move the aqueous droplets containing the magnet beads to positions in closer proximity to the magnetic force at the bead collection area 369.

In Step S3, sample waste (i.e., wash buffer and other materials from which the magnetic beads have been removed in Step S2), is retained by electrowetting droplet manipulation within the sample bead zone 368 (and the sample compartment 266), thereby separating the magnet beads, and the target analyte material bound thereto, from the other constituent substances of the sample bead mixture that was delivered from the sample preparation module 70 to the sample bead zone 368.

In Step S4, an amount of the reconstitution buffer that was dispensed from the rehydration buffer zone 372 in Step S1 may be moved by electrowetting droplet manipulation to the PCR reagent zone 376 (FIG. 59) (and the buffer compartment 296 of the top plate 241 (FIGS. 26, 27)) Resuspension of the dried PCR reagent contained within the PCR reagent zone 376 occurs by oscillating movements of the droplets between the electrowetting pads within the PCR reagent zone 376.

In Step S5, an amount of the reconstitution buffer that was dispensed from the rehydration buffer zone 372 and which was not transported to the PCR reagent zone 376 is transported by electrowetting droplet manipulation over the magnetic beads held by the magnetic force at the bead collection area 369 for a final bead wash. After the final bead wash, the reconstitution buffer is then moved by electrowetting droplet manipulation to an end of the center pathway corresponding to the exonuclease zone 384 where it is held by electrowetting droplet manipulation apart from the magnetic beads held at the bead collection area 369.

In the Step S6, the reconstituted PCR buffer within the PCR reagent zone 376 is distributed by electrowetting droplet manipulation to the primer cocktail positions of each of the thermal cycling tracks 364*a*, 364*b*, 364*c*, and 364*d*. One primer cocktail position 366*a* at a proximal end of the thermal cycling track 364*d* is labeled in FIG. 59. Each of the other thermal cycling tracks 364*a*, 364*b*, and 364*c* has a similar primer cocktail location. The combination of reconstituted PCR reagent with the dried primer cocktail at the primer cocktail position (e.g., position 366) reconstitutes the primer cocktail at that position. In this configuration, the reaction module 240 is configured to perform one PCR reaction in each of the thermal cycling tracks 364*a*, 364*b*, 364*c*, and 364*d*.

In an alternate embodiment, a primer cocktail may also be provided at the distal end of each thermal cycling track 364*a*, 364*b*, 364*c*, and 364*d*. One primer cocktail position 366*b* at a distal end of thermal cycling track 364*d* is labeled in FIG. 59. Each of the other thermal cycling tracks 364*a*, 364*b*, and 364*c* may have a similar primer cocktail location. In such a configuration, the reaction module 240 is configured to perform two PCR reactions in each of the thermal cycling tracks 364*a*, 364*b*, 364*c*, and 364*d*.

In Step S7, the magnetic force is removed from the bead collection area 369 (e.g., by moving the cartridge magnet assembly 552 to its retracted position). Reconstitution/elution buffer is moved by electrowetting droplet manipulation from the central pathway 384 to the bead collection area 369, and a mixture of the magnetic beads and reconstitution/elution buffer from the rehydration buffer zone 372 is shuttled back and forth along the path 384 by electrowetting droplet manipulation t elute the DNA material (or other target analyte) from the magnetic beads.

After a sufficient elution period, in Step S8, the cartridge magnet assembly 552 is again deployed to apply a magnetic force (via the focusing magnet 558) to the bead collection area 369 to attract and retain (immobilize) the magnetic beads from which the DNA material has been eluted, and the eluted DNA material is transferred by electrowetting droplet manipulation to a PCR staging area at a proximal end of each of the thermal cycling tracks 364*a*, 364*b*, 364*c*, and 364*d*. In the embodiment and orientation shown in FIG. 59, the PCR staging area is at the left end of thermal cycling tracks 364*a*, 364*b*, 364*c*, and 364*d*.

In Step S9, PCR droplets—comprising the eluted DNA material, the reconstituted PCR reagent, and the reconstituted PCR primer—are formed by electrowetting droplet manipulation at the PCR staging area of each of the thermal cycling tracks 364*a*, 364*b*, 364*c*, and 364*d*. Each PCR droplet is moved into a corresponding one of the thermal cycling tracks 364*a*, 364*b*, 364*c*, and 364*d*, and a PCR process is performed by shuttling the droplets between two of the PCR (thermal cycling) regions 382*a* (at about, e.g., 60° C. for annealing and extension) and 382*b* (at about, e.g., 95° C. for denaturation) or 382*c* (at about 60° C. for annealing and extension) and 382*b* (at about, e.g., 95° C. for denaturation). In another embodiment, two PCR droplets are transported into each thermal cycling track 364*a*, 364*b*, 364*c*, and 364*d*, and one droplet is shuttled between heater areas 382*c* and 382*b*, whereas the other droplet is shuttled between heater areas 382*a* and 382*b*. The PCR process may last for about 40 minutes or less.

In Step S10, an amount of elution/reconstitution buffer is dispensed by electrowetting droplet manipulation from the rehydration buffer zone 372 and is transported by electrowetting droplet manipulation to the exonuclease reagent zone 374 (FIG. 59) (and the second buffer compartment 300 of the top plate 241 (FIG. 26, 27)) for resuspension of the dried exonuclease reagent. Resuspension of the dried exonuclease reagent contained within the exonuclease reagent zone 374 occurs by oscillating movements of the droplets between the electrowetting pads within the exonuclease reagent zone 374. The reconstituted exonuclease reagent is then transported by electrowetting droplet manipulation from the exonuclease reagent zone 374 to PCR staging areas of the thermal cycling track 364*a*, 364*b*, 364*c*, and 364*d*.

In Step S11, following PCR (Step 9), each droplet that has gone through the PCR process is combined with an amount of the exonuclease agent resuspended in Step S10, transported by electrowetting droplet manipulation to the exonuclease zone 384, and held in a separate location within the exonuclease zone 384. In various embodiments, an amount of elution/reconstitution buffer from the buffer zone 372 is added to each PCR droplet by electrowetting droplet manipulation to bring the total volume of each droplet up to a preferred amount.

In Step S12, the droplet mixtures formed in Step S1*l*, comprising the PCR products and the reconstituted exonuclease reagent, are then incubated within the exonuclease region 380 and the exonuclease zone 384 at a prescribed temperature and for a prescribed period of time.

In Step S13, detection reagent within the hybridization zone 370 (FIG. 59) (and the detection buffer compartment 280 of the top plate 241 (FIGS. 26, 27)) is reconstituted with an amount of rehydration buffer from the rehydration buffer zone 372. In one embodiment, an amount of rehydration buffer from the rehydration buffer zone 372 is moved via electrowetting droplet manipulation through the connecting passage 274 (FIGS. 26, 27) between the detection buffer compartment 280 and the rehydration buffer compartment 276.

In Step S14, an amount of the reconstituted detection reagent (e.g. 25 μl) from the hybridization zone 370 is combined by electrowetting droplet manipulation with each of the PCR droplets. Each PCR droplet is then combined with a signal probe cocktail stored at positions 362*a*, 362*b*, 362*c*, and 362*d* of the fluid processing panel 354. To effect mixing of the PCR droplet and the signal probe cocktail, and to resuspend the signal probe cocktail, each droplets may be transported by electrowetting droplet manipulation around or within one of the detection mixing zones 385*a*, 385*b*, 385*c*, and 385*d*.

In Step S15, the droplets are transported by electrowetting manipulation to the electrosensor arrays 363*a*, 363*b*, 363*c*, and 363*d*, where they are subjected to further incubation within the detection region 378 and various analytes of interest are detected by electrosensing techniques, such as described above and/or described in publications incorporated by reference above.

Figure 65:
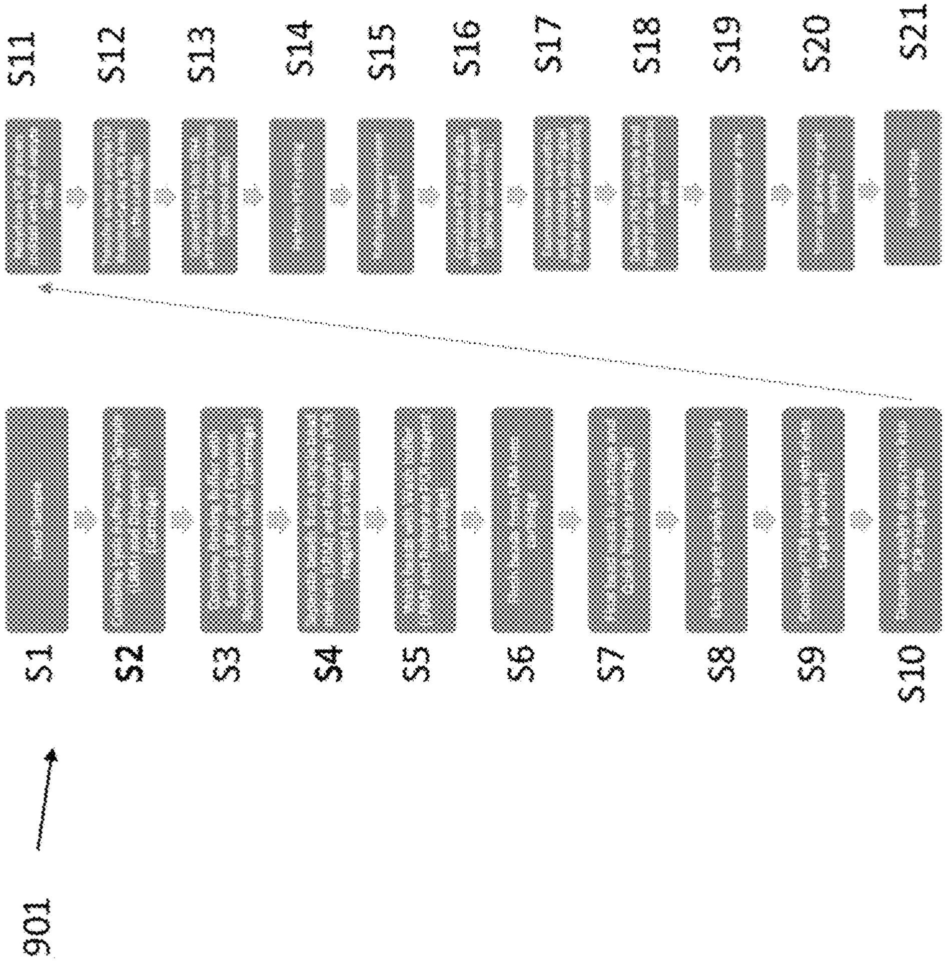
FIG. 65 is a flow chart illustrating an exemplary process that can be performed in the fluidic processing panel.

An exemplary process will be described with reference to flow chart 901 in FIG. 65. Although the various elements (steps) of flow chart 901 in FIG. 65 are shown as sequential steps having a prescribed order, it should be understood that the process 901 as illustrated is exemplary and, not intended to be limiting. Persons of ordinary skill will recognize that many of the various elements (steps) of the process 901 can be performed in different orders than are shown and described herein, can be performed simultaneously or substantially simultaneously with other elements (steps), or can b. omitted altogether. Thus, the order of the elements (steps) as shown in FIG. 65 should not be viewed as limiting unless a specific order for two or more elements (steps) is specifically prescribed or otherwise suggested by the context of the description (e.g., a mixture must first be formed before that mixture can be incubated or otherwise manipulated).

In Step S1, a fluid sample specimen is dispensed into the sample well (also referred to as sample port) 78 (FIG. 16). The fluid sample volume ranges from 1 uL to 500 uL. The sample well 78 may then be closed using the sample cap 84 (see FIG. 6), and the multiplex cartridge 10 is then placed in a processing instrument (e.g., into the processing bay 412 of the processing module 410 of the instrument 400).

In Step S2, within the instrument, the lance blister 34*b* (FIG. 5) associated with the deformable compartment 34*a* (FIG. 5) is compressed by an external actuator (e.g., the compression mechanism 760*a*) to press a bead or other opening device (e.g., as described in U.S. patent application Ser. No. 14/206,867 (U.S. Pat. No. 9,222,623) entitled "Devices and Methods for Manipulating Deformable Fluid Vessels" the contents of which are hereby incorporated by reference) through a closing seal (e.g., lance the seal with the bead or other device), and then the deformable compartment 34*a* is compressed by an external actuator (e.g., the compression mechanism 756*a* of FIG. 54) to force a process fluid contained therein into the first inlet port 136 (FIG. 17). In one embodiment, the process fluid contained in the deformable compartment 34*a* is a lysis buffer (between 100 μl and 400 uL of lysis buffer). The fluid is directed by the first fluid channel 150 from the inlet port 136 to the sample well 78, where the fluid enters the sample well 78 through the inlet snorkel 80. In addition, an external pump (e.g., pump 458) connected to the sample preparation module 70 at the pump port 104 generates pressure that is applied to the contents of the sample well 78 via the pressure conduit 106 and sends sample to the mixing well 90. The mixing well 90 contains pre-dried magnetic beads.

At the same time, the fluid (e.g., oil/Filler Fluid) contained in the deformable compartment 38*a* is used to fill a reaction space 295 within the reaction module 240 between the top plate 241 and the fluidic processing panel 354, as shown in FIG. 30. Specifically, a volume between 2300 μl and 3000 uL of oil/Filler Fluid is dispensed into the reaction space 295.

In Step S3, the sample in lysis buffer is combined with a volume of binding buffer (between 200 μl and 650 uL of binding buffer). Binding buffer in deformable compartment 36*a* is added to the sample preparation module 70 via a second inlet port 138. Pressure from external pump (e.g., pump 458) continues to generate pressure that is applied to the contents of the sample well 78 via the pressure conduit 106 and continues to send sample to the mixing well 90.

At the same time, a volume of reconstitution buffer (between 250 uL and 300 uL) is dispensed into the reaction space 295 within the reaction module 240 containing oil/Filler Fluid.

In Step S4, a pressure is applied to move/transport the sample and bead mixture into the magnetic chamber (100 also referred to herein as the capture compartment) and a magnet is actuated to capture the beads while the supernatant passes through and goes to the waste chamber (102). Magnetic beads are now collected and separated from the waste; the beads and nucleic acids are bound.

At the same time, the reconstitution buffer is dispensed by electrowetting droplet manipulation to rehydrate the PCR reagents in the reaction space 295 within the reaction module 240.

In Step S5, a first aliquot of wash buffer from deformable compartment 42*a* is added to the magnetic chamber (100) via inlet port 146 and passed through the beads to wash and remove contaminants.

At the same time, the reconstitution buffer continues to rehydrate the PCR reagents in the reaction space 295 within the reaction module 240.

In Step S6, the magnet is disengaged. A second aliquot of wash buffer from deformable compartment 42*a* is added to the magnetic chamber (100) via inlet port 146 and passed through the beads a second time to transport the beads from the LRM to the reaction module 240. Sample can exit the module 70 and flow into the reaction module 240. In some instances, the fluid flow is via a first outlet port 182, a second outlet port 188, and a third outlet port 190 formed in a bottom surface of the sample preparation module 70.

In Step S7, inside the reaction module 240, beads are collected by a second magnet in the sample compartment 266 and electrowetting is used to remove the wash buffer. Reconstitution buffer is used to rinse the beads to further reduce contaminants. Beads and nucleic acid are still bound at this stage.

In Step S8, the magnetic force is removed from the bead collection area 369 (FIG. 59 or 68) (e.g., by moving the cartridge magnet assembly 552 to its retracted position). Reconstitution/elution buffer is moved by electrowetting droplet manipulation from the central pathway 384 to the bead collection area 369, and a mixture of the magnetic beads and reconstitution/elution buffer from the rehydration buffer zone 372 is shuttled back and forth along the path 384 by electrowetting droplet manipulation to elute the DNA material (or other target analyte) from the magnetic beads.

In Step S9, the eluted DNA material from S8 is combined with PCR reagents from step S5 along the path 384 (FIG. 59 or 68) by electrowetting droplet manipulation.

In Step S10, PCR droplets—comprising the eluted DNA material, the reconstituted PCR reagent, and the reconstituted PCR primer—are formed by electrowetting droplet manipulation a, the PCR staging area 364.1 (FIGS. 68A-B).

In Step S11, PCR primers are rehydrated by electrowetting. The PCR primers are dry. the drop that comes from step S10 is moved across the dried PCR primers until they are rehydrated.

In Step S12, after primers are suspended, the drops are transferred into the PCR zone where the three heaters are. Specifically, each PCR droplet is moved into a corresponding one of the thermal cycling tracks 364*a*, 364*b*, 364*c*, and 364*d*.

In Step S13, RNA is converted into DNA by reverse transcriptase enzyme.

In Step S14, a PCR process is performed by shuttling the droplets (usually 1-8 drops or 1-4 drops) between two of the PCR (thermal cycling) regions 382*a* (at about, e.g., 50-70° C. for annealing and extension) and 382*b* (at about, e.g., 85-100° C. for denaturation) or 382*c* (at about 50-70° C. for annealing and extension) and 382*b* (at about, e.g., 85-100° C. for denaturation).

In Step S15, an amount of elution/reconstitution buffer is dispensed from the rehydration buffer zone 372 and is transported to the exonuclease reagent zone 374 (FIGS. 68A-B) (and the second buffer compartment 300 of the top plate 241 (FIG. 26, 27)) for resuspension of the dried exonuclease reagent. Resuspension of the dried exonuclease reagent contained within the exonuclease reagent zone 374 occurs by oscillating movements of the droplets between the electrowetting pads within the exonuclease reagent zone 374.

In Step S16, the reconstituted exonuclease reagent is then transported from the exonuclease reagent zone 374 to PCR staging areas 364.1 of the thermal cycling track 364*a*, 364*b*, 364*c*, and 364*d*. Following PCR (Step 14), each droplet that has gone through the PCR process is combined with an amount of the exonuclease agent suspended in Step S15 in the PCR staging area 364.1.

In Step S17, the droplet mixtures formed in Step S11, comprising the PCR products and the reconstituted exonuclease reagent, are then incubated within the exonuclease region 380 and the exonuclease zone 384 at a prescribed temperature and for a prescribed period of time. At the sample time, signal probe is rehydrated in the exonuclease zone 384. Each PCR droplet is then combined with a signal probe cocktail stored at positions 362*a*, 362*b*, 362*c*, and 362*d* of the fluid processing panel 354. To effect mixing of the PCR droplet and the signal probe cocktail, and to resuspend the signal probe cocktail, each droplet may be transported by electrowetting droplet manipulation around or within one of the detection mixing zones 385*a*, 385*b*, 385*c*, and 385*d*.

In Step S18, the droplets containing the exonuclease digested DNA and signal probe cocktail are transported to the electrosensor arrays 363*a*, 363*b*, 363*c*, and 363*d*.

In Step S19, the droplets are subjected to further incubation within the detection region 378 at a prescribed temperature and for a prescribed period of time.

In Step S20, various analytes of interest are detected by electrosensing techniques, such as described above and/or described in publications incorporated by reference above.

In Step S21, the cartridge is ejected from the instrument. The above exemplary processes can be generally applied to detect any target analyte. Below are the specific processes used to detect gram-positive or gram-negative targets in a BCID-Gram negative panel or BCID-gram positive panel i.e, a fully automated, qualitative, nucleic acid, multiplex in vitro diagnostic test for the simultaneous qualitative detection and identification of multiple potentially pathogenic gram-positive bacterial organisms and select determinants of antimicrobial resistance in positive blood culture.

BCID-Gram positive and Gram-negative Assay Process

| Processing Stage | Processing Step | Sample process | Cartridge | Instrument |
|---|---|---|---|---|
| Operator Sample and cartridge Prep | Sample Prep | Operator prepares sample according to assay specific package insert. | N/A | N/A |
| | Cartridge Packaging removal | N/A | Operator Opens Pouch, removes cartridge | N/A |
| | Cartridge Labelling for positive identification | N/A | Operator Places barcode with Accession ID Label onto cartridge | N/A |
| | Sample loading: Operator loads 50 uL of Blood culture specimen into the sample port of the cartridge. | Operator Loads sample into cartridge | N/A | N/A |
| | Cartridge sealing | N/A | Operator Closes cap | N/A |
| | Barcode registration | N/A | Operator scans barcode | Instrument registers barcode information and prepares to receive corresponding cartridge |
| | Cartridge insertion into instrument | N/A | Operator Inserts cartridge into ePlex Bay | Instrument registers presence of cartridge |
| | "Pre-run check" evaluation of cartridge quality | N/A | Cartridge present for evaluation | Interrogation of cartridge electrical function, ability to build pressure, presence of EEPROM, and instrument-cartridge connections. |
| Automated Sample prep: lysis | Sample and lysis buffer pushed. through bead beater and towards mix chamber | Sample lysis by bead beater and moved into mix chamber | Bead beater activates and Lysis buffer dispensed from opened blister into sample chamber | Bead beater motor ON and Lysis foot actuates lysis blister (presses blister to dispense fluid into cartridge) |
| | Sample and lysis buffer combined in mix chamber | N/A (sample stays in mix chamber) | Lysis buffer pushed pneumatically into mix chamber. | Bay pump injects air into cartridge |
| | Sample and lysis buffer mix and incubate, lysing bacteria The lyo pellet is glued to mix paddle during cartridge assembly (therefore it is already present in the mix chamber) | Mixing of sample, lysis, and lyophilized pellet of magnetic beads and *S. pombe* in mix chamber | Mix paddle rotates ~100 rpm to generate mixing | Gear actuates mix paddle |
| | Oil dispensed into PCB Cartridge, to prepare for electro-wetting Oil facilitates final sample preparation stages, and non-sample-prep steps. | N/A | Oil blister dispensed into cartridge | Oil foot actuates oil blister (during above mixing step) |
| Automated Sample prep: nucleic acid capture | Binding buffer added to mixture of sample, lysis buffer and magnetic beads | N/A | Binding buffer dispensed into mix chamber | Binding buffer foot actuates binding buffer blister |
| | Nucleic acids bound to magnetic beads | Nucleic acids from lysed sample bound to magnetic beads. | Mix paddle rotates ~100 rpm to generate mixing | Gear actuates mix paddle |
| | Recon (Reconstitution) buffer dispensed into PCB Cartridge, facilitating upcoming reagent resuspension Occurs during sample prep on the LRM, but Recon Buffer is not used for sample preparation | N/A | Recon buffer dispensed into cartridge | Recon buffer foot actuates recon blister (during above mixing step) |

-continued

| BCID-Gram positive and Gram-negative Assay Process | | | | |
|---|---|---|---|---|
| Automated Sample prep: removal of PCR inhibitors | Preparation to capture magnetic beads | N/A | N/A | Magnet raised inpreparation to capture magnetic beads |
| | Magnetic beads captured to facilitate inhibitor removal | Nucleic acids stay attached to magnetic beads as non-bound inhibitors are washed away. | Magnetic beads captured against flat surface of the Magnet Capture Chamber to maximize contact with fluids. | Pump injects air to force buffer-bead mixture past magnetic capture region. |
| | Removal of PCR inhibitors | Nucleic acids stay attached to magnetic beads as non-bound inhibitors are washed away | Mix of wash buffer and air pushed past magnetic beads to remove inhibitors | Wash blister foot actuates wash blister and pump injects air into cartridge |
| | Preparation to release magnetic beads into electro-wetting area | N/A | N/A | Magnet lowered in preparation to release magnetic beads into electrowetting area |
| | Transfer of magnetic beads (and nucleic acids) into electrowetting area | Nucleic acids from sample transferred to electrowetting area | Mix of wash buffer and air push magnetic beads from the mag capture chamber surface and into the PCB cartridge electrowetting area | Wash blister foot actuates wash blister and pump injects air into cartridge |

| Processing Stage | Processing Step | Sample process | Cartridge process | Instrument Process | Notes |
|---|---|---|---|---|---|
| Automated Sample prep: sample concentration and nucleic acid separation from beads and inhibitors | Sample concentration via bead capture | Magnetic beads (with attached nucleic acids) gathered by magnet | N/A | Magnet raised to capture beads | |
| | Inhibitor removal by washing with buffer. | Magnetic beads held by magnets. | Electrodes actuate electrowetting of buffer | Electrodes energized for electrowetting, and magnet raised to capture beads | This step is repeated 2 times |
| | Inhibitor removal by bead removal from surrounding buffer | Magnetic beads (with bound nucleic acids) are pulled out of surrounding buffer by magnet | Electrodes actuate electrowetting of buffer. Buffer held in place by electro-wetting while beads are pulled back to magnet (bead snap step) | Electrodes energized for electrowetting Magnet is lowered to allow motion of beads, and raised to recapture beads | This step is repeated 2 times |
| | Recon buffer is delivered to beads | Magnetic beads combine with recon buffer | Electrodes actuate electrowetting | Electrodes energized for electrowetting | |
| | Nucleic acids eluted from magnetic beads | Nucleic acids (in recon buffer) moved away from magnetic beads | Electrodes actuate electrowetting Incu-bation at 80 °C | Electrodes energized for electrowetting, and magnet raised to capture beads | |
| | Master Mix reagent resuspension | N/A | Electrodes actuate electrowetting. | Electrodes energized for electrowetting | |
| Nucleic Acid Amplification | Addition of Master Mix to nucleic acids | Master Mix is combined with purified target | Electrodes actuate electrowetting. | Electrodes energized for electrowetting | Master mix is salts, buffer, dNTPs and stabilizers |
| | Droplets are staged for PCR | PCR mix is divided into 8 drops for PCR. | Electrodes actuate electrowetting. Drops are dispensed and staged in PCR staging area. | Electrodes energized for electrowetting. | |
| | Resuspension of primers | Incorporation of primers into Master Mix | Electrodes actuate electrowetting, mixing step | Electrodes energized for electrowetting. | Primers are dried onto PCR staging area where master mix containing target has been |

-continued

| BCID-Gram positive and Gram-negative Assay Process | | | | | |
|---|---|---|---|---|---|
| | PCR entry | The 8 drops are staged in 4 PCR lanes, which are located above heaters. | Electrodes actuate electrowetting. PCR droplets move via electro-wetting to heaters 1 and 3 (4 drops per heater). | Electrodes energized for electrowetting and heaters are energized to controlled temperatures. | |
| | Hot-start Taq activation and initial denature step | The 8 droplets are incubated on heater 2 - at 95.5 for Gram-positive 96.3 °C for Gram-negative | Electrodes activate electrowetting. | Electrodes energized for electrowetting. See above. | |
| | DNA Amplification; 30-35 cycles; 2-step PCR | Amplification - denaturation at for Gram-positive 96.3 °C for Gram-negative and anneal/ extension at 65 for Gram-positive 64.5 °C for Gram-negative | Electrodes activate electrowetting. Droplets travel back and forth from heaters 1 or 3 to heater 2. | Electrodes energized for electrowetting | |
| | Finish PCR | Droplets transported from PCR heater area to staging area | Electrodes activate electrowetting | Electrodes energized for electrowetting | |
| | Merge drops | 8 PCR drops are combined to four 4 uL drops by combining 2 drops of each PCR lane into one drop per lane | Electrodes activate electrowetting | Electrodes energized for electrowetting | |
| Detection | Recon (Reconstitution) buffer dispensed into Reservoir 2, which contains a dry exo-nuclease (Exo) spot. | N/A | Electrodes activate electrowetting, 9 uL of recon fluid is transferred to reservoir 2 to resuspend the Exonuclease | Electrodes energized for electrowetting | Recon buffer blister was actuated during “automated sample prep: nucleic acid capture” processing stage |
| | Delivery of Exo to PCR droplets | 1 uL of Exo is mixed with each of the four 4 uL PCR droplets | Electrodes activate electrowetting | Electrodes energized for electrowetting | |
| | Deliver droplets to detection staging area | Droplets are transferred to detection staging area | Electrodes activate electrowetting | Electrodes energized for electrowetting | |
| | Conversion to single stranded DNA (ssDNA) | Droplets are incubated with Exo | Electrodes activate electrowetting. Incubates at 40 °C | Electrodes energized for electrowetting | |
| | Resuspension of signal probes with Exo-treated droplets | Droplets are agitated over dried signal probe mix spot | Electrodes activate electrowetting | Electrodes energized for electrowetting | This happens concurrently with the step above |
| | Dispense 15 uL of Recon buffer into center lane in preparation for mixing with SSDNA | N/A | Electrodes activate electrowetting | Electrodes energized for electrowetting | |
| | Recon is transported and mixed with droplets; | 15 uL of Recon buffer is transported to the 5 uL of Exo-treated droplets and mixed | Electrodes activate electrowetting | Electrodes energized for electrowetting | |
| | Drop delivery into eSensor zone | Drops are moved from center lane to the eSensor zone | Electrodes activate electrowetting. Incubation at 46.3 for Gram-positive 50 °C for Gram-negative | Electrodes energized for electrowetting | |
| | Collection of digital signals | N/A | Scans electrodes | Collects digital signals | |

-continued

| BCID-Gram positive and Gram-negative Assay Process | | | | |
|---|---|---|---|---|
| Results Reporting and cartridge disposal | Data (digital signals) passed to system for processing and results reporting | N/A | N/A | Bay passes data to Tower for analysis and results reporting |
| | Cartridge ejection | N/A | Cartridge partially ejected from bay | Bay automatically ejects cartridge |
| | Cartridge disposal | N/A | Operator removes the completed cartridge from the bay and disposes of the cartridge according to local regulations | N/A |
| | Instrument reset | N/A | N/A | Instrument automatically resets itself, and is available for another cartridge |

Software Architecture and Operation

Figure 61:
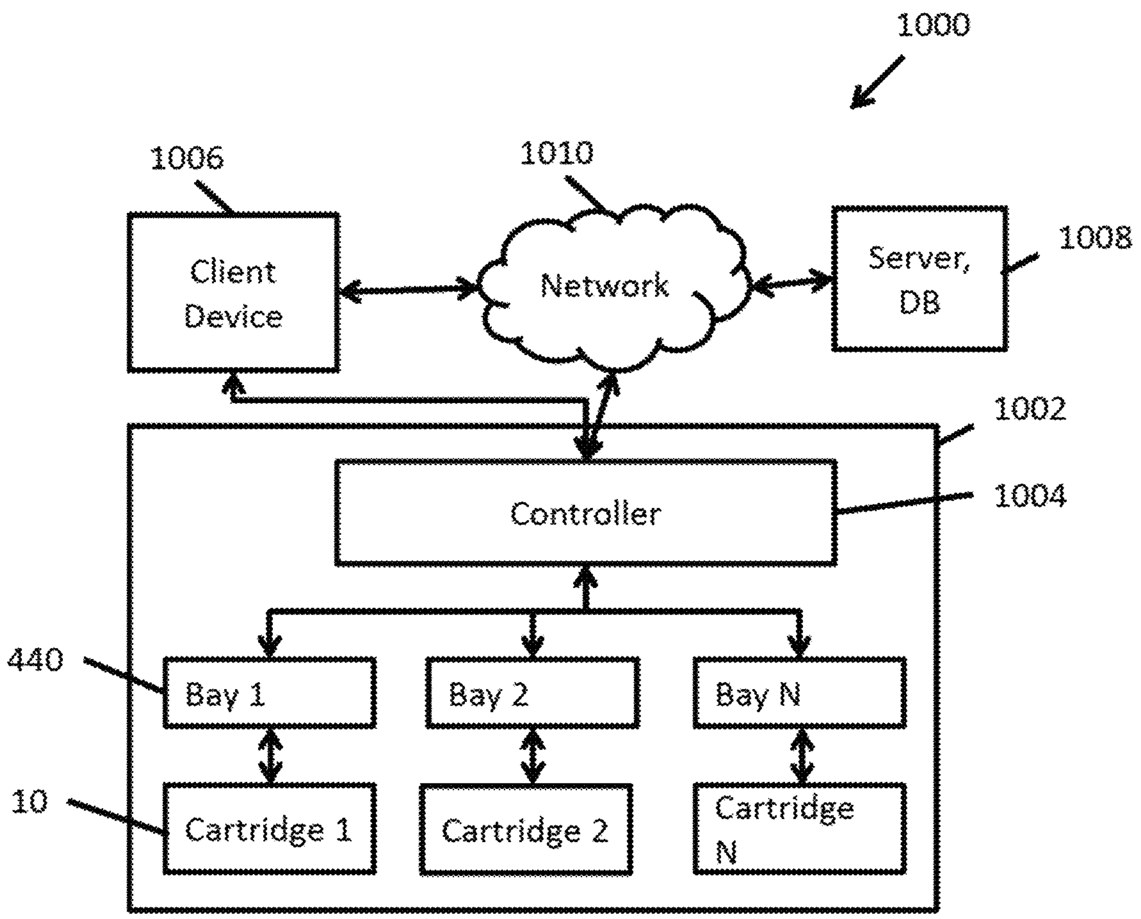
FIG. 61 is a schematic block diagram of the instrument connected to a network or client device.

An exemplary system 1000 according to some embodiments is depicted in electrical block diagram form in FIG. 61. System 1000 may comprise a non-transitory computer readable medium (not specifically shown) storing instructions that when executed by a processor perform steps such as those described in previous figures or described or referred to with respect to FIGS. 61, 62, 63, and 64. The non-transitory computer readable medium storing the instructions may be in one location or distributed among multiple portions of system 1000. The non-transitory computer readable medium storing the instructions may include one or more of a hard disk drive, flash memory, or read-only memory (ROM) to name a few examples. The processor executing the instructions may also be in one location or include processors distributed among multiple portions of system 1000.

The system 1000 may comprise an instrument 1002 having a controller 1004 that may be communicatively coupled to at least one client device 1006 (controller may not be directly communicatively coupled to the client device but may be communicatively coupled to a LIS interchange which is communicatively connected to a Hospital LIS which is communicatively connected to the client device) and at least one server 1008 having an associated database (DB). The controller 1004 may be directly coupled to client device 1006 and/or server 1008 via a communication interface such as a USB (universal serial bus) or a firewire (IEEE 1394) interface to name two examples. Alternatively, the controller may be indirectly coupled to the client device 1006 and/or server 1008 via a network 1010 such as the Internet. In yet another embodiment the controller 1004 may be coupled to client device 1006 and/or server 1008 via a wireless interface protocol such as 802.11 or Bluetooth (IEEE 802 standards) to name two examples. Yet further embodiments comprise combinations of direct couplings, wireless couplings, and indirect network couplings within system 1000.

Client device 1006 may be one or more of a desktop computer, laptop computer, tablet computer, smartphone, or other device or software application to name some examples. Server 1008 together with client 1006 may operate with a client server model. Server 1008 may comprise one or more of a database server or a file server to name two examples.

An example of instrument 1002 has been described with respect to FIGS. 32-37. Instrument 1002 includes sample processing bays 440 (also referred to throughout as "processing bays"). While FIG. 61 depicts only three processing bays 440 for ease of illustration, it is to be understood that instrument 1002 can have any number of processing bays 440. Examples of processing bays 440 are illustrated and described with respect to at least FIGS. 35-43. Each processing bay may electrically coupled to controller 1004 whereby controller 1004 can control and receive information from each processing bay 440.

Each processing bay 440 may be configured to receive a cartridge 10. An exemplary embodiment of cartridge 10 has been extensively described with respect to at least FIGS. 1-31. In some embodiments instrument 1002 may receive different cartridges 10 that are different according to different specific tests to be run on similar or different fluid samples.

Figure 62:
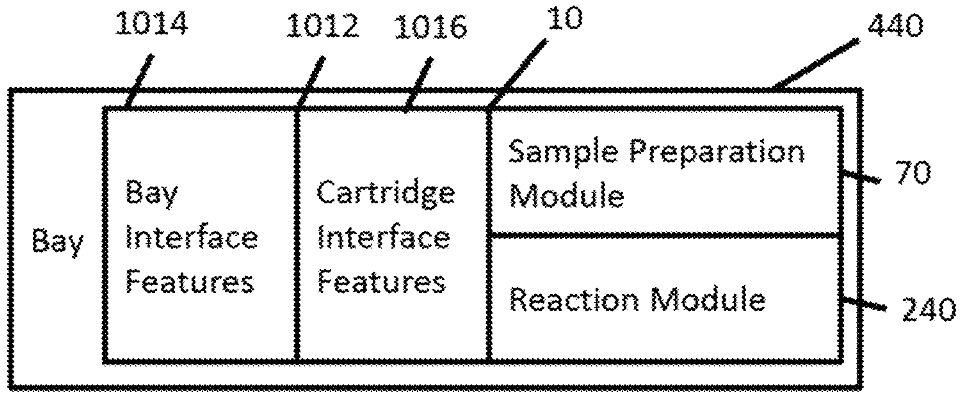
FIG. 62 is a schematic block diagram of a cartridge installed into a processing bay.

FIG. 62 is a schematic block diagram of a cartridge 10 installed into a processing bay 440, according to some embodiments. Cartridge 10 may comprise a sample preparation module 70 and a reaction module 240 as described earlier. An exemplary sample preparation module 70 has been described earlier including being described with respect to FIGS. 6-15. With reference to FIG. 6, the sample preparation module may comprise a sample well 78 for receiving a fluid sample to be processed by the sample preparation module 70. Within the sample preparation module 70, a series of sample preparation process steps may be performed on the sample before the processed sample is passed from the sample preparation module to the reaction module 240. The sample preparation process steps may comprise steps such as removing debris, lysis, and removing other portions of the sample that are not useful for the subsequent steps to be performed in the reaction module 240.

An exemplary reaction module 240 is described with respect to FIGS. 24-31. Sample reaction module 240 may performs process steps on the previously processed sample such as isolating an analyte, amplification to increase a number of target molecules available for analysis, and molecular detection. Exemplary process steps performed by reaction module 240 are described with respect to FIG. 60.

When cartridge 10 is installed in bay 440, an interface 1012 may be defined between cartridge 10 and bay 440

(defined further below). Interface 1012 may provide various functions comprising, for example: (1) receiving, aligning, and securing cartridge 10 within processing bay 440, (2) enabling processing bay 440 to mechanically actuate portions of cartridge 10, (3) enabling bay 440 to heat and/or cool portions of cartridge 10, and (4) allowing electrical signals to pass between bay 440 and cartridge 10. These functions may be partially or entirely performed and controlled by controller 1004 that operates according to instructions executed by controller 1004. These instructions may be defined entirely or in part by an ADF (assay definition file) to be described further with respect to FIGS. 63 and 64.

Interface 1012 may be defined by mutually complementary interface features including bay interface features 1014 that engage and are mutually complementary to cartridge interface features 1016. An exemplary interface 1012 between cartridge 10 and bay 440 has been described earlier including being described with respect to FIGS. 38-55. The complementary interface features may comprise (1) aligning and latching interface features, (2) mechanical actuation features, (3) thermal heat transfer features, and (4) electrical interface features.

Exemplary aligning and latching interface features may comprise cartridge latch 654, cartridge ejector assembly 670, and other features described with respect to FIG. 46. Aligning and latching features may perform various functions that include: (a) guiding and aligning the cartridge 10 as it is installed into bay 440, (b) securing cartridge 10 in bay 440 during an assay process, and (c) ejecting the cartridge 10 from the bay 440 when all assay-related processes are complete.

A first exemplary embodiment of complementary mechanical actuation features includes mixing motor assembly 700 described with respect to FIGS. 50A and 50B in combination with cartridge 10. More particularly the interface includes bevel-level spur 710 that engages peripheral gear teeth 198 of rotary mixer 192 to actuate rotary mixer 192. The bevel-level spur 710 is an example of a bay interface feature 1014. The gear teeth 198 provide an example of a cartridge interface feature 1016. The spur 710 and gear teeth 198 are complementary in the sense that together they provide an interface between bay 440 and cartridge 10 that enables the bay to mix a fluid sample, under control of controller 1004.

Figure 5:
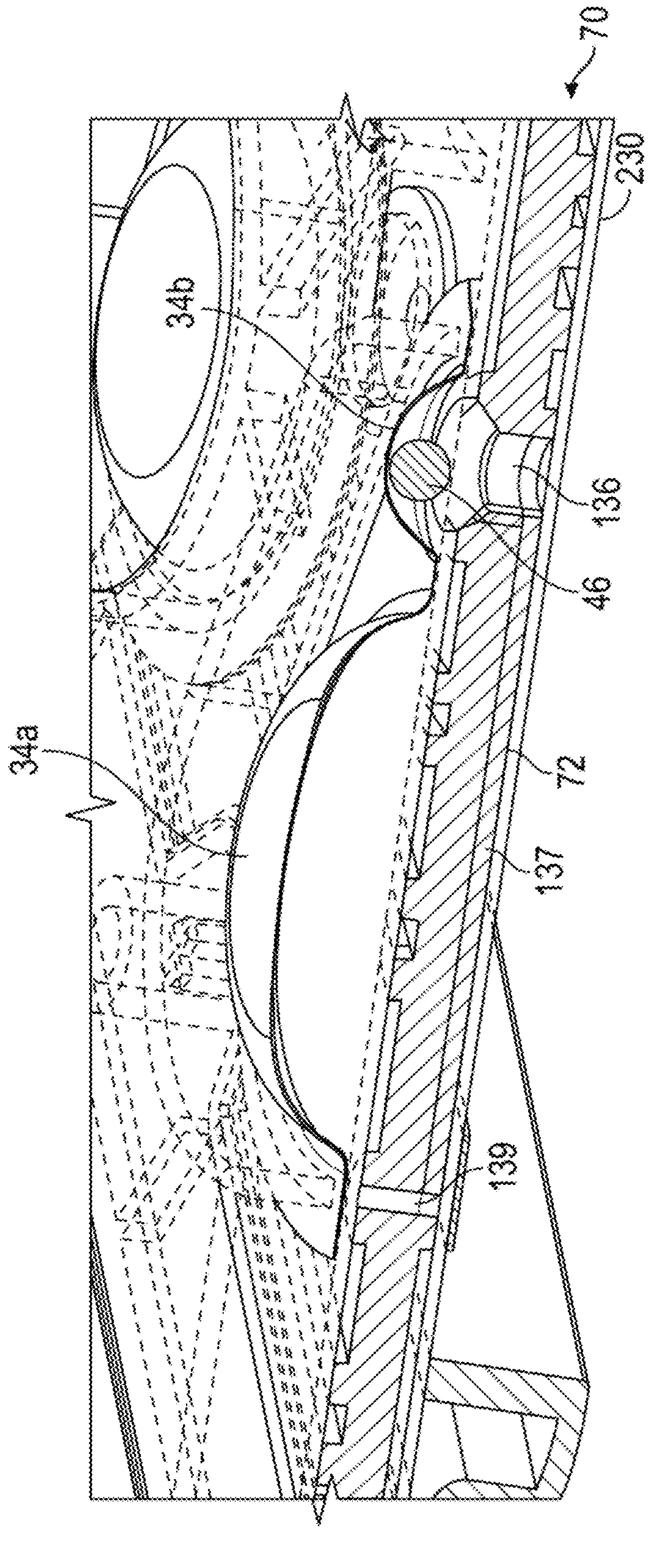
FIG. 5 is a partial perspective view in cross-section of a deformable fluid compartment (or blister) of the multiplex cartridge.

A second exemplary embodiment of complementary mechanical actuation features includes blister compression assembly 750 described with respect to FIGS. 51-54 and deformable blisters or compartments (34*a*, 36*a*, 38*a*, etc.) described with respect to FIG. 5. The blister compression mechanisms (756*a*, 756*b*, 756*c* etc.) are examples of bay interface features 1014. The deformable compartments (34*a*, 36*a*, 38*a*, etc.) are examples of cartridge interface features 1016. The blister compression mechanisms (756*a*, 756*b*, 756*c* etc.) engage the deformable compartments (34*a*, 36*a*, 38*a*, etc.) under control of controller 1004.

An exemplary embodiment of a thermal heat transfer feature is the heating and control assembly 500 described with respect to FIGS. 43 and 44. This enables bay 440 to heat portions of cartridge 10 under control of controller 1004.

An exemplary embodiment of electrical interface features include connector pin arrays 510*a*-510*g* described with respect to FIG. 44 that are configured to electrically couple to connector pad arrays 358*a*-358*g* described with respect to FIG. 58. The connector pin arrays 510*a*-510*g* are examples of bay interface features 1004. The connector pad arrays 358*a*-358*g* are examples of cartridge interface features 1006. These enable controller 1004 to send and receive signals to and from cartridge 10.

Other examples of interface 1012 features are described with respect to earlier figures. In an exemplary embodiment controller 1004 can control some or all of the interactions of bay interface features 1014 with cartridge interface features 1016. Control parameters that partially or completely define these interactions are contained in a control portion (OPUS) of an ADF file to be described below.

Figure 63:
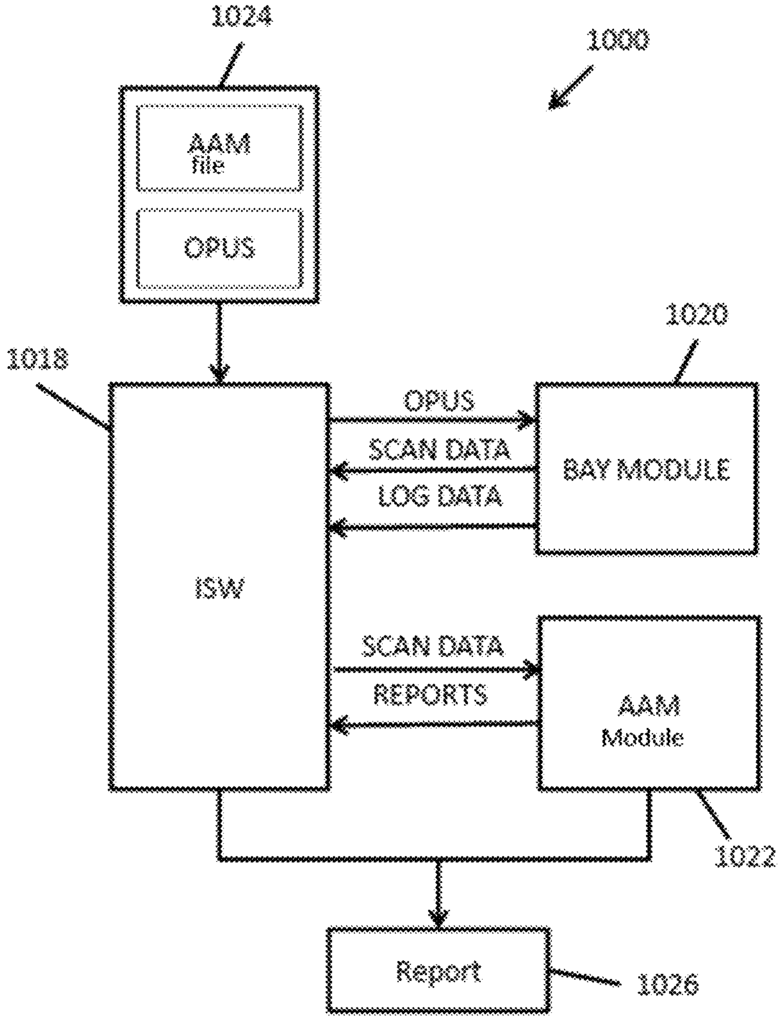
FIG. 63 is a block diagram representing an exemplary software architecture for the system of the present invention.

FIG. 63 is a block diagram representing an exemplary software architecture and information flow for system 1000, according to some embodiments. System 1000 may comprise instrument software module (ISW) 1018, bay software module 1020, and an assay analysis module (AAM module) 1022. The ISW 1018 may generally reside in instrument 1002 although portions of ISW 1018 may also reside in client device 1006. The bay software module 1020 resides in processing bay 440 although portions or all of software module can also reside in other portions of instrument 1002. The AAM module 1022 can reside in one or more of instrument 1002, client device 1006, and server 1008.

To perform a test, an assay definition file (ADF) 1024 may be received by the ISW 1018. The ADF 1024 may typically be defined by client device 1006 before being transferred to ISW 1018. The ADF 1024 may comprise two portions including an OPUS file and an AAM file. The OPUS file may include parameters that define all operations controlled by the execution of bay software module 1020. The AAM file may include parameters that define analysis performed by AAM module 1022.

The OPUS file may be transferred from the ISW 1018 to the bay software module 1020. In some embodiments, the contents of the OPUS file may be structured in an XML format. In some embodiments, the OPUS file comprises an ordered set of execution commands that instruct the bay software interface features 1014. In some embodiments, the OPUS file comprises control parameters including a first set of control parameters pertaining to the sample preparation module 70 and a second set of control parameters pertaining to the reaction module 240. The first set of control parameters may define the operation of certain bay interface features 1014 upon the cartridge interface features 1016 as they pertain to the sample preparation module 70. The OPUS file control parameters may affect aligning and latching features, mechanical actuation features, and/or thermal heat transfer features as discussed with respect to FIG. 62. A few examples of the OPUS file control parameters are now discussed.

The first set of OPUS file control parameters may comprise motor parameters controlling the mixing motor 706 (see FIGS. 50A and 50B) that drives the rotary mixer 192. A first motor parameter example is number of seconds for mixing the sample received by sample well 78. A second motor parameter example may define an electrical power level (e.g., duty cycle and pulse width) delivered to mixing motor 706.

The first set of OPUS control parameters may also define the operation of the blister compression assembly 750. An exemplary blister compression parameter determines which deformable compartments (34*a*, 36*a*, 38*a*, etc.) are compressed by blister compression mechanisms (756*a*, 756*b*, 756*c* etc.)

The first set of OPUS control parameters may also define a heating operation of heating and control assembly 500 (FIGS. 43 and 44). This can further determine temperature of portions of cartridge 10 during the operation of sample preparation module 70.

The second set of OPUS control parameters may comprise parameters that pertain to signals passed between the bay interface features 1014 and the cartridge interface features 1016. More particularly the signals may be passed from the bay 440 to the cartridge 10 via the electrical interface features described with respect to FIGS. 44 and 58. The signals may define a second set of control parameters for controlling the reaction module 240.

The second set of OPUS control parameters may comprise electrowetting parameters which define the operation of electrowetting electrodes within the reaction module 240 for transporting and manipulating fluid droplets. A first example of an electrowetting parameter is an electrowetting pad drive voltage. A second example of an electrowetting parameter is an electrowetting frequency which is the frequency at which the electrowetting voltages are changed during operation. A third example of an electrowetting parameter is an electrowetting phase shift which defines a relative phase of the voltage signal being applied to an electrowetting pad. However, the electrowetting parameters are not limited to these examples.

The second set of OPUS control parameters may comprise electrosensing parameters that are a function of the particular molecular detection taking place. These enable the software to properly interpret whether a given analyte or molecule has been detected. A first example is a number of electrons exchanged in a given redox reaction during detection. A second example is the activation energy of a reaction measured in volts. However, the electrosensing parameters are not limited to these examples.

The second set of OPUS control parameters may define a heating operation of heating and control assembly 500 (FIGS. 43 and 44). This may further determine temperature of portions of cartridge 10 during the operation of reaction module 240.

In some embodiments, the OPUS control parameters in the OPUS file may comprise, for example, one or more of the following: Heater Control (e.g., heater type, heater state, heater feedback control, target in degrees Celsius, proportional gain, integral gain, derivative gain, open loop gain, time in seconds), Delay Execution (e.g., time in milliseconds), Set Normalization Information (e.g., normalization constant, normalization structures), Set Effector Settings (e.g., voltage in volts, effector mode, frequency in hertz), Set Impedance Analysis Setting (e.g., frequency in hertz, starting frequency, frequency step, settling cycles, amplitude selection), Get Impedance Data, and Assert Vector Array (e.g., pogo pins to be asserted, wait time in milliseconds).

In response to applying the first and second control parameters of the OPUS file, (sensor) scan data may be received by ISW 1018 from the bay software module 1020. The scan data may comprise output data that quantifies results from sensors within reaction module 240. AAM file parameters may then be applied to the scan data. The AAM file may comprise data defining filters, classifiers, call logic, and report generators to analyze scan data from processing bay 440. A filter may be applied to the data to digitally process the data. Classifiers and/or call logic may define data interpretation such as applying a threshold to a result and thereby determining whether a given analyte, organism, or molecular type is present or is counted above some threshold. Classifiers and/or call logic may comprise, for example, determining i) if the internal control signal is valid and above a pre-determined threshold; ii) if the internal control fails, all targets are invalid; iii) if the signal of a target is at or above a pre-determined threshold; and iv) if target A depends on target B, target B determines the detectability of target A. Report generators may put the interpreted data into a user-friendly form, e.g., for display on a graphical user interface.

Figure 64:
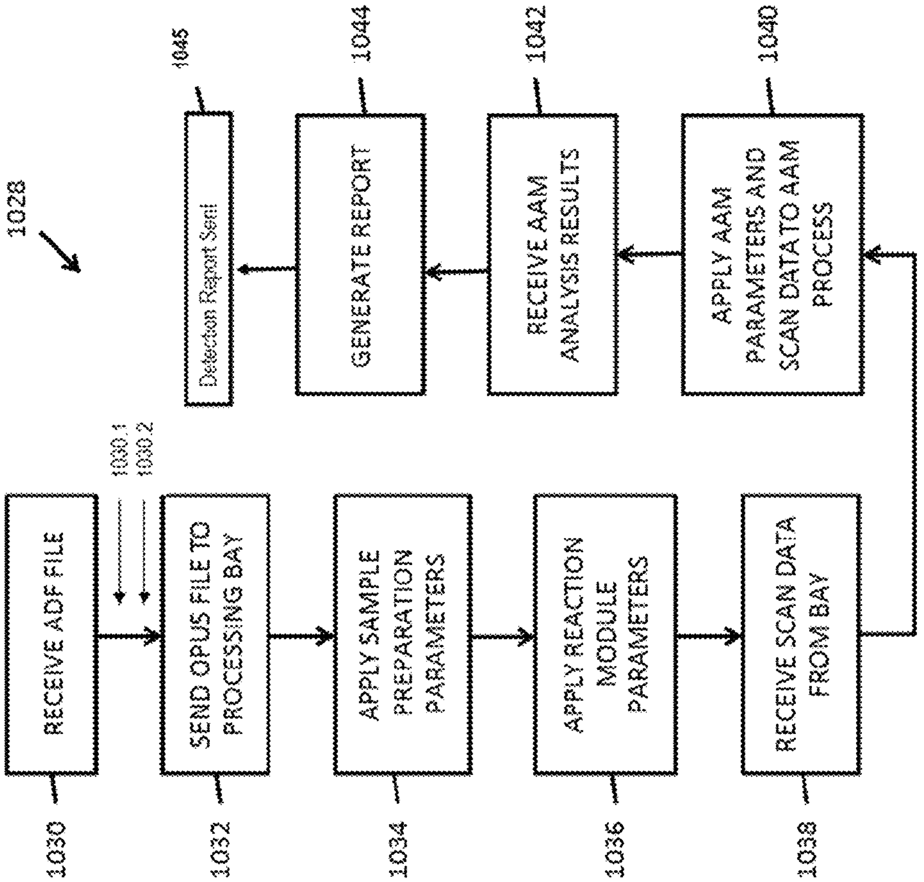
FIG. 64 is a flow chart illustrating an exemplary process performed by the system of the present invention to process a fluid sample.

FIG. 64 is a flowchart representation of an exemplary process 1028 performed by system 1000 to analyze a sample, according to some embodiments. The steps of process 1028 concern software operations that may be concurrent with the sample preparation and sample reaction processes that are described with respect to FIGS. 16-23 (sample preparation) and FIG. 60 (sample reaction). In preferred embodiments, sample preparation precedes sample reaction. As described with respect to FIG. 16, a fluid sample specimen may be dispensed into sample well 78. After sample well 78 is closed the cartridge 10 is placed into the processing bay 440 of instrument 1002. The steps of process 1028 can begin just prior to or after the receipt of cartridge 10 into processing bay 440. According to step 1030, ISW 1018 may receive ADF file 1024.

According to step 1030.1 the ISW 1018 receives a Pending Test Order (PTO). Specifically, when a sample is collected, the physician creates a test order called a physician test order After the physician test order is generated, the physician test order is sent to the hospital's laboratory information system (LIS), a computer software that processes, stores and manages data from all stages of medical processes and tests. The physician test order is accepted by the Hospital LIS and a pending test order (PTO) is created once the patient sample is received and accessioned by the lab into the hospital LIS. The hospital's LIS sends the PTO to an LIS interchange which converts the PTO request from an HL7 or ASTM format to a CSV format and the PTO is now referred to as a test order or an interchange order or formatted test order and the like. The ISW 1018 further supports a "flat file format" i.e. non-standard file support for laboratories without automated interfaces (HL7 or ASTM). As such, tests can be imported and/or exported manually in a text format, CSV, TXT or XML formats. When the LIS interchange receives the PTO and reformats it to a test order, the test order is auto published with information associated with the PTO/sample such as patient identification, accession number, test ordered (Blood Culture Identification—Gram-Negative Panel, Blood Culture Identification—Gram-positive, Blood Culture Identification—fungal etc), patient type (e.g. pediatric, intensive care, maternity), patient location (e.g. pediatrics, ER, maternity), and/or time stamps such as sample collection, sample ordering, time received at central receiving, central receiving sort, transport to lab and/or accession of sample. These time stamps provide real-time monitoring by the instrument software of pending test order turn-around time. After the LIS interchange receives the test order, it sends it to the ISW 1018.

According to step 1030.2 the ISW 1018 receives an assay type from the assay cartridge. Specifically, two machine-readable information tags (or patient identification tags) are arranged on the cartridge and encoded with cartridge-identifying information, where the information encoded in the second tag corresponds to the information encoded in the first tag and is read by a device within the sample processing instrument. After a first machine-readable information tag on the outside of the cartridge is scanned, the cartridge can be loaded into any bay at any time, this is referred to as "random access" or "random and continuous bay access" or "unassigned" or "un-delegated" or "un-allocated" or "unspecified" and the like. Stated another way, the cartridge need not be loaded into a specified bay. In this way, loading errors are avoided. Once the cartridge is loaded, the processing bay module 1020 reads a second machine-readable information tag and confirms it matches the first machine-readable information tag.

According to step 1032, ISW 1018 may send an OPUS portion of ADF file 1024 to the processing bay module 1020. The OPUS portion of the ADF file 1024 may comprise first parameters controlling the sample preparation module 70 and second parameters controlling the sample reaction module 240.

According to step 1034 the first parameters may be applied to the sample preparation module 70 to process the fluid sample specimen so that it is ready for the reaction module 240. In an exemplary embodiment the process steps described with respect to FIGS. 16-23 are performed on the fluid sample specimen by the processing bay 440 and cartridge 10 in response to receiving the first parameters. The first parameters define aspects of at least some process steps described with respect to FIGS. 16-23.

According to step 1036, the second parameters may be applied to the sample reaction module 240 to further process the fluid sample specimen and to generate scan data from sensors in the reaction module 240. In an exemplary embodiment the process steps described with respect to FIG. 60 are performed on the processed fluid sample specimen by the processing bay 440 and cartridge 10 in response to processing bay module 1020 receiving the second parameters.

According to step 1038 the sensor scan data may be transferred from the processing bay module 1020 to the ISW 1018. Also as part of step 1038, log data that can include sensing conditions and other data may be transferred from processing bay module 1020 to ISW 1018.

According to step 1040 the scan data and AAM file parameters that are part of the ADF file 1024 may be transferred to or define the AAM module. In some embodiments, AAM module may already have the AAM file parameters that are part of the ADF file 1024, and thus no transfer is necessary. According to step 1042, the AAM module may generate a test result as a result of the AAM file parameters being applied to the scan data. According to step 1044, a report may be generated that reports the test result from step 1042.

According to step 1045, after exemplary process 1028 is performed by system 1000 to analyze a sample and a report is generated 1044. The ISW 1018 sends (either automatically or manually) a detection report (also referred to as a result report or test results) to either a network folder or the LIS interchange which converts the detection report into a physician test result report and sends the physician test result report directly to the physician or to the hospital's LIS which then sends the physician result report to the physician. The detection report/physician test result sent to the network folder or hospital's LIS or to the physician can include detected targets, non-detected targets, invalid results and/or control data. The ISW 1018 can either auto release all information or hold all information for manual release. Alternatively, the ISW 1018 can auto release some detection reports and hold some detection reports for manual release. For example, detected and non-detected targets can be auto-released while invalids can be manually released (i.e., released only after a lab supervisor. approves for release). If the detection report shows 3 (triple infection) or fewer targets were identified/detected the detection report will automatically release to the hospital's LIS/physician. If the detection report shows greater than 3 (i.e. 4 or more) targets were identified/detected the report will be flagged, a multiple infection error alert (also called an alert notification) can be sent to the operator or physician and the sample can be automatically re-run. The detection report includes the assay ordered. If a cartridge is inserted that does not match the assay ordered (e.g. a gram-negative assay is ordered but a respiratory assay is inserted) a "mismatch alert" is sent to the operator and/or physician and/or the additional target is noted in the detection report. Anomalous results that are not auto-released can require a manager signature before manual release. Such reporting minimizes the risk of reporting errors.

The detection report can include time stamps such as sample collection time, sample ordering time, transport to central receiving time, central receiving sort time, transport to lab time, accession of sample time, time to process, and time to detection.

The automated result reporting (at order entry and results reporting) eliminates transcription errors and ensures actionable results are returned to physicians as soon as possible. Sample results are reported in about 60-90 minutes after the start of running the sample, this is referred to as time to result or sample to result. Preferably, sample results are reported in about 60 minutes after the start of running the sample. Preferably, sample results are reported in under 90 minutes after the start of running the sample. Preferably, sample results are reported upon test completion. A detection report is sent immediately after the pathogen is identified by the detection system.

The ISW 1018 allows the operator to include comments in the detection report called detection report comments, e.g., to specify if the assay ordered matched the target detected, if the assay ordered does not match the target detected, if an additional target was detected in addition to the target for the assay ordered, if a second assay is recommended, if a resistance gene was identified, or suggest a course of treatment such as antibiotic.

In addition to the detection report the ISW 1018 can send a number of alerts and reports.

Control Reports: Control reports or Control summary reports are generated based on the assay, test frequency and lot of cartridges from the supplier. Control reports provide information about the number of samples run, and when control runs are needed. When a control run is processed, the report shows the expected and actual result, if the control passed or failed. Control runs are typically run every 30 days or every lot change. The sample-to-answer system alerts to the operator 48 and/or 24 hours before a control run is needed.

System Usage Report: The system usage report provides analytics around system usage data and performance based on a specified date range. For example, the system usage report will show if higher or lower than average samples were run, if higher or lower than expected samples were run, if a bay has not been utilized, etc. System Usage Reports can be printed from the Clinical Instrument or remotely by the clinical instrument's provider.

Service Notification Report: A service notification report is a report sent to the clinical instrument's provider to request remote access to the clinical instrument to trouble shoot errors such as when a device has exceeded downtime for a month, exceeded invalid runs, mean time to failure is too high, no LIS connectivity etc.

Alerts: The ISW 1018 includes a number of automatic alerts.

A Remote Practitioner Alert is an alert sent to practitioners to notify them that test results are available.

A Non-Operator Alert is an alert sent to non-operators such as lab-managers, directors of labs etc. regarding test results.

A Reportable Organism Alert is an alert sent based on a user-defined reportable organisms. For example, if a patient is diagnosed with an infectious disease, then an alert can be sent to the Department of Health.

A Turnaround Time Violation Alert is an alert sent to the physician, operator or lab manager when the predetermined turnaround time is violated.

A Sample Stability Time Violation Alert is an alert sent to the physician, operator or lab manager that the sample stability time was violated.

A Duplicate Accession ID Alert is an alert notifying the operator that a sample with the same accession number was already run. Since each sample should have its own accession number, the operator should review for a possible error.

A Multiple Infection Error Alert is an alert to notify the operator that there are 4 or more co-infections detected and the sample should be re-run.

A Mismatch Alert is an alert sent to the operator or physician that a target is detected which does not match the assay ordered (e.g. a gram-negative assay is ordered but a fungal infection is identified). The mismatch can be the only target detected or can be in addition to a target expected to be detected by the assay ordered. When a mismatch alert is sent the sample can be automatically re-run on the assay ordered or on another assay which matches the mismatch. For example, if the assay ordered was a BCID-GP assay but a fungal target was identified, the BCID-GP assay can be re-run and/or a BCID-FP assay is run.

User Interface

The system 1000 includes a user interface comprising a touch screen display having a plurality of bay icons, each icon uniquely corresponding to one of said plurality of bays. The user interface further includes hour, minute and second countdown timer on the bay icon to show the time left until a result will be reported.

Additionally, the user interface will display the bay status (whether the bay is empty, the presence or absence of a cartridge, whether the cartridge assay is underway, assay complete, and a process error) even while the user is logged out.

The user interface audible clicks by default on a virtual keyboard.

The user interface allows batch printing of reports.

QC Results

Monitoring and reporting quality control is both a requirement and a best practice to ensure the accuracy of patient testing results and compliance with lab standards. With on-board QC tracking capabilities, the system 1000 provides safeguards to ensure labs not only run controls when required but can easily track and report compliance. Indeed, the base station itself retains onboard QC test records to help ensure the lab runs controls when required. As discussed above, control reports are sent if an external control is due in 48 hours and/or 24 hours.

The system 1000 can prevent new runs if the detection system has not been qualified. This means that if a new lot is provided and a control should be run on the clinical instrument before running a patient sample, the instrument will prevent a patient sample test until the control is run.

The system 1000 further supports the release of QC results to the hospital LIS either automatically or manually.

Further, patient data is automatically removed in all exported run data (troubleshooting logs and raw data calculations such as nA signal from targets, non-detected targets, controls etc) for HIPPA compliance.

The system 1000 tracks and reports required preventative maintenance. Such systems maximize lab efficiency by reducing administrative overhead.

Compliance And Data Management

The system 1000 provides the following compliance and data management tools: Integrated data analytics to easily monitor lab performance, on-demand epidemiology reports for export and simplified analysis in Excel (including disease prevalence in a geographic area); and fully configurable, auto-release of test results (detected targets as well as non-detected targets). All of these unique capabilities of the sample-to-answer system allow Lab Directors to reduce their time spent on routine administrative tasks and focus their limited resources on high-value activities that impact patient care and the bottom line.

Specifically, on demand Epidemiology reports can be run from each base station individually or collectively from all of the base stations run in the laboratory via the LIS.

Remote Service Capability

The system 1000 includes remote service capability to minimize system downtime and ensure patients and physicians have access to rapid test results. Remote service may be needed when the clinical instrument has exceeded downtime for a month, exceeded invalid runs, mean time to failure is too high, no LIS connectivity etc.

Because it combines fluid processing (OPUS), sensing (OPUS), and analysis (AAM file) parameters, the ADF file 1024 enables a wide range of fluid sample specimens to be received and analyzed by system 1000. Moreover, by having multiple processing bays 440, the system 1000 may process, sense, and analyze a wide range of different samples concurrently. This provides a very efficient and versatile analytics laboratory.

The following two examples include a first ADF file 1024-1 and a second ADF file 1024-2. The first ADF file 1024-1 is intended for a first fluid sample type that includes cellular organisms having thick cellular walls that are resistant to chemical lysis. The second ADF file 1024-2 is intended for a second fluid sample type having cellular organisms having thin cellular walls which fully rupture with chemical lysis. The first and second ADF files 1024 differ in both OPUS parameters applied to the processing bay module 1020 and in the AAM parameters applied to sensor scan data. The next two paragraphs only emphasize the differences.

The first ADF file 1024-1 may comprise an OPUS file that further includes "bead mixing" parameters whereby the sample preparation module 70 operates a bead mixer (e.g., FIG. 12 and associated discussion) as part of the lysis process. This assures proper lysis for this sample since the cellular organisms have thick cell walls. Additionally the first ADF file may comprise an AAM file that utilizes a first digital processing filter for analyzing the scan data received from the processing bay 440 for all of the sense electrodes in reaction module 240.

Because the second fluid sample requires only chemical lysis, the second ADF file 1024-2 may comprise an OPUS file that does not include the bead mixing parameters. Thus the bead mixer is not operated for the second fluid sample. The second ADF file may also comprise an AAM file that utilizes the first digital processing filter for some scan data from a subset of the sense electrodes in reaction module 240. This AAM filter may utilize a second digital processing filter for scan data from the remaining sense electrode in reaction module 240.

Of course these are but two examples of different ADF files 1024. These ADF files 1024 may enable both different types of samples to be run concurrently. It is well within the present invention for any number of different fluid samples and their respective assays to be run concurrently on a system 1000.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the scope of this disclosure is intended to include all modifications and variations encompassed within the spirit and scope of the following appended claims.

Exemplary Embodiments

Embodiment 1. An apparatus for processing and analyzing a sample comprising:

- an electronic control system that operates a sample processing bay and analyzes data from the sample processing bay, the electronic control system including a processor coupled to a non-transitory computer readable medium, the non-transitory computer readable medium storing instructions directing the processor to:
- receive and read an assay definition file (ADF) from an external source, the ADF comprising control parameters and analysis parameters;
- send a first set of control instructions to the sample processing bay whereby the sample processing bay operates a sample preparation module to prepare the sample for detection according to a first set of the control parameters;
- send a second set of control instructions to the sample processing bay whereby the sample processing bay operates a sample reaction module to detect a target analyte according to a second set of the control parameters;
- receive detection results from the sample processing bay; and
- analyze and report results of the detection results based upon the analysis parameters.

Embodiment 2. The apparatus of embodiment 1 further comprising the sample processing bay and a cartridge received into the bay, the cartridge including the sample preparation module and the sample reaction module.

Embodiment 3. The apparatus of embodiment 2 wherein the first set of control parameters include a mechanical parameter that at least partly defines operation of mechanical actuation features of the sample processing bay operating on corresponding features of the sample preparation module.

Embodiment 4. The apparatus of embodiment 3 wherein the mechanical parameter defines the operation of a motor within the sample processing bay that drives the mechanical actuation.

Embodiment 5. The apparatus of embodiment 2 wherein the first set of control parameters include a parameter that at least partly defines the operation of a device that changes the temperature of a portion of the cartridge.

Embodiment 6. The apparatus of embodiment 2 further comprising an electrical interface between the sample processing bay and the cartridge, the control parameters define control signals passed from the processing bay to the cartridge through the electrical interface.

Embodiment 7. The apparatus of embodiment 6 wherein the control signals at least partially define the operation of electrowetting electrodes within the cartridge.

Embodiment 8. The apparatus of embodiment 6 wherein the control signals at least partially define the operation of a sensor within the cartridge.

Embodiment 9. The apparatus of embodiment 1 wherein the sample reaction module includes a plurality of sense electrodes, the analysis parameters define the application of a digital filter to scan data generated for at least some of the plurality of sense electrodes.

Embodiment 10. A non-transitory computer readable medium for use with an apparatus for processing and analyzing a sample including an electronic control system coupled to a sample processing bay, the non-transitory computer readable medium storing instructions that when executed on by the processor perform steps comprising:

- receive and read an assay definition file (ADF) from an external source, the ADF comprising control parameters and analysis parameters;
- send a first set of control instructions to the sample processing bay whereby the sample processing bay operates a sample preparation module to prepare the sample for detection according to a first set of the control parameters;
- send a second set of control instructions to the processing bay whereby the processing bay operates a sample reaction module to detect a target analyte according to a second set of the control parameters;
- receive detection results from the sample processing bay; and
- analyze and report results of the detection results based upon the analysis parameters.

Embodiment 11. The non-transitory computer readable medium according to embodiment 10 wherein the sample processing bay is configured to receive a cartridge and wherein the first set of control parameters include a mechanical parameter that at least partly defines a mechanical interaction between the sample processing bay and the sample preparation module.

Embodiment 12. The non-transitory computer readable medium according to embodiment 11 wherein the mechanical parameter defines the operation of a motor within the processing bay that drives the mechanical interaction.

Embodiment 13. The non-transitory computer readable medium according to embodiment 10 wherein the sample processing bay is configured to receive a cartridge, an electrical interface couples the sample processing bay to the cartridge, and the control parameters define control signals passed from the processing bay to the cartridge through the electrical interface.

Embodiment 14. The non-transitory computer readable medium according to embodiment 13 wherein the control signals at least partially define the operation of electrowetting electrodes within the cartridge.

Embodiment 15. The non-transitory computer readable medium according to embodiment 13 wherein the control signals at least partially define the operation of a sensor within the cartridge.

Embodiment 16. The non-transitory computer readable medium according to embodiment 10 wherein the detection results include scan data received from a plurality of electrodes disposed within the reaction module, the analysis parameters define a digital filtering to be applied to the scan data.

Embodiment 17. A method of analyzing a sample in an instrument having a sample processing bay comprising:

receiving and reading an assay definition file (ADF) from an external source, the ADF comprising control parameters and analysis parameters;

sending a first set of control instructions to the sample processing bay whereby the processing bay operates a sample preparation module to prepare the sample for detection according to a first set of the control parameters;

sending a second set of control instructions to the processing bay whereby the processing bay operates a sample reaction module to detect a target analyte according to a second set of the control parameters;

receiving detection results from the sample processing bay; and analyzing and reporting results of the detection results based upon the analysis parameters.

Embodiment 18. The method of embodiment 17 wherein the sample processing bay is configured to receive a cartridge and wherein the first set of control parameters include a mechanical parameter that at least partly defines a mechanical interaction between the sample processing bay and the sample preparation module.

Embodiment 19. The method of embodiment 17 wherein the sample processing bay is configured to receive a cartridge, an electrical interface couples the sample processing bay to the cartridge, and the control parameters define control signals passed from the processing bay to the cartridge through the electrical interface.

Embodiment 20. The method of embodiment 17 wherein the detection results include scan data from a plurality of electrodes disposed within the sample reaction module and the analysis parameters define digital processing of the scan data.

Embodiment 21. An assay definition file (ADF) for processing a fluid sample comprising sensing parameters or analysis parameters.

Embodiment 22. An assay definition file (ADF) for processing a fluid sample comprising sensing parameters and analysis parameters.

Embodiment 23. A method for the detection and/or identification of a hybridization complex comprising a human pathogen and/or genetic material thereof hybridized to a signal probe and a capture probe comprising: receiving an ADF file by the Instrument software module; receiving a test order from a client device; receiving an assay type from the assay cartridge;

processing a fluid sample; sensing an analyte; and generating a detection report.

Embodiment 24. A method for the detection and/or identification of a hybridization complex comprising a human pathogen and/or genetic material thereof hybridized to a signal probe and a capture probe comprising: receiving an ADF file by the Instrument software module; receiving a test order from a client device; receiving an assay type from the assay cartridge; sending an OPUS file to a processing bay; applying sample preparation parameters; applying reaction module parameters; receiving scan data from the bay, applying AAM parameters and scan data to AAM process; receive AAM analysis results; and generating a detection report.

Embodiment 25. A system comprising an instrument software module coupled to a processing bay module and assay analysis module.

Embodiment 26. The system of embodiment 25, wherein the ISW communicates the OPUS portion of the ADF to the processing bay module Embodiment 27. The system of embodiment 26, wherein the processing bay module generates sensor scan data.

Embodiment 28. The system of embodiment 27, wherein the processing bay module communicates sensor scan data to the ISW.

Embodiment 29. The system of embodiment 25, wherein the ISW communicates sensor scan data to the AAM module.

Embodiment 30. The system of embodiment 29, wherein the AAM module applies the AAM file to the sensor scan data and generates a detection report based on the analysis.

Embodiment 31. The system of embodiment 30, wherein the AAM module communicates the detection report to the ISW.

Embodiment 32. The system of embodiment 31, wherein the ISW communicates the detection report to the hospital LIS.

Embodiment 33. The system of embodiment 32, wherein analyzing the scan data by the AAM module comprises applying a digital filter to the scan data.

Embodiment 34. The system of embodiment 33, wherein analyzing the scan data by the AAM module comprises applying a classifier to the scan data.

Embodiment 35. A client device that is communicatively coupled to an instrument.

Embodiment 36. An Assay Definition File (ADF) comprising an assay analysis module (AAM) file and command and control (OPUS) file.

Embodiment 37. The ADF of embodiment 36, wherein the AAM file defines one or more of (1) sense electrode data to be analyzed, (2) apply digital processing filters to the sense electrode data, (3) determine which electrodes are to be processed for a given digital processing filter, (4) a classifier for determining how to interpret digitally processed data, (5) call logic for determining the presence of one or more targets, and (6) report generation.

Embodiment 38. The ADF of embodiment 36, wherein the OPUS file defines one or more of (1) operation of mechanical features of a bay operating on a cartridge, (2) operation of mechanical features of the bay operating on a sample preparation module portion of the cartridge, (3) operation of a motor within the processing bay that drives a mechanical feature that operates upon the sample preparation module portion of the cartridge, (4) electrical signals passed through an electrical interface from the processing bay to the cartridge, (5) operation of a heating or cooling unit in the processing bay that heats or cools one or more portions of the cartridge, (6) operation of electrodes in a reaction module of the cartridge, or (7) operation of a sensor in the reaction module of the cartridge Embodiment 39. An Instrument Software Module (ISM) connected to a bay module and an assay analysis module.

Embodiment 40. The ISM of embodiment 39, wherein the ISM receives an Assay Definition File (ADF) comprising an AAM portion and an OPUS portion, Embodiment 41. The ISM of embodiment 40, wherein the ISW applies the OPUS portion of the ADF to the processing bay module.

Embodiment 42. The ISM of embodiment 41, wherein the OPUS file controls processing of a fluid sample and generates sensor scan data.

Embodiment 43. The ISM of embodiment 39, wherein the ISM receives scan data and sends it to the AAM.

Embodiment 44. The ISM of embodiment 43, wherein the AAM generates a report based on the scan data and sends the report to the ISM.

Embodiment 45. An apparatus for processing and analyzing a sample comprising and instrument wherein the instrument comprises a controller wherein the controller comprises at least one bay for receiving a cartridge and wherein the controller is communicatively coupled to at least one client device.

Embodiment 46. The apparatus of embodiment 45, wherein the controller is communicatively coupled to at least one server having an associated database.

Embodiment 47. A method for the detection and/or identification of a hybridization complex comprising a human pathogen and/or genetic material thereof hybridized to a signal probe and a capture probe comprising: receiving an ADF file by the Instrument software module; sending an OPUS file to a processing bay; applying sample preparation parameters; applying reaction module parameters; receiving scan data from the bay, applying AAM parameters and scan data to AAM process; receive AAM analysis results; and generating a detection report.

Embodiment 48. The method of embodiment 47, wherein the detection report is automatically sent to the hospital LIS.

Embodiment 49. A microfluidic device comprising a wide vent for detecting a human pathogen and/or genetic material thereof comprising: a mixture of oligonucleotides and reagents for carrying out a nucleic acid amplification reaction to detect the human pathogen selected from the group comprising, Influenza A, Adenovirus, Influenza A H1 subtype, Human Bocavirus, Influenza A H3, Human Rhinovirus/Enterovirus, Influenza A 2009 H1N1 subtype, Coronavirus 229E, Influenza B, Coronavirus HKU1, Respiratory Syncytial Virus A, Coronavirus NL63, Respiratory Syncytial Virus B, Coronavirus OC43, Parainfluenza Virus 1, Coronavirus MERS, Parainfluenza Virus 2, *Bordetella pertussis*, Parainfluenza Virus 3, *Chlamydophila pneumoniae*, Parainfluenza Virus 4, *Mycoplasma pneumoniae*, Human Metapneumovirus or *Legionella pneumophila.*

Embodiment 50. An analytical cartridge for use in analysis of fluids, said cartridge comprising: a bottom substrate, a top plate comprising at least one vent spanning at least two thermal zones.

Embodiment 51. A method for sending a test order to an apparatus for processing and analyzing a sample comprising; creating a physician test order; sending the physician test order to the hospital's laboratory information system (LIS); creating a pending test order (PTO); sending the PTO to an LIS interchange; converting the PTO to a test order; auto publishing the test order with information associated with the PTO; sending the test order to an ISW.

Embodiment 52. An Instrument software module (ISW) for processing a sample, the ISW being arranged to: receive at least one ADF file; receive at least one Pending Test Order (PTO); receive an assay cartridge; receive an assay type from the assay cartridge; and perform an amplification and detection procedure on the sample in the assay cartridge, wherein the detection procedure comprises forming a hybridization complex between amplicon, capture probe and signal probe thereby processing the sample.

Embodiment 53. A system for processing an ADF comprising bay control, cartridge control and analysis parameters wherein the system transmits bay control and cartridge control parameters to the bay module; and transmits analysis parameters to the assay analysis module (AAM).

Embodiment 54. The system of embodiment 53 wherein the system receives scan data from the bay module and transmits scan data to the AAM; receives a detection report from the AAM and transmits the detection report to a hospital LIS.

What is claimed is:

1. A method for updating a detection instrument to detect a new analyte, the method comprising:

receiving by the detection instrument an assay definition file (ADF) from an external source to process the new analyte, the ADF comprising at least an assay analysis module (AAM) file that specifies how to process signals generated from the new analyte and a second file;

storing by the detection instrument the ADF on a non-transitory computer-readable medium coupled to a processor and extracting from the ADF at least the AAM file;

sending by the detection instrument analysis instructions based only on the AAM file to an assay analysis module on the detection instrument; and configuring by the processor an assay analysis module on the detection instrument to process signals generated from the new analyte according only to the AAM file thereby remotely updating a detection instrument to detect the new analyte without modifying hardware components.

2. The method of claim 1, wherein the AAM file includes analysis parameters that define selection between two or more digital filters to process scan data generated from processing a sample.

3. The method of claim 1, further comprising: receiving a sample by the detection instrument, processing the sample by the detection instrument, generating scan data by the detection instrument from processing the sample, selecting by the assay analysis module based on the AAM file between two or more digital filters to process the scan data to generate processed scan data.

4. The method of claim 3, further comprising: transmitting information based on the processed scan data to a Laboratory Information System (LIS).

5. The method of claim 2, further comprising: generating by the detection instrument a result based on the analysis parameters.

6. The method of claim 1, further comprising: receiving by the detection instrument a pending test order directly from a hospital LIS.

7. The method of claim 6, further comprising: processing by the detection instrument, a sample based on the pending test order and the ADF.

8. The method of claim 2, wherein configuring the assay analysis module comprises loading, from the AAM file, parameters that define at least one of (i) a selection between two or more digital filters to be applied to scan data received from a plurality of sense electrodes, and (ii) a classifier for determining how to interpret digitally processed scan data.

9. The method of claim 1, wherein the second file comprises an OPUS file that specifies operations of a sample processing system.

10. A method for remotely updating a detection instrument to detect a new analyte, the method comprising:

receiving by the detection instrument an assay definition file (ADF) from an external source to process the new analyte, the ADF comprising at least an OPUS file that specifies operations of a sample processing system and a second file; and storing by the detection instrument the ADF on a non-transitory computer-readable medium coupled to a processor and extracting from the ADF at least the OPUS file;

sending by the detection instrument control instructions based only on the OPUS file to a sample processing bay on the detection instrument; and configuring by the processor a sample processing bay on the detection instrument to execute the assay according to only the OPUS file thereby remotely updating a detection instrument to detect a new analyte without modifying hardware components.

11. The method of claim 10, further comprising: sending a first set of control parameters to a sample processing bay whereby the sample processing bay operates a sample preparation module to prepare a sample for detection according to the first set of the control parameters.

12. The method of claim 11, further comprising: sending a second set of control parameters to the processing bay whereby the processing bay operates a sample reaction module to detect a target analyte according to the second set of the control parameters.

13. The method of claim 12, further comprising: receiving by the detection instrument detection results from the sample processing bay.

14. The method of claim 13, further comprising: analyzing and reporting by the detection instrument the detection results based upon analysis parameters.

15. The method of claim 10, wherein the second file comprises an AAM file that specifies how to process signals generated from the new analyte.

16. A method for updating a detection instrument to detect a new analyte, the method comprising:

receiving by the detection instrument an assay definition file (ADF) from an external source to process the new analyte, the ADF comprising at least an OPUS file that specifies operations of a sample processing system and an AAM file that specifies how to process signals generated from the new analyte;

storing by the detection instrument the ADF on a non-transitory computer-readable medium coupled to a processor and extracting from the ADF at least the OPUS file and AAM file;

sending by the detection instrument control instructions based only on the OPUS file to a sample processing bay on the detection instrument;

configuring by the processor a sample processing bay on the detection instrument to execute the assay according to only the OPUS file;

sending by the detection instrument analysis instructions based only on the AAM file to an assay analysis module on the detection instrument; and configuring by the detection instrument an assay analysis module on the detection instrument to process signals generated from the new analyte according to only the AAM file thereby remotely updating a detection instrument to detect a new analyte without modifying hardware components.

17. The method of claim 16, wherein the OPUS file comprises parameters that define operations controlled by an execution of the sample processing bay on the detection instrument and the AAM file comprises parameters that define an analysis performed by the assay analysis module on the detection instrument.

18. The method of claim 16, further comprising: receiving a sample by the detection instrument, processing the sample by the detection instrument, and generating by the detection instrument sample scan data based on the processing.

19. The method of claim 18, further comprising analyzing by the detection instrument sample scan data wherein analyzing comprises selection between two or more digital filters to process scan data generated from processing a sample.

20. The method of claim 16, wherein the OPUS file comprises parameters for processing the new analyte and the AAM file comprises analysis instructions for analyzing the new analyte.

21. The method of claim 18, further comprising determining by the detection instrument the presence of one or more targets in the sample.

* * * * *